(12) United States Patent
Odate et al.

(10) Patent No.: US 11,549,107 B2
(45) Date of Patent: Jan. 10, 2023

(54) COMPOSITIONS AND METHODS FOR TREATING ALPHA-1 ANTITRYPSIN DEFICIENCY

(71) Applicant: Intellia Therapeutics, Inc., Cambridge, MA (US)

(72) Inventors: Shobu Odate, Arlington, MA (US); Walter Strapps, Dedham, MA (US); Reynald Michael Lescarbeau, Medford, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 586 days.

(21) Appl. No.: 16/446,764

(22) Filed: Jun. 20, 2019

(65) Prior Publication Data

US 2019/0316129 A1    Oct. 17, 2019

Related U.S. Application Data

(63) Continuation of application No. PCT/US2017/067800, filed on Dec. 21, 2017.

(60) Provisional application No. 62/438,219, filed on Dec. 22, 2016.

(51) Int. Cl.

| | | |
|---|---|---|
| *C12N 15/113* | (2010.01) | |
| *A61K 9/14* | (2006.01) | |
| *A61K 47/24* | (2006.01) | |
| *A61K 47/28* | (2006.01) | |
| *C12N 15/86* | (2006.01) | |
| *A61K 9/51* | (2006.01) | |

(52) U.S. Cl.
CPC .............. *C12N 15/113* (2013.01); *A61K 9/14* (2013.01); *A61K 9/5146* (2013.01); *A61K 47/24* (2013.01); *A61K 47/28* (2013.01); *C12N 15/86* (2013.01); *C12N 2310/20* (2017.05)

(58) Field of Classification Search
CPC .......................... C12N 15/113; C12N 2310/20
See application file for complete search history.

(56) References Cited

U.S. PATENT DOCUMENTS

| | | | | |
|---|---|---|---|---|
| 7,250,496 B2 * | 7/2007 | Bentwich | ................ | G16B 15/10 435/320.1 |
| 2015/0059010 A1 * | 2/2015 | Cigan | ................ | C12N 15/8216 800/298 |
| 2015/0166984 A1 | 6/2015 | Liu et al. | | |
| 2018/0273979 A1 * | 9/2018 | Frisch | ................ | C12N 15/111 |

FOREIGN PATENT DOCUMENTS

| | | |
|---|---|---|
| WO | 9313121 A1 | 7/1993 |
| WO | 9532305 A1 | 11/1995 |
| WO | 2016089433 A1 | 6/2016 |
| WO | 2014204726 A9 | 10/2016 |
| WO | 2016164356 A1 | 10/2016 |
| WO | 2017093804 A2 | 6/2017 |
| WO | 2017165862 A1 | 9/2017 |

OTHER PUBLICATIONS

Yusa, Kosuke et al. "Targeted gene corrections of α1-antitryypsin deficiency in induced pluripotent stem cells" Nature 487:391-396 (2011).
Adams et al., "The Biochemistry of the Nucleic Acids", ed., 11th ed., 1992.
Borel et al., "Simultaneous disruption of five Serpina1 genes in mice using CRISPR/Cas9 to generate the first model of alpha-one antitrypsin deficiency, the leading cause of genetic COPD", https://www.umassmed.edu/globalassets/mueller-lab-for-gene-therapy/images/blog-posts/2015-umms-aat.pdf, XP002768895, [retrieved on May 1, 2015].
Carlson, J A et al. "Accumulation of PiZ alpha 1-antitrypsin causes liver damage in transgenic mice." The Journal of clinical investigation vol. 83,4 (1989): 1183-90.
Kelley Melissa L et al: "Versatility of chemically synthesized guide RNAs for CRISPR-Cas9 genome editing", Journal of Biotechnology, Elsevier, vol. 233, (2016), p. 74-83.
Makarova, Kira S, et al., "An updated evolutionary classification of CRISPR-Cas systems." Nature reviews. Microbiology vol. 13,11 (2015): 722-36.
Mefferd et al., "Expression of CRISPR/Cas single guide RNAs using small tRNA promoters", RNA, (2015), 21:1683-9.
Scherer, Lisa J et al. "Optimization and characterization of tRNA-shRNA expression constructs." Nucleic acids research vol. 35,8 (2007): 2620-8.
Shmakov, Sergey et al. "Discovery and Functional Characterization of Diverse Class 2 CRISPR-Cas Systems." Molecular cell vol. 60,3 (2015): 385-97.
Smith, Cory et al. "Efficient and allele-specific genome editing of disease loci in human iPSCs." Molecular therapy : the journal of the American Society of Gene Therapy vol. 23,3 (2014): 570-577.
Tsai, Shengdar Q et al. "GUIDE-seq enables genome-wide profiling of off-target cleavage by CRISPR-Cas nucleases." Nature biotechnology vol. 33,2 (2015): 187-197.
Turner, A.M., "Alpha-1 Antitrypsin Deficiency: New Developments in Augmentation and Other Therapies", BioDrugs (2013) 27: 547-558.
Vester and Wengel, "LNA (locked nucleic acid): high-affinity targeting of complementary RNA and DNA", Biochemistry, (2004), 43(42):13233-41.

(Continued)

*Primary Examiner* — Brian Whiteman
(74) *Attorney, Agent, or Firm* — McNeill Baur PLLC

(57) ABSTRACT

Compositions and methods for introducing double-stranded breaks within the SERPINA1 gene are provided. Compositions and methods for reducing and eliminating mutant forms of α1-antitrypsin (AAT), such as seen in subjects having α1-antitrypsin deficiency (AATD), are provided.

21 Claims, 15 Drawing Sheets

Specification includes a Sequence Listing.

(56) References Cited

OTHER PUBLICATIONS

Zetsche et al., "Cpf1 is a Single RNA-Guided Endonuclease of a Class 2 CRISPR-Cas System," Cell, (2015) 163, 3:759-771.
International Search Report and Written Opinion for PCT/US2017/067800 dated Mar. 14, 2018.

* cited by examiner

```
                              SEQUENCE LISTING

<160> NUMBER OF SEQ ID NOS: 424

<210> SEQ ID NO 1
<211> LENGTH: 20
<212> TYPE: RNA
<213> ORGANISM: Artificial Sequence
<220> FEATURE:
<223> OTHER INFORMATION: Synthetic

<400> SEQUENCE: 1
gccagacucc aaguucugcc                                                    20

<210> SEQ ID NO 2
<211> LENGTH: 20
<212> TYPE: RNA
<213> ORGANISM: Artificial Sequence
<220> FEATURE:
<223> OTHER INFORMATION: Synthetic

<400> SEQUENCE: 2
uaaggccagu ggaaagaauu                                                    20

<210> SEQ ID NO 3
<211> LENGTH: 20
<212> TYPE: RNA
<213> ORGANISM: Artificial Sequence
<220> FEATURE:
<223> OTHER INFORMATION: Synthetic

<400> SEQUENCE: 3
ggcagcgagg aguccacagu                                                    20

<210> SEQ ID NO 4
<211> LENGTH: 20
<212> TYPE: RNA
<213> ORGANISM: Artificial Sequence
<220> FEATURE:
<223> OTHER INFORMATION: Synthetic

<400> SEQUENCE: 4
ucuuuccacu ggccuuaacc                                                    20

<210> SEQ ID NO 5
<211> LENGTH: 20
<212> TYPE: RNA
<213> ORGANISM: Artificial Sequence
<220> FEATURE:
<223> OTHER INFORMATION: Synthetic

<400> SEQUENCE: 5
caaugccguc uucugucucg                                                    20

<210> SEQ ID NO 6
<211> LENGTH: 20
<212> TYPE: RNA
<213> ORGANISM: Artificial Sequence
<220> FEATURE:
<223> OTHER INFORMATION: Synthetic

<400> SEQUENCE: 6
```
aaugccgucu ucugucucgu                                              20

<210> SEQ ID NO 7
<211> LENGTH: 20
<212> TYPE: RNA
<213> ORGANISM: Artificial Sequence
<220> FEATURE:
<223> OTHER INFORMATION: Synthetic

<400> SEQUENCE: 7
augccgucuu cugucucgug                                              20

<210> SEQ ID NO 8
<211> LENGTH: 20
<212> TYPE: RNA
<213> ORGANISM: Artificial Sequence
<220> FEATURE:
<223> OTHER INFORMATION: Synthetic

<400> SEQUENCE: 8
augccccacg agacagaaga                                              20

<210> SEQ ID NO 9
<211> LENGTH: 20
<212> TYPE: RNA
<213> ORGANISM: Artificial Sequence
<220> FEATURE:
<223> OTHER INFORMATION: Synthetic

<400> SEQUENCE: 9 cucgugggc auccuccugc                                               20

<210> SEQ ID NO 10
<211> LENGTH: 20
<212> TYPE: RNA
<213> ORGANISM: Artificial Sequence
<220> FEATURE:
<223> OTHER INFORMATION: Synthetic

<400> SEQUENCE: 10
ggauccucag ccagggagac                                              20

<210> SEQ ID NO 11
<211> LENGTH: 20
<212> TYPE: RNA
<213> ORGANISM: Artificial Sequence
<220> FEATURE:
<223> OTHER INFORMATION: Synthetic

<400> SEQUENCE: 11
ucccuggcug aggauccca                                               20

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12
ucccugggga uccucagcca                                              20

<210> SEQ ID NO 13
<211> LENGTH: 20
<212> TYPE: RNA
<213> ORGANISM: Artificial Sequence -continued
<220> FEATURE:
<223> OTHER INFORMATION: Synthetic

<400> SEQUENCE: 13
cucccugggg auccucagcc                                                    20

<210> SEQ ID NO 14
<211> LENGTH: 20
<212> TYPE: RNA
<213> ORGANISM: Artificial Sequence
<220> FEATURE:
<223> OTHER INFORMATION: Synthetic

<400> SEQUENCE: 14
gugggaugua ucugucuucu                                                    20

<210> SEQ ID NO 15
<211> LENGTH: 20
<212> TYPE: RNA
<213> ORGANISM: Artificial Sequence
<220> FEATURE:
<223> OTHER INFORMATION: Synthetic

<400> SEQUENCE: 15
ggugggaugu aucugucuuc                                                    20

<210> SEQ ID NO 16
<211> LENGTH: 20
<212> TYPE: RNA
<213> ORGANISM: Artificial Sequence
<220> FEATURE:
<223> OTHER INFORMATION: Synthetic

<400> SEQUENCE: 16
agauacaucc caccaugauc                                                    20

<210> SEQ ID NO 17
<211> LENGTH: 20
<212> TYPE: RNA
<213> ORGANISM: Artificial Sequence
<220> FEATURE:
<223> OTHER INFORMATION: Synthetic

<400> SEQUENCE: 17
ugggugaucc ugaucauggu                                                    20

<210> SEQ ID NO 18
<211> LENGTH: 20
<212> TYPE: RNA
<213> ORGANISM: Artificial Sequence
<220> FEATURE:
<223> OTHER INFORMATION: Synthetic

<400> SEQUENCE: 18
uugggugauc cugaucaugg                                                    20

<210> SEQ ID NO 19
<211> LENGTH: 20
<212> TYPE: RNA
<213> ORGANISM: Artificial Sequence
<220> FEATURE:
<223> OTHER INFORMATION: Synthetic

<400> SEQUENCE: 19
agguugggug auccugauca                                                    20

```
<210> SEQ ID NO 20
<211> LENGTH: 20
<212> TYPE: RNA
<213> ORGANISM: Artificial Sequence
<220> FEATURE:
<223> OTHER INFORMATION: Synthetic

<400> SEQUENCE: 20
gggugaucuu guugaagguu                                                    20

<210> SEQ ID NO 21
<211> LENGTH: 20
<212> TYPE: RNA
<213> ORGANISM: Artificial Sequence
<220> FEATURE:
<223> OTHER INFORMATION: Synthetic

<400> SEQUENCE: 21
ggggugaucu uguugaaggu                                                    20

<210> SEQ ID NO 22
<211> LENGTH: 20
<212> TYPE: RNA
<213> ORGANISM: Artificial Sequence
<220> FEATURE:
<223> OTHER INFORMATION: Synthetic

<400> SEQUENCE: 22
caacaagauc accccccaacc                                                   20

<210> SEQ ID NO 23
<211> LENGTH: 20
<212> TYPE: RNA
<213> ORGANISM: Artificial Sequence
<220> FEATURE:
<223> OTHER INFORMATION: Synthetic

<400> SEQUENCE: 23
aggcgaacuc agccagguug                                                    20

<210> SEQ ID NO 24
<211> LENGTH: 20
<212> TYPE: RNA
<213> ORGANISM: Artificial Sequence
<220> FEATURE:
<223> OTHER INFORMATION: Synthetic

<400> SEQUENCE: 24
gaaggcgaac ucagccaggu                                                    20

<210> SEQ ID NO 25
<211> LENGTH: 20
<212> TYPE: RNA
<213> ORGANISM: Artificial Sequence
<220> FEATURE:
<223> OTHER INFORMATION: Synthetic

<400> SEQUENCE: 25
ggcugaaggc gaacucagcc                                                    20

<210> SEQ ID NO 26
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 26
cagcuggcgg uauaggcuga                                                    20

<210> SEQ ID NO 27
<211> LENGTH: 20
<212> TYPE: RNA
<213> ORGANISM: Artificial Sequence
<220> FEATURE:
<223> OTHER INFORMATION: Synthetic

<400> SEQUENCE: 27
cuucagccua uaccgccagc                                                    20

<210> SEQ ID NO 28
<211> LENGTH: 20
<212> TYPE: RNA
<213> ORGANISM: Artificial Sequence
<220> FEATURE:
<223> OTHER INFORMATION: Synthetic

<400> SEQUENCE: 28
ggugugccag cuggcgguau                                                    20

<210> SEQ ID NO 29
<211> LENGTH: 20
<212> TYPE: RNA
<213> ORGANISM: Artificial Sequence
<220> FEATURE:
<223> OTHER INFORMATION: Synthetic

<400> SEQUENCE: 29
uguuggacug gugugccagc                                                    20

<210> SEQ ID NO 30
<211> LENGTH: 20
<212> TYPE: RNA
<213> ORGANISM: Artificial Sequence
<220> FEATURE:
<223> OTHER INFORMATION: Synthetic

<400> SEQUENCE: 30
agauauuggu gcuguuggac                                                    20

<210> SEQ ID NO 31
<211> LENGTH: 20
<212> TYPE: RNA
<213> ORGANISM: Artificial Sequence
<220> FEATURE:
<223> OTHER INFORMATION: Synthetic

<400> SEQUENCE: 31
gaagaagaua uuggugcugu                                                    20

<210> SEQ ID NO 32
<211> LENGTH: 20
<212> TYPE: RNA
<213> ORGANISM: Artificial Sequence
<220> FEATURE:
<223> OTHER INFORMATION: Synthetic

<400> SEQUENCE: 32
cacuggggag aagaagauau                                                    20

<210> SEQ ID NO 33
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 33
ggcuguagcg augcucacug                                               20

<210> SEQ ID NO 34
<211> LENGTH: 20
<212> TYPE: RNA
<213> ORGANISM: Artificial Sequence
<220> FEATURE:
<223> OTHER INFORMATION: Synthetic

<400> SEQUENCE: 34
aggcuguagc gaugcucacu                                               20

<210> SEQ ID NO 35
<211> LENGTH: 20
<212> TYPE: RNA
<213> ORGANISM: Artificial Sequence
<220> FEATURE:
<223> OTHER INFORMATION: Synthetic

<400> SEQUENCE: 35
aaggcuguag cgaugcucac                                               20

<210> SEQ ID NO 36
<211> LENGTH: 20
<212> TYPE: RNA
<213> ORGANISM: Artificial Sequence
<220> FEATURE:
<223> OTHER INFORMATION: Synthetic

<400> SEQUENCE: 36
ugacacucac gaugaaaucc                                               20

<210> SEQ ID NO 37
<211> LENGTH: 20
<212> TYPE: RNA
<213> ORGANISM: Artificial Sequence
<220> FEATURE:
<223> OTHER INFORMATION: Synthetic

<400> SEQUENCE: 37
cacucacgau gaaauccugg                                               20

<210> SEQ ID NO 38
<211> LENGTH: 20
<212> TYPE: RNA
<213> ORGANISM: Artificial Sequence
<220> FEATURE:
<223> OTHER INFORMATION: Synthetic

<400> SEQUENCE: 38
acucacgaug aaauccugga                                               20

<210> SEQ ID NO 39
<211> LENGTH: 20
<212> TYPE: RNA
<213> ORGANISM: Artificial Sequence
<220> FEATURE:
<223> OTHER INFORMATION: Synthetic

<400> SEQUENCE: 39
```

```
gguugaaauu caggcccucc                                           20

<210> SEQ ID NO 40
<211> LENGTH: 20
<212> TYPE: RNA
<213> ORGANISM: Artificial Sequence
<220> FEATURE:
<223> OTHER INFORMATION: Synthetic

<400> SEQUENCE: 40
gggccugaau uucaaccuca                                           20

<210> SEQ ID NO 41
<211> LENGTH: 20
<212> TYPE: RNA
<213> ORGANISM: Artificial Sequence
<220> FEATURE:
<223> OTHER INFORMATION: Synthetic

<400> SEQUENCE: 41
uuucaaccuc acggagauuc                                           20

<210> SEQ ID NO 42
<211> LENGTH: 20
<212> TYPE: RNA
<213> ORGANISM: Artificial Sequence
<220> FEATURE:
<223> OTHER INFORMATION: Synthetic

<400> SEQUENCE: 42
caaccucacg gagauuccgg                                           20

<210> SEQ ID NO 43
<211> LENGTH: 20
<212> TYPE: RNA
<213> ORGANISM: Artificial Sequence
<220> FEATURE:
<223> OTHER INFORMATION: Synthetic

<400> SEQUENCE: 43
gagccuccgg aaucuccgug                                           20

<210> SEQ ID NO 44
<211> LENGTH: 20
<212> TYPE: RNA
<213> ORGANISM: Artificial Sequence
<220> FEATURE:
<223> OTHER INFORMATION: Synthetic

<400> SEQUENCE: 44
ccggaggcuc agauccauga                                           20

<210> SEQ ID NO 45
<211> LENGTH: 20
<212> TYPE: RNA
<213> ORGANISM: Artificial Sequence
<220> FEATURE:
<223> OTHER INFORMATION: Synthetic

<400> SEQUENCE: 45
ugaggguacg gaggaguucc                                           20

<210> SEQ ID NO 46
<211> LENGTH: 20
<212> TYPE: RNA
```

```
<213> ORGANISM: Artificial Sequence
<220> FEATURE:
<223> OTHER INFORMATION: Synthetic

<400> SEQUENCE: 46
cuggcugguu gaggguacgg                                                   20

<210> SEQ ID NO 47
<211> LENGTH: 20
<212> TYPE: RNA
<213> ORGANISM: Artificial Sequence
<220> FEATURE:
<223> OTHER INFORMATION: Synthetic

<400> SEQUENCE: 47
cuggcugucu ggcugguuga                                                   20

<210> SEQ ID NO 48
<211> LENGTH: 20
<212> TYPE: RNA
<213> ORGANISM: Artificial Sequence
<220> FEATURE:
<223> OTHER INFORMATION: Synthetic

<400> SEQUENCE: 48
cuccagcuga ccaccggcaa                                                   20

<210> SEQ ID NO 49
<211> LENGTH: 20
<212> TYPE: RNA
<213> ORGANISM: Artificial Sequence
<220> FEATURE:
<223> OTHER INFORMATION: Synthetic

<400> SEQUENCE: 49
ggccauugcc gguggucagc                                                   20

<210> SEQ ID NO 50
<211> LENGTH: 20
<212> TYPE: RNA
<213> ORGANISM: Artificial Sequence
<220> FEATURE:
<223> OTHER INFORMATION: Synthetic

<400> SEQUENCE: 50
gaggaacagg ccauugccgg                                                   20

<210> SEQ ID NO 51
<211> LENGTH: 20
<212> TYPE: RNA
<213> ORGANISM: Artificial Sequence
<220> FEATURE:
<223> OTHER INFORMATION: Synthetic

<400> SEQUENCE: 51
gcugaggaac aggccauugc                                                   20

<210> SEQ ID NO 52
<211> LENGTH: 20
<212> TYPE: RNA
<213> ORGANISM: Artificial Sequence
<220> FEATURE:
<223> OTHER INFORMATION: Synthetic

<400> SEQUENCE: 52
caauggccug uuccucagcg                                                   20
```

<210> SEQ ID NO 53
<211> LENGTH: 20
<212> TYPE: RNA
<213> ORGANISM: Artificial Sequence
<220> FEATURE:
<223> OTHER INFORMATION: Synthetic

<400> SEQUENCE: 53
aauggccugu uccucagcga                                              20

<210> SEQ ID NO 54
<211> LENGTH: 20
<212> TYPE: RNA
<213> ORGANISM: Artificial Sequence
<220> FEATURE:
<223> OTHER INFORMATION: Synthetic

<400> SEQUENCE: 54
ucaggcccuc gcugaggaac                                              20

<210> SEQ ID NO 55
<211> LENGTH: 20
<212> TYPE: RNA
<213> ORGANISM: Artificial Sequence
<220> FEATURE:
<223> OTHER INFORMATION: Synthetic

<400> SEQUENCE: 55
cuagcuucag gcccucgcug                                              20

<210> SEQ ID NO 56
<211> LENGTH: 20
<212> TYPE: RNA
<213> ORGANISM: Artificial Sequence
<220> FEATURE:
<223> OTHER INFORMATION: Synthetic

<400> SEQUENCE: 56
cagcgagggc cugaagcuag                                              20

<210> SEQ ID NO 57
<211> LENGTH: 20
<212> TYPE: RNA
<213> ORGANISM: Artificial Sequence
<220> FEATURE:
<223> OTHER INFORMATION: Synthetic

<400> SEQUENCE: 57
aaaacuuauc cacuagcuuc                                              20

<210> SEQ ID NO 58
<211> LENGTH: 20
<212> TYPE: RNA
<213> ORGANISM: Artificial Sequence
<220> FEATURE:
<223> OTHER INFORMATION: Synthetic

<400> SEQUENCE: 58
gaagcuagug gauaaguuuu                                              20

<210> SEQ ID NO 59
<211> LENGTH: 20
<212> TYPE: RNA
<213> ORGANISM: Artificial Sequence
<220> FEATURE:

<223> OTHER INFORMATION: Synthetic

<400> SEQUENCE: 59
gcuaguggau aaguuuuugg					20

<210> SEQ ID NO 60
<211> LENGTH: 20
<212> TYPE: RNA
<213> ORGANISM: Artificial Sequence
<220> FEATURE:
<223> OTHER INFORMATION: Synthetic

<400> SEQUENCE: 60
ugacagugaa ggcuucugag					20

<210> SEQ ID NO 61
<211> LENGTH: 20
<212> TYPE: RNA
<213> ORGANISM: Artificial Sequence
<220> FEATURE:
<223> OTHER INFORMATION: Synthetic

<400> SEQUENCE: 61
aagccuucac ugucaacuuc					20

<210> SEQ ID NO 62
<211> LENGTH: 20
<212> TYPE: RNA
<213> ORGANISM: Artificial Sequence
<220> FEATURE:
<223> OTHER INFORMATION: Synthetic

<400> SEQUENCE: 62
agccuucacu gucaacuucg					20

<210> SEQ ID NO 63
<211> LENGTH: 20
<212> TYPE: RNA
<213> ORGANISM: Artificial Sequence
<220> FEATURE:
<223> OTHER INFORMATION: Synthetic

<400> SEQUENCE: 63 gucccgaag uugacaguga					20

<210> SEQ ID NO 64
<211> LENGTH: 20
<212> TYPE: RNA
<213> ORGANISM: Artificial Sequence
<220> FEATURE:
<223> OTHER INFORMATION: Synthetic

<400> SEQUENCE: 64
caacuucggg gacaccgaag					20

<210> SEQ ID NO 65
<211> LENGTH: 20
<212> TYPE: RNA
<213> ORGANISM: Artificial Sequence
<220> FEATURE:
<223> OTHER INFORMATION: Synthetic

<400> SEQUENCE: 65
gaucuguuuc uuggccucuu					20

```
<210> SEQ ID NO 66
<211> LENGTH: 20
<212> TYPE: RNA
<213> ORGANISM: Artificial Sequence
<220> FEATURE:
<223> OTHER INFORMATION: Synthetic

<400> SEQUENCE: 66
guaaucguug aucuguuucu                                                   20

<210> SEQ ID NO 67
<211> LENGTH: 20
<212> TYPE: RNA
<213> ORGANISM: Artificial Sequence
<220> FEATURE:
<223> OTHER INFORMATION: Synthetic

<400> SEQUENCE: 67
gaaacagauc aacgauuacg                                                   20

<210> SEQ ID NO 68
<211> LENGTH: 20
<212> TYPE: RNA
<213> ORGANISM: Artificial Sequence
<220> FEATURE:
<223> OTHER INFORMATION: Synthetic

<400> SEQUENCE: 68
gaucaacgau uacguggaga                                                   20

<210> SEQ ID NO 69
<211> LENGTH: 20
<212> TYPE: RNA
<213> ORGANISM: Artificial Sequence
<220> FEATURE:
<223> OTHER INFORMATION: Synthetic

<400> SEQUENCE: 69
aucaacgauu acguggagaa                                                   20

<210> SEQ ID NO 70
<211> LENGTH: 20
<212> TYPE: RNA
<213> ORGANISM: Artificial Sequence
<220> FEATURE:
<223> OTHER INFORMATION: Synthetic

<400> SEQUENCE: 70
uacguggaga aggguacuca                                                   20

<210> SEQ ID NO 71
<211> LENGTH: 20
<212> TYPE: RNA
<213> ORGANISM: Artificial Sequence
<220> FEATURE:
<223> OTHER INFORMATION: Synthetic

<400> SEQUENCE: 71
acguggagaa ggguacucaa                                                   20

<210> SEQ ID NO 72
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 72
ucaagggaaa auuguggauu                                               20

<210> SEQ ID NO 73
<211> LENGTH: 20
<212> TYPE: RNA
<213> ORGANISM: Artificial Sequence
<220> FEATURE:
<223> OTHER INFORMATION: Synthetic

<400> SEQUENCE: 73
gaaaauugug gauuugguca                                               20

<210> SEQ ID NO 74
<211> LENGTH: 20
<212> TYPE: RNA
<213> ORGANISM: Artificial Sequence
<220> FEATURE:
<223> OTHER INFORMATION: Synthetic

<400> SEQUENCE: 74
cagagacaca guuuuugcuc                                               20

<210> SEQ ID NO 75
<211> LENGTH: 20
<212> TYPE: RNA
<213> ORGANISM: Artificial Sequence
<220> FEATURE:
<223> OTHER INFORMATION: Synthetic

<400> SEQUENCE: 75
uccccucucu ccaggcaaau                                               20

<210> SEQ ID NO 76
<211> LENGTH: 20
<212> TYPE: RNA
<213> ORGANISM: Artificial Sequence
<220> FEATURE:
<223> OTHER INFORMATION: Synthetic

<400> SEQUENCE: 76 cucgugucc uugacuucaa                                                20

<210> SEQ ID NO 77
<211> LENGTH: 20
<212> TYPE: RNA
<213> ORGANISM: Artificial Sequence
<220> FEATURE:
<223> OTHER INFORMATION: Synthetic

<400> SEQUENCE: 77
cuuugaaguc aaggacaccg                                               20

<210> SEQ ID NO 78
<211> LENGTH: 20
<212> TYPE: RNA
<213> ORGANISM: Artificial Sequence
<220> FEATURE:
<223> OTHER INFORMATION: Synthetic

<400> SEQUENCE: 78
cacguggaag uccucuuccu                                               20

<210> SEQ ID NO 79
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 79
cgaggaagag gacuuccacg                                                    20

<210> SEQ ID NO 80
<211> LENGTH: 20
<212> TYPE: RNA
<213> ORGANISM: Artificial Sequence
<220> FEATURE:
<223> OTHER INFORMATION: Synthetic

<400> SEQUENCE: 80
agaggacuuc cacguggacc                                                    20

<210> SEQ ID NO 81
<211> LENGTH: 20
<212> TYPE: RNA
<213> ORGANISM: Artificial Sequence
<220> FEATURE:
<223> OTHER INFORMATION: Synthetic

<400> SEQUENCE: 81
cgguggucac cugguccacg                                                    20

<210> SEQ ID NO 82
<211> LENGTH: 20
<212> TYPE: RNA
<213> ORGANISM: Artificial Sequence
<220> FEATURE:
<223> OTHER INFORMATION: Synthetic

<400> SEQUENCE: 82
ggaccaggug accaccguga                                                    20

<210> SEQ ID NO 83
<211> LENGTH: 20
<212> TYPE: RNA
<213> ORGANISM: Artificial Sequence
<220> FEATURE:
<223> OTHER INFORMATION: Synthetic

<400> SEQUENCE: 83
gcaccuucac gguggucacc                                                    20

<210> SEQ ID NO 84
<211> LENGTH: 20
<212> TYPE: RNA
<213> ORGANISM: Artificial Sequence
<220> FEATURE:
<223> OTHER INFORMATION: Synthetic

<400> SEQUENCE: 84
caucauaggc accuucacgg                                                    20

<210> SEQ ID NO 85
<211> LENGTH: 20
<212> TYPE: RNA
<213> ORGANISM: Artificial Sequence
<220> FEATURE:
<223> OTHER INFORMATION: Synthetic

<400> SEQUENCE: 85
```
gugccuauga ugaagcguuu                                              20

<210> SEQ ID NO 86
<211> LENGTH: 20
<212> TYPE: RNA
<213> ORGANISM: Artificial Sequence
<220> FEATURE:
<223> OTHER INFORMATION: Synthetic

<400> SEQUENCE: 86
augccuaaac gcuucaucau                                              20

<210> SEQ ID NO 87
<211> LENGTH: 20
<212> TYPE: RNA
<213> ORGANISM: Artificial Sequence
<220> FEATURE:
<223> OTHER INFORMATION: Synthetic

<400> SEQUENCE: 87
uggacagcuu cuuacagugc                                              20

<210> SEQ ID NO 88
<211> LENGTH: 20
<212> TYPE: RNA
<213> ORGANISM: Artificial Sequence
<220> FEATURE:
<223> OTHER INFORMATION: Synthetic

<400> SEQUENCE: 88
cuguaagaag cuguccagcu                                              20

<210> SEQ ID NO 89
<211> LENGTH: 20
<212> TYPE: RNA
<213> ORGANISM: Artificial Sequence
<220> FEATURE:
<223> OTHER INFORMATION: Synthetic

<400> SEQUENCE: 89
ggugcugcug augaaauacc                                              20

<210> SEQ ID NO 90
<211> LENGTH: 20
<212> TYPE: RNA
<213> ORGANISM: Artificial Sequence
<220> FEATURE:
<223> OTHER INFORMATION: Synthetic

<400> SEQUENCE: 90
gugcugcuga ugaaauaccu                                              20

<210> SEQ ID NO 91
<211> LENGTH: 20
<212> TYPE: RNA
<213> ORGANISM: Artificial Sequence
<220> FEATURE:
<223> OTHER INFORMATION: Synthetic

<400> SEQUENCE: 91
agauggcggu ggcauugccc                                              20

<210> SEQ ID NO 92
<211> LENGTH: 20
<212> TYPE: RNA
<213> ORGANISM: Artificial Sequence
<220> FEATURE:
<223> OTHER INFORMATION: Synthetic

<400> SEQUENCE: 92
aggcaggaag aagauggcgg                                                    20

<210> SEQ ID NO 93
<211> LENGTH: 20
<212> TYPE: RNA
<213> ORGANISM: Artificial Sequence
<220> FEATURE:
<223> OTHER INFORMATION: Synthetic

<400> SEQUENCE: 93
ggucagcaca gccuuaugca                                                    20

<210> SEQ ID NO 94
<211> LENGTH: 20
<212> TYPE: RNA
<213> ORGANISM: Artificial Sequence
<220> FEATURE:
<223> OTHER INFORMATION: Synthetic

<400> SEQUENCE: 94
agaaagggac ugaagcugcu                                                    20

<210> SEQ ID NO 95
<211> LENGTH: 20
<212> TYPE: RNA
<213> ORGANISM: Artificial Sequence
<220> FEATURE:
<223> OTHER INFORMATION: Synthetic

<400> SEQUENCE: 95
gaaagggacu gaagcugcug                                                    20

<210> SEQ ID NO 96
<211> LENGTH: 20
<212> TYPE: RNA
<213> ORGANISM: Artificial Sequence
<220> FEATURE:
<223> OTHER INFORMATION: Synthetic

<400> SEQUENCE: 96
ugcuggggcc auguuuuuag                                                    20

<210> SEQ ID NO 97
<211> LENGTH: 20
<212> TYPE: RNA
<213> ORGANISM: Artificial Sequence
<220> FEATURE:
<223> OTHER INFORMATION: Synthetic

<400> SEQUENCE: 97
ggguauggcc ucuaaaaaca                                                    20

<210> SEQ ID NO 98
<211> LENGTH: 20
<212> TYPE: RNA
<213> ORGANISM: Artificial Sequence
<220> FEATURE:
<223> OTHER INFORMATION: Synthetic

<400> SEQUENCE: 98
uguugaacuu gaccucgggg                                                    20

```
<210> SEQ ID NO 99
<211> LENGTH: 20
<212> TYPE: RNA
<213> ORGANISM: Artificial Sequence
<220> FEATURE:
<223> OTHER INFORMATION: Synthetic

<400> SEQUENCE: 99
ggguuuguug aacuugaccu                                               20

<210> SEQ ID NO 100
<211> LENGTH: 20
<212> TYPE: RNA
<213> ORGANISM: Artificial Sequence
<220> FEATURE:
<223> OTHER INFORMATION: Synthetic

<400> SEQUENCE: 100
uucugggcag caucucccug                                               20

<210> SEQ ID NO 101
<211> LENGTH: 20
<212> TYPE: RNA
<213> ORGANISM: Artificial Sequence
<220> FEATURE:
<223> OTHER INFORMATION: Synthetic

<400> SEQUENCE: 101 ucuucgggc agcaucuccc                                                20

<210> SEQ ID NO 102
<211> LENGTH: 20
<212> TYPE: RNA
<213> ORGANISM: Artificial Sequence
<220> FEATURE:
<223> OTHER INFORMATION: Synthetic

<400> SEQUENCE: 102
uggacuggug ugccagcugg                                               20

<210> SEQ ID NO 103
<211> LENGTH: 20
<212> TYPE: RNA
<213> ORGANISM: Artificial Sequence
<220> FEATURE:
<223> OTHER INFORMATION: Synthetic

<400> SEQUENCE: 103
agccuuugca augcucuccc                                               20

<210> SEQ ID NO 104
<211> LENGTH: 20
<212> TYPE: RNA
<213> ORGANISM: Artificial Sequence
<220> FEATURE:
<223> OTHER INFORMATION: Synthetic

<400> SEQUENCE: 104
uucaucguga gugucagccu                                               20

<210> SEQ ID NO 105
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 105
ucuccgugag guugaaauuc                                         20

<210> SEQ ID NO 106
<211> LENGTH: 20
<212> TYPE: RNA
<213> ORGANISM: Artificial Sequence
<220> FEATURE:
<223> OTHER INFORMATION: Synthetic

<400> SEQUENCE: 106
gucagcugga gcuggcuguc                                         20

<210> SEQ ID NO 107
<211> LENGTH: 20
<212> TYPE: RNA
<213> ORGANISM: Artificial Sequence
<220> FEATURE:
<223> OTHER INFORMATION: Synthetic

<400> SEQUENCE: 107
agccagcucc agcugaccac                                         20

<210> SEQ ID NO 108
<211> LENGTH: 20
<212> TYPE: RNA
<213> ORGANISM: Artificial Sequence
<220> FEATURE:
<223> OTHER INFORMATION: Synthetic

<400> SEQUENCE: 108
aucaggcagg aagaagaugg                                         20

<210> SEQ ID NO 109
<211> LENGTH: 20
<212> TYPE: RNA
<213> ORGANISM: Artificial Sequence
<220> FEATURE:
<223> OTHER INFORMATION: Synthetic

<400> SEQUENCE: 109
caucuucuuc cugccugaug                                         20

<210> SEQ ID NO 110
<211> LENGTH: 20
<212> TYPE: RNA
<213> ORGANISM: Artificial Sequence
<220> FEATURE:
<223> OTHER INFORMATION: Synthetic

<400> SEQUENCE: 110
aucuucuucc ugccugauga                                         20

<210> SEQ ID NO 111
<211> LENGTH: 20
<212> TYPE: RNA
<213> ORGANISM: Artificial Sequence
<220> FEATURE:
<223> OTHER INFORMATION: Synthetic

<400> SEQUENCE: 111
cgauaucauc accaaguucc                                         20

<210> SEQ ID NO 112
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 112
cagaucauag guuccaguaa                                                     20

<210> SEQ ID NO 113
<211> LENGTH: 20
<212> TYPE: RNA
<213> ORGANISM: Artificial Sequence
<220> FEATURE:
<223> OTHER INFORMATION: Synthetic

<400> SEQUENCE: 113
aucacuaagg ucuucagcaa                                                     20

<210> SEQ ID NO 114
<211> LENGTH: 20
<212> TYPE: RNA
<213> ORGANISM: Artificial Sequence
<220> FEATURE:
<223> OTHER INFORMATION: Synthetic

<400> SEQUENCE: 114
ucacuaaggu cuucagcaau                                                     20

<210> SEQ ID NO 115
<211> LENGTH: 20
<212> TYPE: RNA
<213> ORGANISM: Artificial Sequence
<220> FEATURE:
<223> OTHER INFORMATION: Synthetic

<400> SEQUENCE: 115
cacuaagguc uucagcaaug                                                     20

<210> SEQ ID NO 116
<211> LENGTH: 20
<212> TYPE: RNA
<213> ORGANISM: Artificial Sequence
<220> FEATURE:
<223> OTHER INFORMATION: Synthetic

<400> SEQUENCE: 116
cucaccuugg agagcuucag                                                     20

<210> SEQ ID NO 117
<211> LENGTH: 20
<212> TYPE: RNA
<213> ORGANISM: Artificial Sequence
<220> FEATURE:
<223> OTHER INFORMATION: Synthetic

<400> SEQUENCE: 117
ucucaccuug gagagcuuca                                                     20

<210> SEQ ID NO 118
<211> LENGTH: 20
<212> TYPE: RNA
<213> ORGANISM: Artificial Sequence
<220> FEATURE:
<223> OTHER INFORMATION: Synthetic

<400> SEQUENCE: 118
```
aucucaccuu ggagagcuuc                                              20

<210> SEQ ID NO 119
<211> LENGTH: 20
<212> TYPE: RNA
<213> ORGANISM: Artificial Sequence
<220> FEATURE:
<223> OTHER INFORMATION: Synthetic

<400> SEQUENCE: 119
uuguugaacu ugaccucggg                                              20

<210> SEQ ID NO 120
<211> LENGTH: 20
<212> TYPE: RNA
<213> ORGANISM: Artificial Sequence
<220> FEATURE:
<223> OTHER INFORMATION: Synthetic

<400> SEQUENCE: 120
uuuguugaac uugaccucgg                                              20

<210> SEQ ID NO 121
<211> LENGTH: 20
<212> TYPE: RNA
<213> ORGANISM: Artificial Sequence
<220> FEATURE:
<223> OTHER INFORMATION: Synthetic

<400> SEQUENCE: 121
guuuguugaa cuugaccucg                                              20

<210> SEQ ID NO 122
<211> LENGTH: 20
<212> TYPE: RNA
<213> ORGANISM: Artificial Sequence
<220> FEATURE:
<223> OTHER INFORMATION: Synthetic

<400> SEQUENCE: 122
gguuuguuga acuugaccuc                                              20

<210> SEQ ID NO 123
<211> LENGTH: 20
<212> TYPE: RNA
<213> ORGANISM: Artificial Sequence
<220> FEATURE:
<223> OTHER INFORMATION: Synthetic

<400> SEQUENCE: 123
ucaaucauua agaagacaaa                                              20

<210> SEQ ID NO 124
<211> LENGTH: 20
<212> TYPE: RNA
<213> ORGANISM: Artificial Sequence
<220> FEATURE:
<223> OTHER INFORMATION: Synthetic

<400> SEQUENCE: 124
uucaaucauu aagaagacaa                                              20

<210> SEQ ID NO 125
<211> LENGTH: 20
<212> TYPE: RNA

```
<213> ORGANISM: Artificial Sequence
<220> FEATURE:
<223> OTHER INFORMATION: Synthetic

<400> SEQUENCE: 125
uaccaagucu ccccucuuca                                               20

<210> SEQ ID NO 126
<211> LENGTH: 20
<212> TYPE: RNA
<213> ORGANISM: Artificial Sequence
<220> FEATURE:
<223> OTHER INFORMATION: Synthetic

<400> SEQUENCE: 126
accaagucuc cccucuucau                                               20

<210> SEQ ID NO 127
<211> LENGTH: 20
<212> TYPE: RNA
<213> ORGANISM: Artificial Sequence
<220> FEATURE:
<223> OTHER INFORMATION: Synthetic

<400> SEQUENCE: 127
uccccucuuc augggaaaag                                               20

<210> SEQ ID NO 128
<211> LENGTH: 20
<212> TYPE: RNA
<213> ORGANISM: Artificial Sequence
<220> FEATURE:
<223> OTHER INFORMATION: Synthetic

<400> SEQUENCE: 128
caccacuuuu cccaugaaga                                               20

<210> SEQ ID NO 129
<211> LENGTH: 20
<212> TYPE: RNA
<213> ORGANISM: Artificial Sequence
<220> FEATURE:
<223> OTHER INFORMATION: Synthetic

<400> SEQUENCE: 129
ucaccacuuu ucccaugaag                                               20

<210> SEQ ID NO 130
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 130
nnnnnnnnnn nnnnnnnnnn guuuuagagc uagaaauagc aaguuaaaau aaggcuaguc   60
cguuaucaac uugaaaaagu ggcaccgagu cggugcuuuu                        100

<210> SEQ ID NO 131
<211> LENGTH: 100
<212> TYPE: RNA
<213> ORGANISM: Artificial Sequence
```

```
<220> FEATURE:
<223> OTHER INFORMATION: Synthetic

<400> SEQUENCE: 131
agccagcucc agcugaccac guuuuagagc uagaaauagc aaguuaaaau aaggcuaguc      60
cguuaucaac uugaaaaagu ggcaccgagu cggugcuuuu                          100

<210> SEQ ID NO 132
<211> LENGTH: 100
<212> TYPE: RNA
<213> ORGANISM: Artificial Sequence
<220> FEATURE:
<223> OTHER INFORMATION: Synthetic

<400> SEQUENCE: 132
gcugaggaac aggccauugc guuuuagagc uagaaauagc aaguuaaaau aaggcuaguc      60
cguuaucaac uugaaaaagu ggcaccgagu cggugcuuuu                          100

<210> SEQ ID NO 133
<211> LENGTH: 100
<212> TYPE: RNA
<213> ORGANISM: Artificial Sequence
<220> FEATURE:
<223> OTHER INFORMATION: Synthetic

<400> SEQUENCE: 133
acucacgaug aaauccugga guuuuagagc uagaaauagc aaguuaaaau aaggcuaguc      60
cguuaucaac uugaaaaagu ggcaccgagu cggugcuuuu                          100

<210> SEQ ID NO 134
<211> LENGTH: 100
<212> TYPE: RNA
<213> ORGANISM: Artificial Sequence
<220> FEATURE:
<223> OTHER INFORMATION: Synthetic

<400> SEQUENCE: 134
uugggugauc cugaucaugg guuuuagagc uagaaauagc aaguuaaaau aaggcuaguc      60
cguuaucaac uugaaaaagu ggcaccgagu cggugcuuuu                          100

<210> SEQ ID NO 135
<211> LENGTH: 100
<212> TYPE: RNA
<213> ORGANISM: Artificial Sequence
<220> FEATURE:
<223> OTHER INFORMATION: Synthetic

<400> SEQUENCE: 135
ugggugaucc ugaucauggu guuuuagagc uagaaauagc aaguuaaaau aaggcuaguc      60
cguuaucaac uugaaaaagu ggcaccgagu cggugcuuuu                          100

<210> SEQ ID NO 136
<211> LENGTH: 100
<212> TYPE: RNA
<213> ORGANISM: Artificial Sequence
<220> FEATURE:
<223> OTHER INFORMATION: Synthetic

<400> SEQUENCE: 136
gaucuguuuc uuggccucuu guuuuagagc uagaaauagc aaguuaaaau aaggcuaguc      60
cguuaucaac uugaaaaagu ggcaccgagu cggugcuuuu                          100
```

```
<210> SEQ ID NO 137
<211> LENGTH: 100
<212> TYPE: RNA
<213> ORGANISM: Artificial Sequence
<220> FEATURE:
<223> OTHER INFORMATION: Synthetic

<400> SEQUENCE: 137
gaaggcgaac ucagccaggu guuuuagagc uagaaauagc aaguuaaaau aaggcuaguc      60
cguuaucaac uugaaaaagu ggcaccgagu cggugcuuuu                          100

<210> SEQ ID NO 138
<211> LENGTH: 100
<212> TYPE: RNA
<213> ORGANISM: Artificial Sequence
<220> FEATURE:
<223> OTHER INFORMATION: Synthetic

<400> SEQUENCE: 138
caaccucacg gagauuccgg guuuuagagc uagaaauagc aaguuaaaau aaggcuaguc      60
cguuaucaac uugaaaaagu ggcaccgagu cggugcuuuu                          100

<210> SEQ ID NO 139
<211> LENGTH: 100
<212> TYPE: RNA
<213> ORGANISM: Artificial Sequence
<220> FEATURE:
<223> OTHER INFORMATION: Synthetic

<400> SEQUENCE: 139
uguuggacug gugugccagc guuuuagagc uagaaauagc aaguuaaaau aaggcuaguc      60
cguuaucaac uugaaaaagu ggcaccgagu cggugcuuuu                          100

<210> SEQ ID NO 140
<211> LENGTH: 22
<212> TYPE: RNA
<213> ORGANISM: Artificial Sequence
<220> FEATURE:
<223> OTHER INFORMATION: Synthetic

<400> SEQUENCE: 140
guuuuagagc uaugcuguuu ug                                              22

<210> SEQ ID NO 141
<211> LENGTH: 80
<212> TYPE: RNA
<213> ORGANISM: Artificial Sequence
<220> FEATURE:
<223> OTHER INFORMATION: Synthetic

<400> SEQUENCE: 141
guuuuagagc uagaaauagc aaguuaaaau aaggcuaguc cguuaucaac uugaaaaagu      60
ggcaccgagu cggugcuuuu                                                 80

<210> SEQ ID NO 142
<211> LENGTH: 24
<212> TYPE: DNA
<213> ORGANISM: Artificial Sequence
<220> FEATURE:
<223> OTHER INFORMATION: Synthetic

<400> SEQUENCE: 142
gaggagtcca cagtaggatt gatt                                            24
```

<210> SEQ ID NO 143
<211> LENGTH: 23
<212> TYPE: DNA
<213> ORGANISM: Artificial Sequence
<220> FEATURE:
<223> OTHER INFORMATION: Synthetic

<400> SEQUENCE: 143
agctagttgg taaggtcagt gtg                                              23

<210> SEQ ID NO 144
<211> LENGTH: 23
<212> TYPE: DNA
<213> ORGANISM: Artificial Sequence
<220> FEATURE:
<223> OTHER INFORMATION: Synthetic

<400> SEQUENCE: 144
agctagttgg taaggtcagt gtg                                              23

<210> SEQ ID NO 145
<211> LENGTH: 23
<212> TYPE: DNA
<213> ORGANISM: Artificial Sequence
<220> FEATURE:
<223> OTHER INFORMATION: Synthetic

<400> SEQUENCE: 145
agctagttgg taaggtcagt gtg                                              23

<210> SEQ ID NO 146
<211> LENGTH: 24
<212> TYPE: DNA
<213> ORGANISM: Artificial Sequence
<220> FEATURE:
<223> OTHER INFORMATION: Synthetic

<400> SEQUENCE: 146
tcatggtggg atgtatctgt cttc                                             24

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
tcatggtggg atgtatctgt cttc                                             24

<210> SEQ ID NO 148
<211> LENGTH: 24
<212> TYPE: DNA
<213> ORGANISM: Artificial Sequence
<220> FEATURE:
<223> OTHER INFORMATION: Synthetic

<400> SEQUENCE: 148
tcatggtggg atgtatctgt cttc                                             24

<210> SEQ ID NO 149
<211> LENGTH: 24
<212> TYPE: DNA
<213> ORGANISM: Artificial Sequence
<220> FEATURE:

<223> OTHER INFORMATION: Synthetic

<400> SEQUENCE: 149
gatcctgatc atggtgggat gtat                                              24

<210> SEQ ID NO 150
<211> LENGTH: 24
<212> TYPE: DNA
<213> ORGANISM: Artificial Sequence
<220> FEATURE:
<223> OTHER INFORMATION: Synthetic

<400> SEQUENCE: 150
tcatggtggg atgtatctgt cttc                                              24

<210> SEQ ID NO 151
<211> LENGTH: 24
<212> TYPE: DNA
<213> ORGANISM: Artificial Sequence
<220> FEATURE:
<223> OTHER INFORMATION: Synthetic

<400> SEQUENCE: 151
gatattggtg ctgttggact ggtg                                              24

<210> SEQ ID NO 152
<211> LENGTH: 24
<212> TYPE: DNA
<213> ORGANISM: Artificial Sequence
<220> FEATURE:
<223> OTHER INFORMATION: Synthetic

<400> SEQUENCE: 152
atgctcactg gggagaagaa gata                                              24

<210> SEQ ID NO 153
<211> LENGTH: 24
<212> TYPE: DNA
<213> ORGANISM: Artificial Sequence
<220> FEATURE:
<223> OTHER INFORMATION: Synthetic

<400> SEQUENCE: 153
atgctcactg gggagaagaa gata                                              24

<210> SEQ ID NO 154
<211> LENGTH: 24
<212> TYPE: DNA
<213> ORGANISM: Artificial Sequence
<220> FEATURE:
<223> OTHER INFORMATION: Synthetic

<400> SEQUENCE: 154
atgctcactg gggagaagaa gata                                              24

<210> SEQ ID NO 155
<211> LENGTH: 24
<212> TYPE: DNA
<213> ORGANISM: Artificial Sequence
<220> FEATURE:
<223> OTHER INFORMATION: Synthetic

<400> SEQUENCE: 155
gggagaagaa gatattggtg ctgt                                              24

```
<210> SEQ ID NO 156
<211> LENGTH: 24
<212> TYPE: DNA
<213> ORGANISM: Artificial Sequence
<220> FEATURE:
<223> OTHER INFORMATION: Synthetic

<400> SEQUENCE: 156
gggagaagaa gatattggtg ctgt                                          24

<210> SEQ ID NO 157
<211> LENGTH: 24
<212> TYPE: DNA
<213> ORGANISM: Artificial Sequence
<220> FEATURE:
<223> OTHER INFORMATION: Synthetic

<400> SEQUENCE: 157
gggagaagaa gatattggtg ctgt                                          24

<210> SEQ ID NO 158
<211> LENGTH: 24
<212> TYPE: DNA
<213> ORGANISM: Artificial Sequence
<220> FEATURE:
<223> OTHER INFORMATION: Synthetic

<400> SEQUENCE: 158
gggagaagaa gatattggtg ctgt                                          24

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159
gggagaagaa gatattggtg ctgt                                          24

<210> SEQ ID NO 160
<211> LENGTH: 24
<212> TYPE: DNA
<213> ORGANISM: Artificial Sequence
<220> FEATURE:
<223> OTHER INFORMATION: Synthetic

<400> SEQUENCE: 160
gatattggtg ctgttggact ggtg                                          24

<210> SEQ ID NO 161
<211> LENGTH: 24
<212> TYPE: DNA
<213> ORGANISM: Artificial Sequence
<220> FEATURE:
<223> OTHER INFORMATION: Synthetic

<400> SEQUENCE: 161
gggagaagaa gatattggtg ctgt                                          24

<210> SEQ ID NO 162
<211> LENGTH: 24
<212> TYPE: DNA
<213> ORGANISM: Artificial Sequence
<220> FEATURE:
<223> OTHER INFORMATION: Synthetic
```

<400> SEQUENCE: 162
gggagaagaa gatattggtg ctgt                                              24

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
attgcaaagg ctgtagcgat gctc                                              24

<210> SEQ ID NO 164
<211> LENGTH: 24
<212> TYPE: DNA
<213> ORGANISM: Artificial Sequence
<220> FEATURE:
<223> OTHER INFORMATION: Synthetic

<400> SEQUENCE: 164
attgcaaagg ctgtagcgat gctc                                              24

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attgcaaagg ctgtagcgat gctc                                              24

<210> SEQ ID NO 166
<211> LENGTH: 24
<212> TYPE: DNA
<213> ORGANISM: Artificial Sequence
<220> FEATURE:
<223> OTHER INFORMATION: Synthetic

<400> SEQUENCE: 166
attgcaaagg ctgtagcgat gctc                                              24

<210> SEQ ID NO 167
<211> LENGTH: 23
<212> TYPE: DNA
<213> ORGANISM: Artificial Sequence
<220> FEATURE:
<223> OTHER INFORMATION: Synthetic

<400> SEQUENCE: 167
atttcatcgt gagtgtcagc ctt                                               23

<210> SEQ ID NO 168
<211> LENGTH: 23
<212> TYPE: DNA
<213> ORGANISM: Artificial Sequence
<220> FEATURE:
<223> OTHER INFORMATION: Synthetic

<400> SEQUENCE: 168
atttcatcgt gagtgtcagc ctt                                               23

<210> SEQ ID NO 169
<211> LENGTH: 23

```
<212> TYPE: DNA
<213> ORGANISM: Artificial Sequence
<220> FEATURE:
<223> OTHER INFORMATION: Synthetic

<400> SEQUENCE: 169
atttcatcgt gagtgtcagc ctt                                              23

<210> SEQ ID NO 170
<211> LENGTH: 23
<212> TYPE: DNA
<213> ORGANISM: Artificial Sequence
<220> FEATURE:
<223> OTHER INFORMATION: Synthetic

<400> SEQUENCE: 170
atttcatcgt gagtgtcagc ctt                                              23

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171
ccaggatttc atcgtgagtg tcag                                             24

<210> SEQ ID NO 172
<211> LENGTH: 24
<212> TYPE: DNA
<213> ORGANISM: Artificial Sequence
<220> FEATURE:
<223> OTHER INFORMATION: Synthetic

<400> SEQUENCE: 172
ctccaggatt tcatcgtgag tgtc                                             24

<210> SEQ ID NO 173
<211> LENGTH: 23
<212> TYPE: DNA
<213> ORGANISM: Artificial Sequence
<220> FEATURE:
<223> OTHER INFORMATION: Synthetic

<400> SEQUENCE: 173
cggaatctcc gtgaggttga aat                                              23

<210> SEQ ID NO 174
<211> LENGTH: 23
<212> TYPE: DNA
<213> ORGANISM: Artificial Sequence
<220> FEATURE:
<223> OTHER INFORMATION: Synthetic

<400> SEQUENCE: 174
cggaatctcc gtgaggttga aat                                              23

<210> SEQ ID NO 175
<211> LENGTH: 23
<212> TYPE: DNA
<213> ORGANISM: Artificial Sequence
<220> FEATURE:
<223> OTHER INFORMATION: Synthetic

<400> SEQUENCE: 175
```

-continued cggaatctcc gtgaggttga aat                                          23

<210> SEQ ID NO 176
<211> LENGTH: 24
<212> TYPE: DNA
<213> ORGANISM: Artificial Sequence
<220> FEATURE:
<223> OTHER INFORMATION: Synthetic

<400> SEQUENCE: 176
ttcatggatc tgagcctccg gaat                                         24

<210> SEQ ID NO 177
<211> LENGTH: 24
<212> TYPE: DNA
<213> ORGANISM: Artificial Sequence
<220> FEATURE:
<223> OTHER INFORMATION: Synthetic

<400> SEQUENCE: 177
aaaacttatc cactagcttc aggc                                         24

<210> SEQ ID NO 178
<211> LENGTH: 24
<212> TYPE: DNA
<213> ORGANISM: Artificial Sequence
<220> FEATURE:
<223> OTHER INFORMATION: Synthetic

<400> SEQUENCE: 178
aaaacttatc cactagcttc aggc                                         24

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
aaaacttatc cactagcttc aggc                                         24

<210> SEQ ID NO 180
<211> LENGTH: 24
<212> TYPE: DNA
<213> ORGANISM: Artificial Sequence
<220> FEATURE:
<223> OTHER INFORMATION: Synthetic

<400> SEQUENCE: 180
aaaacttatc cactagcttc aggc                                         24

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
aaaacttatc cactagcttc aggc                                         24

<210> SEQ ID NO 182
<211> LENGTH: 23
<212> TYPE: DNA
<213> ORGANISM: Artificial Sequence

```
<220> FEATURE:
<223> OTHER INFORMATION: Synthetic

<400> SEQUENCE: 182
ttatccacta gcttcaggcc ctc                                              23

<210> SEQ ID NO 183
<211> LENGTH: 24
<212> TYPE: DNA
<213> ORGANISM: Artificial Sequence
<220> FEATURE:
<223> OTHER INFORMATION: Synthetic

<400> SEQUENCE: 183
aggcttctga gtggtacaac tttt                                             24

<210> SEQ ID NO 184
<211> LENGTH: 24
<212> TYPE: DNA
<213> ORGANISM: Artificial Sequence
<220> FEATURE:
<223> OTHER INFORMATION: Synthetic

<400> SEQUENCE: 184
aaaacttatc cactagcttc aggc                                             24

<210> SEQ ID NO 185
<211> LENGTH: 24
<212> TYPE: DNA
<213> ORGANISM: Artificial Sequence
<220> FEATURE:
<223> OTHER INFORMATION: Synthetic

<400> SEQUENCE: 185
aggcttctga gtggtacaac tttt                                             24

<210> SEQ ID NO 186
<211> LENGTH: 24
<212> TYPE: DNA
<213> ORGANISM: Artificial Sequence
<220> FEATURE:
<223> OTHER INFORMATION: Synthetic

<400> SEQUENCE: 186
aggcttctga gtggtacaac tttt                                             24

<210> SEQ ID NO 187
<211> LENGTH: 24
<212> TYPE: DNA
<213> ORGANISM: Artificial Sequence
<220> FEATURE:
<223> OTHER INFORMATION: Synthetic

<400> SEQUENCE: 187
aggcttctga gtggtacaac tttt                                             24

<210> SEQ ID NO 188
<211> LENGTH: 24
<212> TYPE: DNA
<213> ORGANISM: Artificial Sequence
<220> FEATURE:
<223> OTHER INFORMATION: Synthetic

<400> SEQUENCE: 188
aggcttctga gtggtacaac tttt                                             24
```

<210> SEQ ID NO 189
<211> LENGTH: 24
<212> TYPE: DNA
<213> ORGANISM: Artificial Sequence
<220> FEATURE:
<223> OTHER INFORMATION: Synthetic

<400> SEQUENCE: 189 attttcccttt gagtaccctt ctcc                                      24

<210> SEQ ID NO 190
<211> LENGTH: 24
<212> TYPE: DNA
<213> ORGANISM: Artificial Sequence
<220> FEATURE:
<223> OTHER INFORMATION: Synthetic

<400> SEQUENCE: 190
attttccctt gagtaccctt ctcc                                       24

<210> SEQ ID NO 191
<211> LENGTH: 24
<212> TYPE: DNA
<213> ORGANISM: Artificial Sequence
<220> FEATURE:
<223> OTHER INFORMATION: Synthetic

<400> SEQUENCE: 191
ttgagtaccc ttctccacgt aatc                                       24

<210> SEQ ID NO 192
<211> LENGTH: 24
<212> TYPE: DNA
<213> ORGANISM: Artificial Sequence
<220> FEATURE:
<223> OTHER INFORMATION: Synthetic

<400> SEQUENCE: 192
attttccctt gagtaccctt ctcc                                       24

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193
ccacaatttt cccttgagta ccct                                       24

<210> SEQ ID NO 194
<211> LENGTH: 24
<212> TYPE: DNA
<213> ORGANISM: Artificial Sequence
<220> FEATURE:
<223> OTHER INFORMATION: Synthetic

<400> SEQUENCE: 194
tctccacgta atcgttgatc tgtt                                       24

<210> SEQ ID NO 195
<211> LENGTH: 24
<212> TYPE: DNA
<213> ORGANISM: Artificial Sequence
<220> FEATURE:
<223> OTHER INFORMATION: Synthetic

```
<400> SEQUENCE: 195
tctccacgta atcgttgatc tgtt                                            24

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
tctccacgta atcgttgatc tgtt                                            24

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attttccctt gagtaccctt ctcc                                            24

<210> SEQ ID NO 198
<211> LENGTH: 24
<212> TYPE: DNA
<213> ORGANISM: Artificial Sequence
<220> FEATURE:
<223> OTHER INFORMATION: Synthetic

<400> SEQUENCE: 198
tctccacgta atcgttgatc tgtt                                            24

<210> SEQ ID NO 199
<211> LENGTH: 24
<212> TYPE: DNA
<213> ORGANISM: Artificial Sequence
<220> FEATURE:
<223> OTHER INFORMATION: Synthetic

<400> SEQUENCE: 199
tctccacgta atcgttgatc tgtt                                            24

<210> SEQ ID NO 200
<211> LENGTH: 24
<212> TYPE: DNA
<213> ORGANISM: Artificial Sequence
<220> FEATURE:
<223> OTHER INFORMATION: Synthetic

<400> SEQUENCE: 200
aaaactgtgt ctctgtcaag ctcc                                            24

<210> SEQ ID NO 201
<211> LENGTH: 24
<212> TYPE: DNA
<213> ORGANISM: Artificial Sequence
<220> FEATURE:
<223> OTHER INFORMATION: Synthetic

<400> SEQUENCE: 201
ccacaatttt cccttgagta ccct                                            24

<210> SEQ ID NO 202
```

```
<211> LENGTH: 28
<212> TYPE: DNA
<213> ORGANISM: Artificial Sequence
<220> FEATURE:
<223> OTHER INFORMATION: Synthetic

<400> SEQUENCE: 202
gcaaccttac ctttaaagaa gatgtaat                                        28

<210> SEQ ID NO 203
<211> LENGTH: 28
<212> TYPE: DNA
<213> ORGANISM: Artificial Sequence
<220> FEATURE:
<223> OTHER INFORMATION: Synthetic

<400> SEQUENCE: 203
gcaaccttac ctttaaagaa gatgtaat                                        28

<210> SEQ ID NO 204
<211> LENGTH: 28
<212> TYPE: DNA
<213> ORGANISM: Artificial Sequence
<220> FEATURE:
<223> OTHER INFORMATION: Synthetic

<400> SEQUENCE: 204
acctttaaag aagatgtaat tcaccaga                                        28

<210> SEQ ID NO 205
<211> LENGTH: 28
<212> TYPE: DNA
<213> ORGANISM: Artificial Sequence
<220> FEATURE:
<223> OTHER INFORMATION: Synthetic

<400> SEQUENCE: 205
acctttaaag aagatgtaat tcaccaga                                        28

<210> SEQ ID NO 206
<211> LENGTH: 28
<212> TYPE: DNA
<213> ORGANISM: Artificial Sequence
<220> FEATURE:
<223> OTHER INFORMATION: Synthetic

<400> SEQUENCE: 206
acctttaaag aagatgtaat tcaccaga                                        28

<210> SEQ ID NO 207
<211> LENGTH: 28
<212> TYPE: DNA
<213> ORGANISM: Artificial Sequence
<220> FEATURE:
<223> OTHER INFORMATION: Synthetic

<400> SEQUENCE: 207
acctttaaag aagatgtaat tcaccaga                                        28

<210> SEQ ID NO 208
<211> LENGTH: 28
<212> TYPE: DNA
<213> ORGANISM: Artificial Sequence
<220> FEATURE:
<223> OTHER INFORMATION: Synthetic

<400> SEQUENCE: 208
```
gcaaccttac ctttaaagaa gatgtaat                                              28

<210> SEQ ID NO 209
<211> LENGTH: 24
<212> TYPE: DNA
<213> ORGANISM: Artificial Sequence
<220> FEATURE:
<223> OTHER INFORMATION: Synthetic

<400> SEQUENCE: 209
cttgtttcta tgggaacagc tcag                                                  24

<210> SEQ ID NO 210
<211> LENGTH: 24
<212> TYPE: DNA
<213> ORGANISM: Artificial Sequence
<220> FEATURE:
<223> OTHER INFORMATION: Synthetic

<400> SEQUENCE: 210
cttgtttcta tgggaacagc tcag                                                  24

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
cttgtttcta tgggaacagc tcag                                                  24

<210> SEQ ID NO 212
<211> LENGTH: 24
<212> TYPE: DNA
<213> ORGANISM: Artificial Sequence
<220> FEATURE:
<223> OTHER INFORMATION: Synthetic

<400> SEQUENCE: 212
cttgtttcta tgggaacagc tcag                                                  24

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
cttgtttcta tgggaacagc tcag                                                  24

<210> SEQ ID NO 214
<211> LENGTH: 24
<212> TYPE: DNA
<213> ORGANISM: Artificial Sequence
<220> FEATURE:
<223> OTHER INFORMATION: Synthetic

<400> SEQUENCE: 214
cttgtttcta tgggaacagc tcag                                                  24

<210> SEQ ID NO 215
<211> LENGTH: 24
<212> TYPE: DNA

<213> ORGANISM: Artificial Sequence
<220> FEATURE:
<223> OTHER INFORMATION: Synthetic

<400> SEQUENCE: 215
aactgaagaa tccacgctga aaag                                    24

<210> SEQ ID NO 216
<211> LENGTH: 24
<212> TYPE: DNA
<213> ORGANISM: Artificial Sequence
<220> FEATURE:
<223> OTHER INFORMATION: Synthetic

<400> SEQUENCE: 216
catgcctaaa cgcttcatca tagg                                    24

<210> SEQ ID NO 217
<211> LENGTH: 22
<212> TYPE: DNA
<213> ORGANISM: Artificial Sequence
<220> FEATURE:
<223> OTHER INFORMATION: Synthetic

<400> SEQUENCE: 217
ggcattgccc aggtatttca tc                                      22

<210> SEQ ID NO 218
<211> LENGTH: 22
<212> TYPE: DNA
<213> ORGANISM: Artificial Sequence
<220> FEATURE:
<223> OTHER INFORMATION: Synthetic

<400> SEQUENCE: 218
ggcattgccc aggtatttca tc                                      22

<210> SEQ ID NO 219
<211> LENGTH: 23
<212> TYPE: DNA
<213> ORGANISM: Artificial Sequence
<220> FEATURE:
<223> OTHER INFORMATION: Synthetic

<400> SEQUENCE: 219
cattgcccag gtatttcatc agc                                     23

<210> SEQ ID NO 220
<211> LENGTH: 24
<212> TYPE: DNA
<213> ORGANISM: Artificial Sequence
<220> FEATURE:
<223> OTHER INFORMATION: Synthetic

<400> SEQUENCE: 220
gttcattttc caggtgctgt agtt                                    24

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
gagttcattt tccaggtgct gtag                                    24

<210> SEQ ID NO 222
<211> LENGTH: 24
<212> TYPE: DNA
<213> ORGANISM: Artificial Sequence
<220> FEATURE:
<223> OTHER INFORMATION: Synthetic

<400> SEQUENCE: 222
gagttcattt tccaggtgct gtag                                          24

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223
gagttcattt tccaggtgct gtag                                          24

<210> SEQ ID NO 224
<211> LENGTH: 24
<212> TYPE: DNA
<213> ORGANISM: Artificial Sequence
<220> FEATURE:
<223> OTHER INFORMATION: Synthetic

<400> SEQUENCE: 224
tatcgtgggt gagttcattt tcca                                          24

<210> SEQ ID NO 225
<211> LENGTH: 24
<212> TYPE: DNA
<213> ORGANISM: Artificial Sequence
<220> FEATURE:
<223> OTHER INFORMATION: Synthetic

<400> SEQUENCE: 225
tatcgtgggt gagttcattt tcca                                          24

<210> SEQ ID NO 226
<211> LENGTH: 24
<212> TYPE: DNA
<213> ORGANISM: Artificial Sequence
<220> FEATURE:
<223> OTHER INFORMATION: Synthetic

<400> SEQUENCE: 226
gagttcattt tccaggtgct gtag                                          24

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
gagttcattt tccaggtgct gtag                                          24

<210> SEQ ID NO 228
<211> LENGTH: 24
<212> TYPE: DNA
<213> ORGANISM: Artificial Sequence
<220> FEATURE:

<223> OTHER INFORMATION: Synthetic

<400> SEQUENCE: 228
tatcgtgggt gagttcattt tcca 24

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
tatcgtgggt gagttcattt tcca 24

<210> SEQ ID NO 230
<211> LENGTH: 24
<212> TYPE: DNA
<213> ORGANISM: Artificial Sequence
<220> FEATURE:
<223> OTHER INFORMATION: Synthetic

<400> SEQUENCE: 230
aggaacttgg tgatgatatc gtgg 24

<210> SEQ ID NO 231
<211> LENGTH: 24
<212> TYPE: DNA
<213> ORGANISM: Artificial Sequence
<220> FEATURE:
<223> OTHER INFORMATION: Synthetic

<400> SEQUENCE: 231
cttcattttc caggaacttg gtga 24

<210> SEQ ID NO 232
<211> LENGTH: 26
<212> TYPE: DNA
<213> ORGANISM: Artificial Sequence
<220> FEATURE:
<223> OTHER INFORMATION: Synthetic

<400> SEQUENCE: 232
gggaatcacc ttctgtcttc attttc 26

<210> SEQ ID NO 233
<211> LENGTH: 26
<212> TYPE: DNA
<213> ORGANISM: Artificial Sequence
<220> FEATURE:
<223> OTHER INFORMATION: Synthetic

<400> SEQUENCE: 233
gggaatcacc ttctgtcttc attttc 26

<210> SEQ ID NO 234
<211> LENGTH: 24
<212> TYPE: DNA
<213> ORGANISM: Artificial Sequence
<220> FEATURE:
<223> OTHER INFORMATION: Synthetic

<400> SEQUENCE: 234
caaagggttt gttgaacttg acct 24

```
<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235
aggggagact tggtattttg ttca                                          24

<210> SEQ ID NO 236
<211> LENGTH: 24
<212> TYPE: DNA
<213> ORGANISM: Artificial Sequence
<220> FEATURE:
<223> OTHER INFORMATION: Synthetic

<400> SEQUENCE: 236
aggggagact tggtattttg ttca                                          24

<210> SEQ ID NO 237
<211> LENGTH: 24
<212> TYPE: DNA
<213> ORGANISM: Artificial Sequence
<220> FEATURE:
<223> OTHER INFORMATION: Synthetic

<400> SEQUENCE: 237
aggggagact tggtattttg ttca                                          24

<210> SEQ ID NO 238
<211> LENGTH: 24
<212> TYPE: DNA
<213> ORGANISM: Artificial Sequence
<220> FEATURE:
<223> OTHER INFORMATION: Synthetic

<400> SEQUENCE: 238
aggggagact tggtattttg ttca                                          24

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239
acccttcttt aatgtcatcc aggg                                          24

<210> SEQ ID NO 240
<211> LENGTH: 24
<212> TYPE: DNA
<213> ORGANISM: Artificial Sequence
<220> FEATURE:
<223> OTHER INFORMATION: Synthetic

<400> SEQUENCE: 240
acccttcttt aatgtcatcc aggg                                          24

<210> SEQ ID NO 241
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 241
gatattggtg ctgttggact ggtg                                      24

<210> SEQ ID NO 242
<211> LENGTH: 24
<212> TYPE: DNA
<213> ORGANISM: Artificial Sequence
<220> FEATURE:
<223> OTHER INFORMATION: Synthetic

<400> SEQUENCE: 242
gatattggtg ctgttggact ggtg                                      24

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
caggatttca tcgtgagtgt cagc                                      24

<210> SEQ ID NO 244
<211> LENGTH: 21
<212> TYPE: DNA
<213> ORGANISM: Artificial Sequence
<220> FEATURE:
<223> OTHER INFORMATION: Synthetic

<400> SEQUENCE: 244
gttgagggta cggaggagtt c                                         21

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
aaaacttatc cactagcttc aggc                                      24

<210> SEQ ID NO 246
<211> LENGTH: 24
<212> TYPE: DNA
<213> ORGANISM: Artificial Sequence
<220> FEATURE:
<223> OTHER INFORMATION: Synthetic

<400> SEQUENCE: 246
aaaacttatc cactagcttc aggc                                      24

<210> SEQ ID NO 247
<211> LENGTH: 24
<212> TYPE: DNA
<213> ORGANISM: Artificial Sequence
<220> FEATURE:
<223> OTHER INFORMATION: Synthetic

<400> SEQUENCE: 247
aggcttctga gtggtacaac tttt                                      24

<210> SEQ ID NO 248
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 248 attttcccttt gagtaccctt ctcc                                           24

<210> SEQ ID NO 249
<211> LENGTH: 24
<212> TYPE: DNA
<213> ORGANISM: Artificial Sequence
<220> FEATURE:
<223> OTHER INFORMATION: Synthetic

<400> SEQUENCE: 249
tcaccttctg tcttcatttt ccag                                            24

<210> SEQ ID NO 250
<211> LENGTH: 22
<212> TYPE: DNA
<213> ORGANISM: Artificial Sequence
<220> FEATURE:
<223> OTHER INFORMATION: Synthetic

<400> SEQUENCE: 250
gtcccaacat ggctaagagg tg                                              22

<210> SEQ ID NO 251
<211> LENGTH: 22
<212> TYPE: DNA
<213> ORGANISM: Artificial Sequence
<220> FEATURE:
<223> OTHER INFORMATION: Synthetic

<400> SEQUENCE: 251
gtcccaacat ggctaagagg tg                                              22

<210> SEQ ID NO 252
<211> LENGTH: 24
<212> TYPE: DNA
<213> ORGANISM: Artificial Sequence
<220> FEATURE:
<223> OTHER INFORMATION: Synthetic

<400> SEQUENCE: 252
tatacagagt agcagtgacc cagg                                            24

<210> SEQ ID NO 253
<211> LENGTH: 23
<212> TYPE: DNA
<213> ORGANISM: Artificial Sequence
<220> FEATURE:
<223> OTHER INFORMATION: Synthetic

<400> SEQUENCE: 253
tacagatacc agggtgcaac aag                                             23

<210> SEQ ID NO 254
<211> LENGTH: 22
<212> TYPE: DNA
<213> ORGANISM: Artificial Sequence
<220> FEATURE:
<223> OTHER INFORMATION: Synthetic

<400> SEQUENCE: 254
```
ataccagggt gcaacaaggt cg                                          22

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
cccacacatt cttccctaca gata                                        24

<210> SEQ ID NO 256
<211> LENGTH: 24
<212> TYPE: DNA
<213> ORGANISM: Artificial Sequence
<220> FEATURE:
<223> OTHER INFORMATION: Synthetic

<400> SEQUENCE: 256
cccacacatt cttccctaca gata                                        24

<210> SEQ ID NO 257
<211> LENGTH: 22
<212> TYPE: DNA
<213> ORGANISM: Artificial Sequence
<220> FEATURE:
<223> OTHER INFORMATION: Synthetic

<400> SEQUENCE: 257
tcagtgaatc acgggcatct tc                                          22

<210> SEQ ID NO 258
<211> LENGTH: 22
<212> TYPE: DNA
<213> ORGANISM: Artificial Sequence
<220> FEATURE:
<223> OTHER INFORMATION: Synthetic

<400> SEQUENCE: 258
gaatcacggg catcttcagg ag                                          22

<210> SEQ ID NO 259
<211> LENGTH: 22
<212> TYPE: DNA
<213> ORGANISM: Artificial Sequence
<220> FEATURE:
<223> OTHER INFORMATION: Synthetic

<400> SEQUENCE: 259
tcagtgaatc acgggcatct tc                                          22

<210> SEQ ID NO 260
<211> LENGTH: 25
<212> TYPE: DNA
<213> ORGANISM: Artificial Sequence
<220> FEATURE:
<223> OTHER INFORMATION: Synthetic

<400> SEQUENCE: 260
gctcaaccct tctttaatgt catcc                                       25

<210> SEQ ID NO 261
<211> LENGTH: 24
<212> TYPE: DNA
<213> ORGANISM: Artificial Sequence

```
<220> FEATURE:
<223> OTHER INFORMATION: Synthetic

<400> SEQUENCE: 261
acccttcttt aatgtcatcc aggg                                          24

<210> SEQ ID NO 262
<211> LENGTH: 24
<212> TYPE: DNA
<213> ORGANISM: Artificial Sequence
<220> FEATURE:
<223> OTHER INFORMATION: Synthetic

<400> SEQUENCE: 262
acccttcttt aatgtcatcc aggg                                          24

<210> SEQ ID NO 263
<211> LENGTH: 24
<212> TYPE: DNA
<213> ORGANISM: Artificial Sequence
<220> FEATURE:
<223> OTHER INFORMATION: Synthetic

<400> SEQUENCE: 263
acccttcttt aatgtcatcc aggg                                          24

<210> SEQ ID NO 264
<211> LENGTH: 24
<212> TYPE: DNA
<213> ORGANISM: Artificial Sequence
<220> FEATURE:
<223> OTHER INFORMATION: Synthetic

<400> SEQUENCE: 264
acccttcttt aatgtcatcc aggg                                          24

<210> SEQ ID NO 265
<211> LENGTH: 24
<212> TYPE: DNA
<213> ORGANISM: Artificial Sequence
<220> FEATURE:
<223> OTHER INFORMATION: Synthetic

<400> SEQUENCE: 265
acccttcttt aatgtcatcc aggg                                          24

<210> SEQ ID NO 266
<211> LENGTH: 25
<212> TYPE: DNA
<213> ORGANISM: Artificial Sequence
<220> FEATURE:
<223> OTHER INFORMATION: Synthetic

<400> SEQUENCE: 266
gctcaaccct tctttaatgt catcc                                         25

<210> SEQ ID NO 267
<211> LENGTH: 25
<212> TYPE: DNA
<213> ORGANISM: Artificial Sequence
<220> FEATURE:
<223> OTHER INFORMATION: Synthetic

<400> SEQUENCE: 267
gctcaaccct tctttaatgt catcc                                         25
```

<210> SEQ ID NO 268
<211> LENGTH: 24
<212> TYPE: DNA
<213> ORGANISM: Artificial Sequence
<220> FEATURE:
<223> OTHER INFORMATION: Synthetic

<400> SEQUENCE: 268
aaacatggga gggatttaca gtca                                            24

<210> SEQ ID NO 269
<211> LENGTH: 25
<212> TYPE: DNA
<213> ORGANISM: Artificial Sequence
<220> FEATURE:
<223> OTHER INFORMATION: Synthetic

<400> SEQUENCE: 269
gctcaaccct tctttaatgt catcc                                           25

<210> SEQ ID NO 270
<211> LENGTH: 25
<212> TYPE: DNA
<213> ORGANISM: Artificial Sequence
<220> FEATURE:
<223> OTHER INFORMATION: Synthetic

<400> SEQUENCE: 270
gctcaaccct tctttaatgt catcc                                           25

<210> SEQ ID NO 271
<211> LENGTH: 20
<212> TYPE: RNA
<213> ORGANISM: Artificial Sequence
<220> FEATURE:
<223> OTHER INFORMATION: Synthetic

<400> SEQUENCE: 271
guugaggaac aggccguugc                                                 20

<210> SEQ ID NO 272
<211> LENGTH: 20
<212> TYPE: RNA
<213> ORGANISM: Artificial Sequence
<220> FEATURE:
<223> OTHER INFORMATION: Synthetic

<400> SEQUENCE: 272
acucacagug aaauccugga                                                 20

<210> SEQ ID NO 273
<211> LENGTH: 20
<212> TYPE: RNA
<213> ORGANISM: Artificial Sequence
<220> FEATURE:
<223> OTHER INFORMATION: Synthetic

<400> SEQUENCE: 273
gaagccgaac ucagccaggc                                                 20

<210> SEQ ID NO 274
<211> LENGTH: 20
<212> TYPE: RNA
<213> ORGANISM: Artificial Sequence
<220> FEATURE:
<223> OTHER INFORMATION: Synthetic

<400> SEQUENCE: 274
caacgucacg gagauuccgg     20

<210> SEQ ID NO 275
<400> SEQUENCE: 275

000

<210> SEQ ID NO 276
<400> SEQUENCE: 276

000

<210> SEQ ID NO 277
<400> SEQUENCE: 277

000

<210> SEQ ID NO 278
<400> SEQUENCE: 278

000

<210> SEQ ID NO 279
<400> SEQUENCE: 279

000

<210> SEQ ID NO 280
<211> LENGTH: 24
<212> TYPE: DNA
<213> ORGANISM: Artificial Sequence
<220> FEATURE:
<223> OTHER INFORMATION: Synthetic

<400> SEQUENCE: 280
ccatcggacg atcctatctg atta     24

<210> SEQ ID NO 281
<211> LENGTH: 22
<212> TYPE: DNA
<213> ORGANISM: Artificial Sequence
<220> FEATURE:
<223> OTHER INFORMATION: Synthetic

<400> SEQUENCE: 281
aaatcctaac tgggctggaa gg     22

<210> SEQ ID NO 282
<211> LENGTH: 22
<212> TYPE: DNA
<213> ORGANISM: Artificial Sequence
<220> FEATURE:
<223> OTHER INFORMATION: Synthetic

<400> SEQUENCE: 282
aaatcctaac tgggctggaa gg     22

<210> SEQ ID NO 283
<211> LENGTH: 22

```
<212> TYPE: DNA
<213> ORGANISM: Artificial Sequence
<220> FEATURE:
<223> OTHER INFORMATION: Synthetic

<400> SEQUENCE: 283
aaatcctaac tgggctggaa gg                                              22

<210> SEQ ID NO 284
<211> LENGTH: 24
<212> TYPE: DNA
<213> ORGANISM: Artificial Sequence
<220> FEATURE:
<223> OTHER INFORMATION: Synthetic

<400> SEQUENCE: 284
cttggcacag gctggtttaa taat                                            24

<210> SEQ ID NO 285
<211> LENGTH: 24
<212> TYPE: DNA
<213> ORGANISM: Artificial Sequence
<220> FEATURE:
<223> OTHER INFORMATION: Synthetic

<400> SEQUENCE: 285
cttggcacag gctggtttaa taat                                            24

<210> SEQ ID NO 286
<211> LENGTH: 24
<212> TYPE: DNA
<213> ORGANISM: Artificial Sequence
<220> FEATURE:
<223> OTHER INFORMATION: Synthetic

<400> SEQUENCE: 286
cttggcacag gctggtttaa taat                                            24

<210> SEQ ID NO 287
<211> LENGTH: 24
<212> TYPE: DNA
<213> ORGANISM: Artificial Sequence
<220> FEATURE:
<223> OTHER INFORMATION: Synthetic

<400> SEQUENCE: 287
ttctttcagt gttactgatg tcgg                                            24

<210> SEQ ID NO 288
<211> LENGTH: 24
<212> TYPE: DNA
<213> ORGANISM: Artificial Sequence
<220> FEATURE:
<223> OTHER INFORMATION: Synthetic

<400> SEQUENCE: 288
cttggcacag gctggtttaa taat                                            24

<210> SEQ ID NO 289
<211> LENGTH: 22
<212> TYPE: DNA
<213> ORGANISM: Artificial Sequence
<220> FEATURE:
<223> OTHER INFORMATION: Synthetic

<400> SEQUENCE: 289
```
gtgtcaatcc ctgatcactg gg                                                    22

<210> SEQ ID NO 290
<211> LENGTH: 21
<212> TYPE: DNA
<213> ORGANISM: Artificial Sequence
<220> FEATURE:
<223> OTHER INFORMATION: Synthetic

<400> SEQUENCE: 290
tcatcatgtg ccttgactcg g                                                     21

<210> SEQ ID NO 291
<211> LENGTH: 21
<212> TYPE: DNA
<213> ORGANISM: Artificial Sequence
<220> FEATURE:
<223> OTHER INFORMATION: Synthetic

<400> SEQUENCE: 291
tcatcatgtg ccttgactcg g                                                     21

<210> SEQ ID NO 292
<211> LENGTH: 21
<212> TYPE: DNA
<213> ORGANISM: Artificial Sequence
<220> FEATURE:
<223> OTHER INFORMATION: Synthetic

<400> SEQUENCE: 292
tcatcatgtg ccttgactcg g                                                     21

<210> SEQ ID NO 293
<211> LENGTH: 23
<212> TYPE: DNA
<213> ORGANISM: Artificial Sequence
<220> FEATURE:
<223> OTHER INFORMATION: Synthetic

<400> SEQUENCE: 293
gatcactggg agtcatcatg tgc                                                   23

<210> SEQ ID NO 294
<211> LENGTH: 23
<212> TYPE: DNA
<213> ORGANISM: Artificial Sequence
<220> FEATURE:
<223> OTHER INFORMATION: Synthetic

<400> SEQUENCE: 294
gatcactggg agtcatcatg tgc                                                   23

<210> SEQ ID NO 295
<211> LENGTH: 23
<212> TYPE: DNA
<213> ORGANISM: Artificial Sequence
<220> FEATURE:
<223> OTHER INFORMATION: Synthetic

<400> SEQUENCE: 295
gatcactggg agtcatcatg tgc                                                   23

<210> SEQ ID NO 296
<211> LENGTH: 23
<212> TYPE: DNA
<213> ORGANISM: Artificial Sequence

```
<220> FEATURE:
<223> OTHER INFORMATION: Synthetic

<400> SEQUENCE: 296
gatcactggg agtcatcatg tgc                                           23

<210> SEQ ID NO 297
<211> LENGTH: 23
<212> TYPE: DNA
<213> ORGANISM: Artificial Sequence
<220> FEATURE:
<223> OTHER INFORMATION: Synthetic

<400> SEQUENCE: 297
gatcactggg agtcatcatg tgc                                           23

<210> SEQ ID NO 298
<211> LENGTH: 22
<212> TYPE: DNA
<213> ORGANISM: Artificial Sequence
<220> FEATURE:
<223> OTHER INFORMATION: Synthetic

<400> SEQUENCE: 298
gtgtcaatcc ctgatcactg gg                                            22

<210> SEQ ID NO 299
<211> LENGTH: 23
<212> TYPE: DNA
<213> ORGANISM: Artificial Sequence
<220> FEATURE:
<223> OTHER INFORMATION: Synthetic

<400> SEQUENCE: 299
gatcactggg agtcatcatg tgc                                           23

<210> SEQ ID NO 300
<211> LENGTH: 23
<212> TYPE: DNA
<213> ORGANISM: Artificial Sequence
<220> FEATURE:
<223> OTHER INFORMATION: Synthetic

<400> SEQUENCE: 300
gatcactggg agtcatcatg tgc                                           23

<210> SEQ ID NO 301
<211> LENGTH: 21
<212> TYPE: DNA
<213> ORGANISM: Artificial Sequence
<220> FEATURE:
<223> OTHER INFORMATION: Synthetic

<400> SEQUENCE: 301
gtcttgcagg acaatgccgt c                                             21

<210> SEQ ID NO 302
<211> LENGTH: 21
<212> TYPE: DNA
<213> ORGANISM: Artificial Sequence
<220> FEATURE:
<223> OTHER INFORMATION: Synthetic

<400> SEQUENCE: 302
gtcttgcagg acaatgccgt c                                             21
```

```
<210> SEQ ID NO 303
<211> LENGTH: 21
<212> TYPE: DNA
<213> ORGANISM: Artificial Sequence
<220> FEATURE:
<223> OTHER INFORMATION: Synthetic

<400> SEQUENCE: 303
gtcttgcagg acaatgccgt c                                              21

<210> SEQ ID NO 304
<211> LENGTH: 21
<212> TYPE: DNA
<213> ORGANISM: Artificial Sequence
<220> FEATURE:
<223> OTHER INFORMATION: Synthetic

<400> SEQUENCE: 304
gtcttgcagg acaatgccgt c                                              21

<210> SEQ ID NO 305
<211> LENGTH: 21
<212> TYPE: DNA
<213> ORGANISM: Artificial Sequence
<220> FEATURE:
<223> OTHER INFORMATION: Synthetic

<400> SEQUENCE: 305
aatgccgtct tctgtctcgt g                                              21

<210> SEQ ID NO 306
<211> LENGTH: 21
<212> TYPE: DNA
<213> ORGANISM: Artificial Sequence
<220> FEATURE:
<223> OTHER INFORMATION: Synthetic

<400> SEQUENCE: 306
aatgccgtct tctgtctcgt g                                              21

<210> SEQ ID NO 307
<211> LENGTH: 21
<212> TYPE: DNA
<213> ORGANISM: Artificial Sequence
<220> FEATURE:
<223> OTHER INFORMATION: Synthetic

<400> SEQUENCE: 307
aatgccgtct tctgtctcgt g                                              21

<210> SEQ ID NO 308
<211> LENGTH: 21
<212> TYPE: DNA
<213> ORGANISM: Artificial Sequence
<220> FEATURE:
<223> OTHER INFORMATION: Synthetic

<400> SEQUENCE: 308
aatgccgtct tctgtctcgt g                                              21

<210> SEQ ID NO 309
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 309
gagatgctgc ccagaagaca gata                                          24

<210> SEQ ID NO 310
<211> LENGTH: 23
<212> TYPE: DNA
<213> ORGANISM: Artificial Sequence
<220> FEATURE:
<223> OTHER INFORMATION: Synthetic

<400> SEQUENCE: 310
ccagaagaca gatacatccc acc                                           23

<210> SEQ ID NO 311
<211> LENGTH: 23
<212> TYPE: DNA
<213> ORGANISM: Artificial Sequence
<220> FEATURE:
<223> OTHER INFORMATION: Synthetic

<400> SEQUENCE: 311
ctgcccagaa gacagataca tcc                                           23

<210> SEQ ID NO 312
<211> LENGTH: 23
<212> TYPE: DNA
<213> ORGANISM: Artificial Sequence
<220> FEATURE:
<223> OTHER INFORMATION: Synthetic

<400> SEQUENCE: 312
atgatcagga tcacccaacc ttc                                           23

<210> SEQ ID NO 313
<211> LENGTH: 23
<212> TYPE: DNA
<213> ORGANISM: Artificial Sequence
<220> FEATURE:
<223> OTHER INFORMATION: Synthetic

<400> SEQUENCE: 313
atgatcagga tcacccaacc ttc                                           23

<210> SEQ ID NO 314
<211> LENGTH: 23
<212> TYPE: DNA
<213> ORGANISM: Artificial Sequence
<220> FEATURE:
<223> OTHER INFORMATION: Synthetic

<400> SEQUENCE: 314
caccatgatc aggatcaccc aac                                           23

<210> SEQ ID NO 315
<211> LENGTH: 23
<212> TYPE: DNA
<213> ORGANISM: Artificial Sequence
<220> FEATURE:
<223> OTHER INFORMATION: Synthetic

<400> SEQUENCE: 315
ctgagttcgc cttcagccta tac                                           23

<210> SEQ ID NO 316
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 316
ctgagttcgc cttcagccta tac                                              23

<210> SEQ ID NO 317
<211> LENGTH: 23
<212> TYPE: DNA
<213> ORGANISM: Artificial Sequence
<220> FEATURE:
<223> OTHER INFORMATION: Synthetic

<400> SEQUENCE: 317
ctgagttcgc cttcagccta tac                                              23

<210> SEQ ID NO 318
<211> LENGTH: 23
<212> TYPE: DNA
<213> ORGANISM: Artificial Sequence
<220> FEATURE:
<223> OTHER INFORMATION: Synthetic

<400> SEQUENCE: 318
ctgagttcgc cttcagccta tac                                              23

<210> SEQ ID NO 319
<211> LENGTH: 24
<212> TYPE: DNA
<213> ORGANISM: Artificial Sequence
<220> FEATURE:
<223> OTHER INFORMATION: Synthetic

<400> SEQUENCE: 319
ccaacagcac caatatcttc ttct                                             24

<210> SEQ ID NO 320
<211> LENGTH: 24
<212> TYPE: DNA
<213> ORGANISM: Artificial Sequence
<220> FEATURE:
<223> OTHER INFORMATION: Synthetic

<400> SEQUENCE: 320
ccaacagcac caatatcttc ttct                                             24

<210> SEQ ID NO 321
<211> LENGTH: 24
<212> TYPE: DNA
<213> ORGANISM: Artificial Sequence
<220> FEATURE:
<223> OTHER INFORMATION: Synthetic

<400> SEQUENCE: 321
agtccaacag caccaatatc ttct                                             24

<210> SEQ ID NO 322
<211> LENGTH: 24
<212> TYPE: DNA
<213> ORGANISM: Artificial Sequence
<220> FEATURE:
<223> OTHER INFORMATION: Synthetic

<400> SEQUENCE: 322
```
acagcaccaa tatcttcttc tccc 24

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
agtccaacag caccaatatc ttct 24

<210> SEQ ID NO 324
<211> LENGTH: 24
<212> TYPE: DNA
<213> ORGANISM: Artificial Sequence
<220> FEATURE:
<223> OTHER INFORMATION: Synthetic

<400> SEQUENCE: 324
agtccaacag caccaatatc ttct 24

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
agtccaacag caccaatatc ttct 24

<210> SEQ ID NO 326
<211> LENGTH: 24
<212> TYPE: DNA
<213> ORGANISM: Artificial Sequence
<220> FEATURE:
<223> OTHER INFORMATION: Synthetic

<400> SEQUENCE: 326
agtccaacag caccaatatc ttct 24

<210> SEQ ID NO 327
<211> LENGTH: 24
<212> TYPE: DNA
<213> ORGANISM: Artificial Sequence
<220> FEATURE:
<223> OTHER INFORMATION: Synthetic

<400> SEQUENCE: 327
ctgacactca cgatgaaatc ctgg 24

<210> SEQ ID NO 328
<211> LENGTH: 24
<212> TYPE: DNA
<213> ORGANISM: Artificial Sequence
<220> FEATURE:
<223> OTHER INFORMATION: Synthetic

<400> SEQUENCE: 328
ctgacactca cgatgaaatc ctgg 24

<210> SEQ ID NO 329
<211> LENGTH: 24
<212> TYPE: DNA

<213> ORGANISM: Artificial Sequence
<220> FEATURE:
<223> OTHER INFORMATION: Synthetic

<400> SEQUENCE: 329
gatgaaatcc tggagggcct gaat         24

<210> SEQ ID NO 330
<211> LENGTH: 24
<212> TYPE: DNA
<213> ORGANISM: Artificial Sequence
<220> FEATURE:
<223> OTHER INFORMATION: Synthetic

<400> SEQUENCE: 330
ctgacactca cgatgaaatc ctgg         24

<210> SEQ ID NO 331
<211> LENGTH: 24
<212> TYPE: DNA
<213> ORGANISM: Artificial Sequence
<220> FEATURE:
<223> OTHER INFORMATION: Synthetic

<400> SEQUENCE: 331
atcctggagg gcctgaattt caac         24

<210> SEQ ID NO 332
<211> LENGTH: 24
<212> TYPE: DNA
<213> ORGANISM: Artificial Sequence
<220> FEATURE:
<223> OTHER INFORMATION: Synthetic

<400> SEQUENCE: 332
aaggctgaca ctcacgatga aatc         24

<210> SEQ ID NO 333
<211> LENGTH: 24
<212> TYPE: DNA
<213> ORGANISM: Artificial Sequence
<220> FEATURE:
<223> OTHER INFORMATION: Synthetic

<400> SEQUENCE: 333
aaggctgaca ctcacgatga aatc         24

<210> SEQ ID NO 334
<211> LENGTH: 24
<212> TYPE: DNA
<213> ORGANISM: Artificial Sequence
<220> FEATURE:
<223> OTHER INFORMATION: Synthetic

<400> SEQUENCE: 334
aaggctgaca ctcacgatga aatc         24

<210> SEQ ID NO 335
<211> LENGTH: 24
<212> TYPE: DNA
<213> ORGANISM: Artificial Sequence
<220> FEATURE:
<223> OTHER INFORMATION: Synthetic

<400> SEQUENCE: 335
ctgacactca cgatgaaatc ctgg         24

```
<210> SEQ ID NO 336
<211> LENGTH: 24
<212> TYPE: DNA
<213> ORGANISM: Artificial Sequence
<220> FEATURE:
<223> OTHER INFORMATION: Synthetic

<400> SEQUENCE: 336
aaggctgaca ctcacgatga aatc                                          24

<210> SEQ ID NO 337
<211> LENGTH: 24
<212> TYPE: DNA
<213> ORGANISM: Artificial Sequence
<220> FEATURE:
<223> OTHER INFORMATION: Synthetic

<400> SEQUENCE: 337
aaggctgaca ctcacgatga aatc                                          24

<210> SEQ ID NO 338
<211> LENGTH: 24
<212> TYPE: DNA
<213> ORGANISM: Artificial Sequence
<220> FEATURE:
<223> OTHER INFORMATION: Synthetic

<400> SEQUENCE: 338
gagattccgg aggctcagat ccat                                          24

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
gatgaaatcc tggagggcct gaat                                          24

<210> SEQ ID NO 340
<211> LENGTH: 21
<212> TYPE: DNA
<213> ORGANISM: Artificial Sequence
<220> FEATURE:
<223> OTHER INFORMATION: Synthetic

<400> SEQUENCE: 340
ggaactcctc cgtaccctca a                                             21

<210> SEQ ID NO 341
<211> LENGTH: 21
<212> TYPE: DNA
<213> ORGANISM: Artificial Sequence
<220> FEATURE:
<223> OTHER INFORMATION: Synthetic

<400> SEQUENCE: 341
ggaactcctc cgtaccctca a                                             21

<210> SEQ ID NO 342
<211> LENGTH: 22
<212> TYPE: DNA
<213> ORGANISM: Artificial Sequence
<220> FEATURE:
```

```
<223> OTHER INFORMATION: Synthetic

<400> SEQUENCE: 342
cttccaggaa ctcctccgta cc                                              22

<210> SEQ ID NO 343
<211> LENGTH: 22
<212> TYPE: DNA
<213> ORGANISM: Artificial Sequence
<220> FEATURE:
<223> OTHER INFORMATION: Synthetic

<400> SEQUENCE: 343
cttccaggaa ctcctccgta cc                                              22

<210> SEQ ID NO 344
<211> LENGTH: 22
<212> TYPE: DNA
<213> ORGANISM: Artificial Sequence
<220> FEATURE:
<223> OTHER INFORMATION: Synthetic

<400> SEQUENCE: 344
cttccaggaa ctcctccgta cc                                              22

<210> SEQ ID NO 345
<211> LENGTH: 22
<212> TYPE: DNA
<213> ORGANISM: Artificial Sequence
<220> FEATURE:
<223> OTHER INFORMATION: Synthetic

<400> SEQUENCE: 345
cttccaggaa ctcctccgta cc                                              22

<210> SEQ ID NO 346
<211> LENGTH: 21
<212> TYPE: DNA
<213> ORGANISM: Artificial Sequence
<220> FEATURE:
<223> OTHER INFORMATION: Synthetic

<400> SEQUENCE: 346
ggaactcctc cgtaccctca a                                               21

<210> SEQ ID NO 347
<211> LENGTH: 22
<212> TYPE: DNA
<213> ORGANISM: Artificial Sequence
<220> FEATURE:
<223> OTHER INFORMATION: Synthetic

<400> SEQUENCE: 347
gggcctgaag ctagtggata ag                                              22

<210> SEQ ID NO 348
<211> LENGTH: 22
<212> TYPE: DNA
<213> ORGANISM: Artificial Sequence
<220> FEATURE:
<223> OTHER INFORMATION: Synthetic

<400> SEQUENCE: 348
gggcctgaag ctagtggata ag                                              22
```

```
<210> SEQ ID NO 349
<211> LENGTH: 22
<212> TYPE: DNA
<213> ORGANISM: Artificial Sequence
<220> FEATURE:
<223> OTHER INFORMATION: Synthetic

<400> SEQUENCE: 349
gggcctgaag ctagtggata ag                                              22

<210> SEQ ID NO 350
<211> LENGTH: 22
<212> TYPE: DNA
<213> ORGANISM: Artificial Sequence
<220> FEATURE:
<223> OTHER INFORMATION: Synthetic

<400> SEQUENCE: 350
gggcctgaag ctagtggata ag                                              22

<210> SEQ ID NO 351
<211> LENGTH: 22
<212> TYPE: DNA
<213> ORGANISM: Artificial Sequence
<220> FEATURE:
<223> OTHER INFORMATION: Synthetic

<400> SEQUENCE: 351
gggcctgaag ctagtggata ag                                              22

<210> SEQ ID NO 352
<211> LENGTH: 22
<212> TYPE: DNA
<213> ORGANISM: Artificial Sequence
<220> FEATURE:
<223> OTHER INFORMATION: Synthetic

<400> SEQUENCE: 352
gggcctgaag ctagtggata ag                                              22

<210> SEQ ID NO 353
<211> LENGTH: 24
<212> TYPE: DNA
<213> ORGANISM: Artificial Sequence
<220> FEATURE:
<223> OTHER INFORMATION: Synthetic

<400> SEQUENCE: 353
tcagaagcct tcactgtcaa cttc                                            24

<210> SEQ ID NO 354
<211> LENGTH: 24
<212> TYPE: DNA
<213> ORGANISM: Artificial Sequence
<220> FEATURE:
<223> OTHER INFORMATION: Synthetic

<400> SEQUENCE: 354
gatggtcagt ttcagcacct ttta                                            24

<210> SEQ ID NO 355
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 355
gagggatgtg tgtcgtcaag g                                          21

<210> SEQ ID NO 356
<211> LENGTH: 21
<212> TYPE: DNA
<213> ORGANISM: Artificial Sequence
<220> FEATURE:
<223> OTHER INFORMATION: Synthetic

<400> SEQUENCE: 356
gagggatgtg tgtcgtcaag g                                          21

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
ggaggggact catggtttct ttat                                       24

<210> SEQ ID NO 358
<211> LENGTH: 25
<212> TYPE: DNA
<213> ORGANISM: Artificial Sequence
<220> FEATURE:
<223> OTHER INFORMATION: Synthetic

<400> SEQUENCE: 358
tggtttcttt attctgctac actct                                      25

<210> SEQ ID NO 359
<211> LENGTH: 24
<212> TYPE: DNA
<213> ORGANISM: Artificial Sequence
<220> FEATURE:
<223> OTHER INFORMATION: Synthetic

<400> SEQUENCE: 359
attctgctac actcttccaa acct                                       24

<210> SEQ ID NO 360
<211> LENGTH: 24
<212> TYPE: DNA
<213> ORGANISM: Artificial Sequence
<220> FEATURE:
<223> OTHER INFORMATION: Synthetic

<400> SEQUENCE: 360
attctgctac actcttccaa acct                                       24

<210> SEQ ID NO 361
<211> LENGTH: 24
<212> TYPE: DNA
<213> ORGANISM: Artificial Sequence
<220> FEATURE:
<223> OTHER INFORMATION: Synthetic

<400> SEQUENCE: 361
attctgctac actcttccaa acct                                       24

<210> SEQ ID NO 362
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 362
tacactcttc caaaccttca ctca                                              24

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
tacactcttc caaaccttca ctca                                              24

<210> SEQ ID NO 364
<211> LENGTH: 24
<212> TYPE: DNA
<213> ORGANISM: Artificial Sequence
<220> FEATURE:
<223> OTHER INFORMATION: Synthetic

<400> SEQUENCE: 364
attctgctac actcttccaa acct                                              24

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attctgctac actcttccaa acct                                              24

<210> SEQ ID NO 366
<211> LENGTH: 24
<212> TYPE: DNA
<213> ORGANISM: Artificial Sequence
<220> FEATURE:
<223> OTHER INFORMATION: Synthetic

<400> SEQUENCE: 366
tacactcttc caaaccttca ctca                                              24

<210> SEQ ID NO 367
<211> LENGTH: 24
<212> TYPE: DNA
<213> ORGANISM: Artificial Sequence
<220> FEATURE:
<223> OTHER INFORMATION: Synthetic

<400> SEQUENCE: 367
tacactcttc caaaccttca ctca                                              24

<210> SEQ ID NO 368
<211> LENGTH: 24
<212> TYPE: DNA
<213> ORGANISM: Artificial Sequence
<220> FEATURE:
<223> OTHER INFORMATION: Synthetic

<400> SEQUENCE: 368
```
aaatgggaga gacccttga agtc                                              24

<210> SEQ ID NO 369
<211> LENGTH: 24
<212> TYPE: DNA
<213> ORGANISM: Artificial Sequence
<220> FEATURE:
<223> OTHER INFORMATION: Synthetic

<400> SEQUENCE: 369
tttgaagtca aggacaccga ggaa                                              24

<210> SEQ ID NO 370
<211> LENGTH: 23
<212> TYPE: DNA
<213> ORGANISM: Artificial Sequence
<220> FEATURE:
<223> OTHER INFORMATION: Synthetic

<400> SEQUENCE: 370
cctttgaagt caaggacacc gag                                               23

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
tttgaagtca aggacaccga ggaa                                              24

<210> SEQ ID NO 372
<211> LENGTH: 24
<212> TYPE: DNA
<213> ORGANISM: Artificial Sequence
<220> FEATURE:
<223> OTHER INFORMATION: Synthetic

<400> SEQUENCE: 372
ctatgtgaca gggagggaga ggat                                              24

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
ctatgtgaca gggagggaga ggat                                              24

<210> SEQ ID NO 374
<211> LENGTH: 24
<212> TYPE: DNA
<213> ORGANISM: Artificial Sequence
<220> FEATURE:
<223> OTHER INFORMATION: Synthetic

<400> SEQUENCE: 374
ctatgtgaca gggagggaga ggat                                              24

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
ctatgtgaca gggagggaga ggat         24

<210> SEQ ID NO 376
<211> LENGTH: 24
<212> TYPE: DNA
<213> ORGANISM: Artificial Sequence
<220> FEATURE:
<223> OTHER INFORMATION: Synthetic

<400> SEQUENCE: 376
ctatgtgaca gggagggaga ggat         24

<210> SEQ ID NO 377
<211> LENGTH: 23
<212> TYPE: DNA
<213> ORGANISM: Artificial Sequence
<220> FEATURE:
<223> OTHER INFORMATION: Synthetic

<400> SEQUENCE: 377
gatcagcctt acaacgtgtc tct          23

<210> SEQ ID NO 378
<211> LENGTH: 23
<212> TYPE: DNA
<213> ORGANISM: Artificial Sequence
<220> FEATURE:
<223> OTHER INFORMATION: Synthetic

<400> SEQUENCE: 378
gatcagcctt acaacgtgtc tct          23

<210> SEQ ID NO 379
<211> LENGTH: 22
<212> TYPE: DNA
<213> ORGANISM: Artificial Sequence
<220> FEATURE:
<223> OTHER INFORMATION: Synthetic

<400> SEQUENCE: 379
gtgtcaatcc ctgatcactg gg           22

<210> SEQ ID NO 380
<211> LENGTH: 22
<212> TYPE: DNA
<213> ORGANISM: Artificial Sequence
<220> FEATURE:
<223> OTHER INFORMATION: Synthetic

<400> SEQUENCE: 380
gtgtcaatcc ctgatcactg gg           22

<210> SEQ ID NO 381
<211> LENGTH: 23
<212> TYPE: DNA
<213> ORGANISM: Artificial Sequence
<220> FEATURE:
<223> OTHER INFORMATION: Synthetic

<400> SEQUENCE: 381
cttctgtctc gtggggcatc ctc          23

```
<210> SEQ ID NO 382
<211> LENGTH: 23
<212> TYPE: DNA
<213> ORGANISM: Artificial Sequence
<220> FEATURE:
<223> OTHER INFORMATION: Synthetic

<400> SEQUENCE: 382
atgatcagga tcacccaacc ttc                                       23

<210> SEQ ID NO 383
<211> LENGTH: 23
<212> TYPE: DNA
<213> ORGANISM: Artificial Sequence
<220> FEATURE:
<223> OTHER INFORMATION: Synthetic

<400> SEQUENCE: 383
ctgagttcgc cttcagccta tac                                       23

<210> SEQ ID NO 384
<211> LENGTH: 23
<212> TYPE: DNA
<213> ORGANISM: Artificial Sequence
<220> FEATURE:
<223> OTHER INFORMATION: Synthetic

<400> SEQUENCE: 384
ctgagttcgc cttcagccta tac                                       23

<210> SEQ ID NO 385
<211> LENGTH: 24
<212> TYPE: DNA
<213> ORGANISM: Artificial Sequence
<220> FEATURE:
<223> OTHER INFORMATION: Synthetic

<400> SEQUENCE: 385
agtccaacag caccaatatc ttct                                      24

<210> SEQ ID NO 386
<211> LENGTH: 24
<212> TYPE: DNA
<213> ORGANISM: Artificial Sequence
<220> FEATURE:
<223> OTHER INFORMATION: Synthetic

<400> SEQUENCE: 386
ctgacactca cgatgaaatc ctgg                                      24

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
gagagaccct ttgaagtcaa ggac                                      24

<210> SEQ ID NO 388
<211> LENGTH: 22
<212> TYPE: DNA
<213> ORGANISM: Artificial Sequence
<220> FEATURE:
<223> OTHER INFORMATION: Synthetic
```

<400> SEQUENCE: 388
gaaggtgcct atgatgaagc gt                                          22

<210> SEQ ID NO 389
<211> LENGTH: 22
<212> TYPE: DNA
<213> ORGANISM: Artificial Sequence
<220> FEATURE:
<223> OTHER INFORMATION: Synthetic

<400> SEQUENCE: 389
gaaggtgcct atgatgaagc gt                                          22

<210> SEQ ID NO 390
<211> LENGTH: 24
<212> TYPE: DNA
<213> ORGANISM: Artificial Sequence
<220> FEATURE:
<223> OTHER INFORMATION: Synthetic

<400> SEQUENCE: 390
ttaacatcca gcactgtaag aagc                                        24

<210> SEQ ID NO 391
<211> LENGTH: 26
<212> TYPE: DNA
<213> ORGANISM: Artificial Sequence
<220> FEATURE:
<223> OTHER INFORMATION: Synthetic

<400> SEQUENCE: 391
aggagtaagt ggcagaaata atcaga                                      26

<210> SEQ ID NO 392
<211> LENGTH: 24
<212> TYPE: DNA
<213> ORGANISM: Artificial Sequence
<220> FEATURE:
<223> OTHER INFORMATION: Synthetic

<400> SEQUENCE: 392
gacacaggag taagtggcag aaat                                        24

<210> SEQ ID NO 393
<211> LENGTH: 24
<212> TYPE: DNA
<213> ORGANISM: Artificial Sequence
<220> FEATURE:
<223> OTHER INFORMATION: Synthetic

<400> SEQUENCE: 393
cagaagaaca agaggaatgc tgtg                                        24

<210> SEQ ID NO 394
<211> LENGTH: 24
<212> TYPE: DNA
<213> ORGANISM: Artificial Sequence
<220> FEATURE:
<223> OTHER INFORMATION: Synthetic

<400> SEQUENCE: 394
cagaagaaca agaggaatgc tgtg                                        24

<210> SEQ ID NO 395

```
<211> LENGTH: 24
<212> TYPE: DNA
<213> ORGANISM: Artificial Sequence
<220> FEATURE:
<223> OTHER INFORMATION: Synthetic

<400> SEQUENCE: 395
tctgccagct tacatttacc caaa                                          24

<210> SEQ ID NO 396
<211> LENGTH: 24
<212> TYPE: DNA
<213> ORGANISM: Artificial Sequence
<220> FEATURE:
<223> OTHER INFORMATION: Synthetic

<400> SEQUENCE: 396
acaggtctgc cagcttacat ttac                                          24

<210> SEQ ID NO 397
<211> LENGTH: 24
<212> TYPE: DNA
<213> ORGANISM: Artificial Sequence
<220> FEATURE:
<223> OTHER INFORMATION: Synthetic

<400> SEQUENCE: 397
tctgccagct tacatttacc caaa                                          24

<210> SEQ ID NO 398
<211> LENGTH: 23
<212> TYPE: DNA
<213> ORGANISM: Artificial Sequence
<220> FEATURE:
<223> OTHER INFORMATION: Synthetic

<400> SEQUENCE: 398
ccttacaacg tgtctctgct tct                                           23

<210> SEQ ID NO 399
<211> LENGTH: 23
<212> TYPE: DNA
<213> ORGANISM: Artificial Sequence
<220> FEATURE:
<223> OTHER INFORMATION: Synthetic

<400> SEQUENCE: 399
gatcagcctt acaacgtgtc tct                                           23

<210> SEQ ID NO 400
<211> LENGTH: 23
<212> TYPE: DNA
<213> ORGANISM: Artificial Sequence
<220> FEATURE:
<223> OTHER INFORMATION: Synthetic

<400> SEQUENCE: 400
gatcagcctt acaacgtgtc tct                                           23

<210> SEQ ID NO 401
<211> LENGTH: 23
<212> TYPE: DNA
<213> ORGANISM: Artificial Sequence
<220> FEATURE:
<223> OTHER INFORMATION: Synthetic

<400> SEQUENCE: 401
```

-continued gatcagcctt acaacgtgtc tct                                              23

<210> SEQ ID NO 402
<211> LENGTH: 23
<212> TYPE: DNA
<213> ORGANISM: Artificial Sequence
<220> FEATURE:
<223> OTHER INFORMATION: Synthetic

<400> SEQUENCE: 402
gatcagcctt acaacgtgtc tct                                              23

<210> SEQ ID NO 403
<211> LENGTH: 23
<212> TYPE: DNA
<213> ORGANISM: Artificial Sequence
<220> FEATURE:
<223> OTHER INFORMATION: Synthetic

<400> SEQUENCE: 403
gatcagcctt acaacgtgtc tct                                              23

<210> SEQ ID NO 404
<211> LENGTH: 23
<212> TYPE: DNA
<213> ORGANISM: Artificial Sequence
<220> FEATURE:
<223> OTHER INFORMATION: Synthetic

<400> SEQUENCE: 404
ccttacaacg tgtctctgct tct                                              23

<210> SEQ ID NO 405
<211> LENGTH: 23
<212> TYPE: DNA
<213> ORGANISM: Artificial Sequence
<220> FEATURE:
<223> OTHER INFORMATION: Synthetic

<400> SEQUENCE: 405
ccttacaacg tgtctctgct tct                                              23

<210> SEQ ID NO 406
<211> LENGTH: 23
<212> TYPE: DNA
<213> ORGANISM: Artificial Sequence
<220> FEATURE:
<223> OTHER INFORMATION: Synthetic

<400> SEQUENCE: 406
catcgacgag aaagggactg aag                                              23

<210> SEQ ID NO 407
<211> LENGTH: 23
<212> TYPE: DNA
<213> ORGANISM: Artificial Sequence
<220> FEATURE:
<223> OTHER INFORMATION: Synthetic

<400> SEQUENCE: 407
ccttacaacg tgtctctgct tct                                              23

<210> SEQ ID NO 408
<211> LENGTH: 80
<212> TYPE: RNA

```
<213> ORGANISM: Artificial Sequence
<220> FEATURE:
<223> OTHER INFORMATION: Synthetic

<400> SEQUENCE: 408
guuuuagagc uagaaauagc aaguuaaaau aaggcuaguc cguuaucaac uugaaaagu      60 ggcaccgagu cggugcuuuu                                                 80

<210> SEQ ID NO 409
<211> LENGTH: 23
<212> TYPE: DNA
<213> ORGANISM: Artificial Sequence
<220> FEATURE:
<223> OTHER INFORMATION: Synthetic

<400> SEQUENCE: 409
ccttacaacg tgtctctgct tct                                             23

<210> SEQ ID NO 410
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 410
nnnnnnnnnn nnnnnnnnnn guuuuagagc uagaaauagc aaguuaaaau aaggcuaguc     60
cguuaucaac uugaaaaagu ggcaccgagu cggugcuuuu                          100

<210> SEQ ID NO 411
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 411
nnnnnnnnnn nnnnnnnnnn guuuuagagc uagaaauagc aaguuaaaau aaggcuaguc     60
cguuaucaac uugaaaaagu ggcaccgagu cggugcuuuu                          100

<210> SEQ ID NO 412
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 412
nnnnnnnnnn nnnnnnnnnn guuuuagagc uagaaauagc aaguuaaaau aaggcuaguc     60
cguuaucaac uugaaaaagu ggcaccgagu cggugcuuuu                          100

<210> SEQ ID NO 413
<211> LENGTH: 100
```

<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 413
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 414
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 414
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 415
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 415
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 416
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 416
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 417
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)

<223> OTHER INFORMATION: n is a, c, g, or u

<400> SEQUENCE: 417
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 418
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 418
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 419
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 419
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 420
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 420
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 421
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 421
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 422
<211> LENGTH: 4526
<212> TYPE: DNA
<213> ORGANISM: Artificial Sequence
<220> FEATURE:
<223> OTHER INFORMATION: Synthetic

<400> SEQUENCE: 422

| | | | | | |
|---|---|---|---|---|---|
| taatacgact | cactataggg | tcccgcagtc | ggcgtccagc | ggctctgctt | gttcgtgtgt | 60 |
| gtgtcgttgc | aggccttatt | cggatccatg | gataagaagt | actcaatcgg | gctggatatc | 120 |
| ggaactaatt | ccgtgggttg | ggcagtgatc | acggatgaat | acaaagtgcc | gtccaagaag | 180 |
| ttcaaggtcc | tggggaacac | cgatagacac | agcatcaaga | aaaatctcat | cggagccctg | 240 |
| ctgtttgact | ccggcgaaac | cgcagaagcg | acccggctca | acgtaccgc | gaggcgacgc | 300 |
| tacacccggc | ggaagaatcg | catctgctat | ctgcaagaga | tcttttcgaa | cgaaatggca | 360 |
| aaggtcgacg | acagcttctt | ccaccgcctg | gaagaatctt | tcctggtgga | ggaggacaag | 420 |
| aagcatgaac | ggcatcctat | ctttggaaac | atcgtcgacg | aagtggcgta | ccacgaaaag | 480 |
| tacccgacca | tctaccatct | gcggaagaag | ttggttgact | caactgacaa | ggccgacctc | 540 |
| agattgatct | acttggccct | cgcccatatg | atcaaattcc | gcggacactt | cctgatcgaa | 600 |
| ggcgatctga | accctgataa | ctccgacgtg | gataagcttt | tcattcaact | ggtgcagacc | 660 |
| tacaaccaac | tgttcgaaga | aaacccaatc | aatgctagcg | gcgtcgatgc | caaggccatc | 720 |
| ctgtccgccc | ggctgtcgaa | gtcgcggcgc | ctcgaaaacc | tgatcgcaca | gctgccggga | 780 |
| gagaaaaaga | acggactttt | cggcaacttg | atcgctctct | cactgggact | cactcccaat | 840 |
| ttcaagtcca | attttgacct | ggccgaggac | gcgaagctgc | aactctcaaa | ggacacctac | 900 |
| gacgacgact | tggacaattt | gctggcacaa | attggcgatc | agtacgcgga | tctgttcctt | 960 |
| gccgctaaga | acctttcgga | cgcaatcttg | ctgtccgata | tcctgcgcgt | gaacaccgaa | 1020 |
| ataaccaaag | cgccgcttag | cgcctcgatg | attaagcggt | acgacgagca | tcaccaggat | 1080 |
| ctcacgctgc | tcaaagcgct | cgtgagacag | caactgcctg | aaaagtacaa | ggagatcttc | 1140 |
| ttcgaccagt | ccaagaatgg | gtacgcaggg | tacatcgatg | gaggcgctag | ccaggaagag | 1200 |
| ttctataagt | tcatcaagcc | aatcctggaa | aagatggacg | gaaccgaaga | actgctggtc | 1260 |
| aagctgaaca | gggaggatct | gctccggaaa | cagagaacct | tgacaacgg | atccattccc | 1320 |
| caccagatcc | atctgggtga | gctgcacgcc | atcttgcggc | gccaggagga | cttttaccca | 1380 |
| ttcctcaagg | acaaccggga | aaagatcgag | aaaattctga | cgttccgcat | cccgtattac | 1440 |
| gtgggcccac | tggcgcgcgg | caattcgcgc | ttcgcgtgga | tgactagaaa | atcagaggaa | 1500 |
| accatcactc | cttggaattt | cgaggaagtt | gtggataagg | gagcttcggc | acaaagcttc | 1560 |
| atcgaacgaa | tgaccaactt | cgacaagaat | ctcccaaacg | agaaggtgct | tcctaagcac | 1620 |
| agcctccttt | acgaatactt | cactgtctac | aacgaactga | ctaaagtgaa | atacgttact | 1680 |
| gaaggaatga | ggaagccggc | ctttctgtcc | ggagaacaga | gaaagcaat | tgtcgatctg | 1740 |
| ctgttcaaga | ccaaccgcaa | ggtgaccgtc | aagcagctta | agaggacta | cttcaagaag | 1800 |
| atcgagtgtt | tcgactcagt | ggaaatcagc | ggggtggagg | acagattcaa | cgcttcgctg | 1860 |
| ggaacctatc | atgatctcct | gaagatcatc | aaggacaagg | acttccttga | caacgaggag | 1920 |
| aacgaggaca | tcctggaaga | tatcgtcctg | accttgaccc | ttttcgagga | tcgcgagatg | 1980 |
| atcgaggaga | ggcttaagac | ctacgctcat | ctcttcgacg | ataaggtcat | gaaacaactc | 2040 |

```
aagcgccgcc ggtacactgg ttggggccgc ctctcccgca agctgatcaa cggtattcgc    2100
gataaacaga gcggtaaaac tatcctggat ttcctcaaat cggatggctt cgctaatcgt    2160
aacttcatgc aattgatcca cgacgacagc ctgaccttta aggaggacat ccaaaaagca    2220
caagtgtccg gacagggaga ctcactccat gaacacatcg cgaatctggc cggttcgccg    2280
gcgattaaga agggaattct gcaaactgtg aaggtggtcg acgagctggt gaaggtcatg    2340
ggacggcaca aaccggagaa tatcgtgatt gaaatggccc gagaaaacca gactacccag    2400
aagggccaga aaaactcccg cgaaaggatg aagcggatcg aagaaggaat caaggagctg    2460
ggcagccaga tcctgaaaga gcacccggtg gaaaacacgc agctgcagaa cgagaagctc    2520
tacctgtact atttgcaaaa tggacgggac atgtacgtgg accaagagct ggacatcaat    2580
cggttgtctg attacgacgt ggaccacatc gttccacagt cctttctgaa ggatgactcg    2640
atcgataaca aggtgttgac tcgcagcgac aagaacagag ggaagtcaga taatgtgcca    2700
tcggaggagg tcgtgaagaa gatgaagaat tactggcggc agctcctgaa tgcgaagctg    2760
attcccaga gaaagtttga caatctcact aaagccgagc gcggcggact ctcagagctg    2820
gataaggctg gattcatcaa acggcagctg gtcgagactc ggcagattac caagcacgtg    2880
gcgcagatct ggactcccg catgaacact aaatacgacg agaacgataa gctcatccgg    2940
gaagtgaagg tgattaccct gaaaagcaaa cttgtgtcgg actttcggaa ggactttcag    3000
ttttacaaag tgagagaaat caacaactac catcacgcgc atgacgcata cctcaacgct    3060
gtggtcggta ccgccctgat caaaaagtac cctaaacttg aatcggagtt tgtgtacgga    3120
gactacaagg tctacgacgt gaggaagatg atagccaagt ccgaacagga aatcgggaaa    3180
gcaactgcga aatacttctt ttactcaaac atcatgaact ttttcaagac tgaaattacg    3240
ctggccaatg gagaaatcag gaagaggcca ctgatcgaaa ctaacggaga aacgggcgaa    3300
atcgtgtggg acaagggcag ggacttcgca actgttcgca aagtgctctc tatgccgcaa    3360
gtcaatattg tgaagaaaac cgaagtgcaa accggcggat tttcaaagga atcgatcctc    3420
ccaaagagaa atagcgacaa gctcattgca cgcaagaaag actgggaccc gaagaagtac    3480
ggaggattcg attcgccgac tgtcgcatac tccgtcctcg tggtggccaa ggtggagaag    3540
ggaaagagca aaaagctcaa atccgtcaaa gagctgctgg ggattaccat catggaacga    3600
tcctcgttcg agaagaaccc gattgatttc ctcgaggcga agggttacaa ggaggtgaag    3660
aaggatctga tcatcaaact ccccaagtac tcactgttcg aactggaaaa tggtcggaag    3720
cgcatgctgg cttcggccgg agaactccaa aaaggaaatg agctggcctt gcctagcaag    3780
tacgtcaact tcctctatct tgcttcgcac tacgaaaaac tcaaagggtc accggaagat    3840
aacgaacaga agcagctttt cgtggagcag cacaagcatt atctggatga atcatcgaa     3900
caaatctccg agttttcaaa gcgcgtgatc ctcgccgacg ccaacctcga caaagtcctg    3960
tcggcctaca ataagcatag agataagccg atcagagaac aggccgagaa cattatccac    4020
ttgttcaccc tgactaaccl gggagcccca gccgccttca agtacttcga tactactatc    4080
gatcgcaaaa gatacacgtc caccaaggaa gttctggacg cgaccctgat ccaccaaagc    4140
atcactggac tctacgaaac taggatcgat ctgtcgcagc tgggtggcga tggcggtgga    4200
tctccgaaaa agaagagaaa ggtgtaatga gctagccatc acatttaaaa gcatctcagc    4260
ctaccatgag aataagagaa agaaaatgaa gatcaatagc ttattcatct ctttttcttt    4320
ttcgttggtg taaagccaac accctgtcta aaaaacataa atttctttaa tcattttgcc    4380
tcttttctct gtgcttcaat taataaaaaa tggaaagaac ctcgagaaaa aaaaaaaaaa    4440
```

```
aaaaaaaaaa aaaaaaaaaa aaaaaaaaaa aaaaaaaaaa aaaaaaaaaa aaaaaaaaaa    4500
aaaaaaaaaa aaaaaaaaaa aaaaa                                          4526

<210> SEQ ID NO 423
<211> LENGTH: 4615
<212> TYPE: DNA
<213> ORGANISM: Artificial Sequence
<220> FEATURE:
<223> OTHER INFORMATION: Synthetic

<400> SEQUENCE: 423
taatacgact cactataggg tcccgcagtc ggcgtccagc ggctctgctt gttcgtgtgt      60
gtgtcgttgc aggccttatt cggatccatg gataagaagt actcaatcgg gctggatatc     120
ggaactaatt ccgtgggttg ggcagtgatc acggatgaat acaaagtgcc gtccaagaag     180
ttcaaggtcc tggggaacac cgatagacac agcatcaaga aaaatctcat cggagccctg     240
ctgtttgact ccgcgaaaac cgcagaagcg acccggctca acgtaccgc gaggcgacgc      300 tacacccggc ggaagaatcg catctgctat ctgcaagaga tcttttcgaa cgaaatggca     360
aaggtcgacg acagcttctt ccaccgcctg gaagaatctt tcctggtgga ggaggacaag     420
aagcatgaac ggcatcctat cttttggaaac atcgtcgacg aagtggcgta ccacgaaaag     480
tacccgacca tctaccatct gcggaagaag ttggttgact caactgacaa ggccgacctc     540
agattgatct acttggccct cgcccatatg atcaaattcc gcggacactt cctgatcgaa     600
ggcgatctga accctgataa ctccgacgtg ataagctttt cattcaact ggtgcagacc      660 tacaaccaac tgttcgaaga aaacccaatc aatgctagcg gcgtcgatgc caaggccatc     720
ctgtccgccc ggctgtcgaa gtcgcggcgc ctcgaaaacc tgatcgcaca gctgccggga     780
gagaaaaaga acggactttt cggcaacttg atcgctctct cactgggact cactcccaat     840
ttcaagtcca attttgacct ggccgaggac gcgaagctgc aactctcaaa ggacacctac     900
gacgacgact ggacaatttt gctggcacaa attggcgatc agtacgcgga tctgttcctt     960
gccgctaaga acctttcgga cgcaatcttg ctgtccgata tcctgcgcgt gaacaccgaa    1020
ataaccaaag cgccgcttag cgcctcgatg attaagcggt acgacgagca tcaccaggat    1080
ctcacgctgc tcaaagcgct cgtgagacag caactgcctg aaaagtacaa ggagatcttc    1140
ttcgaccagt ccaagaatgg gtacgcaggg tacatcgatg gaggcgctag ccaggaagag    1200
ttctataagt tcatcaagcc aatcctggaa aagatggacg gaaccgaaga actgctggtc    1260
aagctgaaca gggaggatct gctccggaaa cagagaacct tgacaacgg atccattccc    1320 caccagatcc atctgggtga gctgcacgcc atcttgcggc gccaggagga ctttttaccca    1380 ttcctcaagg acaaccggga aaagatcgag aaaattctga cgttccgcat cccgtattac    1440
gtgggcccac tggcgcgcgg caattcgcgc ttcgcgtgga tgactagaaa atcagaggaa    1500
accatcactc cttggaattt cgaggaagtt gtggataagg gagcttcggc acaaagcttc    1560
atcgaacgaa tgaccaactt cgacaagaat ctcccaaacg agaaggtgct tcctaagcac    1620
agcctccttt acgaatactt cactgtctac aacgaactga ctaaagtgaa atacgttact    1680
gaaggaatga ggaagccggc cttttctgtcc ggagaacaga agaaagcaat tgtcgatctg    1740
ctgttcaaga ccaaccgcaa ggtgaccgtc aagcagctta agaggacta cttcaagaag    1800 atcgagtgtt tcgactcagt ggaaatcagc ggggtggagg acagattcaa cgcttcgctg    1860
ggaacctatc atgatctcct gaagatcatc aaggacaagg acttccttga caacgaggag    1920
```

```
aacgaggaca tcctggaaga tatcgtcctg accttgaccc ttttcgagga tcgcgagatg   1980
atcgaggaga ggcttaagac ctacgctcat ctcttcgacg ataaggtcat gaaacaactc   2040
aagcgccgcc ggtacactgg ttggggccgc ctctcccgca agctgatcaa cggtattcgc   2100
gataaacaga gcggtaaaac tatcctggat ttcctcaaat cggatggctt cgctaatcgt   2160
aacttcatgc aattgatcca cgacgacagc ctgacctta aggaggacat ccaaaaagca    2220
caagtgtccg acagggaga ctcactccat gaacacatcg cgaatctggc cggttcgccg    2280
gcgattaaga agggaattct gcaaactgtg aaggtggtcg acgagctggt gaaggtcatg   2340
ggacggcaca aaccggagaa tatcgtgatt gaaatggccc gagaaaacca gactacccag   2400
aagggccaga aaaactcccg cgaaaggatg aagcggatcg aagaaggaat caaggagctg   2460
ggcagccaga tcctgaaaga gcacccggtg aaaacacgc agctgcagaa cgagaagctc    2520
tacctgtact atttgcaaaa tggacgggac atgtacgtgg accaagagct ggacatcaat   2580
cggttgtctg attacgacgt ggaccacatc gttccacagt cctttctgaa ggatgactcg   2640
atcgataaca aggtgttgac tcgcagcgac aagaacagag ggaagtcaga taatgtgcca   2700
tcggaggagg tcgtgaagaa gatgaagaat tactggcggc agctcctgaa tgcgaagctg   2760 attcccaga gaaagtttga caatctcact aaagccgagc gcggcggact ctcagagctg     2820
gataaggctg gattcatcaa acggcagctg gtcgagactc ggcagattac caagcacgtg   2880
gcgcagatct tggactcccg catgaacact aaatacgacg agaacgataa gctcatccgg   2940
gaagtgaagg tgattaccct gaaaagcaaa cttgtgtcgg actttcggaa ggactttcag   3000
ttttacaaag tgagagaaat caacaactac catcacgcgc atgacgcata cctcaacgct   3060
gtggtcggta ccgccctgat caaaaagtac cctaaacttg aatcggagtt tgtgtacgga   3120
gactacaagg tctacgacgt gaggaagatg atagccaagt ccgaacagga atcgggaaa    3180 gcaactgcga aatacttctt ttactcaaac atcatgaact ttttcaagac tgaaattacg   3240
ctggccaatg gagaaatcag gaagaggcca ctgatcgaaa ctaacggaga aacgggcgaa   3300
atcgtgtggg acaagggcag ggacttcgca actgttcgca aagtgctctc tatgccgcaa   3360
gtcaatattg tgaagaaaac cgaagtgcaa accggcggat tttcaaagga atcgatcctc   3420
ccaaagagaa atagcgacaa gctcattgca cgcaagaaag actgggaccc gaagaagtac   3480
ggaggattcg attcgccgac tgtcgcatac tccgtcctcg tggtggccaa ggtggagaag   3540
ggaaagagca aaaagctcaa atccgtcaaa gagctgctgg ggattaccat catggaacga   3600
tcctcgttcg agaagaaccc gattgatttc ctcgaggcga agggttacaa ggaggtgaag   3660
aaggatctga tcatcaaact ccccaagtac tcactgttcg aactggaaaa tggtcggaag   3720
cgcatgctgg cttcggccgg agaactccaa aaaggaaatg agctggcctt gcctagcaag   3780
tacgtcaact tcctctatct tgcttcgcac tacgaaaaac tcaaagggtc accggaagat   3840
aacgaacaga agcagctttt cgtggagcag cacaagcatt atctggatga aatcatcgaa   3900
caaatctccg agttttcaaa gcgcgtgatc ctcgccgacg ccaacctcga caaagtcctg   3960
tcggcctaca ataagcatag agataagccg atcagagaac aggccgagaa cattatccac   4020
ttgttcaccc tgactaacct gggagcccca gccgccttca agtacttcga tactactatc   4080
gatcgcaaaa gatacacgtc caccaaggaa gttctggacg cgaccctgat ccaccaaagc   4140
atcactggac tctacgaaac taggatcgat ctgtcgcagc tgggtggcga tggctcggct   4200
tacccatacg acgtgcctga ctacgcctcg ctcggatcgg gctcccccaa aaagaaacgg   4260
aaggtggacg gatccccgaa aaagaagaga aaggtggact ccggatgaga attatgcagt   4320
```

```
ctagccatca catttaaaag catctcagcc taccatgaga ataagagaaa gaaaatgaag    4380
atcaatagct tattcatctc tttttctttt tcgttggtgt aaagccaaca ccctgtctaa    4440
aaaacataaa tttctttaat cattttgcct cttttctctg tgcttcaatt aataaaaaat    4500
ggaaagaacc tcgagaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaa         4615
```

<210> SEQ ID NO 424
<211> LENGTH: 100
<212> TYPE: RNA
<213> ORGANISM: Artificial Sequence
<220> FEATURE:
<223> OTHER INFORMATION: Synthetic

<400> SEQUENCE: 424

```
uuacagccac gucuacagca guuuuagagc uagaaauagc aaguuaaaau aaggcuaguc     60
cguuaucaac uugaaaaagu ggcaccgagu cggugcuuuu                          100
```

COMPOSITIONS AND METHODS FOR TREATING ALPHA-1 ANTITRYPSIN DEFICIENCY

This application is a Continuation of International Application No. PCT/US2017/067800, which was filed on Dec. 21, 2017 and claims the benefit of priority to U.S. Provisional Application No. 62/438,219, which was filed on Dec. 22, 2016, both of which are incorporated by reference in their entirety.

Alpha-1 antitrypsin (AAT or A1AT) or serum trypsin inhibitor is a type of serine protease inhibitor (also termed a serpin) encoded by the SERPINA1 gene. AAT is primarily synthesized and secreted by hepatocytes, and functions to inhibit the activity of neutrophil elastase in the lung. Without sufficient quantities of functioning AAT, neutrophil elastase is uncontrolled and damages alveoli in the lung. Thus, mutations in SERPINA1 that result in decreased levels of AAT, or decreased levels of properly functioning AAT, lead to lung pathology. Moreover, mutations in SERPINA1 that lead to production of misformed AAT that does not exit the liver leads to liver pathology due to accumulation of AAT in the hepatocytes. Thus, insufficient and improperly formed AAT caused by SERPINA1 mutation leads to both lung and liver pathology.

More than one hundred allelic variants have been described for the SERPINA1 gene. Variants are generally classified according to their effect on serum levels of AAT. For example, M alleles are normal variants associated with normal serum AAT levels, whereas Z and S alleles are mutant variants associated with decreased AAT levels. The presence of Z and S alleles is associated α1-antitrypsin deficiency (AATD or A1AD), a genetic disorder characterized by mutations in the SERPINA1 gene that leads to the production of abnormal AAT.

There are many forms and degrees of AATD. The "Z-variant" is the most common, causing severe clinical disease in both liver and lung. The Z-variant is characterized by a single nucleotide change in the 5' end of the 5th exon that results in a missense mutation of glutamic acid to lysine at amino acid position 342 (E342K). Symptoms arise in patients that are both homozygous (ZZ) and heterozygous (MZ or SZ) at the Z allele. The presence of one or two Z alleles results in SERPINA1 mRNA instability, and AAT protein polymerization and aggregation in liver hepatocytes. Patients having at least one Z allele have an increased incidence of liver cancer due to the accumulation of aggregated AAT protein in the liver. In addition to liver pathology, AATD characterized by at least one Z allele is also characterized by lung disease due to the decrease in AAT in the alveoli and the resulting decrease in inhibition of neutrophil elastase. The prevalence of the severe ZZ-form (i.e., homozygous expression of the Z-variant) is 1:2,000 in northern European populations, and 1:4,500 in the United States.

A need exists to ameliorate the negative effects of AATD in both the liver and lung. The present invention provides compositions and methods using the CRISPR/Cas system to knock out the SERPINA1 gene thereby eliminating the production of mutant forms of AAT that are associated with liver symptoms in patients with AATD.

SUMMARY

Embodiment 01

A method of inducing a double-stranded break (DSB) within the SERPINA1 gene, comprising delivering a composition to a cell, wherein the composition comprises a guide RNA comprising a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129.

Embodiment 02

A method of modifying the SERPINA1 gene comprising delivering a composition to a cell, wherein the composition comprises (i) an RNA-guided DNA binding agent or a nucleic acid encoding an RNA-guided DNA binding agent and (ii) a guide RNA comprising a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129.

Embodiment 03

A method of treating alpha-1 antitrypsin deficiency (AATD), comprising administering a composition to a subject in need thereof, wherein the composition comprises (i) an RNA-guided DNA binding agent or a nucleic acid encoding an RNA-guided DNA binding agent and (ii) a guide RNA comprising a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129, thereby treating AATD.

Embodiment 04

A method for reducing or preventing the accumulation of alpha-1 antitrypsin (AAT) in the liver in a subject, comprising administering a composition to a subject in need thereof, wherein the composition comprises (i) an RNA-guided DNA binding agent or a nucleic acid encoding an RNA-guided DNA binding agent and (ii) a guide RNA comprising a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129, thereby reducing accumulation of AAT in the liver.

Embodiment 05

A composition comprising a guide RNA comprising a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129.

Embodiment 06

A composition comprising a vector encoding a guide RNA, wherein the guide RNA comprises a guide sequence selected from SEQ ID NOs: 5-129 or a guide sequence that is at least 99%, 98%, 97%, 96%, 95%, 94%, 93%, 92%, 91%, or 90% identical to a sequence selected from SEQ ID NOs: 5-129.

Embodiment 07

The composition of embodiment 5 or 6, for use in inducing a double-stranded break (DSB) within the SERPINA1 gene in a cell or subject.

Embodiment 08

The composition of embodiment 5 or 6, for use in modifying the SERPINA1 gene in a cell or subject.

Embodiment 09

The composition of embodiment 5 or 6, for use in treating alpha-1 antitrypsin deficiency (AATD) in a subject.

Embodiment 10

The composition of embodiment 5 or 6, for use in reducing AAT serum or liver concentration in a subject.

Embodiment 11

The composition of embodiment 5 or 6, for use in reducing or preventing the accumulation of alpha-1 antitrypsin (AAT) in the liver in a subject.

Embodiment 12

The method of any one of embodiments 1-4 or the composition for use of any one of embodiments 5-11, wherein the composition reduces serum and/or liver AAT levels.

Embodiment 13

The method or composition for use of embodiment 12, wherein the serum and/or liver AAT levels are reduced by at least 50% as compared to serum and/or AAT levels before administration of the composition.

Embodiment 14

The method or composition for use of embodiment 12, wherein the serum and/or AAT levels are reduced by 50-60%, 60-70%, 70-80%, 80-90%, 90-95%, 95-98%, 98-99%, or 99-100% as compared to serum and/or AAT levels before administration of the composition.

Embodiment 15

The method or composition for use of any one of embodiments 1-4 or 7-14, wherein the composition results in editing of the SERPINA1 gene.

Embodiment 16

The method or composition for use of embodiment 15, wherein the editing is calculated as a percentage of the population that is edited (percent editing).

Embodiment 17

The method or composition for use of embodiment 16, wherein the percent editing is between 30 and 99%.

Embodiment 18

The method or composition for use of embodiment 17, wherein the percent editing is between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99%.

Embodiment 19

The method or composition for use of any one of embodiments 1-4 or 7-18, wherein the composition is administered or delivered at least two times.

Embodiment 20

The method or composition for use of embodiment 19, wherein the composition is administered or delivered at least three times.

Embodiment 21

The method or composition for use of embodiment 19, wherein the composition is administered or delivered at least four times.

Embodiment 22

The method or composition for use of embodiment 19, wherein the composition is administered or delivered up to five, six, seven, eight, nine, or ten times.

Embodiment 23

The method or composition for use of any one of embodiments 19-22, wherein the administration or delivery occurs at an interval of 1, 2, 3, 4, 5, 6, 7, 8, 9, 10, 11, 12, 13, 14, or 15 days.

Embodiment 24

The method or composition for use of any one of embodiments 19-22, wherein the administration or delivery occurs at an interval of 1, 2, 3, 4, 5, 6, 7, 8, 9, 10, 11, 12, 13, 14, or 15 weeks.

Embodiment 25

The method or composition for use of any one of embodiments 19-22, wherein the administration or delivery occurs at an interval of 1, 2, 3, 4, 5, 6, 7, 8, 9, 10, 11, 12, 13, 14, or 15 months.

Embodiment 26

The method or composition of any one of the preceding embodiments, wherein the guide sequence is selected from SEQ ID NOs: 5-129.

Embodiment 27

The method or composition of any one of the preceding embodiments, wherein the guide RNA is at least partially complementary to a target sequence present in the human SERPINA1 gene.

Embodiment 28

The method or composition of embodiment 27, wherein the target sequence is in exon 2, 3, 4, or 5 of the human SERPINA1 gene.

Embodiment 29

The method or composition of embodiment 27, wherein the target sequence is in exon 2 of the human SERPINA1 gene.

Embodiment 30

The method or composition of embodiment 27, wherein the target sequence is in exon 3 of the human SERPINA1 gene.

Embodiment 31

The method or composition of embodiment 27, wherein the target sequence is in exon 4 of the human SERPINA1 gene.

Embodiment 32

The method or composition of embodiment 27, wherein the target sequence is in exon 5 of the human SERPINA1 gene.

Embodiment 33

The method or composition of any one of embodiments 1-32, wherein the guide sequence is complementary to a target sequence in the positive strand of SERPINA1.

Embodiment 34

The method or composition of any one of embodiments 1-32, wherein the guide sequence is complementary to a target sequence in the negative strand of SERPINA1.

Embodiment 35

The method or composition of any one of embodiments 1-32, further comprising a second guide sequence, wherein the first guide sequence is complementary to a first target sequence in the positive strand of the SERPINA1 gene, and wherein the second guide sequence is complementary to a second target sequence in the negative strand of the SERPINA1 gene.

Embodiment 36

The method or composition of any one of the preceding embodiments, wherein the guide RNA comprises a crRNA that comprises the guide sequence and further comprises a nucleotide sequence of SEQ ID NO: 140, wherein the nucleotides of SEQ ID NO: 140 follow the guide sequence at its 3' end.

Embodiment 37

The method or composition of any one of the preceding embodiments, wherein the guide RNA is a dual guide (dgRNA).

Embodiment 38

The method or composition of embodiment 37, wherein the dual guide RNA comprises a crRNA comprising a nucleotide sequence of SEQ ID NO: 140, wherein the nucleotides of SEQ ID NO: 140 follow the guide sequence at its 3' end, and a trRNA.

Embodiment 39

The method or composition of any one of embodiments 1-36, wherein the guide RNA is a single guide (sgRNA).

Embodiment 40

The method or composition of embodiment 39, wherein the sgRNA comprises a guide sequence that has the pattern of SEQ ID NO: 130.

Embodiment 41

The method or composition of embodiment 39, wherein the sgRNA comprises the sequence of SEQ ID NO: 130.

Embodiment 42

The method or composition of embodiment 40 or 41, wherein each N in SEQ ID NO: 130 is any natural or non-natural nucleotide, wherein the N's form the guide sequence, and the guide sequence targets an RNA-guided DNA binding agent to the SERPINA1 gene.

Embodiment 43

The method or composition of any one of embodiments 39-42, wherein the sgRNA comprises any one of the guide sequences of SEQ ID NOs: 5-129 and the nucleotides of SEQ ID NO: 140.

Embodiment 44

The method or composition of any one of embodiments 39-43, wherein the sgRNA comprises a guide sequence that is at least 99%, 98%, 97%, 96%, 95%, 94%, 93%, 92%, 91%, or 90% identical to a sequence selected from SEQ ID Nos: 5-129.

Embodiment 45

The method or composition of embodiment 42, wherein each N in SEQ ID NO: 130 are replaced with a sequence selected from SEQ ID Nos: 5-129.

Embodiment 46

The method or composition of any one of the preceding embodiments, wherein the guide RNA comprises at least one modification.

Embodiment 47

The method or composition of embodiment 46, wherein the at least one modification includes a 2'-O-methyl (2'-O-Me) modified nucleotide.

Embodiment 48

The method or composition of embodiment 46 or 47, wherein the at least one modification includes a phosphorothioate (PS) bond between nucleotides.

Embodiment 49

The method or composition of any one of embodiments 46-48, wherein the at least one modification includes a 2'-fluoro (2'-F) modified nucleotide.

Embodiment 50

The method or composition of any one of embodiments 46-49, wherein the at least one modification includes a modification at one or more of the first five nucleotides at the 5' end.

Embodiment 51

The method or composition of any one of embodiments 46-50, wherein the at least one modification includes a modification at one or more of the last five nucleotides at the 3' end.

Embodiment 52

The method or composition of any one of embodiments 46-51, wherein the at least one modification includes PS bonds between the first four nucleotides.

Embodiment 53

The method or composition of any one of embodiments 46-52, wherein the at least one modification includes PS bonds between the last four nucleotides.

Embodiment 54

The method or composition of any one of embodiments 46-53, wherein the at least one modification includes 2'-O-Me modified nucleotides at the first three nucleotides at the 5' end.

Embodiment 55

The method or composition of any one of embodiments 46-54, wherein the at least one modification includes 2'-O-Me modified nucleotides at the last three nucleotides at the 3' end.

Embodiment 56

The method or composition of any one of embodiments 46-55, wherein the guide RNA comprises the modified nucleotides of SEQ ID NO: 130.

Embodiment 57

The method or composition of any one of embodiments 1-56, wherein the composition further comprises a pharmaceutically acceptable excipient.

Embodiment 58

The method or composition of any one of embodiments 1-57, wherein the guide RNA and optionally the RNA-guided DNA binding agent or a nucleic acid encoding an RNA-guided DNA binding agent is/are associated with a lipid nanoparticle (LNP).

Embodiment 59

The method or composition of embodiment 58, wherein the LNP comprises a CCD lipid.

Embodiment 60

The method or composition of embodiment 59, wherein the CCD lipid is Lipid A.

Embodiment 61

The method or composition of embodiment 58-60, wherein the LNP comprises a neutral lipid.

Embodiment 62

The method or composition of embodiment 61, wherein the neutral lipid is DSPC

Embodiment 63

The method or composition of any one of embodiments 58-62, wherein the LNP comprises a helper lipid.

Embodiment 64

The method or composition of embodiment 63, wherein the helper lipid is cholesterol.

Embodiment 65

The method or composition of any one of embodiments 58-64, wherein the LNP comprises a stealth lipid.

Embodiment 66

The method or composition of embodiment 58-65, wherein the stealth lipid is PEG2k-DMG.

Embodiment 67

The method or composition of any one of the preceding embodiments, wherein the composition further comprises an RNA-guided DNA binding agent.

Embodiment 68

The method or composition of any one of the preceding embodiments, wherein the composition further comprises an mRNA that encodes an RNA-guided DNA binding agent.

Embodiment 69

The method or composition of embodiment 67 or 68, wherein the RNA-guided DNA binding agent is a Cas cleavase.

Embodiment 70

The method or composition of embodiment 69, wherein the RNA-guided DNA binding agent is Cas9.

Embodiment 71

The method or composition of any one of embodiments 67-70, wherein the RNA-guided DNA binding agent is modified.

Embodiment 72

The method or composition of any one of embodiments 67-71, wherein the RNA-guided DNA binding agent is a nickase.

Embodiment 73

The method or composition of embodiment 71 or 72, wherein the modified RNA-guided DNA binding agent comprises a nuclear localization signal (NLS).

Embodiment 74

The method or composition of any one of embodiments 67-73, wherein the RNA-guided DNA binding agent is a Cas from a Type-II CRISPR/Cas system.

Embodiment 75

The method or composition of any one of the preceding embodiments, wherein the composition is a pharmaceutical formulation and further comprises a pharmaceutically acceptable carrier.

Embodiment 76

The method or composition for use of any one of embodiments 1-4 or 7-75, wherein the composition reduces or prevents accumulation of alpha-1 antitrypsin (AAT) in the liver.

Embodiment 77

The method or composition for use of embodiment 76, wherein the AAT is misformed.

Embodiment 78

The method or composition for use of any one of embodiments 1-4 or 7-77, wherein non-homologous ending joining (NHEJ) leads to a mutation during repair of a DSB in the SERPINA1 gene.

Embodiment 79

The method or composition for use of embodiment 78, wherein NHEJ leads to a deletion or insertion of a nucleotide (s) during repair of a DSB in the SERPINA1 gene.

Embodiment 80

The method or composition for use of embodiment 80, wherein the deletion or insertion of a nucleotide(s) induces a frame shift or nonsense mutation in the SERPINA1 gene.

Embodiment 81

The method or composition for use of embodiment 80, wherein a frame shift or nonsense mutation is induced in the SERPINA1 gene of at least 50% of liver cells.

Embodiment 82

The method or composition for use of embodiment 81, wherein a frame shift or nonsense mutation is induced in the SERPINA1 gene of 50%-60%, 60%-70%, 70% or 80%, 80%-90%, 90-95%, 95%-99%, or 99%-100% of liver cells.

Embodiment 83

The method or composition for use of any one of embodiments 79-82, wherein a deletion or insertion of a nucleotide (s) occurs in the SERPINA1 gene at least 50-fold or more than in off-target sites.

Embodiment 84

The method or composition for use of embodiment 83, wherein the deletion or insertion of a nucleotide(s) occurs in the SERPINA1 gene 50-fold to 150-fold, 150-fold to 500-fold, 500-fold to 1500-fold, 1500-fold to 5000-fold, 5000-fold to 15000-fold, 15000-fold to 30000-fold, or 30000-fold to 60000-fold more than in off-target sites.

Embodiment 85

The method or composition for use of any one of embodiments 1-4 or 7-84, wherein administering the composition reduces levels of AAT in the subject.

Embodiment 86

The method or composition for use of embodiment 85, wherein the levels of AAT are reduced by at least 40%.

Embodiment 87

The method or composition for use of embodiment 86, wherein the levels of AAT are reduced by 40-50%, 50%-60%, 60%-70%, 70% or 80%, 80%-90%, 90-95%, 95%-99%, or 99%-100%.

Embodiment 88

The method or composition for use of embodiment 86 or 87, wherein the levels of AAT are measured in serum, plasma, blood, cerebral spinal fluid, or sputum.

Embodiment 89

The method or composition for use of embodiment 86 or 87, wherein the levels of AAT are measured in liver and/or serum.

Embodiment 90

The method or composition for use of any one of embodiments 85-89, wherein the levels of AAT are measured via enzyme-linked immunosorbent assay (ELISA).

Embodiment 91

The method or composition for use of any one of embodiments 1-4 or 7-90, wherein the subject has AATD.

Embodiment 92

The method or composition for use of any one of embodiments 1-4 or 7-91, wherein the subject is human.

Embodiment 93

The method or composition for use of embodiment 91 or 92, wherein the subject has AATD wt.

Embodiment 94

The method or composition for use of embodiment 91 or 92, wherein the subject has hereditary AATD.

Embodiment 95

The method or composition for use of any one of embodiments 1-4, 7-92, or 94, wherein the subject has a family history of AATD.

Embodiment 96

The method or composition for use of any one of embodiments 1-4 or 7-95, wherein the subject has only or predominantly liver symptoms of AATD.

Embodiment 97

The method or composition for use of any one of embodiments 1-4 or 7-96, wherein the subject is heterozygous for the Z allele at the SERPINA1 locus.

Embodiment 98

The method of embodiment 97, wherein the subject has one Z allele and one S allele at the SERPINA1 locus.

Embodiment 99

The method or composition for use of any one of embodiments 1-4 or 7-98, wherein the subject does not have a E342K mutation in the amino acid sequence of AAT, but has reduced levels of wildtype AAT.

Embodiment 100

The method or composition for use of any one of embodiments 1-4 or 7-99, wherein the subject has an improvement, stabilization, or slowing of edema, ascites, or jaundice, or a delay in need for liver transplantation.

Embodiment 101

The method or composition for use of any one of embodiments 1-4 or 7-99, wherein the subject has an improvement, stabilization, or slowing of change as measured by imaging methods or liver enzyme levels as a result of administration.

Embodiment 102

The method or composition for use of any one of embodiments 1-4 or 7-101, wherein the composition or pharmaceutical formulation is administered via a viral vector.

Embodiment 103

The method or composition for use of any one of embodiments 1-4 or 7-102, wherein the composition or pharmaceutical formulation is administered via lipid nanoparticles.

Embodiment 104

The method or composition for use of any one of embodiments 1-4 or 7-103, wherein the subject is tested for specific mutations in the SERPINA1 gene before administering the composition or formulation.

Embodiment 105

The method or composition of any one of embodiments 1-104, wherein the sequence selected from SEQ ID NOs: 5-129 is SEQ ID NO: 5.

Embodiment 106

The method or composition of any one of embodiments 1-104, wherein the sequence selected from SEQ ID NOs: 5-129 is SEQ ID NO: 6.

Embodiment 107

The method or composition of any one of embodiments 1-104, wherein the sequence selected from SEQ ID NOs: 5-129 is SEQ ID NO: 7.

Embodiment 108

The method or composition of any one of embodiments 1-104, wherein the sequence selected from SEQ ID NOs: 5-129 is SEQ ID NO: 8.

Embodiment 109

The method or composition of any one of embodiments 1-104, wherein the sequence selected from SEQ ID NOs: 5-129 is SEQ ID NO: 9.

Embodiment 110

The method or composition of any one of embodiments 1-104, wherein the sequence selected from SEQ ID NOs: 5-129 is SEQ ID NO: 10.

Embodiment 111

The method or composition of any one of embodiments 1-104, wherein the sequence selected from SEQ ID NOs: 5-129 is SEQ ID NO: 11.

Embodiment 112

The method or composition of any one of embodiments 1-104, wherein the sequence selected from SEQ ID NOs: 5-129 is SEQ ID NO: 12.

Embodiment 113

The method or composition of any one of embodiments 1-104, wherein the sequence selected from SEQ ID NOs: 5-129 is SEQ ID NO: 13.

Embodiment 114

The method or composition of any one of embodiments 1-104, wherein the sequence selected from SEQ ID NOs: 5-129 is SEQ ID NO: 14.

Embodiment 115

The method or composition of any one of embodiments 1-104, wherein the sequence selected from SEQ ID NOs: 5-129 is SEQ ID NO: 15.

Embodiment 116

The method or composition of any one of embodiments 1-104, wherein the sequence selected from SEQ ID NOs: 5-129 is SEQ ID NO: 16.

Embodiment 117

The method or composition of any one of embodiments 1-104, wherein the sequence selected from SEQ ID NOs: 5-129 is SEQ ID NO: 17.

Embodiment 118

The method or composition of any one of embodiments 1-104, wherein the sequence selected from SEQ ID NOs: 5-129 is SEQ ID NO: 18.

Embodiment 119

The method or composition of any one of embodiments 1-104, wherein the sequence selected from SEQ ID NOs: 5-129 is SEQ ID NO: 19.

Embodiment 120

The method or composition of any one of embodiments 1-104, wherein the sequence selected from SEQ ID NOs: 5-129 is SEQ ID NO: 20.

Embodiment 121

The method or composition of any one of embodiments 1-104, wherein the sequence selected from SEQ ID NOs: 5-129 is SEQ ID NO: 21.

Embodiment 122

The method or composition of any one of embodiments 1-104, wherein the sequence selected from SEQ ID NOs: 5-129 is SEQ ID NO: 22.

Embodiment 123

The method or composition of any one of embodiments 1-104, wherein the sequence selected from SEQ ID NOs: 5-129 is SEQ ID NO: 23.

Embodiment 124

The method or composition of any one of embodiments 1-104, wherein the sequence selected from SEQ ID NOs: 5-129 is SEQ ID NO: 24.

Embodiment 125

The method or composition of any one of embodiments 1-104, wherein the sequence selected from SEQ ID NOs: 5-129 is SEQ ID NO: 25.

Embodiment 126

The method or composition of any one of embodiments 1-104, wherein the sequence selected from SEQ ID NOs: 5-129 is SEQ ID NO: 26.

Embodiment 127

The method or composition of any one of embodiments 1-104, wherein the sequence selected from SEQ ID NOs: 5-129 is SEQ ID NO: 27.

Embodiment 128

The method or composition of any one of embodiments 1-104, wherein the sequence selected from SEQ ID NOs: 5-129 is SEQ ID NO: 28.

Embodiment 129

The method or composition of any one of embodiments 1-104, wherein the sequence selected from SEQ ID NOs: 5-129 is SEQ ID NO: 29.

Embodiment 130

The method or composition of any one of embodiments 1-104, wherein the sequence selected from SEQ ID NOs: 5-129 is SEQ ID NO: 30.

Embodiment 131

The method or composition of any one of embodiments 1-104, wherein the sequence selected from SEQ ID NOs: 5-129 is SEQ ID NO: 31.

Embodiment 132

The method or composition of any one of embodiments 1-104, wherein the sequence selected from SEQ ID NOs: 5-129 is SEQ ID NO: 32.

Embodiment 133

The method or composition of any one of embodiments 1-104, wherein the sequence selected from SEQ ID NOs: 5-129 is SEQ ID NO: 33.

Embodiment 134

The method or composition of any one of embodiments 1-104, wherein the sequence selected from SEQ ID NOs: 5-129 is SEQ ID NO: 34.

Embodiment 135

The method or composition of any one of embodiments 1-104, wherein the sequence selected from SEQ ID NOs: 5-129 is SEQ ID NO: 35.

Embodiment 136

The method or composition of any one of embodiments 1-104, wherein the sequence selected from SEQ ID NOs: 5-129 is SEQ ID NO: 36.

Embodiment 137

The method or composition of any one of embodiments 1-104, wherein the sequence selected from SEQ ID NOs: 5-129 is SEQ ID NO: 37.

Embodiment 138

The method or composition of any one of embodiments 1-104, wherein the sequence selected from SEQ ID NOs: 5-129 is SEQ ID NO: 38.

Embodiment 139

The method or composition of any one of embodiments 1-104, wherein the sequence selected from SEQ ID NOs: 5-129 is SEQ ID NO: 39.

Embodiment 140

The method or composition of any one of embodiments 1-104, wherein the sequence selected from SEQ ID NOs: 5-129 is SEQ ID NO: 40.

Embodiment 141

The method or composition of any one of embodiments 1-104, wherein the sequence selected from SEQ ID NOs: 5-129 is SEQ ID NO: 41.

Embodiment 142

The method or composition of any one of embodiments 1-104, wherein the sequence selected from SEQ ID NOs: 5-129 is SEQ ID NO: 42.

Embodiment 143

The method or composition of any one of embodiments 1-104, wherein the sequence selected from SEQ ID NOs: 5-129 is SEQ ID NO: 43.

Embodiment 144

The method or composition of any one of embodiments 1-104, wherein the sequence selected from SEQ ID NOs: 5-129 is SEQ ID NO: 44.

Embodiment 145

The method or composition of any one of embodiments 1-104, wherein the sequence selected from SEQ ID NOs: 5-129 is SEQ ID NO: 45.

Embodiment 146

The method or composition of any one of embodiments 1-104, wherein the sequence selected from SEQ ID NOs: 5-129 is SEQ ID NO: 46.

Embodiment 147

The method or composition of any one of embodiments 1-104, wherein the sequence selected from SEQ ID NOs: 5-129 is SEQ ID NO: 47.

Embodiment 148

The method or composition of any one of embodiments 1-104, wherein the sequence selected from SEQ ID NOs: 5-129 is SEQ ID NO: 48.

Embodiment 149

The method or composition of any one of embodiments 1-104, wherein the sequence selected from SEQ ID NOs: 5-129 is SEQ ID NO: 49.

Embodiment 150

The method or composition of any one of embodiments 1-104, wherein the sequence selected from SEQ ID NOs: 5-129 is SEQ ID NO: 50.

Embodiment 151

The method or composition of any one of embodiments 1-104, wherein the sequence selected from SEQ ID NOs: 5-129 is SEQ ID NO: 51.

Embodiment 152

The method or composition of any one of embodiments 1-104, wherein the sequence selected from SEQ ID NOs: 5-129 is SEQ ID NO: 52.

Embodiment 153

The method or composition of any one of embodiments 1-104, wherein the sequence selected from SEQ ID NOs: 5-129 is SEQ ID NO: 53.

Embodiment 154

The method or composition of any one of embodiments 1-104, wherein the sequence selected from SEQ ID NOs: 5-129 is SEQ ID NO: 54.

Embodiment 155

The method or composition of any one of embodiments 1-104, wherein the sequence selected from SEQ ID NOs: 5-129 is SEQ ID NO: 55.

Embodiment 156

The method or composition of any one of embodiments 1-104, wherein the sequence selected from SEQ ID NOs: 5-129 is SEQ ID NO: 56.

Embodiment 157

The method or composition of any one of embodiments 1-104, wherein the sequence selected from SEQ ID NOs: 5-129 is SEQ ID NO: 57.

Embodiment 158

The method or composition of any one of embodiments 1-104, wherein the sequence selected from SEQ ID NOs: 5-129 is SEQ ID NO: 58.

Embodiment 159

The method or composition of any one of embodiments 1-104, wherein the sequence selected from SEQ ID NOs: 5-129 is SEQ ID NO: 59.

Embodiment 160

The method or composition of any one of embodiments 1-104, wherein the sequence selected from SEQ ID NOs: 5-129 is SEQ ID NO: 60.

Embodiment 161

The method or composition of any one of embodiments 1-104, wherein the sequence selected from SEQ ID NOs: 5-129 is SEQ ID NO: 61.

Embodiment 162

The method or composition of any one of embodiments 1-104, wherein the sequence selected from SEQ ID NOs: 5-129 is SEQ ID NO: 62.

Embodiment 163

The method or composition of any one of embodiments 1-104, wherein the sequence selected from SEQ ID NOs: 5-129 is SEQ ID NO: 63.

Embodiment 164

The method or composition of any one of embodiments 1-104, wherein the sequence selected from SEQ ID NOs: 5-129 is SEQ ID NO: 64.

Embodiment 165

The method or composition of any one of embodiments 1-104, wherein the sequence selected from SEQ ID NOs: 5-129 is SEQ ID NO: 65.

Embodiment 166

The method or composition of any one of embodiments 1-104, wherein the sequence selected from SEQ ID NOs: 5-129 is SEQ ID NO: 66.

Embodiment 167

The method or composition of any one of embodiments 1-104, wherein the sequence selected from SEQ ID NOs: 5-129 is SEQ ID NO: 67.

Embodiment 168

The method or composition of any one of embodiments 1-104, wherein the sequence selected from SEQ ID NOs: 5-129 is SEQ ID NO: 68.

Embodiment 169

The method or composition of any one of embodiments 1-104, wherein the sequence selected from SEQ ID NOs: 5-129 is SEQ ID NO: 69.

Embodiment 170

The method or composition of any one of embodiments 1-104, wherein the sequence selected from SEQ ID NOs: 5-129 is SEQ ID NO: 70.

Embodiment 171

The method or composition of any one of embodiments 1-104, wherein the sequence selected from SEQ ID NOs: 5-129 is SEQ ID NO: 71.

Embodiment 172

The method or composition of any one of embodiments 1-104, wherein the sequence selected from SEQ ID NOs: 5-129 is SEQ ID NO: 72.

Embodiment 173

The method or composition of any one of embodiments 1-104, wherein the sequence selected from SEQ ID NOs: 5-129 is SEQ ID NO: 73.

Embodiment 174

The method or composition of any one of embodiments 1-104, wherein the sequence selected from SEQ ID NOs: 5-129 is SEQ ID NO: 74.

Embodiment 175

The method or composition of any one of embodiments 1-104, wherein the sequence selected from SEQ ID NOs: 5-129 is SEQ ID NO: 75.

Embodiment 176

The method or composition of any one of embodiments 1-104, wherein the sequence selected from SEQ ID NOs: 5-129 is SEQ ID NO: 76.

Embodiment 177

The method or composition of any one of embodiments 1-104, wherein the sequence selected from SEQ ID NOs: 5-129 is SEQ ID NO: 77.

Embodiment 178

The method or composition of any one of embodiments 1-104, wherein the sequence selected from SEQ ID NOs: 5-129 is SEQ ID NO: 78.

Embodiment 179

The method or composition of any one of embodiments 1-104, wherein the sequence selected from SEQ ID NOs: 5-129 is SEQ ID NO: 79.

Embodiment 180

The method or composition of any one of embodiments 1-104, wherein the sequence selected from SEQ ID NOs: 5-129 is SEQ ID NO: 80.

Embodiment 181

The method or composition of any one of embodiments 1-104, wherein the sequence selected from SEQ ID NOs: 5-129 is SEQ ID NO: 81.

Embodiment 182

The method or composition of any one of embodiments 1-104, wherein the sequence selected from SEQ ID NOs: 5-129 is SEQ ID NO: 82.

Embodiment 183

The method or composition of any one of embodiments 1-104, wherein the sequence selected from SEQ ID NOs: 5-129 is SEQ ID NO: 83.

Embodiment 184

The method or composition of any one of embodiments 1-104, wherein the sequence selected from SEQ ID NOs: 5-129 is SEQ ID NO: 84.

Embodiment 185

The method or composition of any one of embodiments 1-104, wherein the sequence selected from SEQ ID NOs: 5-129 is SEQ ID NO: 85.

Embodiment 186

The method or composition of any one of embodiments 1-104, wherein the sequence selected from SEQ ID NOs: 5-129 is SEQ ID NO: 86.

Embodiment 187

The method or composition of any one of embodiments 1-104, wherein the sequence selected from SEQ ID NOs: 5-129 is SEQ ID NO: 87.

Embodiment 188

The method or composition of any one of embodiments 1-104, wherein the sequence selected from SEQ ID NOs: 5-129 is SEQ ID NO: 88.

Embodiment 189

The method or composition of any one of embodiments 1-104, wherein the sequence selected from SEQ ID NOs: 5-129 is SEQ ID NO: 89.

Embodiment 190

The method or composition of any one of embodiments 1-104, wherein the sequence selected from SEQ ID NOs: 5-129 is SEQ ID NO: 90.

Embodiment 191

The method or composition of any one of embodiments 1-104, wherein the sequence selected from SEQ ID NOs: 5-129 is SEQ ID NO: 91.

Embodiment 192

The method or composition of any one of embodiments 1-104, wherein the sequence selected from SEQ ID NOs: 5-129 is SEQ ID NO: 92.

Embodiment 193

The method or composition of any one of embodiments 1-104, wherein the sequence selected from SEQ ID NOs: 5-129 is SEQ ID NO: 93.

Embodiment 194

The method or composition of any one of embodiments 1-104, wherein the sequence selected from SEQ ID NOs: 5-129 is SEQ ID NO: 94.

Embodiment 195

The method or composition of any one of embodiments 1-104, wherein the sequence selected from SEQ ID NOs: 5-129 is SEQ ID NO: 95.

Embodiment 196

The method or composition of any one of embodiments 1-104, wherein the sequence selected from SEQ ID NOs: 5-129 is SEQ ID NO: 96.

Embodiment 197

The method or composition of any one of embodiments 1-104, wherein the sequence selected from SEQ ID NOs: 5-129 is SEQ ID NO: 97.

Embodiment 198

The method or composition of any one of embodiments 1-104, wherein the sequence selected from SEQ ID NOs: 5-129 is SEQ ID NO: 98.

Embodiment 199

The method or composition of any one of embodiments 1-104, wherein the sequence selected from SEQ ID NOs: 5-129 is SEQ ID NO: 99.

Embodiment 200

The method or composition of any one of embodiments 1-104, wherein the sequence selected from SEQ ID NOs: 5-129 is SEQ ID NO: 100.

Embodiment 201

The method or composition of any one of embodiments 1-104, wherein the sequence selected from SEQ ID NOs: 5-129 is SEQ ID NO: 101.

Embodiment 202

The method or composition of any one of embodiments 1-104, wherein the sequence selected from SEQ ID NOs: 5-129 is SEQ ID NO: 102.

Embodiment 203

The method or composition of any one of embodiments 1-104, wherein the sequence selected from SEQ ID NOs: 5-129 is SEQ ID NO: 103.

Embodiment 204

The method or composition of any one of embodiments 1-104, wherein the sequence selected from SEQ ID NOs: 5-129 is SEQ ID NO: 104.

Embodiment 205

The method or composition of any one of embodiments 1-104, wherein the sequence selected from SEQ ID NOs: 5-129 is SEQ ID NO: 105.

Embodiment 206

The method or composition of any one of embodiments 1-104, wherein the sequence selected from SEQ ID NOs: 5-129 is SEQ ID NO: 106.

Embodiment 207

The method or composition of any one of embodiments 1-104, wherein the sequence selected from SEQ ID NOs: 5-129 is SEQ ID NO: 107.

Embodiment 208

The method or composition of any one of embodiments 1-104, wherein the sequence selected from SEQ ID NOs: 5-129 is SEQ ID NO: 108.

Embodiment 209

The method or composition of any one of embodiments 1-104, wherein the sequence selected from SEQ ID NOs: 5-129 is SEQ ID NO: 109.

Embodiment 210

The method or composition of any one of embodiments 1-104, wherein the sequence selected from SEQ ID NOs: 5-129 is SEQ ID NO: 110.

Embodiment 211

The method or composition of any one of embodiments 1-104, wherein the sequence selected from SEQ ID NOs: 5-129 is SEQ ID NO: 111.

Embodiment 212

The method or composition of any one of embodiments 1-104, wherein the sequence selected from SEQ ID NOs: 5-129 is SEQ ID NO: 112.

Embodiment 213

The method or composition of any one of embodiments 1-104, wherein the sequence selected from SEQ ID NOs: 5-129 is SEQ ID NO: 113.

Embodiment 214

The method or composition of any one of embodiments 1-104, wherein the sequence selected from SEQ ID NOs: 5-129 is SEQ ID NO: 114.

Embodiment 215

The method or composition of any one of embodiments 1-104, wherein the sequence selected from SEQ ID NOs: 5-129 is SEQ ID NO: 115.

Embodiment 216

The method or composition of any one of embodiments 1-104, wherein the sequence selected from SEQ ID NOs: 5-129 is SEQ ID NO: 116.

Embodiment 217

The method or composition of any one of embodiments 1-104, wherein the sequence selected from SEQ ID NOs: 5-129 is SEQ ID NO: 117.

Embodiment 218

The method or composition of any one of embodiments 1-104, wherein the sequence selected from SEQ ID NOs: 5-129 is SEQ ID NO: 118.

Embodiment 219

The method or composition of any one of embodiments 1-104, wherein the sequence selected from SEQ ID NOs: 5-129 is SEQ ID NO: 119.

Embodiment 220

The method or composition of any one of embodiments 1-104, wherein the sequence selected from SEQ ID NOs: 5-129 is SEQ ID NO: 120.

Embodiment 221

The method or composition of any one of embodiments 1-104, wherein the sequence selected from SEQ ID NOs: 5-129 is SEQ ID NO: 121.

Embodiment 222

The method or composition of any one of embodiments 1-104, wherein the sequence selected from SEQ ID NOs: 5-129 is SEQ ID NO: 122.

Embodiment 223

The method or composition of any one of embodiments 1-104, wherein the sequence selected from SEQ ID NOs: 5-129 is SEQ ID NO: 123.

Embodiment 224

The method or composition of any one of embodiments 1-104, wherein the sequence selected from SEQ ID NOs: 5-129 is SEQ ID NO: 124.

23

Embodiment 225

The method or composition of any one of embodiments 1-104, wherein the sequence selected from SEQ ID NOs: 5-129 is SEQ ID NO: 125.

Embodiment 226

The method or composition of any one of embodiments 1-104, wherein the sequence selected from SEQ ID NOs: 5-129 is SEQ ID NO: 126.

Embodiment 227

The method or composition of any one of embodiments 1-104, wherein the sequence selected from SEQ ID NOs: 5-129 is SEQ ID NO: 127.

Embodiment 228

The method or composition of any one of embodiments 1-104, wherein the sequence selected from SEQ ID NOs: 5-129 is SEQ ID NO: 128.

Embodiment 229

The method or composition of any one of embodiments 1-104, wherein the sequence selected from SEQ ID NOs: 5-129 is SEQ ID NO: 129.

Embodiment 230

The method or composition of any one of embodiments 1-104, further comprising the sequence of SEQ ID NO: 140 or 141.

Embodiment 231

The method or composition of embodiment 230 comprising the modification pattern of SEQ ID NO: 130.

Embodiment 232

The method or composition of any one of embodiments 1-104, wherein the sequence is selected from SEQ ID NO: 131-139.

Embodiment 233

The method or composition of any one of embodiments 1-104, wherein the sequence selected from SEQ ID NOs: 131-139 is SEQ ID NO: 131.

Embodiment 234

The method or composition of any one of embodiments 1-104, wherein the sequence selected from SEQ ID NOs: 131-139 is SEQ ID NO: 132.

Embodiment 235

The method or composition of any one of embodiments 1-104, wherein the sequence selected from SEQ ID NOs: 131-139 is SEQ ID NO: 133.

Embodiment 236

The method or composition of any one of embodiments 1-104, wherein the sequence selected from SEQ ID NOs: 131-139 is SEQ ID NO: 134.

Embodiment 237

The method or composition of any one of embodiments 1-104, wherein the sequence selected from SEQ ID NOs: 131-139 is SEQ ID NO: 135.

Embodiment 238

The method or composition of any one of embodiments 1-104, wherein the sequence selected from SEQ ID NOs: 131-139 is SEQ ID NO: 136.

Embodiment 239

The method or composition of any one of embodiments 1-104, wherein the sequence selected from SEQ ID NOs: 131-139 is SEQ ID NO: 137.

Embodiment 240

The method or composition of any one of embodiments 1-104, wherein the sequence selected from SEQ ID NOs: 131-139 is SEQ ID NO: 138.

Embodiment 241

The method or composition of any one of embodiments 1-104, wherein the sequence selected from SEQ ID NOs: 131-139 is SEQ ID NO: 139.

Embodiment 242

The method or composition of any one of embodiments 232-241, wherein the sequence selected from SEQ ID NOs: 131-139 comprises the modifications shown for the respective sequence in Table 2.

Embodiment 243

Use of a composition or formulation of any of embodiments 5-241 for the preparation of a medicament for treating a human subject having AATD.

FIGURE LEGENDS

Figure 3:
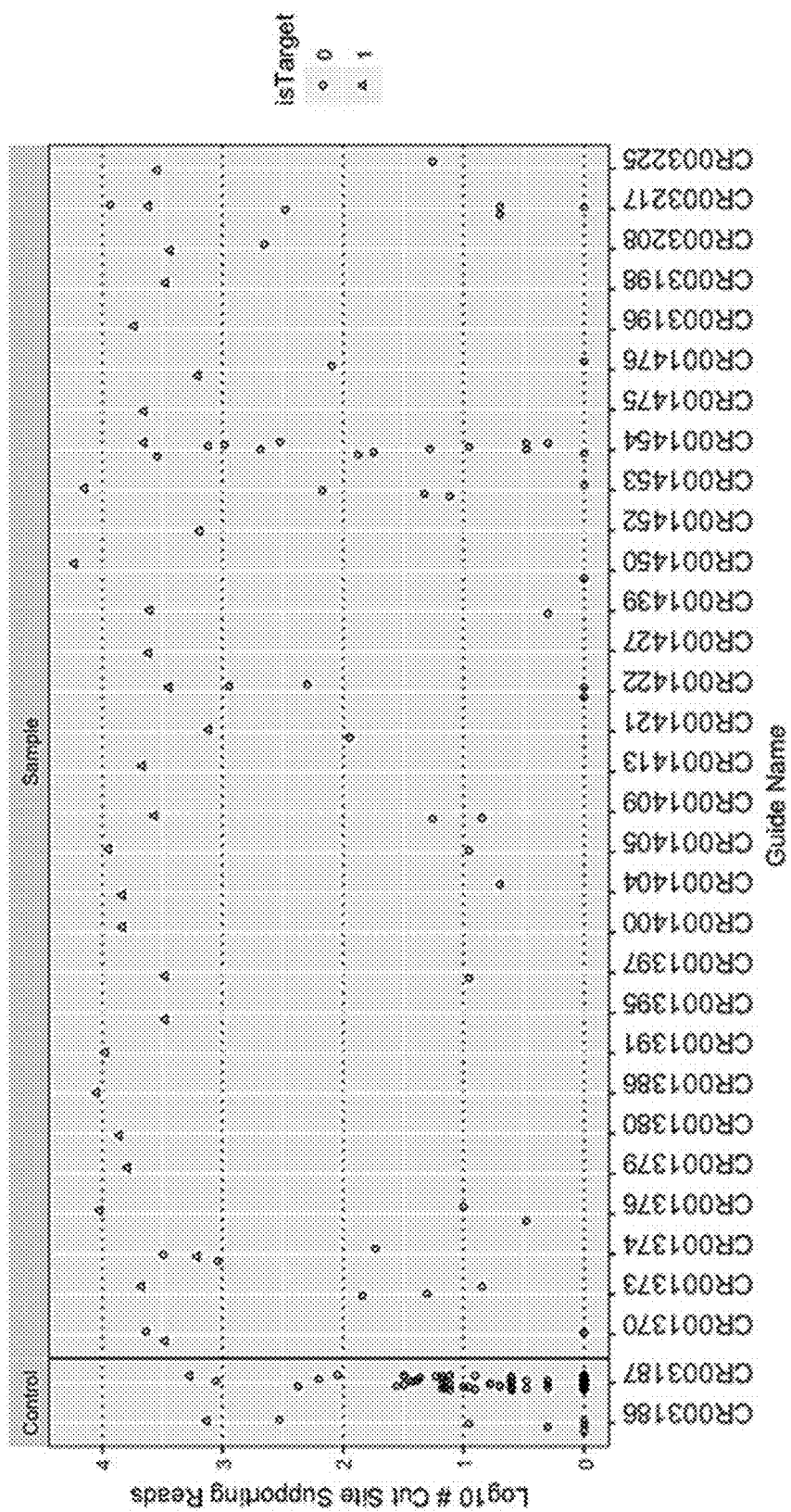
FIG. 3 shows off-target analysis of certain guide RNAs targeting SERPINA1. In the graph, triangles represent the identification of the on-target cut site, while circles represent the identification of potential off-target sites.
Figures 5A, 5B, 5C:
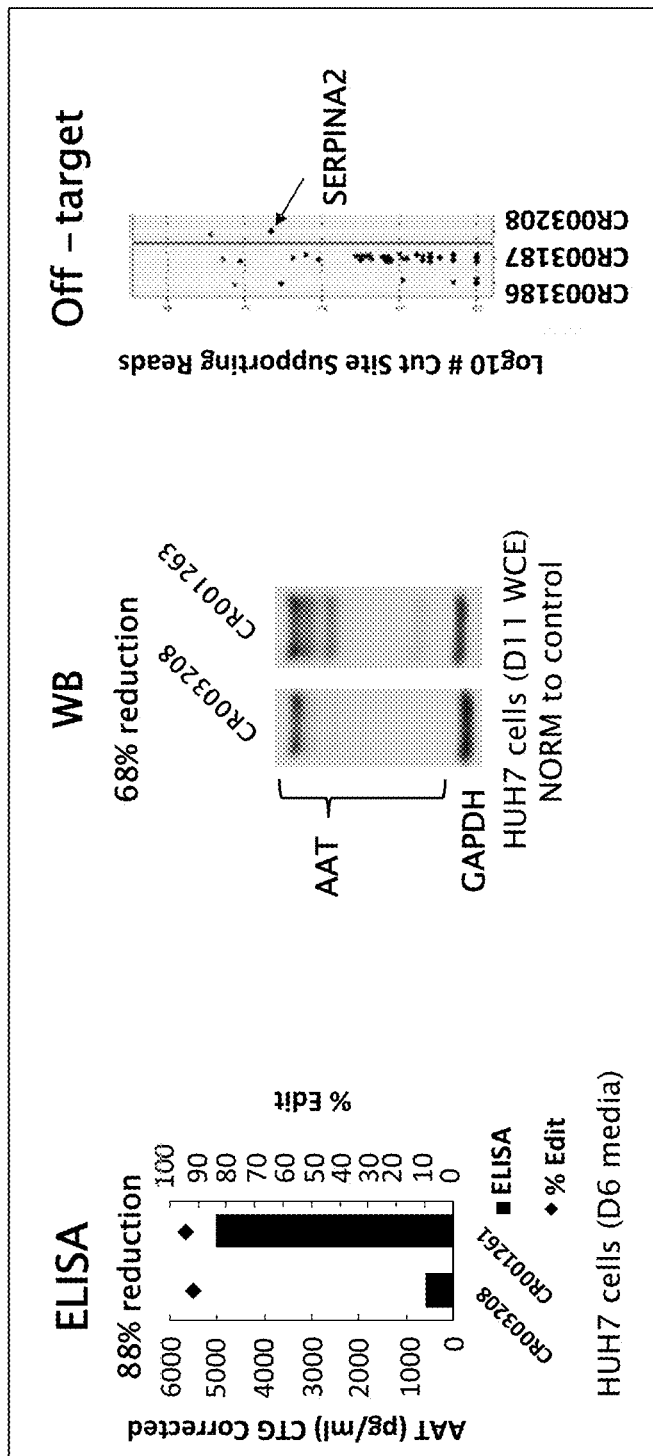

FIGS. 5A-5C show ELISA data for CR003208 and control guide CR001263 showing percent reduction in AAT secretion in HUH7 cells (5A), western blot (WB) analysis of percent reduction in AAT in HUH7 cells (5B), and off-target analysis (5C). In FIG. 5C, a single potential off-target site was identified in the related gene SERPINA2, as denoted by the arrow (see also, FIG. 3). The human guide sequences and the sequence complementary to the corresponding target sequence in cynomolgus monkey are both CR003208 (SEQ ID No: 107). Note that chromosome positions of the target sequence complementary to the human guide sequence are listed in Table 1.

Figures 6A, 6B, 6C:
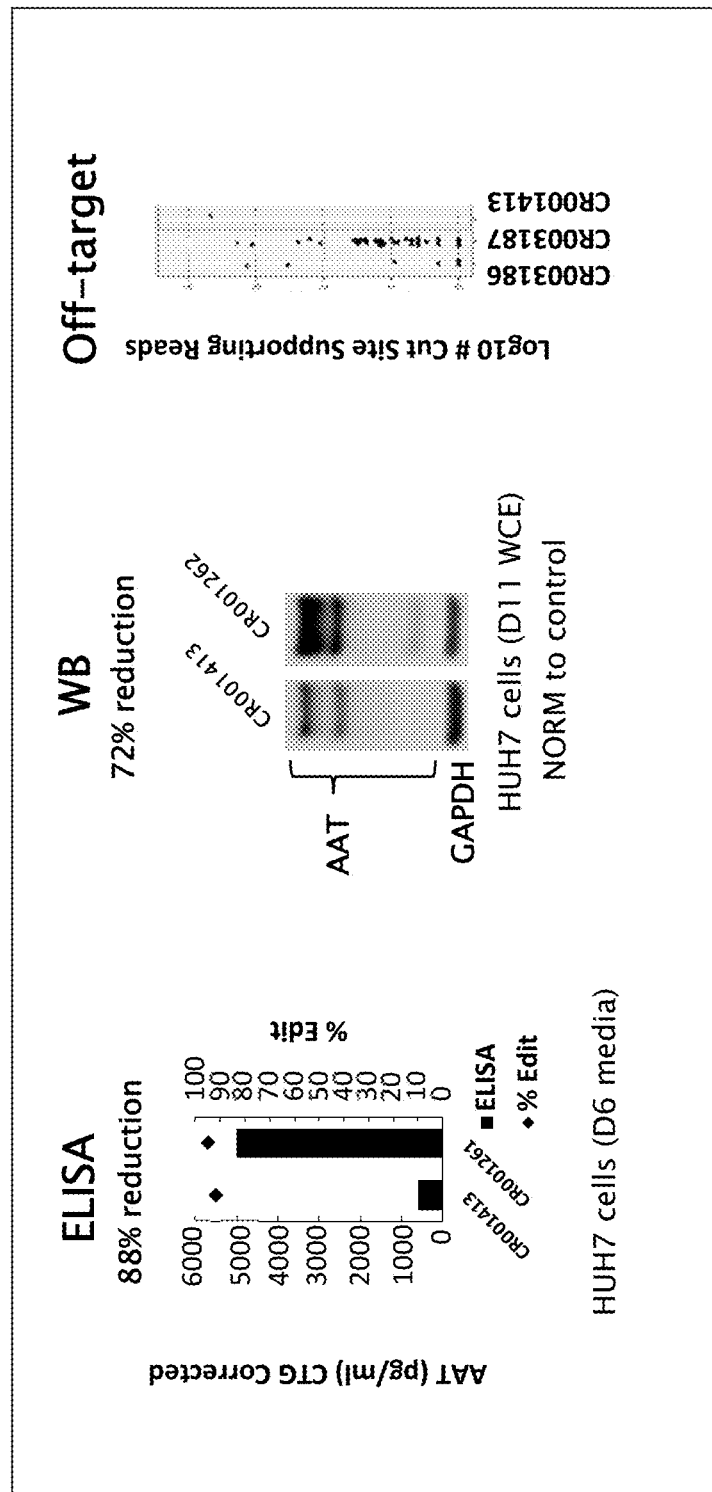

FIGS. 6A-6C show ELISA data for CR001413 and control guide CR001262 showing percent reduction in AAT secretion in HUH7 cells (6A), western blot (WB) analysis of percent reduction in AAT in HUH7 cells (6B), and off-target (6C). The human guide sequences and the sequence complementary to the corresponding target sequence in cynomolgus monkey are CR001413 (SEQ ID No: 51), and GUUGAG-GAACAGGCCGUUGC (SEQ ID No: 271), respectively. Note that chromosome positions of the target sequence complementary to the human guide sequence are listed in Table 1.

Figures 7A, 7B, 7C:
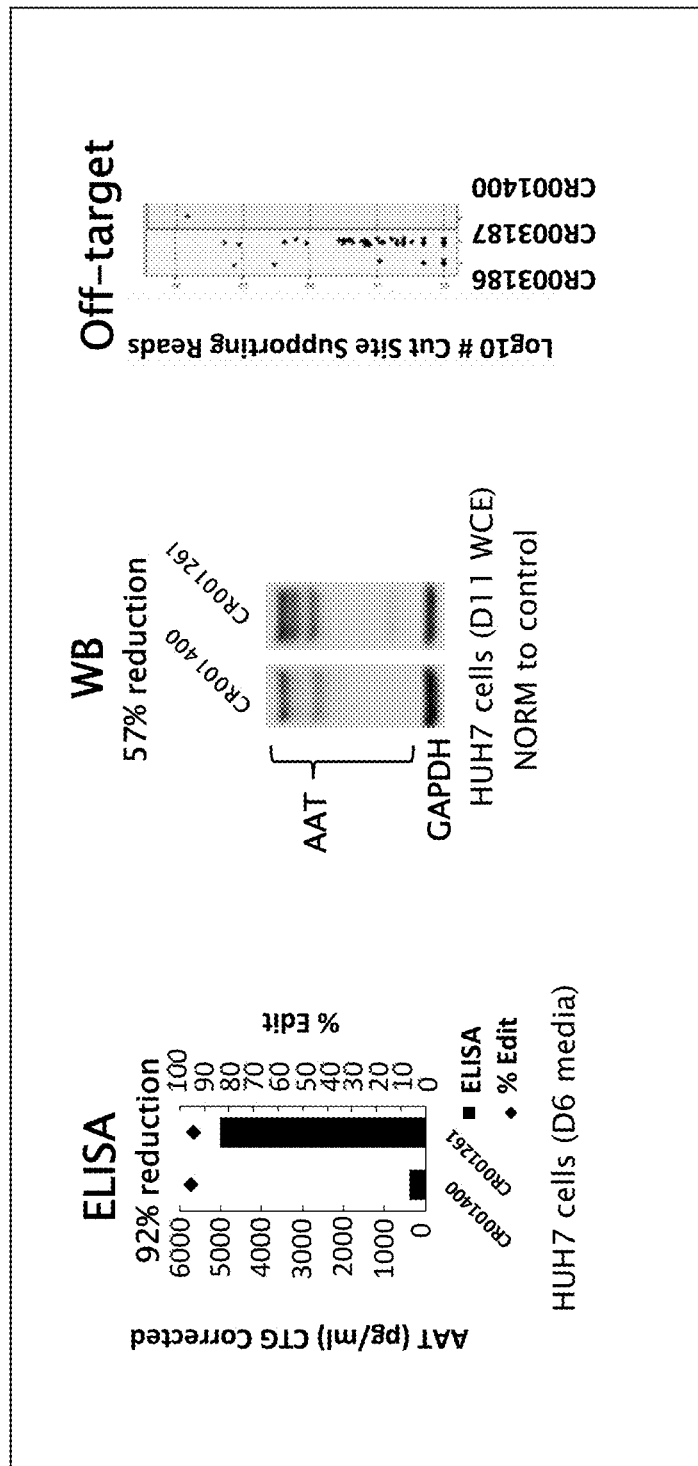

FIGS. 7A-7C show ELISA data for CR001400 and control guide CR001261 showing percent reduction in AAT secretion in HUH7 cells (7A), western blot (WB) analysis of percent reduction in AAT in HUH7 cells (7B), and off-target analysis (7C). The human guide sequences and the sequence complementary to the corresponding target sequence in cynomolgus monkey are SEQ ID No: 38, and ACU-CACAGUGAAAUCCUGGA (SEQ ID No: 272), respectively. Note that chromosome positions of the target sequence complementary to the human guide sequence are listed in Table 1.

Figures 8A, 8B, 8C:
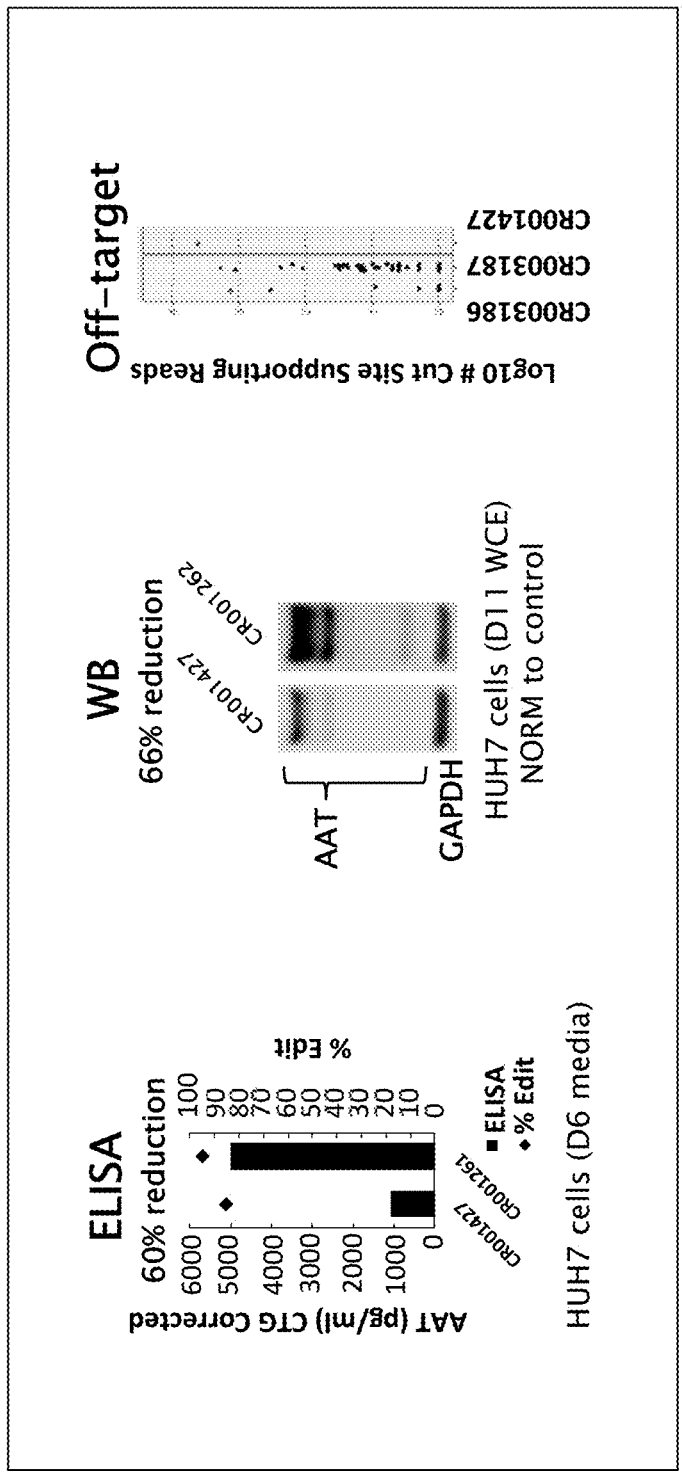

FIGS. 8A-8C show ELISA data for CR001427 and control guide CR001262 showing percent reduction in AAT secretion in HUH7 cells (8A), western blot (WB) analysis of percent reduction in AAT in HUH7 cells (8B), and off-target analysis (8C). The human guide sequences and the sequence complementary to the corresponding target sequence in cynomolgus monkey are both CR001427 (SEQ ID No: 65). Note that chromosome positions of the target sequence complementary to the human guide sequence are listed in Table 1.

Figures 9A, 9B, 9C:
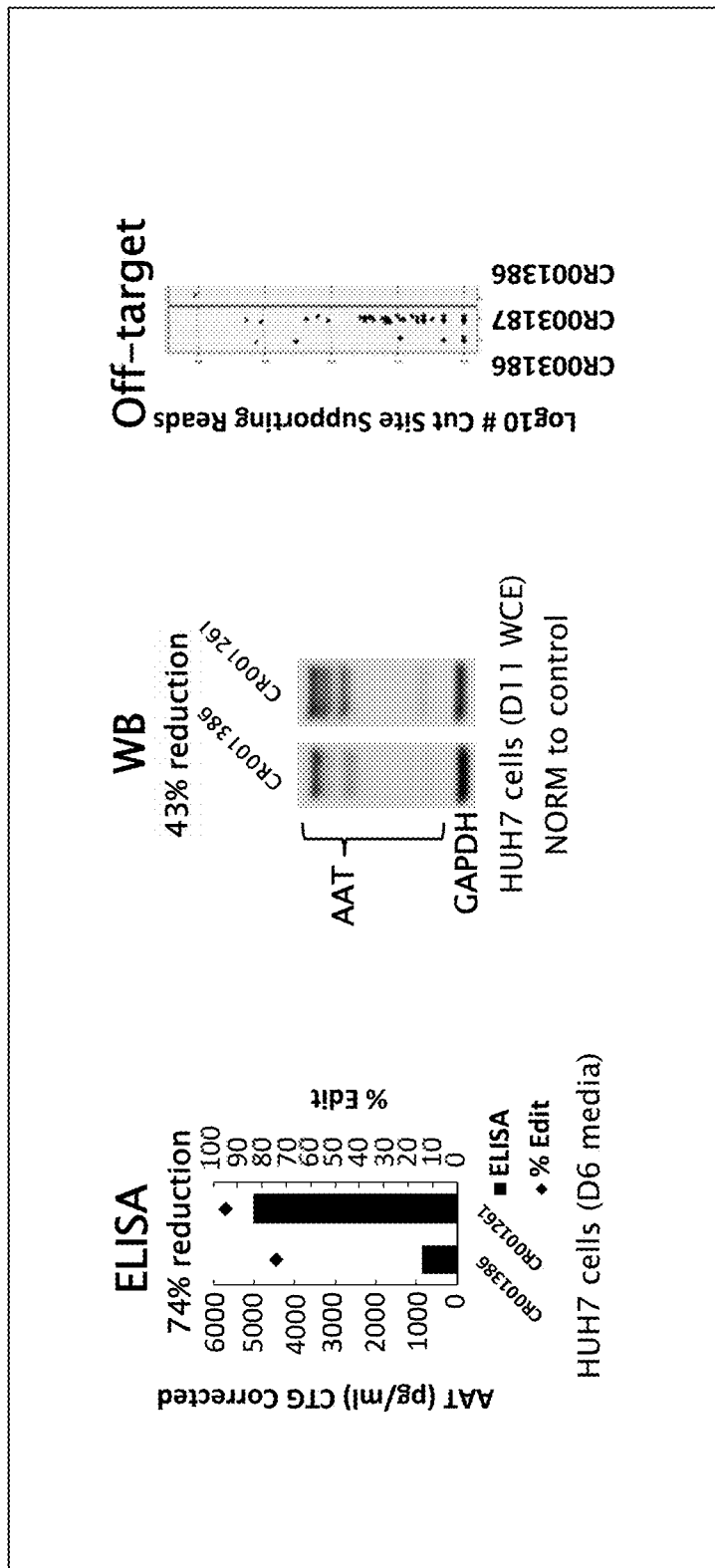

FIGS. 9A-9C show ELISA data for CR001386 and control guide CR001261 showing percent reduction in AAT secretion in HUH7 cells (9A), western blot (WB) analysis of percent reduction in AAT in HUH7 cells (9B), and off-target analysis (9C). The human guide sequences and the sequence complementary to the corresponding target sequence in cynomolgus monkey are CR001386 (SEQ ID No: 24), and GAAGCCGAACUCAGCCAGGC (SEQ ID No: 273), respectively. Note that chromosome positions of the target sequence complementary to the human guide sequence are listed in Table 1.

Figures 10A, 10B, 10C:
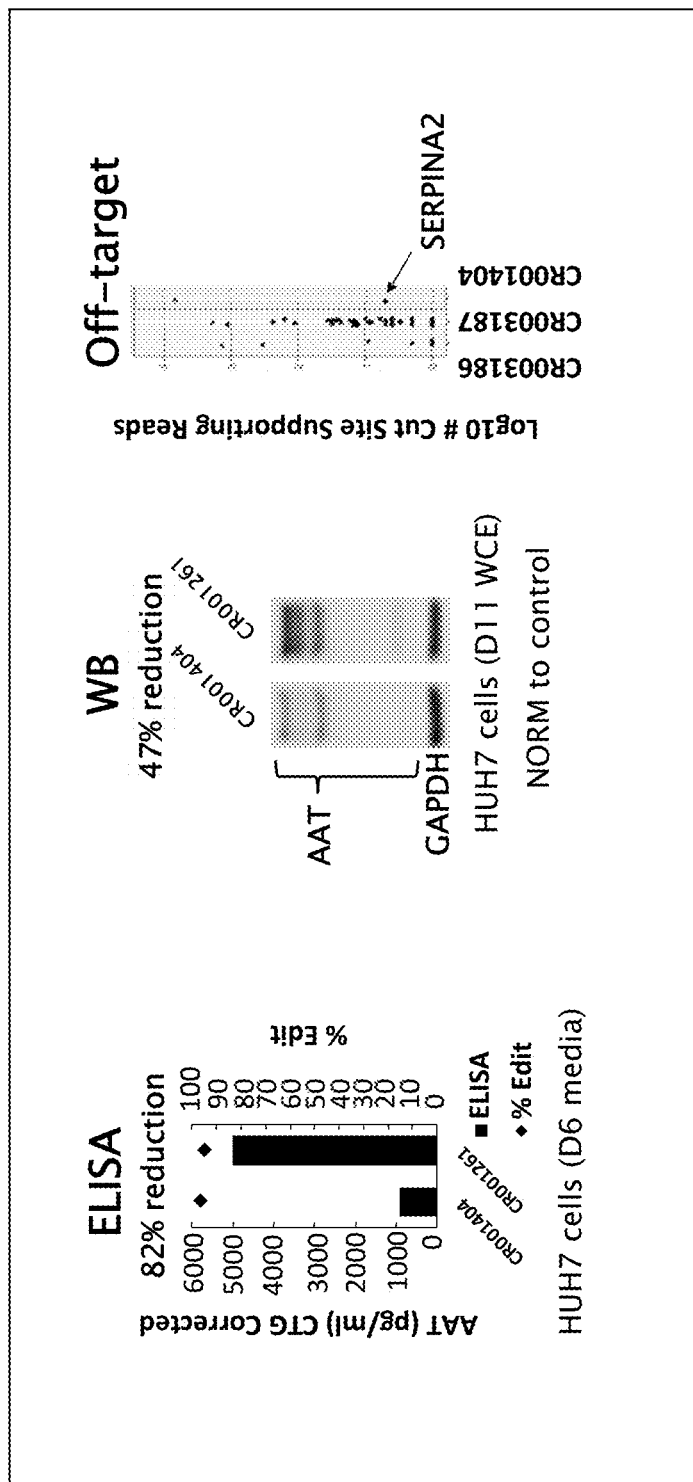

FIGS. 10A-10C show ELISA data for CR001404 and control guide CR001261 showing percent reduction in AAT secretion in HUH7 cells (10A), western blot (WB) analysis of percent reduction in AAT in HUH7 cells (10B), and off-target analysis (10C). In FIG. 10C, a single off-target site was identified, as denoted by the arrow (see also, FIG. 3). The human guide sequences and the sequence complementary to the corresponding target sequence in cynomolgus monkey, are CR001404 (SEQ ID No: 42), and CAACGU-CACGGAGAUUCCGG (SEQ ID No: 274), respectively. Note that chromosome positions of the target sequence complementary to the human guide sequence are listed in Table 1.

Figure 11:
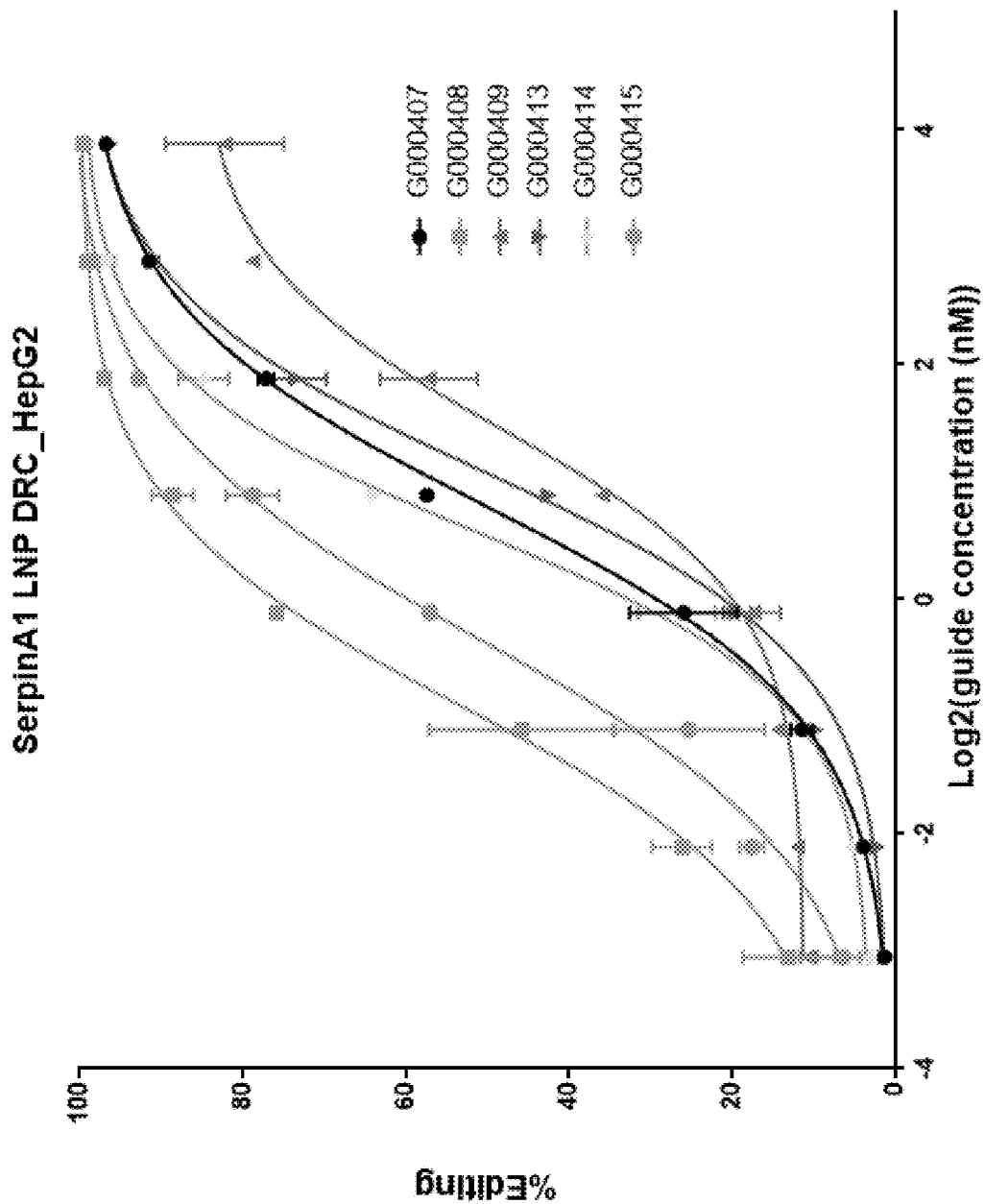

FIG. 11 shows percent editing of AAT in HepG2 cells for various guides at various concentrations in a dose response curve ("DRC").

Figure 12:
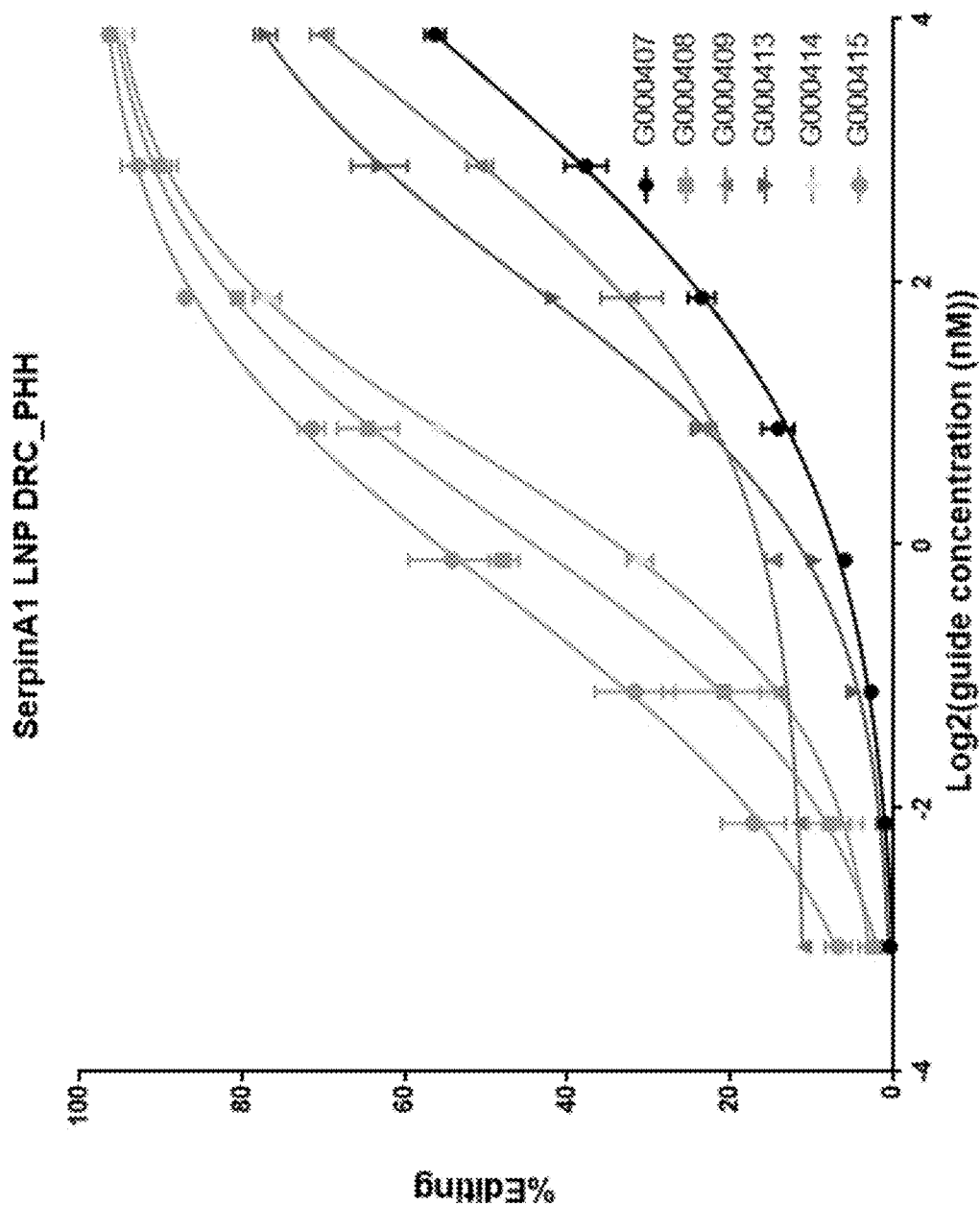

FIG. 12 shows percent editing of AAT in primary human hepatocytes (PHH) cells for various guides at various concentrations in a dose response curve ("DRC").

Figure 13A:
Figure 13B:
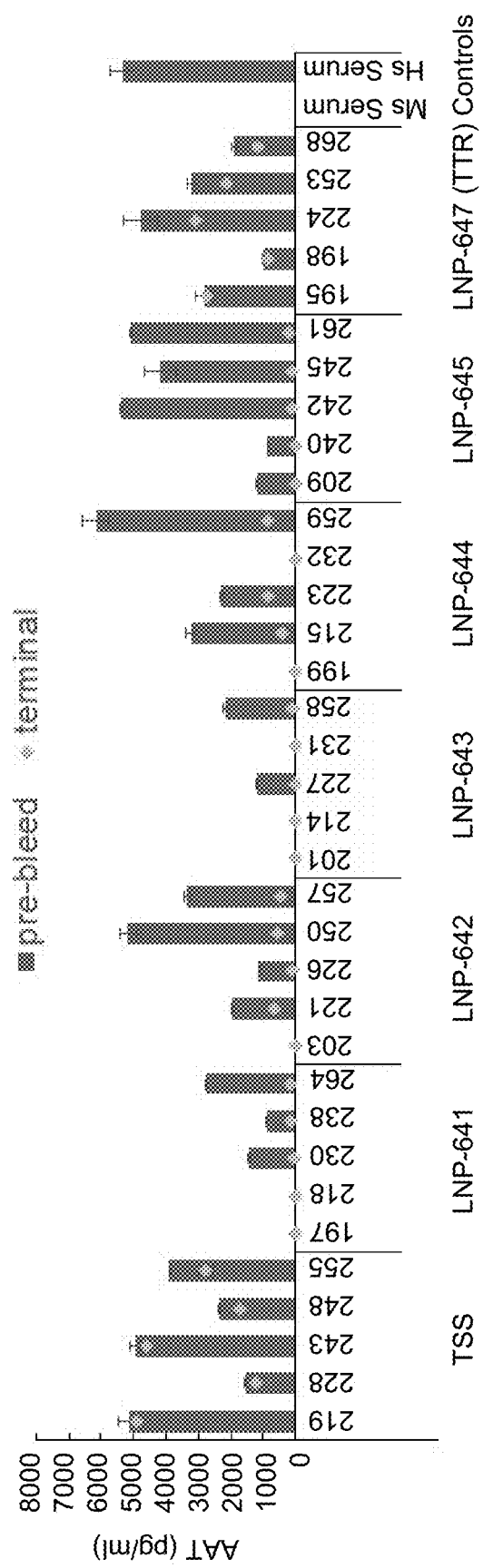
Figure 13C:
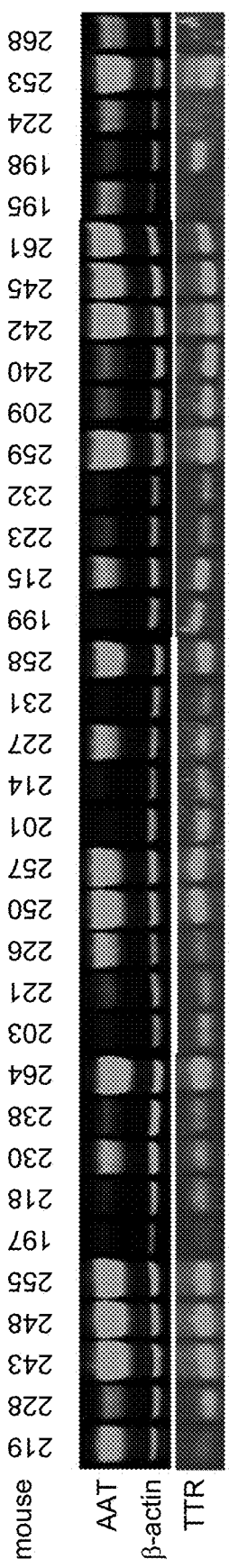

FIGS. 13A-C show the results of an in vivo experiment in transgenic mice harboring copies of the human PiZ variant of SERPINA1. FIG. 13A shows robust editing of the PiZ variant of SERPINA1 across each group, with no editing detected in the vehicle control (TSS). FIG. 13B shows ELISA data from this same experiment, while FIG. 13C shows Western Blot data from this same experiment.

DETAILED DESCRIPTION

Provided herein are guide RNA compositions useful in CRISPR/Cas9 systems to edit the SERPINA1 gene. The guide RNAs, in dual or single guide RNA formats, with RNA-guided DNA binding agents, e.g., Cas9 or mRNA encoding RNA-guided DNA binding agent, e.g., mRNA encoding Cas9, may be administered to subjects having non-wild type SERPINA1 gene sequences, such as, for example, subjects with alpha-1 antitrypsin deficiency ("AATD" or "A1AD"). Guide sequences targeting the SERPINA1 gene are shown in Table 1 at SEQ ID Nos: 5-129. Control guides used in the experiments described herein are shown at SEQ ID Nos: 1-4.

TABLE 1

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 1 | CR001261 | Control 1 | Chr1:55039269-55039291 | GCCAGACUCCAAGUUCUGCC |
| 2 | CR001262 | Control 2 | Chr1:55039155-55039177 | UAAGGCCAGUGGAAAGAAUU |
| 3 | CR001263 | Control 3 | Chr1:55039180-55039202 | GGCAGCGAGGAGUCCACAGU |
| 4 | CR001264 | Control 4 | Chr1:55039149-55039171 | UCUUUCCACUGGCCUUAACC |
| 5 | CR001367 | Exon 2 | Chr14:94383211-94383233 | CAAUGCCGUCUUCUGUCUCG |

TABLE 1-continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 6 | CR001368 | Exon 2 | Chr14:94383210-94383232 | AAUGCCGUCUUCUGUCUCGU |
| 7 | CR001369 | Exon 2 | Chr14:94383209-94383231 | AUGCCGUCUUCUGUCUCGUG |
| 8 | CR001370 | Exon 2 | Chr14:94383206-94383228 | AUGCCCACGAGACAGAAGA |
| 9 | CR001371 | Exon 2 | Chr14:94383195-94383217 | CUCGUGGGCAUCCUCCUGC |
| 10 | CR001372 | Exon 2 | Chr14:94383152-94383174 | GGAUCCUCAGCCAGGGAGAC |
| 11 | CR001373 | Exon 2 | Chr14:94383146-94383168 | UCCCUGGCUGAGGAUCCCCA |
| 12 | CR001374 | Exon 2 | Chr14:94383145-94383167 | UCCCUGGGGAUCCUCAGCCA |
| 13 | CR001375 | Exon 2 | Chr14:94383144-94383166 | CUCCCUGGGGAUCCUCAGCC |
| 14 | CR001376 | Exon 2 | Chr14:94383115-94383137 | GUGGGAUGUAUCUGUCUUCU |
| 15 | CR001377 | Exon 2 | Chr14:94383114-94383136 | GGUGGGAUGUAUCUGUCUUC |
| 16 | CR001378 | Exon 2 | Chr14:94383105-94383127 | AGAUACAUCCCACCAUGAUC |
| 17 | CR001379 | Exon 2 | Chr14:94383097-94383119 | UGGGUGAUCCUGAUCAUGGU |
| 18 | CR001380 | Exon 2 | Chr14:94383096-94383118 | UUGGGUGAUCCUGAUCAUGG |
| 19 | CR001381 | Exon 2 | Chr14:94383093-94383115 | AGGUUGGGUGAUCCUGAUCA |
| 20 | CR001382 | Exon 2 | Chr14:94383078-94383100 | GGGUGAUCUUGUUGAAGGUU |
| 21 | CR001383 | Exon 2 | Chr14:94383077-94383099 | GGGGUGAUCUUGUUGAAGGU |
| 22 | CR001384 | Exon 2 | Chr14:94383069-94383091 | CAACAAGAUCACCCCCAACC |
| 23 | CR001385 | Exon 2 | Chr14:94383057-94383079 | AGGCGAACUCAGCCAGGUUG |
| 24 | CR001386 | Exon 2 | Chr14:94383055-94383077 | GAAGGCGAACUCAGCCAGGU |
| 25 | CR001387 | Exon 2 | Chr14:94383051-94383073 | GGCUGAAGGCGAACUCAGCC |
| 26 | CR001388 | Exon 2 | Chr14:94383037-94383059 | CAGCUGGCGGUAUAGGCUGA |
| 27 | CR001389 | Exon 2 | Chr14:94383036-94383058 | CUUCAGCCUAUACCGCCAGC |
| 28 | CR001390 | Exon 2 | Chr14:94383030-94383052 | GGUGUGCCAGCUGGCGGUAU |
| 29 | CR001391 | Exon 2 | Chr14:94383021-94383043 | UGUUGGACUGGUGUGCCAGC |

TABLE 1-continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 30 | CR001392 | Exon 2 | Chr14:94383009-94383031 | AGAUAUUGGUGCUGUUGGAC |
| 31 | CR001393 | Exon 2 | Chr14:94383004-94383026 | GAAGAAGAUAUUGGUGCUGU |
| 32 | CR001394 | Exon 2 | Chr14:94382995-94383017 | CACUGGGGAGAAGAAGAUAU |
| 33 | CR001395 | Exon 2 | Chr14:94382980-94383002 | GGCUGUAGCGAUGCUCACUG |
| 34 | CR001396 | Exon 2 | Chr14:94382979-94383001 | AGGCUGUAGCGAUGCUCACU |
| 35 | CR001397 | Exon 2 | Chr14:94382978-94383000 | AAGGCUGUAGCGAUGCUCAC |
| 36 | CR001398 | Exon 2 | Chr14:94382928-94382950 | UGACACUCACGAUGAAAUCC |
| 37 | CR001399 | Exon 2 | Chr14:94382925-94382947 | CACUCACGAUGAAAUCCUGG |
| 38 | CR001400 | Exon 2 | Chr14:94382924-94382946 | ACUCACGAUGAAAUCCUGGA |
| 39 | CR001401 | Exon 2 | Chr14:94382910-94382932 | GGUUGAAAUUCAGGCCCUCC |
| 40 | CR001402 | Exon 2 | Chr14:94382904-94382926 | GGGCCUGAAUUUCAACCUCA |
| 41 | CR001403 | Exon 2 | Chr14:94382895-94382917 | UUUCAACCUCACGGAGAUUC |
| 42 | CR001404 | Exon 2 | Chr14:94382892-94382914 | CAACCUCACGGAGAUUCCGG |
| 43 | CR001405 | Exon 2 | Chr14:94382889-94382911 | GAGCCUCCGGAAUCUCCGUG |
| 44 | CR001406 | Exon 2 | Chr14:94382876-94382898 | CCGGAGGCUCAGAUCCAUGA |
| 45 | CR001407 | Exon 2 | Chr14:94382850-94382872 | UGAGGGUACGGAGGAGUUCC |
| 46 | CR001408 | Exon 2 | Chr14:94382841-94382863 | CUGGCUGGUUGAGGGUACGG |
| 47 | CR001409 | Exon 2 | Chr14:94382833-94382855 | CUGGCUGUCUGGCUGGUUGA |
| 48 | CR001410 | Exon 2 | Chr14:94382810-94382832 | CUCCAGCUGACCACCGGCAA |
| 49 | CR001411 | Exon 2 | Chr14:94382808-94382830 | GGCCAUUGCCGGUGGUCAGC |
| 50 | CR001412 | Exon 2 | Chr14:94382800-94382822 | GAGGAACAGGCCAUUGCCGG |
| 51 | CR001413 | Exon 2 | Chr14:94382797-94382819 | GCUGAGGAACAGGCCAUUGC |
| 52 | CR001414 | Exon 2 | Chr14:94382793-94382815 | CAAUGGCCUGUUCCUCAGCG |
| 53 | CR001415 | Exon 2 | Chr14:94382792-94382814 | AAUGGCCUGUUCCUCAGCGA |

TABLE 1 -continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 54 | CR001416 | Exon 2 | Chr14:94382787-94382809 | UCAGGCCCUCGCUGAGGAAC |
| 55 | CR001417 | Exon 2 | Chr14:94382781-94382803 | CUAGCUUCAGGCCCUCGCUG |
| 56 | CR001418 | Exon 2 | Chr14:94382778-94382800 | CAGCGAGGGCCUGAAGCUAG |
| 57 | CR001419 | Exon 2 | Chr14:94382769-94382791 | AAAACUUAUCCACUAGCUUC |
| 58 | CR001420 | Exon 2 | Chr14:94382766-94382788 | GAAGCUAGUGGAUAAGUUUU |
| 59 | CR001421 | Exon 2 | Chr14:94382763-94382785 | GCUAGUGGAUAAGUUUUUGG |
| 60 | CR001422 | Exon 2 | Chr14:94382724-94382746 | UGACAGUGAAGGCUUCUGAG |
| 61 | CR001423 | Exon 2 | Chr14:94382716-94382738 | AAGCCUUCACUGUCAACUUC |
| 62 | CR001424 | Exon 2 | Chr14:94382715-94382737 | AGCCUUCACUGUCAACUUCG |
| 63 | CR001425 | Exon 2 | Chr14:94382713-94382735 | GUCCCCGAAGUUGACAGUGA |
| 64 | CR001426 | Exon 2 | Chr14:94382703-94382725 | CAACUUCGGGGACACCGAAG |
| 65 | CR001427 | Exon 2 | Chr14:94382689-94382711 | GAUCUGUUUCUUGGCCUCUU |
| 66 | CR001428 | Exon 2 | Chr14:94382680-94382702 | GUAAUCGUUGAUCUGUUUCU |
| 67 | CR001429 | Exon 2 | Chr14:94382676-94382698 | GAAACAGAUCAACGAUUACG |
| 68 | CR001430 | Exon 2 | Chr14:94382670-94382692 | GAUCAACGAUUACGUGGAGA |
| 69 | CR001431 | Exon 2 | Chr14:94382669-94382691 | AUCAACGAUUACGUGGAGAA |
| 70 | CR001432 | Exon 2 | Chr14:94382660-94382682 | UACGUGGAGAAGGGUACUCA |
| 71 | CR001433 | Exon 2 | Chr14:94382659-94382681 | ACGUGGAGAAGGGUACUCAA |
| 72 | CR001434 | Exon 2 | Chr14:94382643-94382665 | UCAAGGGAAAAUUGUGGAUU |
| 73 | CR001435 | Exon 2 | Chr14:94382637-94382659 | GAAAAUUGUGGAUUUGGUCA |
| 74 | CR001436 | Exon 2 | Chr14:94382607-94382629 | CAGAGACACAGUUUUUGCUC |
| 75 | CR001437 | Exon 3 | Chr14:94381127-94381149 | UCCCCUCUCUCCAGGCAAAU |
| 76 | CR001438 | Exon 3 | Chr14:94381098-94381120 | CUCGGUGUCCUUGACUUCAA |
| 77 | CR001439 | Exon 3 | Chr14:94381097-94381119 | CUUUGAAGUCAAGGACACCG |

TABLE 1 -continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 78 | CR001440 | Exon 3 | Chr14:94381080-94381102 | CACGUGGAAGUCCUCUUCCU |
| 79 | CR001441 | Exon 3 | Chr14:94381079-94381101 | CGAGGAAGAGGACUUCCACG |
| 80 | CR001442 | Exon 3 | Chr14:94381073-94381095 | AGAGGACUUCCACGUGGACC |
| 81 | CR001443 | Exon 3 | Chr14:94381064-94381086 | CGGUGGUCACCUGGUCCACG |
| 82 | CR001444 | Exon 3 | Chr14:94381058-94381080 | GGACCAGGUGACCACCGUGA |
| 83 | CR001445 | Exon 3 | Chr14:94381055-94381077 | GCACCUUCACGGUGGUCACC |
| 84 | CR001446 | Exon 3 | Chr14:94381047-94381069 | CAUCAUAGGCACCUUCACGG |
| 85 | CR001447 | Exon 3 | Chr14:94381036-94381058 | GUGCCUAUGAUGAAGCGUUU |
| 86 | CR001448 | Exon 3 | Chr14:94381033-94381055 | AUGCCUAAACGCUUCAUCAU |
| 87 | CR001449 | Exon 3 | Chr14:94381001-94381023 | UGGACAGCUUCUUACAGUGC |
| 88 | CR001450 | Exon 3 | Chr14:94380995-94381017 | CUGUAAGAAGCUGUCCAGCU |
| 89 | CR001451 | Exon 3 | Chr14:94380974-94380996 | GGUGCUGCUGAUGAAAUACC |
| 90 | CR001452 | Exon 3 | Chr14:94380973-94380995 | GUGCUGCUGAUGAAAUACCU |
| 91 | CR001453 | Exon 3 | Chr14:94380956-94380978 | AGAUGGCGGUGGCAUUGCCC |
| 92 | CR001454 | Exon 3 | Chr14:94380945-94380967 | AGGCAGGAAGAAGAUGGCGG |
| 93 | CR001474 | Exon 5 | Chr14:94378611-94378633 | GGUCAGCACAGCCUUAUGCA |
| 94 | CR001475 | Exon 5 | Chr14:94378581-94378603 | AGAAAGGGACUGAAGCUGCU |
| 95 | CR001476 | Exon 5 | Chr14:94378580-94378602 | GAAAGGGACUGAAGCUGCUG |
| 96 | CR001477 | Exon 5 | Chr14:94378565-94378587 | UGCUGGGGCCAUGUUUUAG |
| 97 | CR001478 | Exon 5 | Chr14:94378557-94378579 | GGGUAUGGCCUCUAAAAACA |
| 98 | CR001483 | Exon 5 | Chr14:94378526-94378548 | UGUUGAACUUGACCUCGGGG |
| 99 | CR001484 | Exon 5 | Chr14:94378521-94378543 | GGGUUUGUUGAACUUGACCU |
| 100 | CR003190 | Exon 2 | Chr14:94383131-94383153 | UUCUGGGCAGCAUCUCCCUG |
| 101 | CR003191 | Exon 2 | Chr14:94383129-94383151 | UCUUCUGGGCAGCAUCUCCC |

TABLE 1 -continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 102 | CR003196 | Exon 2 | Chr14:94383024-94383046 | UGGACUGGUGUGCCAGCUGG |
| 103 | CR003204 | Exon 2 | Chr14:94382961-94382983 | AGCCUUUGCAAUGCUCUCCC |
| 104 | CR003205 | Exon 2 | Chr14:94382935-94382957 | UUCAUCGUGAGUGUCAGCCU |
| 105 | CR003206 | Exon 2 | Chr14:94382901-94382923 | UCUCCGUGAGGUUGAAAUUC |
| 106 | CR003207 | Exon 2 | Chr14:94382822-94382844 | GUCAGCUGGAGCUGGCUGUC |
| 107 | CR003208 | Exon 2 | Chr14:94382816-94382838 | AGCCAGCUCCAGCUGACCAC |
| 108 | CR003217 | Exon 3 | Chr14:94380942-94380964 | AUCAGGCAGGAAGAAGAUGG |
| 109 | CR003218 | Exon 3 | Chr14:94380938-94380960 | CAUCUUCUUCCUGCCUGAUG |
| 110 | CR003219 | Exon 3 | Chr14:94380937-94380959 | AUCUUCUUCCUGCCUGAUGA |
| 111 | CR003220 | Exon 3 | Chr14:94380881-94380903 | CGAUAUCAUCACCAAGUUCC |
| 112 | CR003221 | Exon 4 | Chr14:94379554-94379576 | CAGAUCAUAGGUUCCAGUAA |
| 113 | CR003222 | Exon 4 | Chr14:94379507-94379529 | AUCACUAAGGUCUUCAGCAA |
| 114 | CR003223 | Exon 4 | Chr14:94379506-94379528 | UCACUAAGGUCUUCAGCAAU |
| 115 | CR003224 | Exon 4 | Chr14:94379505-94379527 | CACUAAGGUCUUCAGCAAUG |
| 116 | CR003225 | Exon 4 | Chr14:94379453-94379475 | CUCACCUUGGAGAGCUUCAG |
| 117 | CR003226 | Exon 4 | Chr14:94379452-94379474 | UCUCACCUUGGAGAGCUUCA |
| 118 | CR003227 | Exon 4 | Chr14:94379451-94379473 | AUCUCACCUUGGAGAGCUUC |
| 119 | CR003235 | Exon 5 | Chr14:94378525-94378547 | UUGUUGAACUUGACCUCGGG |
| 120 | CR003236 | Exon 5 | Chr14:94378524-94378546 | UUUGUUGAACUUGACCUCGG |
| 121 | CR003237 | Exon 5 | Chr14:94378523-94378545 | GUUUGUUGAACUUGACCUCG |
| 122 | CR003238 | Exon 5 | Chr14:94378522-94378544 | GGUUUGUUGAACUUGACCUC |
| 123 | CR003240 | Exon 5 | Chr14:94378501-94378523 | UCAAUCAUUAAGAAGACAAA |
| 124 | CR003241 | Exon 5 | Chr14:94378500-94378522 | UUCAAUCAUUAAGAAGACAA |
| 125 | CR003242 | Exon 5 | Chr14:94378472-94378494 | UACCAAGUCUCCCCUCUUCA |

TABLE 1 -continued

SERPINA1 targeted and control guide sequence nomenclature, chromosomal coordinates, and sequence

| SEQ ID No | Guide ID | Description | Chromosomal coordinates | Guide Sequences |
|---|---|---|---|---|
| 126 | CR003243 | Exon 5 | Chr14:94378471-94378493 | ACCAAGUCUCCCCUCUUCAU |
| 127 | CR003244 | Exon 5 | Chr14:94378463-94378485 | UCCCCUCUUCAUGGGAAAAG |
| 128 | CR003245 | Exon 5 | Chr14:94378461-94378483 | CACCACUUUUCCCAUGAAGA |
| 129 | CR003246 | Exon 5 | Chr14:94378460-94378482 | UCACCACUUUUCCCAUGAAG |

Each of the Guide Sequences above may further comprise additional nucleotides to form a crRNA, e.g., with the following exemplary nucleotide sequence following the Guide Sequence at its 3' end: GUUUUAGAGCUAUGCU-GUUUUG (SEQ ID NO: 140). In the case of a sgRNA, the above Guide Sequences may further comprise additional nucleotides to form a sgRNA, e.g., with the following exemplary nucleotide sequence following the 3' end of the Guide Sequence: GUUUUAGAGCUA-GAAAUAGCAAGUUAAAAUAAGGCUAGU-CCGUUAUCAACUU GAAAAAGUGGCACCGAGUCG-GUGCUUUU (SEQ ID NO: 141) in 5' to 3' orientation.

In some embodiments, the sgRNA is modified. In some embodiments, the modified sgRNA comprises any one of the sequences recited in Table 2 (SEQ ID Nos: 130-139, 408, and 410-421). In Table 2, "N" may be any natural or non-natural nucleotide. In some embodiments, compositions comprising SEQ ID NO: 130 are encompassed wherein each N in SEQ ID NO: 130 is collectively replaced with a guide sequence selected from SEQ ID NOs: 5-129, wherein the modification pattern shown in SEQ ID NO: 130 remains.

In some embodiments, compositions comprising SEQ ID NO: 410 are encompassed wherein each N in SEQ ID NO: 410 is collectively replaced with a guide sequence selected from SEQ ID NOs: 5-129, wherein the modification pattern shown in SEQ ID NO: 410 remains.

In some embodiments, compositions comprising SEQ ID NO: 411 are encompassed wherein each N in SEQ ID NO: 411 is collectively replaced with a guide sequence selected from SEQ ID NOs: 5-129, wherein the modification pattern shown in SEQ ID NO: 411 remains.

In some embodiments, compositions comprising SEQ ID NO: 412 are encompassed wherein each N in SEQ ID NO: 412 is collectively replaced with a guide sequence selected from SEQ ID NOs: 5-129, wherein the modification pattern shown in SEQ ID NO: 412 remains.

In some embodiments, compositions comprising SEQ ID NO: 413 are encompassed wherein each N in SEQ ID NO: 413 is collectively replaced with a guide sequence selected from SEQ ID NOs: 5-129, wherein the modification pattern shown in SEQ ID NO: 413 remains.

In some embodiments, compositions comprising SEQ ID NO: 414 are encompassed wherein each N in SEQ ID NO: 414 is collectively replaced with a guide sequence selected from SEQ ID NOs: 5-129, wherein the modification pattern shown in SEQ ID NO: 414 remains.

In some embodiments, compositions comprising SEQ ID NO: 415 are encompassed wherein each N in SEQ ID NO: 415 is collectively replaced with a guide sequence selected from SEQ ID NOs: 5-129, wherein the modification pattern shown in SEQ ID NO: 415 remains.

In some embodiments, compositions comprising SEQ ID NO: 416 are encompassed wherein each N in SEQ ID NO: 416 is collectively replaced with a guide sequence selected from SEQ ID NOs: 5-129, wherein the modification pattern shown in SEQ ID NO: 416 remains.

In some embodiments, compositions comprising SEQ ID NO: 417 are encompassed wherein each N in SEQ ID NO: 417 is collectively replaced with a guide sequence selected from SEQ ID NOs: 5-129, wherein the modification pattern shown in SEQ ID NO: 417 remains.

In some embodiments, compositions comprising SEQ ID NO: 418 are encompassed wherein each N in SEQ ID NO: 418 is collectively replaced with a guide sequence selected from SEQ ID NOs: 5-129, wherein the modification pattern shown in SEQ ID NO: 418 remains.

In some embodiments, compositions comprising SEQ ID NO: 419 are encompassed wherein each N in SEQ ID NO: 419 is collectively replaced with a guide sequence selected from SEQ ID NOs: 5-129, wherein the modification pattern shown in SEQ ID NO: 419 remains.

In some embodiments, compositions comprising SEQ ID NO: 420 are encompassed wherein each N in SEQ ID NO: 420 is collectively replaced with a guide sequence selected from SEQ ID NOs: 5-129, wherein the modification pattern shown in SEQ ID NO: 420 remains.

In some embodiments, compositions comprising SEQ ID NO: 421 are encompassed wherein each N in SEQ ID NO: 421 is collectively replaced with a guide sequence selected from SEQ ID NOs: 5-129, wherein the modification pattern shown in SEQ ID NO: 421 remains.

TABLE 2

SERPINA1 targeted sgRNAs

| SEQ ID | sgRNA ID | Description | Sequence |
|---|---|---|---|
| 130 | Mod Only-N | sgRNA modified sequence | mN*mN*mN*NNNNNNNNNNNNNNNNNNNGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 408 | Mod-Only | sgRNA modified sequence | GUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 131 | G000407 | sgRNA modified sequence | mA*mG*mC*CAGCUCCAGCUGACCACGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 132 | G000408 | sgRNA modified sequence | mG*mC*mU*GAGGAACAGGCCAUUGCGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 133 | G000409 | sgRNA modified sequence | mA*mC*mU*CACGAUGAAAUCCUGGAGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 134 | G000410 | sgRNA modified sequence | mU*mU*mG*GGUGAUCCUGAUCAUGGGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 135 | G000411 | sgRNA modified sequence | mU*mG*mG*GUGAUCCUGAUCAUGGUGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 136 | G000412 | sgRNA modified sequence | mG*mA*mU*CUGUUUCUUGGCCUCUUGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 137 | G000413 | sgRNA modified sequence | mG*mA*mA*GGCGAACUCAGCCAGGUGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 138 | G000414 | sgRNA modified sequence | mC*mA*mA*CCUCACGGAGAUUCCGGGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 139 | G000415 | sgRNA modified sequence | mU*mG*mU*UGGACUGGUGUGCCAGCGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 410 | G000537/G211-33 | 5'end 3xOMePS (mod only) | mN*mN*mN*NNNNNNNNNNNNNNNNNNNGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmUmUmUmU |
| 411 | G000538/G211-34 | 3'end 3xOMePS (mod only) | mNmNmNNNNNNNNNNNNNNNNNNNNGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmGmCmU*mU*mU*mU |
| 412 | G000539/G211-35 | 5xOMePS (mod only) | mN*mN*mN*mN*mN*NNNNNNNNNNNNNNNNNGUUUUAGAmGmCmUmAmGmAmAmAmUmAmGmCAAGUUAAAAUAAGGCUAGUCCGUUAUCAmAmCmUmUmGmAmAmAmAmAmGmUmGmCmAmCmCmGmAmGmUmCmGmGmUmG*mC*mU*mU*mU |

TABLE 2 -continued

SERPINA1 targeted sgRNAs

| SEQ ID | sgRNA ID | Description | Sequence |
|---|---|---|---|
| 413 | G000541/G211-37 (mod only) | 3xOMePS+2 PS | mN*mN*mN*N*N*NNNNNNNNNNNNNNNGUUUUAGAmGmC mUmAmGmAmAmAmUmAmGmCAAGUUAAAAUAAGGCUAG UCCGUUAUCAmAmCmUmUmGmAmAmAmAmAmGmUmGmG mCmAmCmCmGmAmGmUmCmGmGmUmG*mC*mU*mU*mU* mU |
| 414 | G000542/G211-38 (mod only) | 3xOMePS+7 PS | mN*mN*mN*N*N*N*N*N*N*NNNNNNNNNNNGUUUUAGA mGmCmUmAmGmAmAmAmUmAmGmCAAGUUAAAAUAAGG CUAGUCCGUUAUCAmAmCmUmUmGmAmAmAmAmAmGmU mGmGmCmAmCmCmGmAmGmU*mC*mG*mG*mU*mG*mC*m U*mU*mU*mU |
| 415 | G000543/G211-39 (mod only) | invd abasic | (invd) NNNNNNNNNNNNNNNNGUUUUAGAmGmCmUmAmG mAmAmAmUmAmGmCAAGUUAAAAUAAGGCUAGUCCGUU AUCAmAmCmUmUmGmAmAmAmAmAmGmUmGmGmCmAm CmCmGmAmGmUmCmGmGmUmGmCmUmUmUmU (invd) |
| 416 | G000544/G211-40 (mod only) | invd abasic + 3xOMePS | (invd) mN*mN*mN*NNNNNNNNNNNNNNNNNGUUUUAGAmG mCmUmAmGmAmAmAmUmAmGmCAAGUUAAAAUAAGGCU AGUCCGUUAUCAmAmCmUmUmGmAmAmAmAmAmGmUmG mGmCmAmCmCmGmAmGmUmCmGmGmUmGmCmU*mU*mU* mU (invd) |
| 417 | G000564/G211-42 (mod only) | 3xMOE-PS | moeN*moeN*moeN*NNNNNNNNNNNNNNNNNGUUUUAGAm GmCmUmAmGmAmAmAmUmAmGmCAAGUUAAAAUAAGGC UAGUCCGUUAUCAmAmCmUmUmGmAmAmAmAmAmGmUm GmGmCmAmCmCmGmAmGmUmCmGmGmUmGmCmoeU*moe U*moeU*mU |
| 418 | G000545/G211-43 (mod only) | US loop PS | mN*mN*mN*NNNNNNNNNNNNNGUUUUAGAmGmCm UmA*mG*mA*mA*mA*mUmAmGmCAAGUUAAAAUAAGGC UAGUCCGUUAUCAmAmCmUmUmGmAmAmAmAmAmGmUm GmGmCmAmCmCmGmAmGmUmCmGmGmUmGmCmU*mU*m U*mU |
| 419 | G000546/G211-44 (mod only) | H1 loop PS | mN*mN*mN*NNNNNNNNNNNNNNNNNGUUUUAGAmGmCm UmAmGmAmAmAmUmAmGmCAAGUUAAAAUAAGGCUAGU CCGUUAUCAmAmCmUmU*mG*mA*mA*mA*mAmAmGmUm GmGmCmAmCmCmGmAmGmUmCmGmGmUmGmCmU*mU*m U*mU |
| 420 | G000547/G211-45 (mod only) | H2 loop PS | mN*mN*mN*NNNNNNNNNNNNNNNNNGUUUUAGAmGmCm UmAmGmAmAmAmUmAmGmCAAGUUAAAAUAAGGCUAGU CCGUUAUCAmAmCmUmUmGmAmAmAmAmAmGmUmGmGm CmAmCmCmG*mA*mG*mU*mCmGmGmUmGmCmU*mU*mU* mU |
| 421 | G000548/G211-46 (mod only) | all loops PS | mN*mN*mN*NNNNNNNNNNNNNNNNNGUUUUAGAmGmCm UmA*mG*mA*mA*mA*mUmAmGmCAAGUUAAAAUAAGGC UAGUCCGUUAUCAmAmCmUmU*mG*mA*mA*mA*mAmAm GmUmGmGmCmAmCmCmG*mA*mG*mU*mCmGmGmUmGmC mU*mU*mU*mU |

*= PS linkage;
'm'= 2'-O-Me nucleotide

Unless stated otherwise, the following terms and phrases as used herein are intended to have the following meanings:

"Polynucleotide" and "nucleic acid" are used herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., N4-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, O6-methylguanine, 4-thio-pyrimidines, 4-amino-pyrimidines, 4-dimethylhydrazine-pyrimidines, and O4-alkyl-pyrimidines; U.S. Pat. No. 5,378,825 and PCT No. WO 93/13121). For general discussion see The Biochemistry of the Nucleic Acids 5-36, Adams et al., ed., 11th ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, Biochemistry 43(42): 13233-41). RNA and DNA have different sugar moieties and can differ by the presence of uracil or analogs thereof in RNA and thymine or analogs thereof in DNA.

"Guide RNA", "gRNA", and simply "guide" are used herein interchangeably to refer to either a crRNA (also known as CRISPR RNA), or the combination of a crRNA and a trRNA (also known as tracrRNA). The crRNA and trRNA may be associated as a single RNA molecule (single guide RNA, sgRNA) or in two separate RNA molecules (dual guide RNA, dgRNA). "Guide RNA" or "gRNA" or "guide" refers to each type. The trRNA may be a naturally-occurring sequence, or a trRNA sequence with modifications or variations compared to naturally-occurring sequences.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of a guide RNA for a *Streptococcus pyogenes* Cas9 (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. In some embodiments, the target sequence is in a gene or on a chromosome, for example, and is complementary to the guide sequence. In some embodiments, the degree of complementarity or identity between a guide sequence and its corresponding target sequence may be about 75%, 80%, 85%, 90%, 95%, 96%, 97%, 98%, 99%, or 100%. In some embodiments, the guide sequence and the target region may be 100% complementary or identical. In other embodiments, the guide sequence and the target region may contain at least one mismatch. For example, the guide sequence and the target sequence may contain 1, 2, 3, or 4 mismatches, where the total length of the target sequence is at least 17, 18, 19, 20 or more base pairs. In some embodiments, the guide sequence and the target region may contain 1-4 mismatches where the guide sequence comprises at least 17, 18, 19, 20 or more nucleotides. In some embodiments, the guide sequence and the target region may contain 1, 2, 3, or 4 mismatches where the guide sequence comprises 20 nucleotides.

Target sequences for Cas proteins include both the positive and negative strands of genomic DNA (i.e., the sequence given and the sequence's reverse compliment), as a nucleic acid substrate for a Cas protein is a double stranded nucleic acid. Accordingly, where a guide sequence is said to be "complementary to a target sequence", it is to be understood that the guide sequence may direct a guide RNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. RNA-guided DNA binding agents include Cas proteins (e.g., Cas9 proteins), such as Cas nucleases (e.g., Cas9 nucleases). "Cas nuclease", also called "Cas protein", as used herein, encompasses Cas cleavases, Cas nickases, and inactivated forms thereof ("dCas DNA binding agents"). Cas proteins further encompass a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity, such as a Cas9 nuclease or a Cpf1 nuclease. Class 2 Cas nucleases include Class 2 Cas cleavases/nickases (e.g., H840A, D10A, or N863A variants), which further have RNA-guided DNA cleavase or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A/R661A/Q695A/Q926A variants), HypaCas9 (e.g., N692A/M694A/Q695A/H698A variants), eSPCas9(1.0) (e.g, K810A/K1003A/R1060A variants), and eSPCas9(1.1) (e.g., K848A/K1003A/R1060A variants) proteins and modifications thereof. Cpf1 protein, Zetsche et al., Cell, 163: 1-13 (2015), is homologous to Cas9, and contains a RuvC-like nuclease domain. The Cpf1 sequences of Zetsche et al. are incorporated by reference in their entirety. See, e.g., Zetsche et al. at Tables S1 and S3. "Cas9" encompasses Spy Cas9, the variants of Cas9 listed herein, and equivalents thereof. See, e.g., Makarova et al., Nat Rev Microbiol, 13(11): 722-36 (2015); Shmakov et al., Molecular Cell, 60:385-397 (2015).

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides (such as thymidine, uridine, or modified uridine) have the same complement (e.g., adenosine for all of thymidine, uridine, or modified uridine; another example is cytosine and 5-methylcytosine, both of which have guanosine or modified guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity>50% for amino acids or >75% for nucleotides, the Needleman- Wunsch algorithm with default settings of the Needleman-Wunsch algorithm interface provided by the EBI at the www.ebi.ac.uk web server is generally appropriate.

"mRNA" is used herein to refer to a polynucleotide that is not DNA and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof In general, mRNAs do not contain a substantial quantity of thymidine residues (e.g., 0 residues or fewer than 30, 20, 10, 5, 4, 3, or 2 thymidine residues; or less than 10%, 9%, 8%, 7%, 6%, 5%, 4%, 4%, 3%, 2%, 1%, 0.5%, 0.2%, or 0.1% thymidine content). An mRNA can contain modified uridines at some or all of its uridine positions.

As used herein, "AAT" or "A1AT" refer to alpha-1 antitrypsin, which is the gene product of the SERPINA1 gene.

As used herein, "AATD" or "A1AD" refers to alpha-1 antitrypsin deficiency. AATD comprises diseases and disorders caused by a variety of different genetic mutations in SERPINA1 AATD may refer to a disease where decreased levels of AAT are expressed, AAT is not expressed, or a mutant or non-functional AAT is expressed.

Guide sequences useful in the guide RNA compositions and methods described herein are shown in Table 1.

As used herein, "indels" refer to insertion/deletion mutations consisting of a number of nucleotides that are either inserted or deleted at the site of double-stranded breaks (DSBs) in the nucleic acid.

As used herein, "knockdown" refers to a decrease in expression of a particular gene product (e.g., protein, mRNA, or both). Knockdown of a protein can be measured either by detecting protein secreted by tissue or population of cells (e.g., in serum or cell media) or by detecting total cellular amount of the protein from a tissue or cell population of interest. Methods for measuring knockdown of mRNA are known, and include sequencing of mRNA isolated from a tissue or cell population of interest. In some embodiments, "knockdown" may refer to some loss of expression of a particular gene product, for example a decrease in the amount of mRNA transcribed or a decrease in the amount of protein expressed or secreted by a population of cells (including in vivo populations such as those found in tissues).

As used herein, "knockout" refers to a loss of expression of a particular protein in a cell. Knockout can be measured either by detecting the amount of protein secretion from a tissue or population of cells (e.g., in serum or cell media) or by detecting total cellular amount of a protein a tissue or a population of cells. In some embodiments, the methods of the invention "knockout" AAT in one or more cells (e.g., in a population of cells including in vivo populations such as those found in tissues). In some embodiments, a knockout is not the formation of mutant AAT protein, for example, created by indels, but rather the complete loss of expression of AAT protein in a cell.

As used herein, "mutant AAT" refers to a gene product of SERPINA1 (i.e., the AAT protein) having a change in the amino acid sequence of AAT compared to the wildtype amino acid sequence of SERPINA1 (NCBI Gene ID: 5265; Ensembl: Ensembl:ENSG00000197249).

As used herein, "mutant SERPINA1" or "mutant SERPINA1 allele" refers to a SERPINA1 sequence having a change in the nucleotide sequence of SERPINA1 compared to the wildtype sequence (NCBI Gene ID: 5265; Ensembl: Ensembl:ENSG00000197249).

As used herein, "ribonucleoprotein" (RNP) or "RNP complex" refers to a guide RNA together with an RNA-guided DNA binding agent, such as a Cas protein. In some embodiments, the guide RNA guides an RNA-guided DNA binding agent such as Cas9 to a target sequence, and the guide RNA hybridizes with and an RNA-guided DNA binding agent cleaves the target sequence.

As used herein, a "target sequence" refers to a sequence of nucleic acid in a target gene that has complementarity to the guide sequence of the gRNA. The interaction of the target sequence and the guide sequence directs an RNA-guided DNA binding agent to bind, and potentially nick or cleave (depending on the activity of the agent), within the target sequence.

As used herein, "treatment" refers to any administration or application of a therapeutic for disease or disorder in a subject, and includes inhibiting the disease, arresting its development, relieving one or more symptoms of the disease, curing the disease, or preventing reoccurrence of one or more symptoms of the disease. For example, treatment of AATD may comprise alleviating symptoms of AATD.

As used herein, the "Z mutant", "Z form mutant", "Z variant", "PiZ variant", or the "ZZ-form" of AAT refer to a mutation in the SERPINA1 gene sequence that leads to a missense mutation of glutamic acid to lysine (E342K mutation) in the amino acid sequence of AAT.

The term "about" or "approximately" means an acceptable error for a particular value as determined by one of ordinary skill in the art, which depends in part on how the value is measured or determined.

I. Compositions

A. Guide RNA (gRNAs)

In some embodiments, the invention comprises a composition comprising one or more guide RNA (gRNA) comprising guide sequences that direct a RNA-guided DNA binding agent (e.g., Cas9) to a target DNA sequence in SERPINA1. The gRNA may comprise one or more of the guide sequences shown in Table 1. The guide sequences of Table 1 may further comprise a crRNA and/or a trRNA. In each composition and method embodiment described herein, the crRNA and trRNA may be associated on one RNA (sgRNA), or may be on separate RNAs (dgRNA).

In each of the composition and method embodiments described herein, the guide RNA may comprise two RNA molecules as a "dual guide RNA" or "dgRNA". The dgRNA comprises a first RNA molecule (e.g. a crRNA) comprising a guide sequence comprising any one of the guide sequences described in Table 1, and a second RNA molecule comprising a trRNA. The first and second RNA molecules are not covalently linked, but may form a RNA duplex via the base pairing between portions of the crRNA and the trRNA.

In each of the composition and method embodiments described herein, the guide RNA may comprise a single RNA molecule as a "single guide RNA" or "sgRNA". The sgRNA comprises a crRNA (or a portion thereof) comprising any one of the guide sequences described in Table 1 covalently linked to a trRNA (or a portion thereof). In some embodiments, the crRNA and the trRNA are covalently linked via a linker. In some embodiments, the sgRNA forms a stem-loop structure via the base pairing between portions of the crRNA and the trRNA.

In some embodiments, the trRNA may comprise all or a portion of a wild type trRNA sequence from a naturally-occurring CRISPR/Cas system. In some embodiments, the trRNA comprises a truncated or modified wild type trRNA. The length of the trRNA depends on the CRISPR/Cas system used. In some embodiments, the trRNA comprises or consists of 5, 6, 7, 8, 9, 10, 11, 12, 13, 14, 15, 16, 17, 18, 19, 20, 25, 30, 40, 50, 60, 70, 80, 90, 100, or more than 100 nucleotides. In some embodiments, the trRNA may comprise certain secondary structures, such as, for example, one or more hairpin or stem-loop structures, or one or more bulge structures.

In some embodiments, the invention comprises one or more guide RNAs comprising a guide sequence of any one of SEQ ID NOs: 5-129.

In one aspect, the invention comprises a gRNA that comprises a guide sequence that is at least 99%, 98%, 97%, 96%, 95%, 94%, 93%, 92%, 91%, or 90% identical to a sequence selected from SEQ ID NOs: 5-129.

In other embodiments, the composition comprises at least two gRNA's comprising guide sequences selected from any two or more of the guide sequences of SEQ ID NOs: 5-129. In some embodiments, the composition comprises at least two gRNA's that each are at least 99%, 98%, 97%, 96%, 95%, 94%, 93%, 92%, 91%, or 90% identical to any of the nucleic acids of SEQ ID NOs: 5-129.

In some embodiments, the gRNA is a sgRNA comprising any one of the sequences shown in Table 2 (SEQ ID Nos. 130-139, 408, and 410-421). In some embodiments, the sgRNA comprises a sequence that is at least 99%, 98%, 97%, 96%, 95%, 94%, 93%, 92%, 91%, or 90% identical to any of the nucleic acids of SEQ ID Nos. 130-139, and 408. In some embodiments, the sgRNA comprises any one of the guide sequences shown in Table 1 in place of the guide sequences shown in the sgRNA sequences of Table 2 at SEQ ID Nos: 130-139, 408, and 410-421 with or without the modifications.

Guide RNAs are encompassed that comprise the modifications of any of the sequences shown in Table 2, and identified therein by SEQ ID No. That is, the nucleotides may be the same or different, but the modification pattern shown may be the same or similar to a modification pattern of a gRNA of Table 2. A modification pattern includes the relative position and identity of modifications of the gRNA or a region of the gRNA. In some embodiments, the modification pattern is at least 50%, 55%, 60%, 70%, 75%, 80%, 85%, 90%, 95%, 96%, 97%, 98%, and 99% identical to the modification pattern of any one of the sequences shown in the sequence column of Table 2. In some embodiments, the modification pattern differs from the modification pattern of a sequence of Table 2, or a region of such a sequence, at 0, 1, 2, 3, 4, 5, or 6 nucleotides. In some embodiments, the gRNA comprises modifications that differ from the modifications of a sequence of Table 2, at 0, 1, 2, 3, 4, 5, or 6 nucleotides.

The guide RNA compositions of the present invention are designed to recognize a target sequence in the SERPINA1 gene. For example, the SERPINA1 target sequence may be recognized and cleaved by the provided RNA-guided DNA binding agent. In some embodiments, a Cas protein may be directed by a guide RNA to a target sequence of the SERPINA1 gene, where the guide sequence of the guide RNA hybridizes with the target sequence and the Cas protein cleaves the target sequence.

In some embodiments, the selection of the one or more guide RNAs is determined based on target sequences within the SERPINA1 gene.

Without being bound by any particular theory, mutations in critical regions of the gene may be less tolerable than mutations in non-critical regions of the gene, thus the location of a DSB is an important factor in the amount or type of protein knockdown or knockout that may result. In some embodiments, a gRNA complementary or having complementarity to a target sequence within SERPINA1 is used to direct the Cas protein to a particular location in the SERPINA1 gene. In some embodiments, gRNAs are designed to have guide sequences that are complementary or have complementarity to target sequences in exons 2, 3, 4, or 5 of SERPINA1.

In some embodiments, gRNAs are designed to be complementary or have complementarity to target sequences in exons of SERPINA1 that code for the N-terminal region of AAT.

B. Chemically Modified gRNAs

In some embodiments, the invention comprises a gRNA comprising one or more modifications. In some embodiments, the modification comprises a 2'-O-methyl (2'-O-Me) modified nucleotide. In some embodiments, the modification comprises a phosphorothioate (PS) bond between nucleotides.

Modified sugars are believed to control the puckering of nucleotide sugar rings, a physical property that influences oligonucleotide binding affinity for complementary strands, duplex formation, and interaction with nucleases. Substitutions on sugar rings can therefore alter the confirmation and puckering of these sugars. For example, 2'-O-methyl (2'-O-Me) modifications can increase binding affinity and nuclease stability of oligonucleotides, though the effect of any modification at a given position in an oligonucleotide needs to be empirically determined.

The terms "mA," "mC," "mU," or "mG" may be used to denote a nucleotide that has been modified with 2'-O-Me.

Modification of 2'-O-methyl can be depicted as follows:

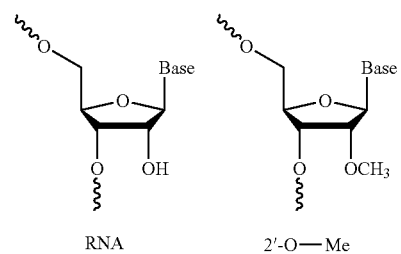

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

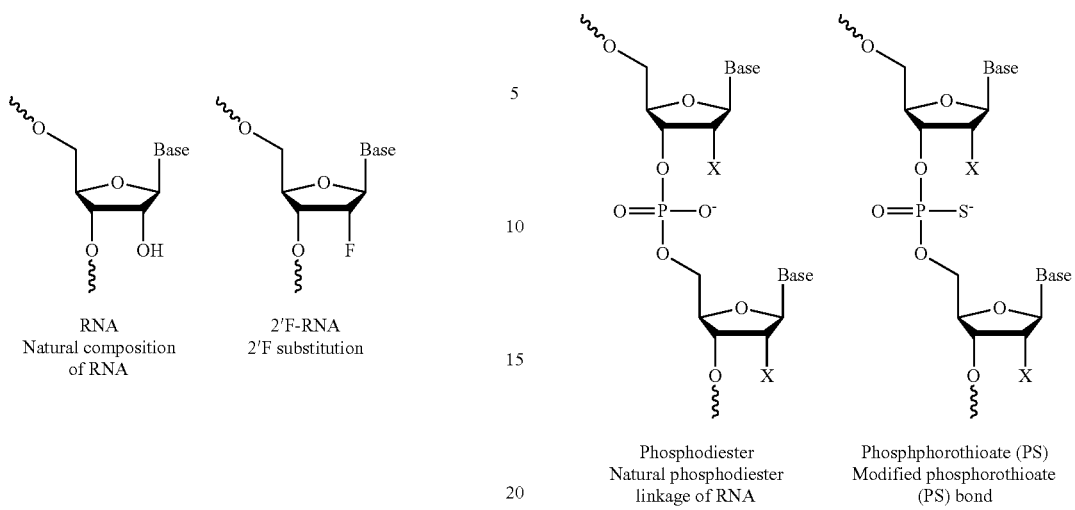

RNA
Natural composition of RNA

2'F-RNA
2'F substitution

In some embodiments, the modification may be 2'-O-(2-methoxyethyl) (2'-O-moe). Modification of a ribonucleotide as a 2'-O-moe ribonucleotide can be depicted as follows:

MOE

The terms "moeA," "moeC," "moeU," or "moeG" may be used to denote a nucleotide that has been modified with 2'-O-moe.

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

The diagram below shows the substitution of S-into a nonbridging phosphate oxygen, generating a PS bond in lieu of a phosphodiester bond:

Phosphodiester
Natural phosphodiester linkage of RNA

Phosphphorothioate (PS)
Modified phosphorothioate (PS) bond

Abasic nucleotides refer to those which lack nitrogenous bases. The figure below depicts an oligonucleotide with an abasic (also known as apurinic) site that lacks a base:

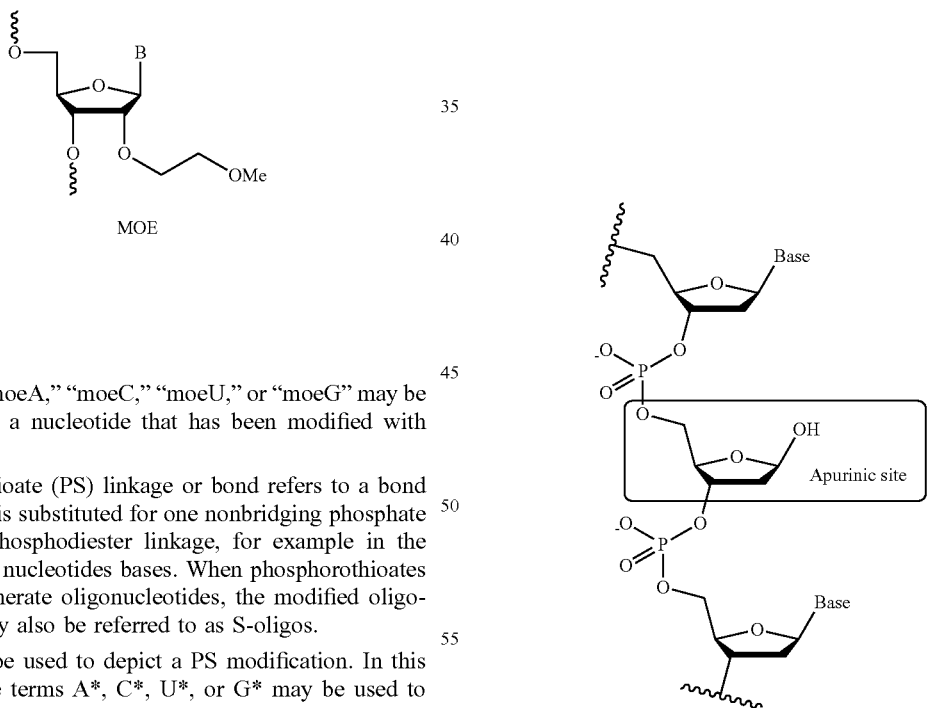

Inverted bases refer to those with linkages that are inverted from the normal 5' to 3' linkage (i.e., either a 5' to 5' linkage or a 3' to 3' linkage). For example:

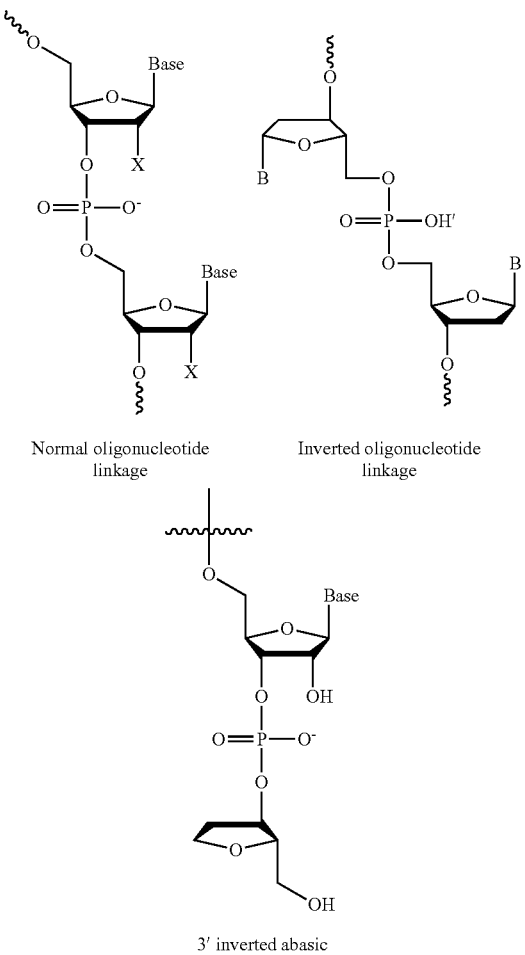

Normal oligonucleotide linkage

Inverted oligonucleotide linkage

3' inverted abasic

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap.

In some embodiments, one or more of the first three, four, or five nucleotides at the 5' end of the 5' terminus, and one or more of the last three, four, or five nucleotides at the 3' end of the 3' terminus are modified. In some embodiments, the modification is a 2'-O-Me, 2'-F, 2'-O-moe, inverted abasic nucleotide, PS bond, or other nucleotide modification well known in the art to increase stability and/or performance.

In some embodiments, the first four nucleotides at the 5' end of the 5' terminus, and the last four nucleotides at the 3' end of the 3' terminus are linked with phosphorothioate (PS) bonds.

In some embodiments, the first three nucleotides at the 5' end of the 5' terminus, and the last three nucleotides at the 3' end of the 3' terminus comprise a 2'-O-methyl (2'-O-Me) modified nucleotide. In some embodiments, the first three nucleotides at the 5' end of the 5' terminus, and the last three nucleotides at the 3' end of the 3' terminus comprise a 2'-fluoro (2'-F) modified nucleotide. In some embodiments, the first three nucleotides at the 5' end of the 5' terminus, and the last three nucleotides at the 3' end of the 3' terminus comprise an inverted abasic nucleotide.

In some embodiments, the guide RNA comprises a modified sgRNA. In some embodiments, the sgRNA comprises the modification pattern shown in SEQ ID No: 130, where N is any natural or non-natural nucleotide, and where the totality of the N's comprise a guide sequence that directs a RNA-guided DNA binding agent (e.g., Cas9) to a target sequence. In some embodiments, the sgRNA comprises the modification pattern shown in any one of SEQ ID No: 410-421, where N is any natural or non-natural nucleotide, and where the totality of the N's comprise a guide sequence that directs a RNA-guided DNA binding agent (e.g., Cas9) to a target sequence. In some embodiments, the guide RNA comprises a sgRNA shown in any one of SEQ ID No: 131-139. In some embodiments, the guide RNA comprises a sgRNA comprising any one of the guide sequences of SEQ ID No: 5-129 and the nucleotides of SEQ ID No: 408, wherein the nucleotides of SEQ ID No: 408 are on the 3' end of the guide sequence, and wherein the guide sequence may be modified as shown in SEQ ID No: 130. In some embodiments, the guide RNA comprises a sgRNA comprising any one of the guide sequences of SEQ ID No: 5-129 and the nucleotides of SEQ ID No: 141, wherein the nucleotides of SEQ ID No: 141 are on the 3' end of the guide sequence, and wherein the guide sequence may be modified as shown in SEQ ID No: 130.

In some embodiments, the guide RNAs disclosed herein comprise one of the modification pattern disclosed in U.S. 62/431,756, filed Dec. 8, 2016, and PCT/US17/65306, filed Dec. 8, 2017, titled "Chemically Modified Guide RNAs," the contents of which are hereby incorporated by reference in their entirety.

C. Vectors

In certain embodiments, the invention comprises DNA vectors comprising any of the guide RNAs comprising any one or more of the guide sequences described herein. In some embodiments, in addition to guide RNA sequences, the vectors further comprise nucleic acids that do not encode guide RNAs. Nucleic acids that do not encode guide RNA include, but are not limited to, promoters, enhancers, regulatory sequences, and nucleic acids encoding a RNA-guided DNA binding agent (e.g., Cas9). In some embodiments, the vector comprises a nucleotide sequence encoding a crRNA, a trRNA, or a crRNA and trRNA. In some embodiments, the vector comprises a nucleotide sequence encoding a sgRNA. In some embodiments, the vector comprises a nucleotide sequence encoding a crRNA and an mRNA encoding a Cas protein, such as, Cas9. In some embodiments, the vector comprises a nucleotide sequence encoding a crRNA, a trRNA, and an mRNA encoding a Cas protein, such as, Cas9. In some embodiments, the vector comprises a nucleotide sequence encoding a sgRNA and an mRNA encoding a Cas protein, such as, Cas9. In one embodiment, the Cas9 is from *Streptococcus pyogenes* (i.e., Spy Cas9). In some embodiments, the nucleotide sequence encoding the crRNA, trRNA, or crRNA and trRNA comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the crRNA and the trRNA are encoded by non-contiguous nucleic acids within one vector. In other embodiments, the crRNA and the trRNA may be encoded by a contiguous nucleic acid. In some embodiments, the crRNA and the trRNA are encoded by opposite strands of a single nucleic acid. In other embodiments, the crRNA and the trRNA are encoded by the same strand of a single nucleic acid.

D. Ribonucleoprotein Complex

In some embodiments, a composition is encompassed comprising one or more gRNAs comprising one or more guide sequences from Table 1 or Table 2 and a RNA-guided DNA binding agent (e.g., Cas9). In some embodiments, the gRNA together with DNA binding agent such as a Cas9 is called a ribonucleoprotein complex (RNP). In some embodiments, the RNA-guided DNA binding agent is a Cas protein. In some embodiments, the gRNA together with a Cas protein is called a Cas RNP. In some embodiments, the RNP comprises Type-I, Type-II, or Type-III components. In some embodiments, the Cas protein is from the Type-I CRISPR/Cas system. In some embodiments, the Cas protein is from the Type-II CRISPR/Cas system. In some embodiments, the Cas protein is from the Type-III CRISPR/Cas system. In some embodiments, the Cas protein is Cas9. In some embodiments, the Cas protein is Cpf1. In some embodiments, the Cas protein is the Cas9 protein from the Type-II CRISPR/Cas system. In some embodiment, the gRNA together with Cas9 is called a Cas9 RNP.

In embodiments encompassing a Cas nuclease, the Cas nuclease may be from a Type-IIA, Type-IIB, or Type-IIC system. Non-limiting exemplary species that the Cas nuclease or other RNP components may be derived from include *Streptococcus pyogenes, Streptococcus thermophilus, Streptococcus* sp., *Staphylococcus aureus, Listeria innocua, Lactobacillus gasseri, Francisella novicida, Wolinella succinogenes, Sutterella wadsworthensis, Gammaproteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anaebaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria, Acidaminococcus* sp., *Lachnospiraceae bacterium* ND2006, and *Acaryochloris marina*. In some embodiments, the Cas nuclease is the Cas9 protein from *Streptococcus pyogenes*. In some embodiments, the Cas nuclease is the Cas9 protein from *Streptococcus thermophilus*. In some embodiments, the Cas nuclease is the Cas9 protein from *Neisseria meningitidis*. In some embodiments, the Cas nuclease is the Cas9 protein is from *Staphylococcus aureus*. In some embodiments, the Cas nuclease is the Cpf1 protein from *Francisella novicida*. In some embodiments, the Cas nuclease is the Cpf1 protein from *Acidaminococcus* sp. In some embodiments, the Cas nuclease is the Cpf1 protein from *Lachnospiraceae bacterium* ND2006.

Wild type Cas9 has two nuclease domains: RuvC and HNH. The RuvC domain cleaves the non-target DNA strand, and the HNH domain cleaves the target strand of DNA. In some embodiments, the Cas9 protein comprises more than one RuvC domain and/or more than one HNH domain. In some embodiments, the Cas9 protein is a wild type Cas9. In each of the composition and method embodiments, the Cas induces a double strand break in target DNA.

Modified versions of Cas9 having one catalytic domain, either RuvC or HNH, that is inactive are termed "nickases". Nickases cut only one strand on the target DNA, thus creating a single-strand break. A single-strand break may also be known as a "nick." In some embodiments, the compositions and methods comprise nickases. In some embodiments, the compositions and methods comprise a nickase Cas9 that induces a nick rather than a double strand break in the target DNA.

In some embodiments, the Cas protein may be modified to contain only one functional nuclease domain. For example, the Cas protein may be modified such that one of the nuclease domains is mutated or fully or partially deleted to reduce its nucleic acid cleavage activity. In some embodiments, a nickase Cas is used having a RuvC domain with reduced activity. In some embodiments, a nickase Cas is used having an inactive RuvC domain. In some embodiments, a nickase Cas is used having an HNH domain with reduced activity. In some embodiments, a nickase Cas is used having an inactive HNH domain.

In some embodiments, a conserved amino acid within a Cas protein nuclease domain is substituted to reduce or alter nuclease activity. In some embodiments, a Cas protein may comprise an amino acid substitution in the RuvC or RuvC-like nuclease domain. Exemplary amino acid substitutions in the RuvC or RuvC-like nuclease domain include D10A (based on the *S. pyogenes* Cas9 protein). See, e.g., Zetsche et al. (2015) Cell Oct 22:163(3): 759-771. In some embodiments, the Cas protein may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein). See, e.g., Zetsche et al (2015).

In some embodiments, the RNP complex described herein comprises a nickase and a pair of guide RNAs that are complementary to the sense and antisense strands of the target sequence, respectively. In this embodiment, the guide RNAs direct the nickase to a target sequence and introduce a DSB by generating a nick on opposite strands of the target sequence (i.e., double nicking). In some embodiments, use of double nicking may improve specificity and reduce off-target effects. In some embodiments, a nickase Cas is used together with two separate guide RNAs targeting opposite strands of DNA to produce a double nick in the target DNA. In some embodiments, a nickase Cas is used together with two separate guide RNAs that are selected to be in close proximity to produce a double nick in the target DNA.

In some embodiments, chimeric Cas proteins are used, where one domain or region of the protein is replaced by a portion of a different protein. In some embodiments, a Cas nuclease domain may be replaced with a domain from a different nuclease such as Fok1. In some embodiments, a Cas protein may be a modified nuclease.

In other embodiments, the Cas protein may be from a Type-I CRISPR/Cas system. In some embodiments, the Cas protein may be a component of the Cascade complex of a Type-I CRISPR/Cas system. In some embodiments, the Cas protein may be a Cas3 protein. In some embodiments, the Cas protein may be from a Type-III CRISPR/Cas system. In some embodiments, the Cas protein may have an RNA cleavage activity.

E. Determination of Efficacy of gRNAs

In some embodiments, the efficacy of a gRNA is determined when expressed together with other components of an RNP. In some embodiments, the gRNA is expressed together with a Cas. In some embodiments, the gRNA is expressed in a cell line that already stably expresses Cas.

Use of the Cas RNP system can lead to double-stranded breaks in the DNA. Nonhomologous end joining (NHEJ) is a process whereby double-stranded breaks (DSBs) in the DNA are repaired via re-ligation of the break ends, which can produce errors in the form of insertion/deletion (indel) mutations. The DNA ends of the DSB frequently have been subjected to enzymatic processing, resulting in the addition or removal of nucleotides at one or both strands before the rejoining of the ends. These additions or removals prior to rejoining result in the presence of insertion or deletion (indel) mutations in the DNA sequence at the site of the NHEJ repair. Many mutations due to indels alter the reading frame or introduce premature stop codons and, therefore, produce a non-functional protein.

In some embodiments, the efficacy of particular gRNAs is determined based on in vitro models. In some embodiments, the in vitro model is HEK293 cells stably expressing Cas9 (HEK293_Cas9). In some embodiments, the in vitro model is HUH7 human hepatocarcinoma cells. In some embodiments, the in vitro model is sk-Hep human hepatic adenocarcinoma cells. In some embodiments, the in vitro model is primary human hepatocytes. In some embodiments, the in vitro model is HepG2 cells.

In some embodiments, the efficacy of particular guide sequences is determined across multiple in vitro cell models for a gRNA selection process. In some embodiments, a cell line comparison of data with selected gRNAs is performed. In some embodiments, cross screening in multiple cell models is performed.

In some embodiments, the efficacy of a guide RNA is measured by percent editing of SERPINA1. In some embodiments, the percent editing of SERPINA1 is compared to the percent editing of a control gene (e.g., a gene that the gRNA is not targeted to). In some embodiments, the control gene is Control 1, 2, 3, or 4 as shown in Table 1. In some embodiments, the editing percentage (e.g., the "editing efficiency" or "percent editing") is defined as the total number of sequence reads with insertions/deletions ("indels") or substitutions over the total number of sequence reads, including wild type. In some embodiments, the guide RNA has a percent editing that is about 100%. In some embodiments, the percent editing is, for example, between 5 and 10%, 10 and 15%, 15 and 20%, 20 and 25%, 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99%.

In some embodiments, the methods and compositions described herein comprise guide RNA having a reduction in off-target cleavage. In some embodiments, there are no detectable off-target cleavages. In some embodiments, a deletion or insertion of a nucleotide(s) occurs in the SERPINA1 gene at least 50-fold or more than in off-target sites. In some embodiments, the deletion or insertion of a nucleotide(s) occurs in the SERPINA1 gene 50-fold to 150-fold, 150-fold to 500-fold, 500-fold to 1500-fold, 1500-fold to 5000-fold, 5000-fold to 15000-fold, 15000-fold to 30000-fold, or 30000-fold to 60000-fold more than in off-target sites.

In some embodiments, the efficacy of a guide RNA is measured by secretion of AAT. In some embodiments, secretion of AAT is measured using an enzyme-linked immunosorbent assay (ELISA) assay with culture media. In some embodiments, secretion of AAT is measured in the same in vitro systems used to measure editing. In some embodiments, secretion of AAT is measured in primary human hepatocytes. In some embodiments, secretion of AAT is measured in HUH7 cells.

In some embodiments, the amount of AAT in cells measures efficacy of a gRNA. In some embodiments, the amount of AAT in cells is measured using western blot. In some embodiments, the cell used is HUH7 cells. In some embodiments, the amount of AAT is compared to the amount of glyceraldehyde 3-phosphate dehydrogenase GAPDH (a housekeeping gene) to control for changes in cell number.

II. Treatment of AATD

In some embodiments, a method of inducing a double-stranded break (DSB) within the SERPINA1 gene is provided comprising administering a guide RNA comprising any one or more guide sequences of SEQ ID Nos: 5-129, or any one or more of the sgRNAs of SEQ ID Nos: 130-139. In some embodiments, gRNAs comprising any one or more of the guide sequences of SEQ ID Nos: 5-129 are administered to induce a DSB in the SERPINA1 gene. The guide RNAs may be administered together with a RNA-guided DNA binding agent such as a Cas protein, such as, for example, Cas9, or an mRNA or vector encoding a RNA-guided DNA binding agent such as a Cas protein, such as, for example, Cas9. In some embodiments, the guide RNA administered is one or more of the guide RNA compositions described herein.

In some embodiments, a method of modifying the SERPINA1 gene is provided comprising administering a guide RNA comprising any one or more of the guide sequences of SEQ ID Nos: 5-129, or any one or more of the sgRNAs of SEQ ID Nos: 130-139. In some embodiments, gRNAs comprising any one or more of the guide sequences of SEQ ID Nos: 5-129, or any one or more of the sgRNAs of SEQ ID Nos: 130-139, are administered to modify the SERPINA1 gene. The guide RNAs may be administered together with a Cas protein or an mRNA or vector encoding a Cas protein, such as, for example, Cas9.

In some embodiments, a method of treating AATD is provided comprising administering a guide RNA comprising any one or more of the guide sequences of SEQ ID Nos: 5-129, or any one or more of the sgRNAs of SEQ ID Nos: 130-139. In some embodiments, gRNAs comprising any one or more of the guide sequences of SEQ ID Nos: 5-129, or any one or more of the sgRNAs of SEQ ID Nos: 130-139 are administered to treat AATD. The guide RNAs may be administered together with a Cas protein or an mRNA or vector encoding a Cas protein, such as, for example, Cas9.

In some embodiments, a method of reducing or preventing the accumulation of AAT in the serum, liver, liver tissue, liver cells, and/or hepatocytes of a subject is provided comprising administering a guide RNA comprising any one or more of the guide sequences of SEQ ID Nos 5-129, or any one or more of the sgRNAs of SEQ ID Nos: 130-139. In some embodiments, gRNAs comprising any one or more of the guide sequences of SEQ ID Nos: 5-129 or any one or more of the sgRNAs of SEQ ID Nos: 130-139 are administered to reduce or prevent the accumulation of AAT in the liver, liver tissue, liver cells, and/or hepatocytes. The gRNAs may be administered together with an RNA-guided DNA binding agent such as a Cas protein or an mRNA or vector encoding a Cas protein, such as, for example, Cas9.

In some embodiments, the gRNAs comprising the guide sequences of Table 1 or Table 2 together with a Cas protein induce DSBs, and non-homologous ending joining (NHEJ) during repair leads to a mutation in the SERPINA1 gene. In some embodiments, NHEJ leads to a deletion or insertion of a nucleotide(s), which induces a frame shift or nonsense mutation in the SERPINA1 gene.

In some embodiments, administering the guide RNAs of the invention (e.g., in a composition provided herein) reduces levels of mutated alpha-1 antitrypsin (AAT) produced by the subject, and therefore prevents accumulation and aggregation of AAT in the liver.

In some embodiments, the subject is mammalian. In some embodiments, the subject is human. In some embodiments, the subject is cow, pig, monkey, sheep, dog, cat, fish, or poultry.

In some embodiments, the use of a guide RNAs comprising any one or more of the guide sequences in Table 1 or Table 2 (e.g., in a composition provided herein) is provided for the preparation of a medicament for treating a human subject having AATD.

In some embodiments, the guide RNAs, compositions, and formulations are administered intravenously. In some embodiments, the guide RNAs, compositions, and formulations are administered into the hepatic circulation.

In some embodiments, a single administration of the guide RNA of the invention (e.g., in a composition provided herein) is sufficient to knock down expression of the mutant protein. In some embodiments, a single administration of the guide RNA of the invention (e.g., in a composition provided herein) is sufficient to knock down or knock out expression of the mutant protein. In other embodiments, more than one administration of the guide RNA of the invention (e.g., in a composition provided herein) may be beneficial to maximize editing via cumulative effects.

In some embodiments, the efficacy of treatment with the compositions of the invention is seen at 1 year, 2 years, 3 years, 4 years, 5 years, or 10 years after delivery.

In some embodiments, treatment slows or halts liver disease progression. In some embodiments, treatment improves liver disease measures. In some embodiments, liver disease is measured by changes in liver structure, liver function, or symptoms in the subject.

In some embodiments, efficacy of treatment is measured by the ability to delay or avoid a liver transplantation in the subject. In some embodiments, efficacy of treatment is measured by increased survival time of the subject.

In some embodiments, efficacy of treatment is measured by reduction in liver enzymes in blood. In some embodiments, the liver enzymes are alanine transaminase (ALT) or aspartate transaminase (AST).

In some embodiments, efficacy of treatment is measured by the slowing of development of scar tissue or decrease in scar tissue in the liver based on biopsy results.

In some embodiments, efficacy of treatment is measured using patient-reported results such as fatigue, weakness, itching, loss of appetite, loss of appetite, weight loss, nausea, or bloating. In some embodiments, efficacy of treatment is measured by decreases in edema, ascites, or jaundice. In some embodiments, efficacy of treatment is measured by decreases in portal hypertension. In some embodiments, efficacy of treatment is measured by decreases in rates of liver cancer.

In some embodiments, efficacy of treatment is measured using imaging methods. In some embodiments, the imaging methods are ultrasound, computerized tomography, magnetic resonance imagery, or elastography.

In some embodiments, the serum and/or liver AAT levels are reduced by 40-50%, 50-60%, 60-70%, 70-80%, 80-90%, 90-95%, 95-98%, 98-99%, or 99-100% as compared to serum and/or liver AAT levels before administration of the composition.

In some embodiments, the percent editing of the SERPINA1 gene is between 30 and 99%. In some embodiments, the percent editing is between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99%.

A. Combination Therapy

In some embodiments, the invention comprises combination therapies comprising any one of the gRNAs comprising any one or more of the guide sequences disclosed in Table 1 or any one or more of the sgRNAs in Table 2 (e.g., in a composition provided herein) together with an augmentation therapy suitable for alleviating the lung symptoms of AATD. In some embodiments, the augmentation therapy for lung disease is intravenous therapy with AAT purified from human plasma, as described in Turner, *BioDrugs* 2013 December; 27(6): 547-58. In some embodiments, the augmentation therapy is with Prolastin®, Zemaira®, Aralast®, or Kamada®.

In some embodiments, the combination therapy comprises any one of the gRNAs comprising any one or more of the guide sequences disclosed in Table 1 or any one or more of the sgRNAs in Table 2 (e.g., in a composition provided herein) together with a siRNA that targets ATT or mutant ATT. In some embodiments, the siRNA is any siRNA capable of further reducing or eliminating the expression of wild type or mutant AAT. In some embodiments, the siRNA is administered after any one of the gRNAs comprising any one or more of the guide sequences disclosed in Table 1 or any one or more of the sgRNAs in Table 2 (e.g., in a composition provided herein). In some embodiments, the siRNA is administered on a regular basis following treatment with any of the gRNA compositions provided herein.

B. Delivery of gRNA

In some embodiments, the guide RNA compositions described herein, alone or encoded on one or more vectors, are formulated in or administered via a lipid nanoparticle; see e.g., PCT/US2017/024973, filed Mar. 30, 2017 entitled "LIPID NANOPARTICLE FORMULATIONS FOR CRISPR/CAS COMPONENTS," the contents of which are hereby incorporated by reference in their entirety. Any lipid nanoparticle (LNP) formulation known to those of skill in the art to be capable of delivering nucleotides to subjects may be utilized with the guide RNAs described herein, as well as either mRNA encoding an RNA-guided DNA binding agent such as Cas or Cas9, or an RNA-guided DNA binding agent such as Cas or Cas9 protein itself.

In some embodiments, the invention comprises a method for delivering any one of the gRNAs disclosed herein to a subject, wherein the gRNA is associated with an LNP. In some embodiments, the gRNA/LNP is also associated with an RNA-guided DNA binding agent such as Cas9 or an mRNA encoding an RNA-guided DNA binding agent such as Cas9.

In some embodiments, the invention comprises a composition comprising any one of the gRNAs disclosed and an LNP. In some embodiments, the composition further comprises a Cas9 or an mRNA encoding Cas9.

In some embodiments, the LNPs comprise cationic lipids. In some embodiments, the LNPs comprise a lipid such as a CCD lipid such as Lipid A ((9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate)), Lipid B (((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl) bis(decanoate)), Lipid C (2-((4-(((3-(dimethylamino)propoxy)carbonyl)oxy)hexadecanoyl)oxy)propane-1,3-diyl(9Z,9'Z, 12Z, 12'Z)-bis(octadeca-9,12-dienoate)), or Lipid D (dimethylamino)propoxy)carbonyl)oxy)-13-(octanoyloxy)tridecyl 3-octylundecanoate). In some embodiments, the LNPs comprise molar ratios of a cationic lipid amine to RNA phosphate (N:P) of about 4.5.

In some embodiments, LNPs associated with the gRNAs disclosed herein are for use in preparing a medicament for treating AATD. In some embodiments, LNPs associated with the gRNAs disclosed herein are for use in preparing a medicament for reducing or preventing accumulation and aggregation of AAT in subjects having AATD. In some embodiments, LNPs associated with the gRNAs disclosed herein are for use in preparing a medicament for reducing serum and/or liver AAT concentration. In some embodiments, LNPs associated with the gRNAs disclosed herein are for use in treating AATD in a subject, such as a mammal, e.g., a primate such as a human. In some embodiments, LNPs associated with the gRNAs disclosed herein are for use in reducing or preventing accumulation and aggregation of AAT in subjects having AATD, such as a mammal, e.g., a primate such as a human. In some embodiments, LNPs associated with the gRNAs disclosed herein are for use in reducing serum AAT concentration in a subject, such as a mammal, e.g., a primate such as a human.

Electroporation is also a well-known means for delivery of cargo, and any electroporation methodology may be used for delivery of any one of the gRNAs disclosed herein. In some embodiments, electroporation may be used to deliver any one of the gRNAs disclosed herein and an RNA-guided DNA binding agent such as Cas9 or an mRNA encoding an RNA-guided DNA binding agent such as Cas9.

In some embodiments, the invention comprises a method for delivering any one of the gRNAs disclosed herein to an ex vivo cell, wherein the gRNA is associated with an LNP or not associated with an LNP. In some embodiments, the gRNA/LNP or gRNA is also associated with an RNA-guided DNA binding agent such as Cas9 or an mRNA encoding an RNA-guided DNA agent such as Cas9.

In certain embodiments, the invention comprises DNA or RNA vectors encoding any of the guide RNAs comprising any one or more of the guide sequences described herein. In certain embodiments, the invention comprises DNA or RNA vectors encoding any one or more of the guide sequences described herein. In some embodiments, in addition to guide RNA sequences, the vectors further comprise nucleic acids that do not encode guide RNAs. Nucleic acids that do not encode guide RNA include, but are not limited to, promoters, enhancers, regulatory sequences, and nucleic acids encoding an RNA-guided DNA binding agent, which can be a nuclease such as Cas9. In some embodiments, the vector comprises one or more nucleotide sequence(s) encoding a crRNA, a trRNA, or a crRNA and trRNA. In some embodiments, the vector comprises one or more nucleotide sequence(s) encoding a sgRNA and an mRNA encoding an RNA-guided DNA binding agent, which can be a Cas protein, such as Cas9 or Cpf1. In some embodiments, the vector comprises one or more nucleotide sequence(s) encoding a crRNA, a trRNA, and an mRNA encoding an RNA-guided DNA binding agent, which can be a Cas protein, such as, Cas9 or Cpf1. In one embodiment, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the crRNA and the trRNA are encoded by non-contiguous nucleic acids within one vector. In other embodiments, the crRNA and the trRNA may be encoded by a contiguous nucleic acid. In some embodiments, the crRNA and the trRNA are encoded by opposite strands of a single nucleic acid. In other embodiments, the crRNA and the trRNA are encoded by the same strand of a single nucleic acid.

In some embodiments, the vector may be circular. In other embodiments, the vector may be linear. In some embodiments, the vector may be enclosed in a lipid nanoparticle, liposome, non-lipid nanoparticle, or viral capsid. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, helper dependent adenoviral vectors (HDAd), herpes simplex virus (HSV-1) vectors, bacteriophage T4, baculovirus vectors, and retrovirus vectors. In some embodiments, the viral vector may be an AAV vector. In some embodiments, the viral vector is AAV2, AAV3, AAV3B, AAV5, AAV6, AAV6.2, AAV7, AAVrh.64R1, AAVhu.37, AAVrh.8, AAVrh.32.33, AAV8, AAV9, AAVrh10, or AAVLK03. In other embodiments, the viral vector may a lentivirus vector.

In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal ('I') are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding an RNA-guided DNA binding agent such as a Cas protein (e.g., Cas9), while a second AAV vector may contain one or more guide sequences.

In some embodiments, the vector may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding an RNA-guided DNA binding agent such as a Cas protein (e.g., Cas9) described herein. In some embodiments, the nuclease encoded by the vector may be a Cas protein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1a) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1a promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In some embodiments, the promoter may be a tissue-specific promoter, e.g., a promoter specific for expression in the liver.

The vector may further comprise a nucleotide sequence encoding the guide RNA described herein. In some embodiments, the vector comprises one copy of the guide RNA. In other embodiments, the vector comprises more than one copy of the guide RNA. In embodiments with more than one guide RNA, the guide RNAs may be non-identical such that they target different target sequences, or may be identical in that they target the same target sequence. In some embodiments where the vectors comprise more than one guide RNA, each guide RNA may have other different properties, such as activity or stability within a complex with an RNA-guided DNA nuclease, such as a Cas RNP complex. In some embodiments, the nucleotide sequence encoding the guide RNA may be operably linked to at least one transcriptional or translational control sequence, such as a promoter, a 3' UTR, or a 5' UTR. In one embodiment, the promoter may be a tRNA promoter, e.g., tRNA$^{Lys3}$, or a tRNA chimera. See Mefferd et al., RNA. 2015 21:1683-9; Scherer et al., *Nucleic Acids Res.* 2007 35: 2620-2628. In some embodiments, the promoter may be recognized by RNA polymerase III (Pol III). Non-limiting examples of Pol III promoters include U6 and H1 promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In embodiments with more than one guide RNA, the promoters used to drive expression may be the same or different. In some embodiments, the nucleotide encoding the crRNA of the guide RNA and the nucleotide encoding the trRNA of the guide RNA may be provided on the same vector. In some embodiments, the nucleotide encoding the crRNA and the nucleotide encoding the trRNA may be driven by the same promoter. In some embodiments, the crRNA and trRNA may be transcribed into a single transcript. For example, the crRNA and trRNA may be processed from the single transcript to form a double-molecule guide RNA. Alternatively, the crRNA and trRNA may be transcribed into a single-molecule guide RNA (sgRNA). In other embodiments, the crRNA and the trRNA may be driven by their corresponding promoters on the same vector. In yet other embodiments, the crRNA and the trRNA may be encoded by different vectors.

In some embodiments, the nucleotide sequence encoding the guide RNA may be located on the same vector comprising the nucleotide sequence encoding an RNA-guided DNA binding agent such as a Cas protein. In some embodiments, expression of the guide RNA and of the RNA-guided DNA binding agent such as a Cas protein may be driven by their own corresponding promoters. In some embodiments, expression of the guide RNA may be driven by the same promoter that drives expression of the RNA-guided DNA binding agent such as a Cas protein. In some embodiments, the guide RNA and the RNA-guided DNA binding agent such as a Cas protein transcript may be contained within a single transcript. For example, the guide RNA may be within an untranslated region (UTR) of the RNA-guided DNA binding agent such as a Cas protein transcript. In some embodiments, the guide RNA may be within the 5' UTR of the transcript. In other embodiments, the guide RNA may be within the 3' UTR of the transcript. In some embodiments, the intracellular half-life of the transcript may be reduced by containing the guide RNA within its 3' UTR and thereby shortening the length of its 3' UTR. In additional embodiments, the guide RNA may be within an intron of the transcript. In some embodiments, suitable splice sites may be added at the intron within which the guide RNA is located such that the guide RNA is properly spliced out of the transcript. In some embodiments, expression of the RNA-guided DNA binding agent such as a Cas protein and the guide RNA from the same vector in close temporal proximity may facilitate more efficient formation of the CRISPR RNP complex.

In some embodiments, the compositions comprise a vector system. In some embodiments, the vector system may comprise one single vector. In other embodiments, the vector system may comprise two vectors. In additional embodiments, the vector system may comprise three vectors. When different guide RNAs are used for multiplexing, or when multiple copies of the guide RNA are used, the vector system may comprise more than three vectors.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the vector system may comprise tissue-specific promoters to start expression only after it is delivered into a specific tissue.

The vector may be delivered by liposome, a nanoparticle, an exosome, or a microvesicle. The vector may also be delivered by a lipid nanoparticle (LNP). Any of the LNPs and LNP formulations described herein are suitable for delivery of the guides alone or together a cas nuclease or an mRNA encoding a cas nuclease. In some embodiments, an LNP composition is encompassed comprising: an RNA component and a lipid component, wherein the lipid component comprises an amine lipid, a neutral lipid, a helper lipid, and a stealth lipid; and wherein the N/P ratio is about 1-10.

In some instances, the lipid component comprises Lipid A, cholesterol, DSPC, and PEG-DMG; and wherein the N/P ratio is about 1-10. In some embodiments, the lipid component comprises: about 40-60 mol-% amine lipid; about 5-15 mol-% neutral lipid; and about 1.5-10 mol-% PEG lipid, wherein the remainder of the lipid component is helper lipid, and wherein the N/P ratio of the LNP composition is about 3-10. In some embodiments, the lipid component comprises about 50-60 mol-% amine lipid; about 8-10 mol-% neutral lipid; and about 2.5-4 mol-% PEG lipid, wherein the remainder of the lipid component is helper lipid, and wherein the N/P ratio of the LNP composition is about 3-8. In some instances, the lipid component comprises: about 50-60 mol-% amine lipid; about 5-15 mol-% DSPC; and about 2.5-4 mol-% PEG lipid, wherein the remainder of the lipid component is cholesterol, and wherein the N/P ratio of the LNP composition is about 3-8. In some instances, the lipid component comprises: 48-53 mol-% Lipid A; about 8-10 mol-% DSPC; and 1.5-10 mol-% PEG lipid, wherein the remainder of the lipid component is cholesterol, and wherein the N/P ratio of the LNP composition is 3-8±0.2.

In some embodiments, the vector may be delivered systemically. In some embodiments, the vector may be delivered into the hepatic circulation.

In some embodiments, the vector may be delivered systemically. In some embodiments, the vector may be delivered into the hepatic circulation.

III. Recitation of Certain Embodiments

In some embodiments, the invention comprises a composition comprising a guide RNA comprising a guide sequence selected from SEQ ID NOs: 5-129. In some instances, a composition comprising a guide RNA comprising a guide sequence that is at least 99%, 98%, 97%, 96%, 95%, 94%, 93%, 92%, 91%, or 90% identical to a sequence selected from SEQ ID NOs: 5-129 is provided.

The guide RNA may be at least partially complementary to a target sequence present in the human SERPINA1 gene.

The guide RNA may direct a nuclease to a target sequence that is in exon 2, 3, 4, or 5 of the human SERPINA1 gene.

In some embodiments, the guide RNA directs a nuclease to a target sequence that is in exon 2 of the human SERPINA1 gene. In some instances, the guide RNA that targets exon 2 is selected from CR001370, CR001373, CR001374, CR001376, CR001379, CR001380, CR001386, CR001386, CR003196, CR001391, CR003198, CR001395, CR001397, CR001400, CR001404, CR001405, CR003208, CR001409, CR001413, CR001421, CR001422, and CR001427.

In some embodiments, the guide RNA directs a nuclease to a target sequence that is in exon 3 of the human SERPINA1 gene. In some instances, the guide RNA that targets exon 3 is selected from CR001450, CR003214, CR001453, CR001454, and CR003217.

In some embodiments, the guide RNA directs a nuclease to a target sequence that is in exon 4 of the human SERPINA1 gene. In some instances, the guide RNA that targets exon 4 is selected from CR003225 and CR003226.

In some embodiments, the guide RNA directs a nuclease to a target sequence that is in exon 5 of the human SERPINA1 gene. In some instances, the guide RNA that targets exon 5 is selected from CR001475 and CR001476.

In some instances, the guide RNA is a dual guide (dgRNA). The guide may also be a single guide RNA (sgRNA).

In some embodiments, the invention comprises a crRNA comprising any one of the guide sequence disclosed herein, and further comprising a nucleotide sequence of SEQ ID No: 140, wherein the nucleotides of SEQ ID NO: 140 follow the guide sequence at its 3' end. In some embodiments, a dual guide RNA further comprises a tRNA.

In some embodiments, the invention comprises a sgRNA comprising a sequence selected from SEQ ID Nos: 130-139, or 408.

In some instances, the sgRNA comprises a guide sequence that is at least 99%, 98%, 97%, 96%, 95%, 94%, 93%, 92%, 91%, or 90% identical to a sequence selected from SEQ ID Nos: 130-139, or 408.

The invention comprises a sgRNA comprising the nucleotides of SEQ ID NO: 130, wherein N is any natural or non-natural nucleotide, and wherein the N's collectively form a guide sequence that targets Cas9 to the SERPINA1 gene.

In some embodiments, the sgRNA comprises a guide sequence selected from any one of SEQ ID Nos: 5-129.

In some embodiments, a sgRNA comprising any one of the guide sequences of SEQ ID Nos: 5-129 and the nucleotides of SEQ ID NO: 408 is provided.

In some embodiments, the guide sequence is encoded on a vector. In some embodiments, the guide RNA comprises a guide sequence that is complementary to a target sequence in the positive strand of SERPINA1. In some embodiments, the guide RNA comprises a guide sequence that is complementary to a target sequence in the negative strand of SERPINA1.

In some embodiments, the guide RNAs comprising a guide sequence further comprising a second guide sequence, wherein the first guide sequence is complementary to a first target sequence in the positive strand of the SERPINA1 gene and the second guide sequence is complementary to a second target sequence in the negative strand of the SERPINA1 gene.

The guide RNAs of the invention may be modified. In some embodiments, the modification comprises a 2'-O-methyl (2'-O-Me) modified nucleotide. In some embodiments, the modification comprises a phosphorothioate (PS) bond between nucleotides. In some embodiments, the modification comprises a 2'-fluoro (2'-F) modified nucleotide. In some embodiments, the modification comprises an inverted abasic nucleotide.

In some embodiments, the modification is at one or more of the first five nucleotides at the 5' end. In some embodiments, the modification is at one or more of the last five nucleotides at the 3' end.

In some embodiments, the modification comprises PS bonds between the first four nucleotides. In some embodiments, the modification comprises PS bonds between the last four nucleotides. The PS-modified guide may further comprise 2'-O-Me modified nucleotides at the first three nucleotides at the 5' end and the last three nucleotides at the 3' end.

In some embodiments, the guide RNA comprises the modified nucleotides of SEQ ID NO: 408.

In some embodiments, a composition or formulation comprising any of the described guide RNAs and a pharmaceutically acceptable excipient or carrier is provided.

In some embodiments, a composition is provided comprising a guide RNA as described herein associated with a lipid nanoparticle (LNP).

The composition may further comprise a nuclease protein or an mRNA that encodes a nuclease.

In some embodiments, the nuclease is a Cas. In some embodiments, the Cas is Cas9. In some embodiments, the Cas is Cpf1. In some embodiments, the nuclease is a nickase. In some embodiments, the nuclease is modified. In some embodiments, the modified nuclease comprises a nuclear localization signal (NLS).

In some embodiments, the Cas is from the Type-I, Type-II, or Type-III CR1SPR/Cas system.

In some embodiments, a method of inducing a double-stranded break (DSB) within the SERPINA1 gene is provided comprising administering any one or more of the guide RNAs, compositions, or formulations described herein.

In some embodiments, a method of modifying the SERPINA1 gene is provided comprising, delivering a Cas protein or a nucleic acid encoding a Cas protein, and any one or more of the guide RNAs, compositions, or formulations described herein.

In some embodiments, a method of treating AATD is provided comprising, administering a Cas protein or a nucleic acid encoding a Cas protein, and any one or more of the guide RNAs, compositions, or formulations described herein, thereby treating AATD.

In some embodiments, a method for reducing or preventing the accumulation of AAT in the liver of a subject is provided comprising, administering a Cas protein or a nucleic acid encoding a Cas protein, and any one or more of the guide RNAs, compositions, or formulations described herein, thereby reducing accumulation of AAT in the liver.

In some embodiments, ATT is reduced or prevented in liver cells. In some embodiments, the liver cells are hepatocytes.

In some method and use embodiments, the subject has AATD.

In some embodiments, non-homologous ending joining (NHEJ) leads to a mutation during repair of a DSB in the SERPINA1 gene. In some instances, NHEJ leads to a deletion or insertion of a nucleotide(s) during repair of a DSB in the SERPINA1 gene. In some embodiments, the deletion or insertion of a nucleotide(s) induces a frame shift or nonsense mutation in the SERPINA1 gene.

In some embodiments, the administering reduces levels of alpha-1 antitrypsin (AAT). The levels of AAT may be measured in serum, plasma, blood, cerebral spinal fluid, or sputum. The levels of AAT may be measured in liver tissue.

In some method and use embodiments, the subject is human. The human subject may have alpha-1 antitrypsin deficiency (AATD). The subject may have a family history of AATD. The subject may have both liver and lung symptoms of AATD. The subject may have only or predominantly liver symptoms of AATD.

In some embodiments, the subject expresses AAT having a E342K mutation. In some embodiments, the subject has at least one Z allele at the SERPINA1 locus. In some embodiments, the subject has at least one S allele at the SERPINA1 locus. In some embodiments, the subject is homozygous for the Z allele at the SERPINA1 locus. In some embodiments, the subject is heterozygous for the Z allele at the SERPINA1 locus. In some embodiments, the subject has one Z allele and one S allele at the SERPINA1 locus.

The subject may not have a E342K mutation in the amino acid sequence of AAT, but still have a reduced level of wildtype AAT.

In some embodiments, after administration, the subject may have an improvement, stabilization, or slowing of edema, ascites, or jaundice, or a delay in need for liver transplantation. In some embodiments, after administration, the subject has an improvement, stabilization, or slowing of change as measured by imaging methods or liver enzyme levels as a result of administration.

Any of the guide, composition or pharmaceutical formulations described herein may be administered via a viral vector.

Any of the guide, composition or pharmaceutical formulations described herein may be administered via lipid nanoparticles.

In some embodiments, the subject is tested for specific mutations in the SERPINA1 gene before administering the guide, composition, or formulation.

In some embodiments, uses of any of the guide, composition, or formulations described herein for the preparation of a medicament for treating a human subject having AATD are encompassed.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1—Materials and Methods

1. In Vitro Transcription ("IVT") of Nuclease mRNA

Capped and polyadenylated *Streptococcus pyogenes* ("Spy") Cas9 mRNA containing N1-methyl pseudo-U was generated by in vitro transcription using a linearized plasmid DNA template and T7 RNA polymerase. Plasmid DNA containing a T7 promoter and a 100 nt poly (A/T) region was linearized by incubating at 37° C. for 2 hours with XbaI with the following conditions: 200 ng/µL plasmid, 2 U/µL XbaI (NEB), and 1× reaction buffer. The XbaI was inactivated by heating the reaction at 65° C. for 20 min. The linearized plasmid was purified from enzyme and buffer salts using a silica maxi spin column (Epoch Life Sciences) and analyzed by agarose gel to confirm linearization. The IVT reaction to generate Cas9 modified mRNA was incubated at 37° C. for 4 hours in the following conditions: 50 ng/4 linearized plasmid; 2 mM each of GTP, ATP, CTP, and N1-methyl pseudo-UTP (Trilink); 10 mM ARCA (Trilink); 5 U/µL T7 RNA polymerase (NEB); 1 U/µL Murine RNase inhibitor (NEB); 0.004 U/µL Inorganic *E. coli* pyrophosphatase (NEB); and 1× reaction buffer. After the 4-hour incubation, TURBO DNase (ThermoFisher) was added to a final concentration of 0.01 U/4, and the reaction was incubated for an additional 30 minutes to remove the DNA template. The Cas9 mRNA was purified from enzyme and nucleotides using a MegaClear Transcription Clean-up kit according to the manufacturer's protocol (ThermoFisher). The transcript concentration was determined by measuring the light absorbance at 260 nm (Nanodrop), and the transcript was analyzed by capillary electrophoresis by Bioanlayzer (Agilent).

For the experiments described in Examples 2 and 3, a plasmid DNA template comprising SEQ ID NO:422 was used to generate the IVT Cas9 mRNA. For the experiments described in Examples 4 and 5, a plasmid DNA template comprising SEQ ID NO:423 was used to generate the IVT Cas9 mRNA.

DNA sequence used to generate IVT mRNA used in Examples 2 and 3 (SEQ ID NO: 422):

```
TAATACGACTCACTATAGGGTCCCGCAGTCGGCGTCCAGCGGCTCTGC

TTGTTCGTGTGTGTGTCGTTGCAGGCCTTATTCGGATCCATGGATAAGAAGTACT

CAATCGGGCTGGATATCGGAACTAATTCCGTGGGTTGGGCAGTGATCACGGATG

AATACAAAGTGCCGTCCAAGAAGTTCAAGGTCCTGGGGAACACCGATAGACACA

GCATCAAGAAAAATCTCATCGGAGCCCTGCTGTTTGACTCCGGCGAAACCGCAG

AAGCGACCCGGCTCAAACGTACCGCGAGGCGACGCTACACCCGGCGGAAGAATC

GCATCTGCTATCTGCAAGAGATCTTTTCGAACGAAATGGCAAAGGTCGACGACA

GCTTCTTCCACCGCCTGGAAGAATCTTTCCTGGTGGAGGAGGACAAGAAGCATG

AACGGCATCCTATCTTTGGAAACATCGTCGACGAAGTGGCGTACCACGAAAAGT

ACCCGACCATCTACCATCTGCGGAAGAAGTTGGTTGACTCAACTGACAAGGCCG

ACCTCAGATTGATCTACTTGGCCCTCGCCCATATGATCAAATTCCGCGGACACTT

CCTGATCGAAGGCGATCTGAACCCTGATAACTCCGACGTGGATAAGCTTTTCATT

CAACTGGTGCAGACCTACAACCAACTGTTCGAAGAAAACCCAATCAATGCTAGC
```

-continued

```
GGCGTCGATGCCAAGGCCATCCTGTCCGCCCGGCTGTCGAAGTCGCGGCGCCTCG

AAAACCTGATCGCACAGCTGCCGGAGAGAAAAAGAACGGACTTTTCGGCAACT

TGATCGCTCTCTCACTGGGACTCACTCCCAATTTCAAGTCCAATTTTGACCTGGCC

GAGGACGCGAAGCTGCAACTCTCAAAGGACACCTACGACGACGACTTGGACAAT

TTGCTGGCACAAATTGGCGATCAGTACGCGGATCTGTTCCTTGCCGCTAAGAACC

TTTCGGACGCAATCTTGCTGTCCGATATCCTGCGCGTGAACACCGAAATAACCAA

AGCGCCGCTTAGCGCCTCGATGATTAAGCGGTACGACGAGCATCACCAGGATCT

CACGCTGCTCAAAGCGCTCGTGAGACAGCAACTGCCTGAAAAGTACAAGGAGAT

CTTCTTCGACCAGTCCAAGAATGGGTACGCAGGGTACATCGATGGAGGCGCTAG

CCAGGAAGAGTTCTATAAGTTCATCAAGCCAATCCTGGAAAAGATGGACGGAAC

CGAAGAACTGCTGGTCAAGCTGAACAGGGAGGATCTGCTCCGGAAACAGAGAAC

CTTTGACAACGGATCCATTCCCCACCAGATCCATCTGGGTGAGCTGCACGCCATC

TTGCGGCGCCAGGAGGACTTTTACCCATTCCTCAAGGACAACCGGGAAAAGATC

GAGAAAATTCTGACGTTCCGCATCCCGTATTACGTGGGCCCACTGGCGCGCGGCA

ATTCGCGCTTCGCGTGGATGACTAGAAAATCAGAGGAAACCATCACTCCTTGGA

ATTTCGAGGAAGTTGTGGATAAGGGAGCTTCGGCACAAAGCTTCATCGAACGAA

TGACCAACTTCGACAAGAATCTCCCAAACGAGAAGGTGCTTCCTAAGCACAGCC

TCCTTTACGAATACTTCACTGTCTACAACGAACTGACTAAAGTGAAATACGTTAC

TGAAGGAATGAGGAAGCCGGCCTTTCTGTCCGGAGAACAGAAGAAAGCAATTGT

CGATCTGCTGTTCAAGACCAACCGCAAGGTGACCGTCAAGCAGCTTAAAGAGGA

CTACTTCAAGAAGATCGAGTGTTTCGACTCAGTGGAAATCAGCGGGGTGGAGGA

CAGATTCAACGCTTCGCTGGGAACCTATCATGATCTCCTGAAGATCATCAAGGAC

AAGGACTTCCTTGACAACGAGGAGAACGAGGACATCCTGGAAGATATCGTCCTG

ACCTTGACCCTTTTCGAGGATCGCGAGATGATCGAGGAGAGGCTTAAGACCTAC

GCTCATCTCTTCGACGATAAGGTCATGAAACAACTCAAGCGCCGCCGGTACACTG

GTTGGGGCCGCCTCTCCCGCAAGCTGATCAACGGTATTCGCGATAAACAGAGCG

GTAAAACTATCCTGGATTTCCTCAAATCGGATGGCTTCGCTAATCGTAACTTCAT

GCAATTGATCCACGACGACAGCCTGACCTTTAAGGAGGACATCCAAAAAGCACA

AGTGTCCGGACAGGGAGACTCACTCCATGAACACATCGCGAATCTGGCCGGTTC

GCCGGCGATTAAGAAGGGAATTCTGCAAACTGTGAAGGTGGTCGACGAGCTGGT

GAAGGTCATGGGACGGCACAAACCGGAGAATATCGTGATTGAAATGGCCCGAGA

AAACCAGACTACCCAGAAGGGCCAGAAAAACTCCCGCGAAAGGATGAAGCGGA

TCGAAGAAGGAATCAAGGAGCTGGGCAGCCAGATCCTGAAAGAGCACCCGGTG

GAAAACACGCAGCTGCAGAACGAGAAGCTCTACCTGTACTATTTGCAAAATGGA

CGGGACATGTACGTGGACCAAGAGCTGGACATCAATCGGTTGTCTGATTACGAC

GTGGACCACATCGTTCCACAGTCCTTTCTGAAGGATGACTCGATCGATAACAAGG

TGTTGACTCGCAGCGACAAGAACAGAGGGAAGTCAGATAATGTGCCATCGGAGG

AGGTCGTGAAGAAGATGAAGAATTACTGGCGGCAGCTCCTGAATGCGAAGCTGA

TTACCCAGAGAAAGTTTGACAATCTCACTAAAGCCGAGCGCGGCGGACTCTCAG

AGCTGGATAAGGCTGGATTCATCAAACGGCAGCTGGTCGAGACTCGGCAGATTA

CCAAGCACGTGGCGCAGATCTTGGACTCCCGCATGAACACTAAATACGACGAGA
```

-continued

```
ACGATAAGCTCATCCGGGAAGTGAAGGTGATTACCCTGAAAAGCAAACTTGTGT

CGGACTTTCGGAAGGACTTTCAGTTTTACAAAGTGAGAGAAATCAACAACTACC

ATCACGCGCATGACGCATACCTCAACGCTGTGGTCGGTACCGCCCTGATCAAAA

AGTACCCTAAACTTGAATCGGAGTTTGTGTACGGAGACTACAAGGTCTACGACGT

GAGGAAGATGATAGCCAAGTCCGAACAGGAAATCGGGAAAGCAACTGCGAAAT

ACTTCTTTTACTCAAACATCATGAACTTTTTCAAGACTGAAATTACGCTGGCCAAT

GGAGAAATCAGGAAGAGGCCACTGATCGAAACTAACGGAGAAACGGGCGAAAT

CGTGTGGGACAAGGGCAGGGACTTCGCAACTGTTCGCAAAGTGCTCTCTATGCCG

CAAGTCAATATTGTGAAGAAAACCGAAGTGCAAACCGGCGGATTTTCAAAGGAA

TCGATCCTCCCAAAGAGAAATAGCGACAAGCTCATTGCACGCAAGAAAGACTGG

GACCCGAAGAAGTACGGAGGATTCGATTCGCCGACTGTCGCATACTCCGTCCTCG

TGGTGGCCAAGGTGGAGAAGGGAAAGAGCAAAAAGCTCAAATCCGTCAAAGAG

CTGCTGGGGATTACCATCATGGAACGATCCTCGTTCGAGAAGAACCCGATTGATT

TCCTCGAGGCGAAGGGTTACAAGGAGGTGAAGAAGGATCTGATCATCAAACTCC

CCAAGTACTCACTGTTCGAACTGGAAAATGGTCGGAAGCGCATGCTGGCTTCGGC

CGGAGAACTCCAAAAAGGAAATGAGCTGGCCTTGCCTAGCAAGTACGTCAACTT

CCTCTATCTTGCTTCGCACTACGAAAAACTCAAAGGGTCACCGGAAGATAACGA

ACAGAAGCAGCTTTTCGTGGAGCAGCACAAGCATTATCTGGATGAAATCATCGA

ACAAATCTCCGAGTTTTCAAAGCGCGTGATCCTCGCCGACGCCAACCTCGACAAA

GTCCTGTCGGCCTACAATAAGCATAGAGATAAGCCGATCAGAGAACAGGCCGAG

AACATTATCCACTTGTTCACCCTGACTAACCTGGGAGCCCCAGCCGCCTTCAAGT

ACTTCGATACTACTATCGATCGCAAAAGATACACGTCCACCAAGGAAGTTCTGGA

CGCGACCCTGATCCACCAAAGCATCACTGGACTCTACGAAACTAGGATCGATCT

GTCGCAGCTGGGTGGCGATGGCGGTGGATCTCCGAAAAAGAAGAGAAAGGTGTA

ATGAGCTAGCCATCACATTTAAAAGCATCTCAGCCTACCATGAGAATAAGAGAA

AGAAAATGAAGATCAATAGCTTATTCATCTCTTTTTCTTTTTCGTTGGTGTAAAGC

CAACACCCTGTCTAAAAAACATAAATTTCTTTAATCATTTTGCCTCTTTTCTCTGT

GCTTCAATTAATAAAAAATGGAAAGAACCTCGAGAAAAAAAAAAAAAAAAAA

AAAAAAAAAAAAAAAAAAAAAAAAAAAAAAAAAAAAAAAAAAAAAA

AAAAAAAAAAAAAAAAAAAAAAAAAA
```

DNA sequence used to generate IVT mRNA used in Examples 4 and 5 (SEQ ID NO: 423):

```
TAATACGACTCACTATAGGGTCCCGCAGTCGGCGTCCAGCGGCTCTGC

TTGTTCGTGTGTGTCGTTGCAGGCCTTATTCGGATCCATGGATAAGAAGTACT

CAATCGGGCTGGATATCGGAACTAATTCCGTGGGTTGGGCAGTGATCACGGATG

AATACAAAGTGCCGTCCAAGAAGTTCAAGGTCCTGGGGAACACCGATAGACACA

GCATCAAGAAAAATCTCATCGGAGCCCTGCTGTTTGACTCCGGCGAAACCGCAG

AAGCGACCCGGCTCAAACGTACCGCGAGGCGACGCTACACCCGGCGGAAGAATC

GCATCTGCTATCTGCAAGAGATCTTTTCGAACGAAATGGCAAAGGTCGACGACA
```

-continued

```
GCTTCTTCCACCGCCTGGAAGAATCTTTCCTGGTGGAGGAGGACAAGAAGCATG
AACGGCATCCTATCTTTGGAAACATCGTCGACGAAGTGGCGTACCACGAAAAGT
ACCCGACCATCTACCATCTGCGGAAGAAGTTGGTTGACTCAACTGACAAGGCCG
ACCTCAGATTGATCTACTTGGCCCTCGCCCATATGATCAAATTCCGCGGACACTT
CCTGATCGAAGGCGATCTGAACCCTGATAACTCCGACGTGGATAAGCTTTTCATT
CAACTGGTGCAGACCTACAACCAACTGTTCGAAGAAAACCCAATCAATGCTAGC
GGCGTCGATGCCAAGGCCATCCTGTCCGCCCGGCTGTCGAAGTCGCGGCGCCTCG
AAAACCTGATCGCACAGCTGCCGGGAGAGAAAAAGAACGGACTTTTCGGCAACT
TGATCGCTCTCTCACTGGGACTCACTCCCAATTTCAAGTCCAATTTTGACCTGGCC
GAGGACGCGAAGCTGCAACTCTCAAAGGACACCTACGACGACGACTTGGACAAT
TTGCTGGCACAAATTGGCGATCAGTACGCGGATCTGTTCCTTGCCGCTAAGAACC
TTTCGGACGCAATCTTGCTGTCCGATATCCTGCGCGTGAACACCGAAATAACCAA
AGCGCCGCTTAGCGCCTCGATGATTAAGCGGTACGACGAGCATCACCAGGATCT
CACGCTGCTCAAAGCGCTCGTGAGACAGCAACTGCCTGAAAAGTACAAGGAGAT
CTTCTTCGACCAGTCCAAGAATGGGTACGCAGGGTACATCGATGGAGGCGCTAG
CCAGGAAGAGTTCTATAAGTTCATCAAGCCAATCCTGGAAAAGATGGACGGAAC
CGAAGAACTGCTGGTCAAGCTGAACAGGGAGGATCTGCTCCGGAAACAGAGAAC
CTTTGACAACGGATCCATTCCCCACCAGATCCATCTGGGTGAGCTGCACGCCATC
TTGCGGCGCCAGGAGGACTTTTACCCATTCCTCAAGGACAACCGGGAAAAGATC
GAGAAAATTCTGACGTTCCGCATCCCGTATTACGTGGGCCCACTGGCGCGCGGCA
ATTCGCGCTTCGCGTGGATGACTAGAAAATCAGAGGAAACCATCACTCCTTGGA
ATTTCGAGGAAGTTGTGGATAAGGGAGCTTCGGCACAAAGCTTCATCGAACGAA
TGACCAACTTCGACAAGAATCTCCCAAACGAGAAGGTGCTTCCTAAGCACAGCC
TCCTTTACGAATACTTCACTGTCTACAACGAACTGACTAAAGTGAAATACGTTAC
TGAAGGAATGAGGAAGCCGGCCTTTCTGTCCGGAGAACAGAAGAAAGCAATTGT
CGATCTGCTGTTCAAGACCAACCGCAAGGTGACCGTCAAGCAGCTTAAAGAGGA
CTACTTCAAGAAGATCGAGTGTTTCGACTCAGTGGAAATCAGCGGGGTGGAGGA
CAGATTCAACGCTTCGCTGGGAACCTATCATGATCTCCTGAAGATCATCAAGGAC
AAGGACTTCCTTGACAACGAGGAGAACGAGGACATCCTGGAAGATATCGTCCTG
ACCTTGACCCTTTTCGAGGATCGCGAGATGATCGAGGAGAGGCTTAAGACCTAC
GCTCATCTCTTCGACGATAAGGTCATGAAACAACTCAAGCGCCGCCGGTACACTG
GTTGGGGCCGCCTCTCCCGCAAGCTGATCAACGGTATTCGCGATAAACAGAGCG
GTAAAACTATCCTGGATTTCCTCAAATCGGATGGCTTCGCTAATCGTAACTTCAT
GCAATTGATCCACGACGACAGCCTGACCTTTAAGGAGGACATCCAAAAAGCACA
AGTGTCCGGACAGGGAGACTCACTCCATGAACACATCGCGAATCTGGCCGGTTC
GCCGGCGATTAAGAAGGGAATTCTGCAAACTGTGAAGGTGGTCGACGAGCTGGT
GAAGGTCATGGGACGGCACAAACCGGAGAATATCGTGATTGAAATGGCCCGAGA
AAACCAGACTACCCAGAAGGGCCAGAAAAACTCCCGCGAAAGGATGAAGCGGA
TCGAAGAAGGAATCAAGGAGCTGGGCAGCCAGATCCTGAAAGAGCACCCGGTG
GAAAACACGCAGCTGCAGAACGAGAAGCTCTACCTGTACTATTTGCAAAATGGA
CGGGACATGTACGTGGACCAAGAGCTGGACATCAATCGGTTGTCTGATTACGAC
```

```
GTGGACCACATCGTTCCACAGTCCTTTCTGAAGGATGACTCGATCGATAACAAGG

TGTTGACTCGCAGCGACAAGAACAGAGGGAAGTCAGATAATGTGCCATCGGAGG

AGGTCGTGAAGAAGATGAAGAATTACTGGCGGCAGCTCCTGAATGCGAAGCTGA

TTACCCAGAGAAAGTTTGACAATCTCACTAAAGCCGAGCGCGGCGGACTCTCAG

AGCTGGATAAGGCTGGATTCATCAAACGGCAGCTGGTCGAGACTCGGCAGATTA

CCAAGCACGTGGCGCAGATCTTGGACTCCCGCATGAACACTAAATACGACGAGA

ACGATAAGCTCATCCGGGAAGTGAAGGTGATTACCCTGAAAAGCAAACTTGTGT

CGGACTTTCGGAAGGACTTTCAGTTTTACAAAGTGAGAGAAATCAACAACTACC

ATCACGCGCATGACGCATACCTCAACGCTGTGGTCGGTACCGCCCTGATCAAAA

AGTACCCTAAACTTGAATCGGAGTTTGTGTACGGAGACTACAAGGTCTACGACGT

GAGGAAGATGATAGCCAAGTCCGAACAGGAAATCGGGAAAGCAACTGCGAAAT

ACTTCTTTTACTCAAACATCATGAACTTTTTCAAGACTGAAATTACGCTGGCCAAT

GGAGAAATCAGGAAGAGGCCACTGATCGAAACTAACGGAGAAACGGGCGAAAT

CGTGTGGGACAAGGGCAGGGACTTCGCAACTGTTCGCAAAGTGCTCTCTATGCCG

CAAGTCAATATTGTGAAGAAAACCGAAGTGCAAACCGGCGGATTTTCAAAGGAA

TCGATCCTCCCAAAGAGAAATAGCGACAAGCTCATTGCACGCAAGAAAGACTGG

GACCCGAAGAAGTACGGAGGATTCGATTCGCCGACTGTCGCATACTCCGTCCTCG

TGGTGGCCAAGGTGGAGAAGGGAAAGAGCAAAAAGCTCAAATCCGTCAAAGAG

CTGCTGGGGATTACCATCATGGAACGATCCTCGTTCGAGAAGAACCCGATTGATT

TCCTCGAGGCGAAGGGTTACAAGGAGGTGAAGAAGGATCTGATCATCAAACTCC

CCAAGTACTCACTGTTCGAACTGGAAAATGGTCGGAAGCGCATGCTGGCTTCGGC

CGGAGAACTCCAAAAAGGAAATGAGCTGGCCTTGCCTAGCAAGTACGTCAACTT

CCTCTATCTTGCTTCGCACTACGAAAAACTCAAAGGGTCACCGGAAGATAACGA

ACAGAAGCAGCTTTTCGTGGAGCAGCACAAGCATTATCTGGATGAAATCATCGA

ACAAATCTCCGAGTTTTCAAAGCGCGTGATCCTCGCCGACGCCAACCTCGACAAA

GTCCTGTCGGCCTACAATAAGCATAGAGATAAGCCGATCAGAGAACAGGCCGAG

AACATTATCCACTTGTTCACCCTGACTAACCTGGGAGCCCCAGCCGCCTTCAAGT

ACTTCGATACTACTATCGATCGCAAAAGATACACGTCCACCAAGGAAGTTCTGGA

CGCGACCCTGATCCACCAAAGCATCACTGGACTCTACGAAACTAGGATCGATCT

GTCGCAGCTGGGTGGCGATGGCTCGGCTTACCCATACGACGTGCCTGACTACGCC

TCGCTCGGATCGGGCTCCCCCAAAAAGAAACGGAAGGTGGACGGATCCCCGAAA

AAGAAGAGAAAGGTGGACTCCGGATGAGAATTATGCAGTCTAGCCATCACATTT

AAAAGCATCTCAGCCTACCATGAGAATAAGAGAAAGAAAATGAAGATCAATAGC

TTATTCATCTCTTTTTCTTTTTCGTTGGTGTAAAGCCAACACCCTGTCTAAAAAAC

ATAAATTTCTTTAATCATTTTGCCTCTTTTCTCTGTGCTTCAATTAATAAAAAATG

GAAAGAACCTCGAGAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAA
```

2. Human SERPINA1 Guide Design and Human SERPINA1 with Cynomolgus Homology Guide Design Initial guide selection was performed in silico using a human reference genome (e.g., hg38) and user defined genomic regions of interest (e.g., SERPINA1 protein coding exons), for identifying PAMs in the regions of interest. For each identified PAM, analyses were performed and statistics reported. gRNA molecules were further selected and rank-ordered based on a number of criteria known in the art (e.g., GC content, predicted on-target activity, and potential off-target activity).

A total of 88 guide RNAs were designed toward SERPINA1 (ENSG00000197249.13) targeting the protein coding regions within Exon 2 and 3. These 88 guides plus 4 control guides (in duplicate) were placed in 96 well format. In parallel, 51 guide RNAs targeting Exons 2 through 5 of SERPINA1 with 100% homology in cynomolgus monkey plus the 4 control guides (in duplicate) were placed in 96 well format. Guide sequences in the guide RNAs and corresponding genomic coordinates are provided below (Table 1).

3. Cas9 mRNA and Guide RNA Delivery In Vitro

The human embryonic kidney adenocarcinoma cell line HEK293 constitutively expressing Spy Cas9 ("HEK293_Cas9") was cultured in DMEM media supplemented with 10% fetal bovine serum and 500 µg/ml G418. Cells were plated at a density of 10,000 cells/well in a 96-well plate 20 hours prior to transfection (~70% confluent at time of transfection). Cells were transfected with Lipofectamine RNAiMAX (ThermoFisher, Cat. 13778150) according to the manufacturer's protocol. Cells were transfected with a lipoplex containing individual crRNA (25 nM), trRNA (25 nM), Lipofectamine RNAiMAX (0.3 µL/well) and OptiMem.

The human hepatocellular carcinoma cell line HUH7 (Japanese Collection of Research Bioresources Cell Bank, Cat. JCRB0403) was cultured in DMEM media supplemented with 10% fetal bovine serum. Cells were plated at a density of 15,000 cells/well in a 96-well plate 20 hours prior to transfection (~70% confluent at time of transfection). Cells were transfected with Lipofectamine MessengerMAX (ThermoFisher, Cat. LMRNA003) according to the manufacturer's protocol. Cells were sequentially transfected with a lipoplex containing Spy Cas9 mRNA (100 ng), MessengerMAX (0.3 µL/well) and OptiMem followed by a separate lipoplex containing individual crRNA (25 nM), tracer RNA (25 nM), MessengerMAX (0.3 µL/well) and OptiMem.

Primary human liver hepatocytes (PHH) (Gibco, Lot #Hu8249) were cultured according to the manufacturer's protocol (Invitrogen, protocol 11.28.2012). In brief, the cells were thawed and resuspended in hepatocyte thawing medium with supplements (Gibco, Cat. CM7500) followed by centrifugation. The supernatant was discarded and the pelleted cells resuspended in hepatocyte plating medium plus supplement pack (Invitrogen, Cat. A1217601 and CM3000). Cells were counted and plated on Bio-coat collagen I coated 96-well plates (ThermoFisher, Cat. 877272) at a density of 33,000 cells/well. Plated cells were allowed to settle and adhere for 5 hours in a tissue culture incubator at 37° C. and 5% CO2 atmosphere. After incubation cells were checked for monolayer formation and were washed once with hepatocyte culture medium with serum-free supplement pack (Invitrogen, Cat. A1217601 and CM4000). In parallel, individual crRNA and trRNA was pre-annealed by mixing equivalent amounts of reagent and incubating at 95° C. for 2 min and cooling to room temperature. The dual guide (dgRNA) consisting of pre-annealed crRNA and trRNA, was incubated with Spy Cas9 protein to form a ribonucleoprotein (RNP) complex. Cells were transfected with Lipofectamine RNAiMAX (ThermoFisher, Cat. 13778150) according to the manufacturer's protocol. Cells were transfected with an RNP containing Spy Cas9 (10 nM), individual crRNA (10 nM), tracer RNA (10 nM), Lipofectamine RNAiMAX (1.0 µL/well) and OptiMem.

The human hepatocellular carcinoma cell line HepG2 (American Type Culture Collection, Cat. HB-8065) was cultured in DMEM media supplemented with 10% fetal bovine serum. Cells were counted and plated on Bio-coat collagen I coated 96-well plates (ThermoFisher, Cat. 877272) at a density of 15,000 cells/well in a 96-well plate 24 hours prior to incubation with LNPs, as further described in Example 4.

4. Genomic DNA Isolation

HEK293_Cas9, HUH7 and PHH transfected cells were harvested post-transfection at 24 or 48 hours. The gDNA was extracted from each well of a 96-well plate using 50 µL/well BuccalAmp DNA Extraction solution (Epicentre, Cat. QE09050) according to manufacturer's protocol. All DNA samples were subjected to PCR and subsequent NGS analysis, as described herein.

5. Next-Generation Sequencing ("NGS") and Analysis for On-Target Cleavage Efficiency To quantitatively determine the efficiency of editing at the target location in the genome, deep sequencing was utilized to identify the presence of insertions and deletions introduced by gene editing.

PCR primers were designed around the target site within the gene of interest (e.g. SERPINA1), and the genomic area of interest was amplified. Primer sequences are provided in Table 3

TABLE 3

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| Control 1 | CR001261 | 142 | GAGGAGTCCACAGTAGGATTGATT | 280 | CCATCGGACGATCCTATCTGATTA |
| Control 2 | CR001262 | 143 | AGCTAGTTGGTAAGGTCAGTGTG | 281 | AAATCCTAACTGGGCTGGAAGG |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| Control 3 | CR001263 | 144 | AGCTAGTTGGTAAGGTCAGTGTG | 282 | AAATCCTAACTGGGCTGGAAGG |
| Control 4 | CR001264 | 145 | AGCTAGTTGGTAAGGTCAGTGTG | 283 | AAATCCTAACTGGGCTGGAAGG |
| SERPINA1 | CR001367 | 146 | TCATGGTGGGATGTATCTGTCTTC | 284 | CTTGGCACAGGCTGGTTTAATAAT |
| SERPINA1 | CR001368 | 147 | TCATGGTGGGATGTATCTGTCTTC | 285 | CTTGGCACAGGCTGGTTTAATAAT |
| SERPINA1 | CR001369 | 148 | TCATGGTGGGATGTATCTGTCTTC | 286 | CTTGGCACAGGCTGGTTTAATAAT |
| SERPINA1 | CR001370 | 149 | GATCCTGATCATGGTGGGATGTAT | 287 | TTCTTTCAGTGTTACTGATGTCGG |
| SERPINA1 | CR001371 | 150 | TCATGGTGGGATGTATCTGTCTTC | 288 | CTTGGCACAGGCTGGTTTAATAAT |
| SERPINA1 | CR001372 | 151 | GATATTGGTGCTGTTGGACTGGTG | 289 | GTGTCAATCCCTGATCACTGGG |
| SERPINA1 | CR001373 | 152 | ATGCTCACTGGGGAGAAGAAGATA | 290 | TCATCATGTGCCTTGACTCGG |
| SERPINA1 | CR001374 | 153 | ATGCTCACTGGGGAGAAGAAGATA | 291 | TCATCATGTGCCTTGACTCGG |
| SERPINA1 | CR001375 | 154 | ATGCTCACTGGGGAGAAGAAGATA | 292 | TCATCATGTGCCTTGACTCGG |
| SERPINA1 | CR001376 | 155 | GGGAGAAGAAGATATTGGTGCTGT | 293 | GATCACTGGGAGTCATCATGTGC |
| SERPINA1 | CR001377 | 156 | GGGAGAAGAAGATATTGGTGCTGT | 294 | GATCACTGGGAGTCATCATGTGC |
| SERPINA1 | CR001378 | 157 | GGGAGAAGAAGATATTGGTGCTGT | 295 | GATCACTGGGAGTCATCATGTGC |
| SERPINA1 | CR001379 | 158 | GGGAGAAGAAGATATTGGTGCTGT | 296 | GATCACTGGGAGTCATCATGTGC |
| SERPINA1 | CR001380 | 159 | GGGAGAAGAAGATATTGGTGCTGT | 297 | GATCACTGGGAGTCATCATGTGC |
| SERPINA1 | CR001381 | 160 | GATATTGGTGCTGTTGGACTGGTG | 298 | GTGTCAATCCCTGATCACTGGG |
| SERPINA1 | CR001382 | 161 | GGGAGAAGAAGATATTGGTGCTGT | 299 | GATCACTGGGAGTCATCATGTGC |
| SERPINA1 | CR001383 | 162 | GGGAGAAGAAGATATTGGTGCTGT | 300 | GATCACTGGGAGTCATCATGTGC |
| SERPINA1 | CR001384 | 163 | ATTGCAAAGGCTGTAGCGATGCTC | 301 | GTCTTGCAGGACAATGCCGTC |
| SERPINA1 | CR001385 | 164 | ATTGCAAAGGCTGTAGCGATGCTC | 302 | GTCTTGCAGGACAATGCCGTC |
| SERPINA1 | CR001386 | 165 | ATTGCAAAGGCTGTAGCGATGCTC | 303 | GTCTTGCAGGACAATGCCGTC |
| SERPINA1 | CR001387 | 166 | ATTGCAAAGGCTGTAGCGATGCTC | 304 | GTCTTGCAGGACAATGCCGTC |
| SERPINA1 | CR001388 | 167 | ATTTCATCGTGAGTGTCAGCCTT | 305 | AATGCCGTCTTCTGTCTCGTG |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| SERPINA1 | CR001389 | 168 | ATTTCATCGTGAGTGTCAGCCTT | 306 | AATGCCGTCTTCTGTCTCGTG |
| SERPINA1 | CR001390 | 169 | ATTTCATCGTGAGTGTCAGCCTT | 307 | AATGCCGTCTTCTGTCTCGTG |
| SERPINA1 | CR001391 | 170 | ATTTCATCGTGAGTGTCAGCCTT | 308 | AATGCCGTCTTCTGTCTCGTG |
| SERPINA1 | CR001392 | 171 | CCAGGATTTCATCGTGAGTGTCAG | 309 | GAGATGCTGCCCAGAAGACAGATA |
| SERPINA1 | CR001393 | 172 | CTCCAGGATTTCATCGTGAGTGTC | 310 | CCAGAAGACAGATACATCCCACC |
| SERPINA1 | CR001394 | 173 | CGGAATCTCCGTGAGGTTGAAAT | 311 | CTGCCCAGAAGACAGATACATCC |
| SERPINA1 | CR001395 | 174 | CGGAATCTCCGTGAGGTTGAAAT | 312 | ATGATCAGGATCACCCAACCTTC |
| SERPINA1 | CR001396 | 175 | CGGAATCTCCGTGAGGTTGAAAT | 313 | ATGATCAGGATCACCCAACCTTC |
| SERPINA1 | CR001397 | 176 | TTCATGGATCTGAGCCTCCGGAAT | 314 | CACCATGATCAGGATCACCCAAC |
| SERPINA1 | CR001398 | 177 | AAAACTTATCCACTAGCTTCAGGC | 315 | CTGAGTTCGCCTTCAGCCTATAC |
| SERPINA1 | CR001399 | 178 | AAAACTTATCCACTAGCTTCAGGC | 316 | CTGAGTTCGCCTTCAGCCTATAC |
| SERPINA1 | CR001400 | 179 | AAAACTTATCCACTAGCTTCAGGC | 317 | CTGAGTTCGCCTTCAGCCTATAC |
| SERPINA1 | CR001401 | 180 | AAAACTTATCCACTAGCTTCAGGC | 318 | CTGAGTTCGCCTTCAGCCTATAC |
| SERPINA1 | CR001402 | 181 | AAAACTTATCCACTAGCTTCAGGC | 319 | CCAACAGCACCAATATCTTCTTCT |
| SERPINA1 | CR001403 | 182 | TTATCCACTAGCTTCAGGCCCTC | 320 | CCAACAGCACCAATATCTTCTTCT |
| SERPINA1 | CR001404 | 183 | AGGCTTCTGAGTGGTACAACTTTT | 321 | AGTCCAACAGCACCAATATCTTCT |
| SERPINA1 | CR001405 | 184 | AAAACTTATCCACTAGCTTCAGGC | 322 | ACAGCACCAATATCTTCTTCTCCC |
| SERPINA1 | CR001406 | 185 | AGGCTTCTGAGTGGTACAACTTTT | 323 | AGTCCAACAGCACCAATATCTTCT |
| SERPINA1 | CR001407 | 186 | AGGCTTCTGAGTGGTACAACTTTT | 324 | AGTCCAACAGCACCAATATCTTCT |
| SERPINA1 | CR001408 | 187 | AGGCTTCTGAGTGGTACAACTTTT | 325 | AGTCCAACAGCACCAATATCTTCT |
| SERPINA1 | CR001409 | 188 | AGGCTTCTGAGTGGTACAACTTTT | 326 | AGTCCAACAGCACCAATATCTTCT |
| SERPINA1 | CR001410 | 189 | ATTTTCCCTTGAGTACCCTTCTCC | 327 | CTGACACTCACGATGAAATCCTGG |
| SERPINA1 | CR001411 | 190 | ATTTTCCCTTGAGTACCCTTCTCC | 328 | CTGACACTCACGATGAAATCCTGG |
| SERPINA1 | CR001412 | 191 | TTGAGTACCCTTCTCCACGTAATC | 329 | GATGAAATCCTGGAGGGCCTGAAT |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| SERPINA1 | CR001413 | 192 | ATTTTCCCTTGAGTACCCTTCTCC | 330 | CTGACACTCACGATGAAATCCTGG |
| SERPINA1 | CR001414 | 193 | CCACAATTTTCCCTTGAGTACCCT | 331 | ATCCTGGAGGGCCTGAATTTCAAC |
| SERPINA1 | CR001415 | 194 | TCTCCACGTAATCGTTGATCTGTT | 332 | AAGGCTGACACTCACGATGAAATC |
| SERPINA1 | CR001416 | 195 | TCTCCACGTAATCGTTGATCTGTT | 333 | AAGGCTGACACTCACGATGAAATC |
| SERPINA1 | CR001417 | 196 | TCTCCACGTAATCGTTGATCTGTT | 334 | AAGGCTGACACTCACGATGAAATC |
| SERPINA1 | CR001418 | 197 | ATTTTCCCTTGAGTACCCTTCTCC | 335 | CTGACACTCACGATGAAATCCTGG |
| SERPINA1 | CR001419 | 198 | TCTCCACGTAATCGTTGATCTGTT | 336 | AAGGCTGACACTCACGATGAAATC |
| SERPINA1 | CR001420 | 199 | TCTCCACGTAATCGTTGATCTGTT | 337 | AAGGCTGACACTCACGATGAAATC |
| SERPINA1 | CR001421 | 200 | AAAACTGTGTCTCTGTCAAGCTCC | 338 | GAGATTCCGGAGGCTCAGATCCAT |
| SERPINA1 | CR001422 | 201 | CCACAATTTTCCCTTGAGTACCCT | 339 | GATGAAATCCTGGAGGGCCTGAAT |
| SERPINA1 | CR001423 | 202 | GCAACCTTACCTTTAAAGAAGATGTAAT | 340 | GGAACTCCTCCGTACCCTCAA |
| SERPINA1 | CR001424 | 203 | GCAACCTTACCTTTAAAGAAGATGTAAT | 341 | GGAACTCCTCCGTACCCTCAA |
| SERPINA1 | CR001425 | 204 | ACCTTTAAAGAAGATGTAATTCACCAGA | 342 | CTTCCAGGAACTCCTCCGTACC |
| SERPINA1 | CR001426 | 205 | ACCTTTAAAGAAGATGTAATTCACCAGA | 343 | CTTCCAGGAACTCCTCCGTACC |
| SERPINA1 | CR001427 | 206 | ACCTTTAAAGAAGATGTAATTCACCAGA | 344 | CTTCCAGGAACTCCTCCGTACC |
| SERPINA1 | CR001428 | 207 | ACCTTTAAAGAAGATGTAATTCACCAGA | 345 | CTTCCAGGAACTCCTCCGTACC |
| SERPINA1 | CR001429 | 208 | GCAACCTTACCTTTAAAGAAGATGTAAT | 346 | GGAACTCCTCCGTACCCTCAA |
| SERPINA1 | CR001430 | 209 | CTTGTTTCTATGGAACAGCTCAG | 347 | GGGCCTGAAGCTAGTGGATAAG |
| SERPINA1 | CR001431 | 210 | CTTGTTTCTATGGAACAGCTCAG | 348 | GGGCCTGAAGCTAGTGGATAAG |
| SERPINA1 | CR001432 | 211 | CTTGTTTCTATGGAACAGCTCAG | 349 | GGGCCTGAAGCTAGTGGATAAG |
| SERPINA1 | CR001433 | 212 | CTTGTTTCTATGGAACAGCTCAG | 350 | GGGCCTGAAGCTAGTGGATAAG |
| SERPINA1 | CR001434 | 213 | CTTGTTTCTATGGAACAGCTCAG | 351 | GGGCCTGAAGCTAGTGGATAAG |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| SERPINA1 | CR001435 | 214 | CTTGTTTCTATGGAACAGCTCAG | 352 | GGGCCTGAAGCTAGTGGATAAG |
| SERPINA1 | CR001436 | 215 | AACTGAAGAATCCACGCTGAAAAG | 353 | TCAGAAGCCTTCACTGTCAACTTC |
| SERPINA1 | CR001437 | 216 | CATGCCTAAACGCTTCATCATAGG | 354 | GATGGTCAGTTTCAGCACCTTTTA |
| SERPINA1 | CR001438 | 217 | GGCATTGCCCAGGTATTTCATC | 355 | GAGGGATGTGTGTCGTCAAGG |
| SERPINA1 | CR001439 | 218 | GGCATTGCCCAGGTATTTCATC | 356 | GAGGGATGTGTGTCGTCAAGG |
| SERPINA1 | CR001440 | 219 | CATTGCCCAGGTATTTCATCAGC | 357 | GGAGGGGACTCATGGTTTCTTTAT |
| SERPINA1 | CR001441 | 220 | GTTCATTTTCCAGGTGCTGTAGTT | 358 | TGGTTTCTTTATTCTGCTACACTCT |
| SERPINA1 | CR001442 | 221 | GAGTTCATTTTCCAGGTGCTGTAG | 359 | ATTCTGCTACACTCTTCCAAACCT |
| SERPINA1 | CR001443 | 222 | GAGTTCATTTTCCAGGTGCTGTAG | 360 | ATTCTGCTACACTCTTCCAAACCT |
| SERPINA1 | CR001444 | 223 | GAGTTCATTTTCCAGGTGCTGTAG | 361 | ATTCTGCTACACTCTTCCAAACCT |
| SERPINA1 | CR001445 | 224 | TATCGTGGGTGAGTTCATTTTCCA | 362 | TACACTCTTCCAAACCTTCACTCA |
| SERPINA1 | CR001446 | 225 | TATCGTGGGTGAGTTCATTTTCCA | 363 | TACACTCTTCCAAACCTTCACTCA |
| SERPINA1 | CR001447 | 226 | GAGTTCATTTTCCAGGTGCTGTAG | 364 | ATTCTGCTACACTCTTCCAAACCT |
| SERPINA1 | CR001448 | 227 | GAGTTCATTTTCCAGGTGCTGTAG | 365 | ATTCTGCTACACTCTTCCAAACCT |
| SERPINA1 | CR001449 | 228 | TATCGTGGGTGAGTTCATTTTCCA | 366 | TACACTCTTCCAAACCTTCACTCA |
| SERPINA1 | CR001450 | 229 | TATCGTGGGTGAGTTCATTTTCCA | 367 | TACACTCTTCCAAACCTTCACTCA |
| SERPINA1 | CR001451 | 230 | AGGAACTTGGTGATGATATCGTGG | 368 | AAATGGGAGAGACCCTTTGAAGTC |
| SERPINA1 | CR001452 | 231 | CTTCATTTTCCAGGAACTTGGTGA | 369 | TTTGAAGTCAAGGACACCGAGGAA |
| SERPINA1 | CR001453 | 232 | GGGAATCACCTTCTGTCTTCATTTTC | 370 | CCTTTGAAGTCAAGGACACCGAG |
| SERPINA1 | CR001454 | 233 | GGGAATCACCTTCTGTCTTCATTTTC | 371 | TTTGAAGTCAAGGACACCGAGGAA |
| SERPINA1 | CR001474 | 234 | CAAAGGGTTTGTTGAACTTGACCT | 372 | CTATGTGACAGGGAGGGAGAGGAT |
| SERPINA1 | CR001475 | 235 | AGGGGAGACTTGGTATTTTGTTCA | 373 | CTATGTGACAGGGAGGGAGAGGAT |
| SERPINA1 | CR001476 | 236 | AGGGGAGACTTGGTATTTTGTTCA | 374 | CTATGTGACAGGGAGGGAGAGGAT |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| SERPINA1 | CR001477 | 237 | AGGGGAGACTTGGTATTTGTTCA | 375 | CTATGTGACAGGGAGGGAGAGGAT |
| SERPINA1 | CR001478 | 238 | AGGGGAGACTTGGTATTTGTTCA | 376 | CTATGTGACAGGGAGGGAGAGGAT |
| SERPINA1 | CR001483 | 239 | ACCCTTCTTTAATGTCATCCAGGG | 377 | GATCAGCCTTACAACGTGTCTCT |
| SERPINA1 | CR001484 | 240 | ACCCTTCTTTAATGTCATCCAGGG | 378 | GATCAGCCTTACAACGTGTCTCT |
| SERPINA1 | CR003190 | 241 | GATATTGGTGCTGTTGGACTGGTG | 379 | GTGTCAATCCCTGATCACTGGG |
| SERPINA1 | CR003191 | 242 | GATATTGGTGCTGTTGGACTGGTG | 380 | GTGTCAATCCCTGATCACTGGG |
| SERPINA1 | CR003196 | 243 | CAGGATTTCATCGTGAGTGTCAGC | 381 | CTTCTGTCTCGTGGGGCATCCTC |
| SERPINA1 | CR003204 | 244 | GTTGAGGGTACGGAGGAGTTC | 382 | ATGATCAGGATCACCCAACCTTC |
| SERPINA1 | CR003205 | 245 | AAAACTTATCCACTAGCTTCAGGC | 383 | CTGAGTTCGCCTTCAGCCTATAC |
| SERPINA1 | CR003206 | 246 | AAAACTTATCCACTAGCTTCAGGC | 384 | CTGAGTTCGCCTTCAGCCTATAC |
| SERPINA1 | CR003207 | 247 | AGGCTTCTGAGTGGTACAACTTTT | 385 | AGTCCAACAGCACCAATATCTTCT |
| SERPINA1 | CR003208 | 248 | ATTTTCCCTTGAGTACCCTTCTCC | 386 | CTGACACTCACGATGAAATCCTGG |
| SERPINA1 | CR003217 | 249 | TCACCTTCTGTCTTCATTTTCCAG | 387 | GAGAGACCCTTTGAAGTCAAGGAC |
| SERPINA1 | CR003218 | 250 | GTCCCAACATGGCTAAGAGGTG | 388 | GAAGGTGCCTATGATGAAGCGT |
| SERPINA1 | CR003219 | 251 | GTCCCAACATGGCTAAGAGGTG | 389 | GAAGGTGCCTATGATGAAGCGT |
| SERPINA1 | CR003220 | 252 | TATACAGAGTAGCAGTGACCCAGG | 390 | TTAACATCCAGCACTGTAAGAAGC |
| SERPINA1 | CR003221 | 253 | TACAGATACCAGGGTGCAACAAG | 391 | AGGAGTAAGTGGCAGAAATAATCAGA |
| SERPINA1 | CR003222 | 254 | ATACCAGGGTGCAACAAGGTCG | 392 | GACACAGGAGTAAGTGGCAGAAAT |
| SERPINA1 | CR003223 | 255 | CCCACACATTCTTCCCTACAGATA | 393 | CAGAAGAACAAGAGGAATGCTGTG |
| SERPINA1 | CR003224 | 256 | CCCACACATTCTTCCCTACAGATA | 394 | CAGAAGAACAAGAGGAATGCTGTG |
| SERPINA1 | CR003225 | 257 | TCAGTGAATCACGGGCATCTTC | 395 | TCTGCCAGCTTACATTTACCCAAA |
| SERPINA1 | CR003226 | 258 | GAATCACGGGCATCTTCAGGAG | 396 | ACAGGTCTGCCAGCTTACATTTAC |
| SERPINA1 | CR003227 | 259 | TCAGTGAATCACGGGCATCTTC | 397 | TCTGCCAGCTTACATTTACCCAAA |
| SERPINA1 | CR003235 | 260 | GCTCAACCCTTCTTTAATGTCATCC | 398 | CCTTACAACGTGTCTCTGCTTCT |

TABLE 3 -continued

Sequencing Primers for SERPINA1 targeted and control crRNAs

| Description | Guide ID (Sequence primer designed for) | SEQ ID of forward sequence | Forward Sequence | SEQ ID of reverse sequence | Reverse Sequence |
|---|---|---|---|---|---|
| SERPINA1 | CR003236 | 261 | ACCCTTCTTTAATGTCATCCAGGG | 399 | GATCAGCCTTACAACGTGTCTCT |
| SERPINA1 | CR003237 | 262 | ACCCTTCTTTAATGTCATCCAGGG | 400 | GATCAGCCTTACAACGTGTCTCT |
| SERPINA1 | CR003238 | 263 | ACCCTTCTTTAATGTCATCCAGGG | 401 | GATCAGCCTTACAACGTGTCTCT |
| SERPINA1 | CR003240 | 264 | ACCCTTCTTTAATGTCATCCAGGG | 402 | GATCAGCCTTACAACGTGTCTCT |
| SERPINA1 | CR003241 | 265 | ACCCTTCTTTAATGTCATCCAGGG | 403 | GATCAGCCTTACAACGTGTCTCT |
| SERPINA1 | CR003242 | 266 | GCTCAACCCTTCTTTAATGTCATCC | 404 | CCTTACAACGTGTCTCTGCTTCT |
| SERPINA1 | CR003243 | 267 | GCTCAACCCTTCTTTAATGTCATCC | 405 | CCTTACAACGTGTCTCTGCTTCT |
| SERPINA1 | CR003244 | 268 | AAACATGGGAGGGATTTACAGTCA | 406 | CATCGACGAGAAAGGGACTGAAG |
| SERPINA1 | CR003245 | 269 | GCTCAACCCTTCTTTAATGTCATCC | 407 | CCTTACAACGTGTCTCTGCTTCT |
| SERPINA1 | CR003246 | 270 | GCTCAACCCTTCTTTAATGTCATCC | 409 | CCTTACAACGTGTCTCTGCTTCT |

Additional PCR was performed according to the manufacturer's protocols (Illumina) to add chemistry for sequencing. The amplicons were sequenced on an Illumina MiSeq instrument. The reads were aligned to the human reference genome (e.g., hg38) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing") is defined as the total number of sequence reads with insertions/deletions ("indels") or substitutions over the total number of sequence reads, including wild type.

6. Alpha-1 Antitrypsin ("AAT") ELISA

The hepatocellular carcinoma cell line, HUH7, was transfected as previously described with select guides from Table 1. Six days post-transfection, cells were washed once with PBS and then replaced with 200 µL of standard DMEM media with 10% FBS. Four hours later, media was harvested and stored at −20° C. A CellTiter-Glo ("CTG") assay (Promega, Cat. G7570) was completed on the adherent cells according to the manufacturer's protocol. Total AAT levels were determined using an AAT ELISA Kit (R & D Systems, Cat. DY1268). Kit reagents and standards were prepared using the manufacturer's protocol. Prior to running the ELISA, frozen media was thawed at room temperature and centrifuged at 1000 rpm for 1 minute to pellet debris and then placed on ice. For the ELISA, 30 µL of media was diluted with 70 µL of 1× assay diluent. The ELISA procedure was completed according to the manufacturer's protocol. The plate was read on a SpectraMax M5 plate reader. AAT levels were calculated by SoftMax Pro software ver. 6.4.2 using a four parameter logistic curve fit off of the standard curve. Cell numbers for each well were estimated by comparison to the plate average based on the values obtained from the CTG assay. Final AAT levels (pg/ml) were adjusted for cell number.

7. AAT Protein Analysis by Western Blot

The hepatocellular carcinoma cell line, HUH7, was transfected as previously described with select guides from Table 1. Six-days post-transfection, the media was removed and the cells were lysed with 50 µL/well RIPA buffer (Boston Bio Products, Cat. BP-115) plus freshly added protease inhibitor mixture consisting of complete protease inhibitor cocktail (Sigma, Cat. 11697498001), 1 mM DTT, and 250 U/ml Benzonase (EMD Millipore, Cat. 71206-3). Cells were kept on ice for 30 minutes at which time NaCl (1 M final concentration) was added. Cell lysates were thoroughly mixed and retained on ice for 30 minutes. The whole cell extracts ("WCE") were transferred to a PCR plate and centrifuged to pellet debris. A Bradford assay (Bio-Rad, Cat. 500-0001) was used to assess protein content of the lysates. The Bradford assay procedure was completed according to the manufacturer's protocol. Extracts were stored at −20° C. prior to use. Western blots were performed to assess AAT protein levels. Lysates were mixed with Laemmli buffer and denatured at 95° C. for 10 minutes. Western blots were run using the NuPage system on 4-12% Bis-Tris gels (ThermoFisher) according to the manufacturer's protocol followed by wet transfer onto 0.45 µm nitrocellulose membrane (Bio-Rad, Cat. 1620115). After transfer membranes were rinsed thoroughly with water and stained with Ponceau S solution (Boston Bio Products, Cat. ST-180) to confirm complete and even transfer. Blots were blocked using 5% Dry Milk in TBS for 30 minutes on a lab rocker at room temperature. Blots were rinsed with TBST and probed with rabbit α-AAT polyclonal antibody (Sigma, Cat. HPA001292) at 1:1000 in TBST. GAPDH was used as a loading control (ThermoFisher, Cat. NB600502) at 1:2500 in TBST and incubated simultaneously with the AAT primary antibody. Blots were sealed in a bag and kept overnight at 4° C. on a lab rocker. After incubation, blots were rinsed 3 times for 5 minutes each in TBST and probed with secondary antibodies to Mouse and Rabbit (ThermoFisher, Cat. PI35518 and PISA535571) at 1:25,000 each in TBST for 30 minutes at room temperature. After incubation, blots were rinsed 3 times for 5 minutes each in TBST and 2 times with PBS. Blots were visualized and analyzed using a Licor Odyssey system.

8. Lipid Nanoparticle (LNP) Formulation

LNPs were formulated with an N:P ratio (amine to RNA phosphate) (N:P) of 4.5. The lipid nanoparticle components were dissolved in 100% ethanol with the following molar ratios: 45 mol-% cationic lipid (Lipid A); 44 mol-% cholesterol; 9 mol-% DSPC; and 2 mol-% PEG2k-DMG. The RNA cargo (1:1 mRNA:sgRNA (wt/wt)) were dissolved in 25 Mm sodium acetate buffer at pH 4.5, resulting in a concentration of RNA cargo of approximately 0.45 mg/mL. LNPs were formed by microfluidic mixing of the lipid and RNA solutions using a Precision Nanosystems NanoAssemblr™ Benchtop Instrument, according to the manufacturer's protocol. LNPs were collected in water at a ratio of 3:1. LNPs were incubated for one hour at RT. The remaining buffer was exchanged into 50 mM Tris at pH 7.5 (100-fold excess of sample volume), overnight at 4° C. under gentle stirring using a 10 kDa Slide-a-Lyzer™ G2 Dialysis Cassette (ThermoFisher Scientific). The next day the LNPs were concentrated using an Amicon filter (at 4000 g at 4 C) to twice the desired concentration. They were then mixed 1:1 with 2×TSS (50 mM Tris, 90 mM sodium chloride, 10% w/v sucrose at pH 7.5). The resulting mixture was then filtered using a 0.2 μM filter. The resulting filtrate was stored at 2-8° C.

Example 2—Screening and Guide Qualification

1. Cross Screening of SERPINA1 Guides in Multiple Cell Types

Guides targeting human SERPINA1 and those with homology in cynomolgus monkey were transfected into the HEK293 Cas9 and HUH7 cell lines, as well as primary human hepatocytes as described in Example 1. Percent editing was determined for crRNAs comprising each guide sequence across each cell type and the guide sequences were then rank ordered based on highest % edit. The screening data for the guide sequences in Table 1 in all three cell lines are listed below (Table 4, 5, and 6).

Table 4 shows the average and standard deviation for % Edit, % Insertion (Ins), and % Deletion (Del) for the SERPINA1 and control crRNAs in the human kidney adenocarcinoma cell line, HEK293_Cas9, which constitutively over expresses Spy Cas9 protein.

TABLE 4

SERPINA1 editing data for crRNAs expressed in HEK293_Cas9 cells

| Guide ID | Avg % Edit | Std Dev % Edit | Avg % Ins | Std Dev % Ins | Avg % Del | Std Dev % Del |
|---|---|---|---|---|---|---|
| CR001261 (Control 1) | 37.14 | 10.50 | 29.56 | 7.80 | 7.58 | 2.70 |
| CR001262 (Control 2) | 61.12 | 6.39 | 6.27 | 1.02 | 54.85 | 5.37 |
| CR001263 (Control 2) | 49.83 | 5.97 | 4.14 | 0.71 | 45.70 | 5.75 |
| CR001264 (Control 3) | 63.96 | 2.58 | 12.77 | 1.85 | 51.19 | 2.62 |
| CR001367 | 19.98 | 1.45 | 2.35 | 1.20 | 17.63 | 2.22 |
| CR001368 | 33.11 | 4.48 | 6.16 | 2.34 | 26.95 | 4.20 |
| CR001369 | 39.81 | 1.81 | 18.42 | 1.08 | 21.40 | 1.10 |
| CR001370 | 57.97 | 6.52 | 7.76 | 1.07 | 50.21 | 5.61 |
| CR001371 | 35.04 | 7.59 | 7.13 | 1.42 | 27.92 | 6.25 |
| CR001372 | 15.72 | 3.21 | 8.30 | 1.95 | 7.42 | 1.27 |
| CR001373 | 45.15 | 13.06 | 4.13 | 0.99 | 41.01 | 12.06 |
| CR001374 | 58.18 | 5.41 | 2.56 | 0.13 | 55.62 | 5.54 |
| CR001375 | 7.50 | 2.34 | 2.23 | 0.51 | 5.28 | 1.85 |
| CR001376 | 44.31 | 6.67 | 7.74 | 0.64 | 36.57 | 6.06 |
| CR001377 | 20.40 | 4.28 | 1.27 | 0.29 | 19.13 | 3.99 |
| CR001378 | 28.03 | 11.43 | 3.88 | 0.83 | 24.15 | 10.95 |
| CR001379 | 53.08 | 2.61 | 16.18 | 0.22 | 36.90 | 2.39 |
| CR001380 | 46.85 | 3.14 | 14.28 | 2.62 | 32.57 | 1.47 |
| CR001381 | 36.58 | 17.60 | 8.97 | 3.66 | 27.62 | 14.60 |
| CR001382 | 44.55 | 11.27 | 4.13 | 1.16 | 40.42 | 10.40 |
| CR001383 | 30.09 | 2.46 | 6.47 | 6.04 | 23.62 | 3.58 |
| CR001384 | 33.33 | 12.19 | 6.60 | 2.35 | 26.73 | 10.30 |
| CR001385 | 17.84 | 2.09 | 2.90 | 1.09 | 14.93 | 1.01 |
| CR001386 | 28.33 | 12.64 | 5.41 | 2.41 | 22.91 | 10.28 |
| CR001387 | 1.31 | 0.11 | 0.31 | 0.06 | 1.00 | 0.05 |
| CR001388 | 31.56 | 1.55 | 4.87 | 1.05 | 26.69 | 0.52 |
| CR001389 | 30.25 | 8.10 | 4.39 | 0.27 | 25.86 | 7.94 |
| CR001390 | 38.70 | 7.27 | 2.41 | 1.21 | 36.30 | 6.14 |
| CR001391 | 25.85 | 4.84 | 4.73 | 0.85 | 21.12 | 4.33 |
| CR001392 | 38.90 | 1.94 | 4.31 | 0.40 | 34.59 | 2.11 |
| CR001393 | 24.37 | 5.50 | 3.95 | 0.59 | 20.42 | 5.08 |
| CR001394 | 27.59 | 7.94 | 3.81 | 1.16 | 23.77 | 7.03 |
| CR001395 | 64.14 | 1.93 | 20.99 | 1.21 | 43.16 | 0.93 |
| CR001396 | 48.47 | 0.51 | 4.67 | 0.25 | 43.81 | 0.35 |
| CR001397 | 38.85 | 5.70 | 21.07 | 3.03 | 17.78 | 2.92 |
| CR001398 | 50.87 | 7.83 | 8.89 | 2.03 | 41.98 | 5.80 |
| CR001399 | 56.30 | 4.16 | 7.71 | 0.18 | 48.59 | 4.19 |
| CR001400 | 67.59 | 1.70 | 51.60 | 2.79 | 15.99 | 1.64 |
| CR001401 | 32.28 | 4.65 | 4.97 | 0.38 | 27.31 | 4.28 |
| CR001402 | 31.10 | 5.94 | 5.84 | 0.66 | 25.26 | 5.31 |
| CR001403 | 64.84 | 4.30 | 10.76 | 0.12 | 54.08 | 4.41 |
| CR001404 | 73.28 | 1.88 | 2.66 | 0.78 | 70.63 | 1.72 |
| CR001405 | 48.44 | 3.46 | 23.17 | 2.64 | 25.28 | 3.23 |
| CR001406 | 3.96 | 5.13 | 0.07 | 0.06 | 3.89 | 5.06 |
| CR001407 | 20.24 | 1.38 | 3.13 | 0.21 | 17.11 | 1.35 |
| CR001408 | 47.19 | 1.45 | 5.09 | 0.84 | 42.09 | 0.67 |
| CR001409 | 43.17 | 6.32 | 16.98 | 3.44 | 26.20 | 15.26 |
| CR001410 | 32.14 | 0.53 | 3.19 | 0.33 | 28.95 | 0.73 |
| CR001411 | 8.61 | 3.29 | 1.22 | 0.25 | 7.39 | 3.05 |
| CR001412 | 37.33 | 7.35 | 7.38 | 3.13 | 29.95 | 8.09 |
| CR001413 | 43.98 | 1.38 | 18.27 | 1.59 | 25.72 | 2.54 |
| CR001414 | 11.37 | 1.85 | 7.04 | 1.11 | 4.33 | 0.87 |
| CR001415 | 16.17 | 5.14 | 1.38 | 0.34 | 14.79 | 4.80 |
| CR001416 | 19.41 | 3.54 | 1.51 | 0.14 | 17.90 | 3.44 |
| CR001417 | 24.59 | 3.79 | 1.69 | 0.51 | 22.91 | 3.44 |
| CR001418 | 22.23 | 8.75 | 3.32 | 0.64 | 18.91 | 8.42 |
| CR001419 | 7.16 | 2.43 | 1.96 | 0.59 | 5.20 | 1.84 |
| CR001420 | 16.80 | 0.67 | 3.83 | 0.03 | 12.97 | 0.65 |
| CR001421 | 50.60 | 5.30 | 16.44 | 1.91 | 34.16 | 3.68 |
| CR001422 | 46.78 | 8.39 | 35.12 | 4.87 | 11.65 | 3.75 |
| CR001423 | 5.71 | 2.24 | 3.85 | 1.72 | 1.86 | 0.67 |
| CR001424 | 10.02 | 5.15 | 6.63 | 3.08 | 3.39 | 2.13 |
| CR001425 | 11.80 | 2.11 | 2.71 | 0.73 | 9.09 | 2.60 |
| CR001426 | 8.24 | 0.40 | 1.39 | 0.40 | 6.85 | 0.55 |
| CR001427 | 44.65 | 2.98 | 7.44 | 0.41 | 37.21 | 2.59 |
| CR001428 | 19.94 | 6.39 | 2.17 | 0.33 | 17.77 | 6.07 |
| CR001429 | 29.81 | 5.32 | 12.59 | 2.11 | 17.22 | 3.20 |
| CR001430 | 20.87 | 8.25 | 2.13 | 0.44 | 18.74 | 7.84 |
| CR001431 | 52.49 | 10.52 | 33.80 | 7.35 | 18.69 | 3.61 |
| CR001432 | 21.92 | 5.22 | 5.70 | 0.94 | 16.22 | 4.66 |

TABLE 4-continued

SERPINA1 editing data for crRNAs expressed in HEK293_Cas9 cells

| Guide ID | Avg % Edit | Std Dev % Edit | Avg % Ins | Std Dev % Ins | Avg % Del | Std Dev % Del |
|---|---|---|---|---|---|---|
| CR001433 | 40.95 | 2.95 | 23.21 | 1.30 | 17.75 | 1.66 |
| CR001434 | 5.60 | 1.90 | 0.72 | 0.47 | 4.88 | 1.44 |
| CR001435 | 18.53 | 7.21 | 1.83 | 1.10 | 16.70 | 6.11 |
| CR001436 | 14.88 | 2.43 | 1.37 | 0.16 | 13.51 | 7.96 |
| CR001437 | 39.01 | 8.82 | 13.95 | 3.13 | 25.06 | 6.23 |
| CR001438 | 3.68 | 1.14 | 0.15 | 0.05 | 3.53 | 1.09 |
| CR001439 | 49.03 | 5.18 | 37.60 | 3.67 | 11.43 | 2.08 |
| CR001440 | 34.54 | 4.15 | 1.56 | 0.15 | 32.97 | 4.03 |
| CR001441 | 6.54 | 1.29 | 1.29 | 0.45 | 5.25 | 0.96 |
| CR001442 | 25.65 | 3.34 | 2.78 | 0.34 | 22.87 | 3.09 |
| CR001443 | 25.51 | 1.41 | 7.29 | 0.37 | 18.21 | 1.20 |
| CR001444 | 40.41 | 12.61 | 15.09 | 4.07 | 25.32 | 8.73 |
| CR001445 | 11.00 | 3.16 | 1.94 | 1.00 | 9.07 | 2.70 |
| CR001446 | 53.02 | 4.58 | 22.96 | 2.46 | 30.06 | 2.57 |
| CR001447 | 20.10 | 8.74 | 3.25 | 1.64 | 16.84 | 7.25 |
| CR001448 | 15.52 | 3.15 | 3.20 | 0.75 | 12.32 | 2.45 |
| CR001449 | 27.61 | 5.69 | 3.47 | 1.15 | 24.14 | 4.54 |
| CR001450 | 56.61 | 8.41 | 28.80 | 5.02 | 27.81 | 3.43 |
| CR001451 | 34.18 | 20.33 | 9.40 | 6.81 | 24.78 | 13.52 |
| CR001452 | 51.84 | 13.15 | 1.82 | 0.19 | 50.02 | 12.97 |
| CR001453 | 15.91 | 6.86 | 0.69 | 0.37 | 15.22 | 6.49 |
| CR001454 | 20.19 | 6.08 | 1.36 | 0.51 | 18.83 | 5.70 |
| CR001474 | 25.96 | 6.20 | 12.86 | 3.64 | 13.11 | 2.58 |
| CR001475 | 63.15 | 3.07 | 31.61 | 6.12 | 31.55 | 3.31 |
| CR001476 | 54.31 | 7.67 | 2.67 | 1.04 | 51.64 | 6.65 |
| CR001477 | 25.52 | 10.95 | 6.36 | 2.70 | 19.16 | 8.29 |
| CR001478 | 26.52 | 8.90 | 5.60 | 1.66 | 20.92 | 7.24 |
| CR001483 | 28.12 | 6.12 | 2.09 | 1.65 | 26.03 | 5.09 |
| CR001484 | 19.76 | 4.36 | 3.18 | 1.25 | 16.58 | 3.53 |
| CR003190 | 15.11 | 0.09 | 4.36 | 0.27 | 10.75 | 6.21 |
| CR003191 | 25.88 | 7.98 | 7.44 | 2.32 | 18.45 | 5.69 |
| CR003196 | 50.52 | 7.48 | 9.43 | 3.74 | 41.09 | 4.21 |
| CR003204 | 36.91 | 7.35 | 12.61 | 1.50 | 24.30 | 7.38 |
| CR003205 | 17.97 | 0.98 | 2.23 | 0.64 | 15.74 | 0.38 |
| CR003206 | 2.46 | 0.27 | 0.25 | 0.40 | 2.21 | 0.15 |
| CR003207 | 17.50 | 3.13 | 5.54 | 1.16 | 11.96 | 2.07 |
| CR003208 | 55.48 | 6.45 | 9.94 | 1.08 | 45.54 | 5.58 |
| CR003217 | 46.59 | 4.09 | 8.48 | 2.06 | 38.11 | 5.42 |
| CR003218 | 26.03 | 4.39 | 3.34 | 1.29 | 22.70 | 3.93 |
| CR003219 | 39.80 | 4.38 | 7.42 | 1.66 | 32.38 | 2.85 |
| CR003220 | 12.14 | 1.54 | 2.24 | 0.75 | 9.90 | 5.94 |
| CR003221 | 13.00 | 2.59 | 1.96 | 1.32 | 11.05 | 1.70 |
| CR003222 | 37.01 | 7.33 | 2.90 | 0.98 | 34.11 | 20.55 |
| CR003223 | 10.74 | 1.77 | 2.19 | 0.79 | 8.55 | 1.84 |
| CR003224 | 26.86 | 1.86 | 11.22 | 0.84 | 15.64 | 1.02 |
| CR003225 | 34.08 | 7.08 | 15.46 | 6.18 | 18.61 | 2.36 |
| CR003226 | 38.95 | 10.09 | 23.27 | 8.00 | 15.68 | 2.84 |
| CR003227 | 10.78 | 0.60 | 3.67 | 2.38 | 7.11 | 1.97 |
| CR003235 | 29.83 | 10.98 | 10.64 | 2.88 | 19.20 | 8.19 |
| CR003236 | 38.33 | 1.77 | 12.20 | 2.58 | 26.13 | 1.67 |
| CR003237 | 25.91 | 5.58 | 9.09 | 2.64 | 16.81 | 3.09 |
| CR003238 | 34.15 | 4.88 | 4.18 | 0.67 | 29.96 | 5.16 |
| CR003240 | 20.47 | 3.55 | 9.82 | 2.98 | 10.65 | 0.80 |
| CR003241 | 18.30 | 4.42 | 8.32 | 1.74 | 9.98 | 3.67 |
| CR003242 | 13.42 | 2.02 | 3.78 | 0.73 | 9.63 | 1.34 |
| CR003243 | 12.14 | 6.02 | 1.59 | 1.14 | 10.55 | 4.88 |
| CR003244 | 19.12 | 3.52 | 6.50 | 1.03 | 12.62 | 2.56 |
| CR003245 | 12.70 | 5.33 | 2.63 | 1.64 | 10.06 | 3.69 |
| CR003246 | 16.04 | 15.42 | 0.69 | 0.10 | 15.35 | 15.45 |

Table 5 shows the average and standard deviation for % Edit, % Insertion (Ins), and % Deletion (Del) for the tested SERPINA1 and control crRNAs co-transfected with Spy Cas9 mRNA in the human hepatocellular carcinoma cell line, HUH7.

TABLE 5

SERPINA1 editing data for crRNAs expressed in HUH7 cells

| Guide ID | Avg % Edit | Std Dev % Edit | Avg % Ins | Std Dev % Ins | Avg % Del | Std Dev % Del |
|---|---|---|---|---|---|---|
| CR001261 (Control 1) | 29.28 | 12.67 | 19.87 | 8.98 | 9.41 | 3.70 |
| CR001262 (Control 2) | 41.40 | 7.03 | 3.16 | 1.01 | 38.24 | 6.05 |
| CR001263 (Control 3) | 26.98 | 1.18 | 2.24 | 0.35 | 24.73 | 1.52 |
| CR001264 (Control 4) | 44.08 | 1.15 | 7.53 | 0.75 | 36.55 | 0.46 |
| CR001367 | 5.47 | 5.69 | 0.24 | 0.31 | 5.23 | 5.40 |
| CR001368 | 14.79 | 2.61 | 1.19 | 0.39 | 13.60 | 2.25 |
| CR001369 | 17.25 | 5.72 | 6.70 | 1.98 | 10.56 | 3.75 |
| CR001370 | 38.46 | 6.45 | 5.55 | 0.75 | 32.91 | 5.71 |
| CR001371 | 14.63 | 4.57 | 1.63 | 0.56 | 12.99 | 4.14 |
| CR001372 | 10.15 | 2.06 | 3.91 | 0.98 | 6.24 | 1.15 |
| CR001373 | 34.70 | 4.03 | 1.42 | 0.33 | 33.27 | 3.71 |
| CR001374 | 27.33 | 2.59 | 0.99 | 0.04 | 26.35 | 2.62 |
| CR001375 | 4.11 | 0.21 | 1.04 | 0.15 | 3.07 | 0.24 |
| CR001376 | 23.15 | 6.14 | 5.91 | 2.24 | 17.23 | 3.92 |
| CR001377 | 6.47 | 1.96 | 0.45 | 0.28 | 6.02 | 1.69 |
| CR001378 | 14.10 | 4.19 | 0.93 | 0.39 | 13.16 | 3.83 |
| CR001379 | 21.90 | 8.09 | 7.45 | 2.73 | 14.45 | 5.41 |
| CR001380 | 24.22 | 3.87 | 7.37 | 1.00 | 16.85 | 2.91 |
| CR001381 | 12.32 | 8.87 | 2.73 | 2.20 | 9.59 | 6.69 |
| CR001382 | 17.13 | 8.79 | 2.24 | 1.58 | 14.89 | 7.21 |
| CR001383 | 7.42 | 3.28 | 1.53 | 0.44 | 5.89 | 2.98 |
| CR001384 | 12.96 | 9.79 | 2.51 | 2.03 | 10.45 | 7.77 |
| CR001385 | 7.53 | 4.30 | 0.78 | 0.56 | 6.74 | 3.75 |
| CR001386 | 23.99 | 13.56 | 1.62 | 0.16 | 22.37 | 13.49 |
| CR001387 | 0.90 | 0.31 | 0.09 | 0.07 | 0.80 | 0.24 |
| CR001388 | 9.77 | 3.08 | 1.87 | 0.77 | 7.90 | 2.37 |
| CR001389 | 16.05 | 2.28 | 3.20 | 0.35 | 12.85 | 1.93 |
| CR001390 | 11.73 | 2.36 | 0.54 | 0.20 | 11.20 | 2.17 |
| CR001391 | 21.81 | 6.84 | 5.36 | 1.48 | 16.45 | 5.41 |
| CR001392 | 11.96 | 3.02 | 1.45 | 0.40 | 10.51 | 2.62 |
| CR001393 | 7.00 | 2.17 | 0.93 | 0.44 | 6.07 | 1.89 |
| CR001394 | 16.37 | 7.60 | 1.40 | 0.82 | 14.97 | 6.84 |
| CR001395 | 30.98 | 4.33 | 11.11 | 0.93 | 19.87 | 3.40 |
| CR001396 | 14.50 | 1.19 | 1.16 | 0.11 | 13.34 | 1.10 |
| CR001397 | 16.50 | 9.54 | 6.67 | 4.03 | 9.83 | 5.54 |
| CR001398 | 26.04 | 3.41 | 3.41 | 1.02 | 22.64 | 2.69 |
| CR001399 | 35.04 | 5.14 | 3.48 | 0.52 | 31.56 | 4.65 |
| CR001400 | 35.61 | 1.04 | 24.34 | 0.65 | 11.26 | 0.95 |
| CR001401 | 23.70 | 2.90 | 1.73 | 0.08 | 21.97 | 2.90 |
| CR001402 | 19.71 | 3.39 | 3.93 | 0.71 | 15.78 | 2.69 |
| CR001403 | 28.18 | 3.71 | 4.88 | 0.43 | 23.30 | 3.62 |
| CR001404 | 35.07 | 2.36 | 1.02 | 0.40 | 34.05 | 2.03 |
| CR001405 | 21.48 | 10.19 | 9.91 | 4.25 | 11.57 | 6.01 |
| CR001406 | 1.66 | 0.55 | 0.12 | 0.05 | 1.53 | 0.58 |
| CR001407 | 17.44 | 1.05 | 2.35 | 0.42 | 15.08 | 0.73 |
| CR001408 | 19.90 | 8.27 | 3.29 | 1.30 | 16.61 | 7.08 |
| CR001409 | 26.27 | 7.85 | 12.99 | 4.28 | 13.28 | 3.59 |
| CR001410 | 12.89 | 1.64 | 0.88 | 0.17 | 12.01 | 1.49 |
| CR001411 | 4.14 | 1.05 | 0.47 | 0.21 | 3.68 | 0.84 |
| CR001412 | 18.60 | 1.72 | 3.00 | 0.15 | 15.60 | 1.80 |
| CR001413 | 22.14 | 3.34 | 9.37 | 1.35 | 12.77 | 2.00 |
| CR001414 | 5.48 | 2.42 | 2.53 | 1.06 | 2.95 | 1.37 |
| CR001415 | 10.49 | 6.86 | 0.57 | 0.45 | 9.92 | 6.42 |
| CR001416 | 5.33 | 4.64 | 0.35 | 0.30 | 4.98 | 4.35 |
| CR001417 | 11.24 | 9.48 | 0.59 | 0.45 | 10.64 | 9.04 |
| CR001418 | 8.53 | 4.51 | 1.53 | 0.78 | 7.00 | 3.74 |
| CR001419 | 4.77 | 2.89 | 1.11 | 0.65 | 3.66 | 2.24 |
| CR001420 | 6.16 | 4.38 | 1.12 | 0.96 | 5.04 | 3.43 |
| CR001421 | 18.49 | 1.49 | 6.85 | 0.70 | 11.64 | 0.81 |
| CR001422 | 21.46 | 4.27 | 15.17 | 3.34 | 6.30 | 0.95 |
| CR001423 | 3.81 | 1.50 | 0.94 | 0.30 | 2.87 | 1.22 |
| CR001424 | 5.83 | 2.81 | 2.37 | 1.17 | 3.47 | 1.64 |
| CR001425 | 11.32 | 0.84 | 0.53 | 0.05 | 10.79 | 0.86 |
| CR001426 | 3.21 | 1.21 | 0.31 | 0.24 | 2.91 | 0.97 |
| CR001427 | 35.32 | 7.09 | 3.54 | 1.13 | 31.78 | 5.96 |
| CR001428 | 6.98 | 1.67 | 0.73 | 0.27 | 6.25 | 1.40 |
| CR001429 | 9.58 | 5.60 | 3.38 | 2.03 | 6.20 | 3.57 |
| CR001430 | 3.23 | 1.18 | 0.27 | 0.17 | 2.96 | 1.02 |
| CR001431 | 17.90 | 4.70 | 11.23 | 3.22 | 6.67 | 1.62 |
| CR001432 | 5.57 | 1.26 | 1.22 | 0.52 | 4.35 | 0.74 |
| CR001433 | 19.93 | 5.08 | 6.78 | 2.31 | 13.15 | 2.99 |

TABLE 5-continued

SERPINA1 editing data for crRNAs expressed in HUH7 cells

| Guide ID | Avg % Edit | Std Dev % Edit | Avg % Ins | Std Dev % Ins | Avg % Del | Std Dev % Del |
|---|---|---|---|---|---|---|
| CR001434 | 2.72 | 0.05 | 0.17 | 0.04 | 2.55 | 0.08 |
| CR001435 | 12.35 | 2.33 | 1.24 | 0.15 | 11.10 | 2.21 |
| CR001436 | 4.89 | 0.68 | 0.25 | 0.11 | 4.64 | 0.62 |
| CR001437 | 13.47 | 6.01 | 4.01 | 1.94 | 9.46 | 4.11 |
| CR001438 | 3.26 | 0.83 | 0.07 | 0.03 | 3.19 | 0.80 |
| CR001439 | 38.53 | 4.67 | 27.41 | 2.79 | 11.12 | 1.99 |
| CR001440 | 14.29 | 4.38 | 0.97 | 0.37 | 13.32 | 4.02 |
| CR001441 | 5.04 | 0.88 | 0.86 | 0.04 | 4.18 | 0.87 |
| CR001442 | 11.04 | 2.22 | 0.68 | 0.19 | 10.36 | 2.33 |
| CR001443 | 10.38 | 0.63 | 2.83 | 0.20 | 7.55 | 0.74 |
| CR001444 | 20.77 | 3.79 | 2.94 | 0.53 | 17.83 | 3.30 |
| CR001445 | 3.59 | 0.21 | 0.42 | 0.05 | 3.17 | 0.16 |
| CR001446 | 14.52 | 2.62 | 5.36 | 1.04 | 9.16 | 1.59 |
| CR001447 | 9.86 | 2.39 | 1.04 | 0.10 | 8.82 | 2.29 |
| CR001448 | 6.67 | 0.41 | 1.64 | 0.05 | 5.02 | 0.37 |
| CR001449 | 10.66 | 0.26 | 0.83 | 0.19 | 9.83 | 0.26 |
| CR001450 | 12.69 | 2.95 | 6.73 | 1.61 | 5.96 | 1.40 |
| CR001451 | 11.11 | 3.69 | 2.83 | 1.12 | 8.27 | 2.59 |
| CR001452 | 19.02 | 4.47 | 0.45 | 0.18 | 18.57 | 4.29 |
| CR001453 | 6.70 | 3.10 | 0.13 | 0.06 | 6.56 | 3.09 |
| CR001454 | 6.93 | 3.29 | 0.19 | 0.10 | 6.73 | 3.19 |
| CR001474 | 14.47 | 0.59 | 9.31 | 0.55 | 5.16 | 0.24 |
| CR001475 | 43.17 | 2.46 | 13.96 | 0.38 | 29.22 | 2.18 |
| CR001476 | 42.34 | 3.55 | 0.92 | 0.16 | 41.43 | 3.69 |
| CR001477 | 11.25 | 1.22 | 3.62 | 0.45 | 7.63 | 0.82 |
| CR001478 | 12.03 | 1.27 | 1.61 | 0.20 | 10.41 | 1.17 |
| CR001483 | 8.69 | 0.35 | 1.12 | 0.06 | 7.58 | 0.33 |
| CR001484 | 11.22 | 1.44 | 1.38 | 0.49 | 9.83 | 0.96 |
| CR003190 | 7.94 | 1.93 | 1.78 | 0.42 | 6.16 | 1.56 |
| CR003191 | 11.92 | 0.19 | 2.62 | 0.12 | 9.31 | 0.29 |
| CR003196 | 12.60 | 3.00 | 3.39 | 0.80 | 9.21 | 2.21 |
| CR003204 | 9.27 | 0.75 | 3.20 | 0.35 | 6.08 | 0.41 |
| CR003205 | 10.52 | 2.42 | 0.71 | 0.13 | 9.81 | 2.29 |
| CR003206 | 1.82 | 0.33 | 0.06 | 0.03 | 1.77 | 0.31 |
| CR003207 | 6.73 | 0.60 | 2.91 | 0.35 | 3.82 | 0.25 |
| CR003208 | 19.01 | 0.99 | 4.05 | 0.39 | 14.96 | 0.62 |
| CR003217 | 19.38 | 2.40 | 2.33 | 0.49 | 17.04 | 1.95 |
| CR003218 | 8.49 | 0.87 | 0.67 | 0.14 | 7.82 | 0.75 |
| CR003219 | 15.02 | 2.15 | 3.33 | 0.20 | 11.69 | 2.06 |
| CR003220 | 4.42 | 1.05 | 0.52 | 0.02 | 3.90 | 1.03 |
| CR003221 | 8.04 | 1.18 | 0.43 | 0.15 | 7.62 | 1.05 |
| CR003222 | 6.01 | 1.09 | 0.38 | 0.08 | 5.63 | 1.02 |
| CR003223 | 4.66 | 0.97 | 0.54 | 0.12 | 4.11 | 0.85 |
| CR003224 | 5.16 | 1.47 | 2.22 | 0.84 | 2.94 | 0.63 |
| CR003225 | 13.66 | 1.72 | 3.50 | 0.64 | 10.16 | 1.09 |
| CR003226 | 12.33 | 5.09 | 4.46 | 1.99 | 7.87 | 3.20 |
| CR003227 | 2.83 | 0.97 | 0.61 | 0.38 | 2.21 | 0.60 |
| CR003235 | 12.45 | 0.76 | 4.56 | 0.47 | 7.90 | 0.43 |
| CR003236 | 28.21 | 3.13 | 2.74 | 0.30 | 25.47 | 2.86 |
| CR003237 | 8.44 | 0.95 | 1.90 | 0.28 | 6.55 | 0.70 |
| CR003238 | 9.29 | 1.35 | 1.53 | 0.44 | 7.76 | 1.02 |
| CR003240 | 13.29 | 1.41 | 5.54 | 0.39 | 7.75 | 1.05 |
| CR003241 | 9.17 | 4.27 | 3.34 | 1.98 | 5.83 | 2.29 |
| CR003242 | 4.81 | 0.93 | 0.90 | 0.20 | 3.91 | 0.74 |
| CR003243 | 6.14 | 0.75 | 0.60 | 0.10 | 5.54 | 0.68 |
| CR003244 | 9.75 | 1.10 | 2.27 | 0.23 | 7.48 | 0.87 |
| CR003245 | 4.08 | 1.73 | 0.50 | 0.17 | 3.58 | 1.58 |
| CR003246 | 6.50 | 0.38 | 0.46 | 0.09 | 6.04 | 0.30 |

Table 6 shows the average and standard deviation for % Edit, % Insertion (Ins), and % Deletion (Del) for the tested SERPINA1 and control crRNAs co-transfected with Spy Cas9 protein in primary human hepatocytes.

TABLE 6

SERPINA1 editing data for crRNAs expressed in primary human hepatocytes

| GUIDE ID | Avg % Edit | Std Dev % Edit | Avg % Ins | Std Dev % Ins | Avg % Del | Std Dev % Del |
|---|---|---|---|---|---|---|
| CR001261 (Control 1) | 40.90 | 0.60 | 19.27 | 0.70 | 21.64 | 0.84 |
| CR001262 (Control 2) | 51.93 | 5.15 | 3.78 | 1.65 | 48.15 | 3.60 |
| CR001263 (Control 3) | 20.68 | 2.81 | 1.05 | 0.70 | 19.63 | 2.57 |
| CR001264 (Control 4) | 53.15 | 2.78 | 24.01 | 1.21 | 29.14 | 1.82 |
| CR001367 | 16.20 | 1.54 | 0.49 | 0.07 | 15.71 | 1.47 |
| CR001368 | 26.12 | 3.04 | 1.06 | 0.50 | 25.06 | 3.41 |
| CR001369 | 16.05 | 0.57 | 2.04 | 0.27 | 14.01 | 0.60 |
| CR001370 | NA | NA | NA | NA | NA | NA |
| CR001371 | 27.11 | 4.39 | 1.10 | 0.11 | 26.01 | 4.49 |
| CR001372 | 10.72 | 1.40 | 1.81 | 0.46 | 8.91 | 1.30 |
| CR001373 | 71.53 | 3.97 | 0.36 | 0.11 | 71.18 | 3.89 |
| CR001374 | 53.75 | 6.02 | 0.87 | 0.30 | 52.87 | 5.91 |
| CR001375 | 3.93 | 0.44 | 0.57 | 0.13 | 3.37 | 0.38 |
| CR001376 | 25.88 | 0.80 | 7.04 | 1.20 | 18.84 | 0.42 |
| CR001377 | 7.05 | 2.73 | 0.24 | 0.08 | 6.81 | 2.69 |
| CR001378 | 23.42 | 1.52 | 0.45 | 0.21 | 22.97 | 1.60 |
| CR001379 | 37.64 | 3.89 | 4.21 | 0.10 | 33.43 | 3.81 |
| CR001380 | 30.46 | 7.98 | 5.22 | 1.32 | 25.24 | 7.02 |
| CR001381 | 43.15 | 2.52 | 10.64 | 1.92 | 32.51 | 1.59 |
| CR001382 | 24.10 | 3.15 | 1.03 | 0.36 | 23.08 | 3.45 |
| CR001383 | 11.16 | 4.85 | 0.54 | 0.35 | 10.61 | 4.50 |
| CR001384 | 25.99 | 5.70 | 3.88 | 0.44 | 22.11 | 5.43 |
| CR001385 | 16.36 | 2.74 | 1.03 | 0.39 | 15.33 | 2.62 |
| CR001386 | 20.42 | 1.44 | 0.96 | 0.10 | 19.46 | 1.45 |
| CR001387 | 0.88 | 0.15 | 0.06 | 0.03 | 0.82 | 0.12 |
| CR001388 | 10.54 | 2.37 | 1.83 | 0.56 | 8.71 | 1.81 |
| CR001389 | 29.43 | 11.67 | 1.08 | 0.77 | 28.35 | 10.93 |
| CR001390 | 11.70 | 2.08 | 0.25 | 0.17 | 11.45 | 2.05 |
| CR001391 | 36.78 | 12.41 | 1.96 | 1.01 | 34.82 | 11.56 |
| CR001392 | 11.80 | 0.47 | 0.48 | 0.22 | 11.32 | 0.48 |
| CR001393 | 12.28 | 1.22 | 1.16 | 0.07 | 11.12 | 1.15 |
| CR001394 | 37.48 | 2.80 | 6.22 | 0.23 | 31.26 | 2.58 |
| CR001395 | 45.91 | 0.19 | 12.56 | 0.92 | 33.36 | 0.83 |
| CR001396 | 25.05 | 3.21 | 1.64 | 0.96 | 23.41 | 2.25 |
| CR001397 | 37.76 | 0.32 | 5.62 | 0.22 | 32.14 | 0.29 |
| CR001398 | 35.27 | 1.82 | 6.28 | 0.46 | 28.99 | 2.04 |
| CR001399 | 71.45 | 1.71 | 1.67 | 0.45 | 69.79 | 1.33 |
| CR001400 | 64.89 | 0.27 | 32.88 | 1.98 | 32.01 | 2.25 |
| CR001401 | 31.26 | 5.01 | 1.71 | 0.54 | 29.56 | 5.45 |
| CR001402 | 26.57 | 3.19 | 0.98 | 0.82 | 25.58 | 3.74 |
| CR001403 | 24.34 | 3.84 | 10.35 | 4.25 | 13.99 | 0.41 |
| CR001404 | 53.91 | 3.12 | 0.72 | 0.04 | 53.20 | 3.08 |
| CR001405 | 24.19 | 5.35 | 2.28 | 1.12 | 21.91 | 4.32 |
| CR001406 | 1.66 | 0.46 | 0.07 | 0.05 | 1.59 | 0.42 |
| CR001407 | 27.19 | 2.85 | 3.42 | 0.54 | 23.78 | 2.54 |
| CR001408 | 36.36 | 1.15 | 5.34 | 0.31 | 31.02 | 0.84 |
| CR001409 | 26.69 | 2.03 | 15.78 | 1.89 | 10.91 | 0.67 |
| CR001410 | 12.88 | 1.12 | 0.40 | 0.10 | 12.47 | 1.03 |
| CR001411 | 4.85 | 0.52 | 0.11 | 0.08 | 4.74 | 0.46 |
| CR001412 | 23.60 | 1.98 | 0.94 | 0.07 | 22.66 | 2.01 |
| CR001413 | 31.95 | 8.50 | 4.83 | 1.47 | 27.12 | 7.22 |
| CR001414 | 4.05 | 0.64 | 1.42 | 0.26 | 2.63 | 0.55 |
| CR001415 | 24.47 | 3.35 | 0.47 | 0.32 | 24.00 | 3.04 |
| CR001416 | 16.10 | 4.60 | 0.09 | 0.07 | 16.01 | 4.54 |
| CR001417 | 23.38 | 5.00 | 0.70 | 0.27 | 22.68 | 4.75 |
| CR001418 | 13.00 | 2.18 | 1.92 | 0.47 | 11.08 | 2.23 |
| CR001419 | 2.37 | 0.30 | 0.33 | 0.13 | 2.04 | 0.22 |
| CR001420 | 2.44 | 0.52 | 0.28 | 0.19 | 2.16 | 0.42 |
| CR001421 | 31.76 | 7.50 | 7.01 | 0.99 | 24.75 | 6.58 |
| CR001422 | 23.24 | 5.45 | 14.63 | 2.09 | 8.61 | 5.36 |
| CR001423 | 3.76 | 1.80 | 0.36 | 0.02 | 3.40 | 1.79 |
| CR001424 | 11.27 | 2.71 | 1.36 | 0.55 | 9.91 | 2.17 |
| CR001425 | 38.20 | 1.94 | 0.45 | 0.12 | 37.75 | 2.05 |
| CR001426 | 8.90 | 0.45 | 0.28 | 0.07 | 8.63 | 0.38 |
| CR001427 | 33.70 | 0.91 | 0.77 | 0.26 | 32.93 | 0.76 |
| CR001428 | 5.41 | 0.66 | 0.68 | 0.26 | 4.74 | 0.88 |
| CR001429 | 20.46 | 5.24 | 1.21 | 0.80 | 19.24 | 4.50 |
| CR001430 | 4.53 | 0.30 | 0.23 | 0.15 | 4.30 | 0.37 |
| CR001431 | 10.56 | 2.64 | 4.04 | 0.34 | 6.53 | 2.58 |
| CR001432 | 7.20 | 1.54 | 1.35 | 0.09 | 5.85 | 1.46 |

TABLE 6-continued

SERPINA1 editing data for crRNAs expressed in primary human hepatocytes

| GUIDE ID | Avg % Edit | Std Dev % Edit | Avg % Ins | Std Dev % Ins | Avg % Del | Std Dev % Del |
|---|---|---|---|---|---|---|
| CR001433 | 42.38 | 4.26 | 4.77 | 0.54 | 37.61 | 3.88 |
| CR001434 | 1.65 | 0.46 | 0.10 | 0.04 | 1.56 | 0.43 |
| CR001435 | 11.24 | 1.60 | 0.67 | 0.19 | 10.58 | 1.41 |
| CR001436 | 7.02 | 0.29 | 0.22 | 0.15 | 6.80 | 0.24 |
| CR001437 | 15.86 | 1.38 | 1.98 | 0.45 | 13.88 | 1.81 |
| CR001438 | 12.27 | 0.91 | 0.12 | 0.12 | 12.16 | 0.96 |
| CR001439 | 49.32 | 2.14 | 11.45 | 1.62 | 37.86 | 2.53 |
| CR001440 | 12.73 | 2.81 | 0.67 | 0.19 | 12.06 | 2.75 |
| CR001441 | 7.62 | 0.65 | 0.55 | 0.21 | 7.06 | 0.44 |
| CR001442 | 10.28 | 1.71 | 0.44 | 0.22 | 9.84 | 1.90 |
| CR001443 | 11.67 | 0.45 | 0.86 | 0.18 | 10.81 | 0.27 |
| CR001444 | 69.19 | 1.49 | 7.18 | 0.17 | 62.02 | 1.38 |
| CR001445 | 3.54 | 1.36 | 0.51 | 0.56 | 3.03 | 0.81 |
| CR001446 | 33.58 | 3.50 | 13.36 | 3.73 | 20.21 | 3.54 |
| CR001447 | 36.92 | 3.24 | 2.06 | 0.75 | 34.86 | 3.49 |
| CR001448 | 17.57 | 1.15 | 1.61 | 0.18 | 15.96 | 1.25 |
| CR001449 | 39.92 | 4.34 | 0.42 | 0.30 | 39.50 | 4.04 |
| CR001450 | 29.49 | 4.02 | 11.36 | 1.31 | 18.12 | 4.58 |
| CR001451 | 36.02 | 6.92 | 3.93 | 0.78 | 32.09 | 6.14 |
| CR001452 | 58.47 | 3.95 | 0.35 | 0.29 | 58.12 | 3.79 |
| CR001453 | 12.20 | 0.67 | 0.18 | 0.05 | 12.02 | 0.63 |
| CR001454 | 42.15 | 6.39 | 0.18 | 0.07 | 41.96 | 6.32 |
| CR001474 | 3.50 | 0.55 | 1.10 | 0.15 | 2.40 | 0.44 |
| CR001475 | 39.50 | 5.84 | 12.54 | 1.80 | 26.96 | 7.64 |
| CR001476 | 61.10 | 7.94 | 0.40 | 0.07 | 60.70 | 7.99 |
| CR001477 | 20.94 | 2.91 | 3.45 | 0.64 | 17.49 | 2.34 |
| CR001478 | 14.40 | 3.43 | 0.72 | 0.13 | 13.67 | 3.30 |
| CR001483 | 16.05 | 2.18 | 0.88 | 0.28 | 15.17 | 2.14 |
| CR001484 | 7.21 | 2.01 | 0.48 | 0.33 | 6.74 | 1.71 |
| CR003190 | 5.33 | 0.84 | 0.39 | 0.17 | 4.94 | 0.85 |
| CR003191 | 10.58 | 1.38 | 1.02 | 0.29 | 9.56 | 1.38 |
| CR003196 | 13.42 | 3.85 | 1.00 | 0.81 | 12.42 | 3.07 |
| CR003204 | 9.35 | 2.05 | 0.91 | 0.37 | 8.44 | 1.74 |
| CR003205 | 9.17 | 1.25 | 0.19 | 0.12 | 8.98 | 1.14 |
| CR003206 | 1.85 | 0.04 | 0.07 | 0.03 | 1.78 | 0.02 |
| CR003207 | 5.18 | 0.82 | 1.33 | 0.42 | 3.85 | 0.78 |
| CR003208 | 25.18 | 6.59 | 2.17 | 0.88 | 23.01 | 5.82 |
| CR003217 | 28.65 | 5.18 | 2.72 | 0.28 | 25.92 | 5.23 |
| CR003218 | 19.42 | 2.62 | 0.61 | 0.32 | 18.80 | 2.80 |
| CR003219 | 23.05 | 3.77 | 6.65 | 1.74 | 16.41 | 2.02 |
| CR003220 | 4.47 | 0.58 | 0.73 | 0.24 | 3.75 | 0.55 |
| CR003221 | 27.28 | 6.03 | 0.34 | 0.12 | 26.95 | 6.00 |
| CR003222 | 8.96 | 3.22 | 0.20 | 0.20 | 8.76 | 3.11 |
| CR003223 | 2.34 | 0.63 | 0.08 | 0.05 | 2.25 | 0.58 |
| CR003224 | 6.15 | 0.89 | 1.40 | 0.35 | 4.75 | 0.55 |
| CR003225 | 37.34 | 5.44 | 2.36 | 0.26 | 34.98 | 5.45 |
| CR003226 | 40.66 | 8.86 | 11.85 | 2.34 | 28.81 | 7.97 |
| CR003227 | 4.49 | 0.87 | 0.37 | 0.30 | 4.12 | 1.17 |
| CR003235 | 14.85 | 3.18 | 0.89 | 0.55 | 13.96 | 2.78 |
| CR003236 | 49.76 | 2.18 | 0.67 | 0.34 | 49.09 | 1.84 |
| CR003237 | 16.95 | 3.22 | 2.23 | 0.62 | 14.72 | 2.86 |
| CR003238 | 8.94 | 1.34 | 0.52 | 0.10 | 8.42 | 1.26 |
| CR003240 | 18.79 | 3.80 | 2.29 | 0.42 | 16.50 | 3.38 |
| CR003241 | 9.49 | 1.91 | 1.62 | 0.50 | 7.88 | 1.43 |
| CR003242 | 4.86 | 0.69 | 0.53 | 0.21 | 4.32 | 0.82 |
| CR003243 | 4.02 | 1.43 | 0.22 | 0.17 | 3.80 | 1.27 |
| CR003244 | 4.61 | 1.51 | 0.36 | 0.30 | 4.25 | 1.22 |
| CR003245 | 6.01 | 3.48 | 0.44 | 0.11 | 5.56 | 3.41 |
| CR003246 | 8.91 | 2.65 | 0.23 | 0.16 | 8.67 | 2.50 |

Figure 1:
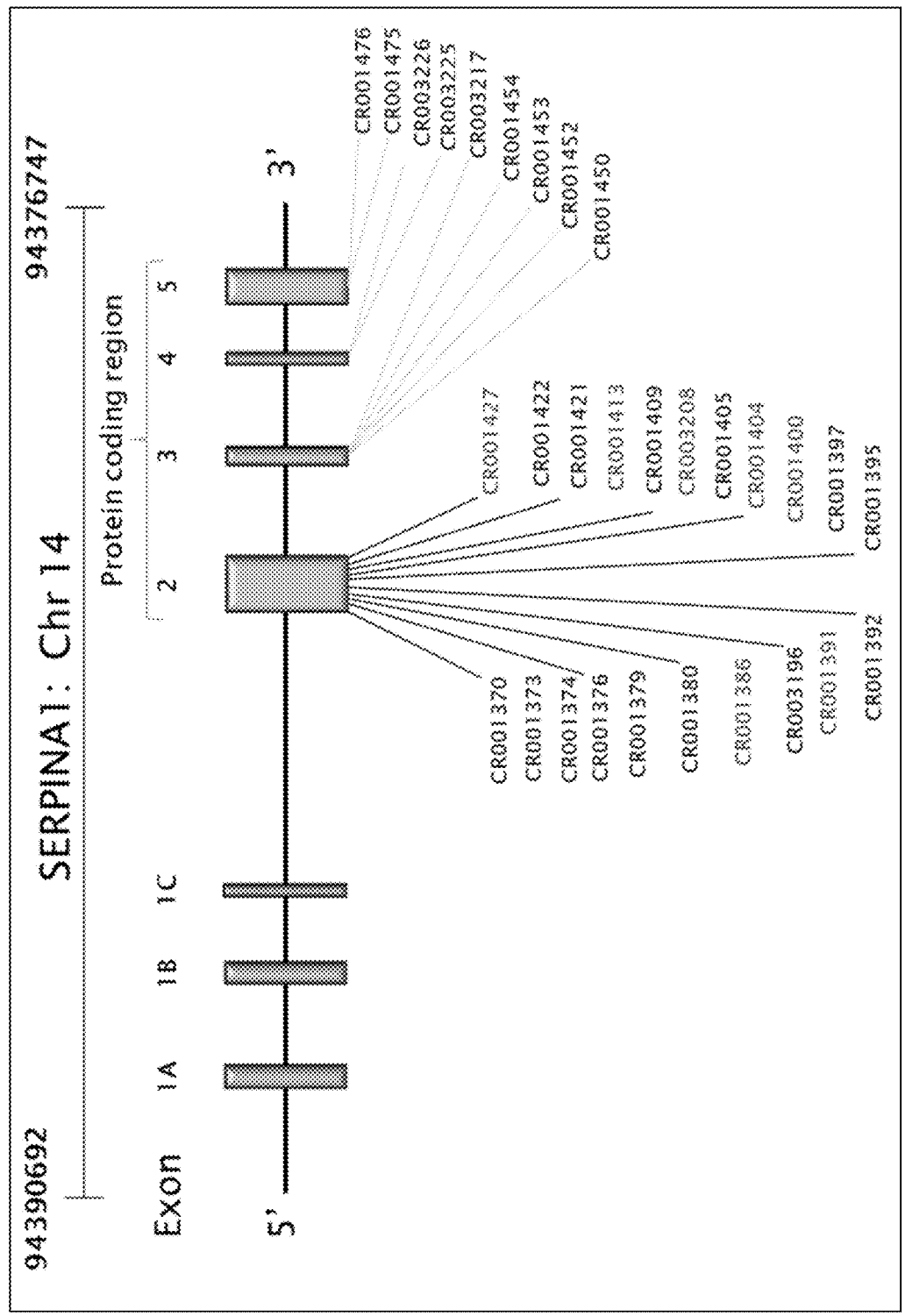
FIG. 1 shows a schematic of chromosome 14 with the regions of the SERPINA1 gene that are targeted by the guide sequences provided in Table 7.
Figure 2:
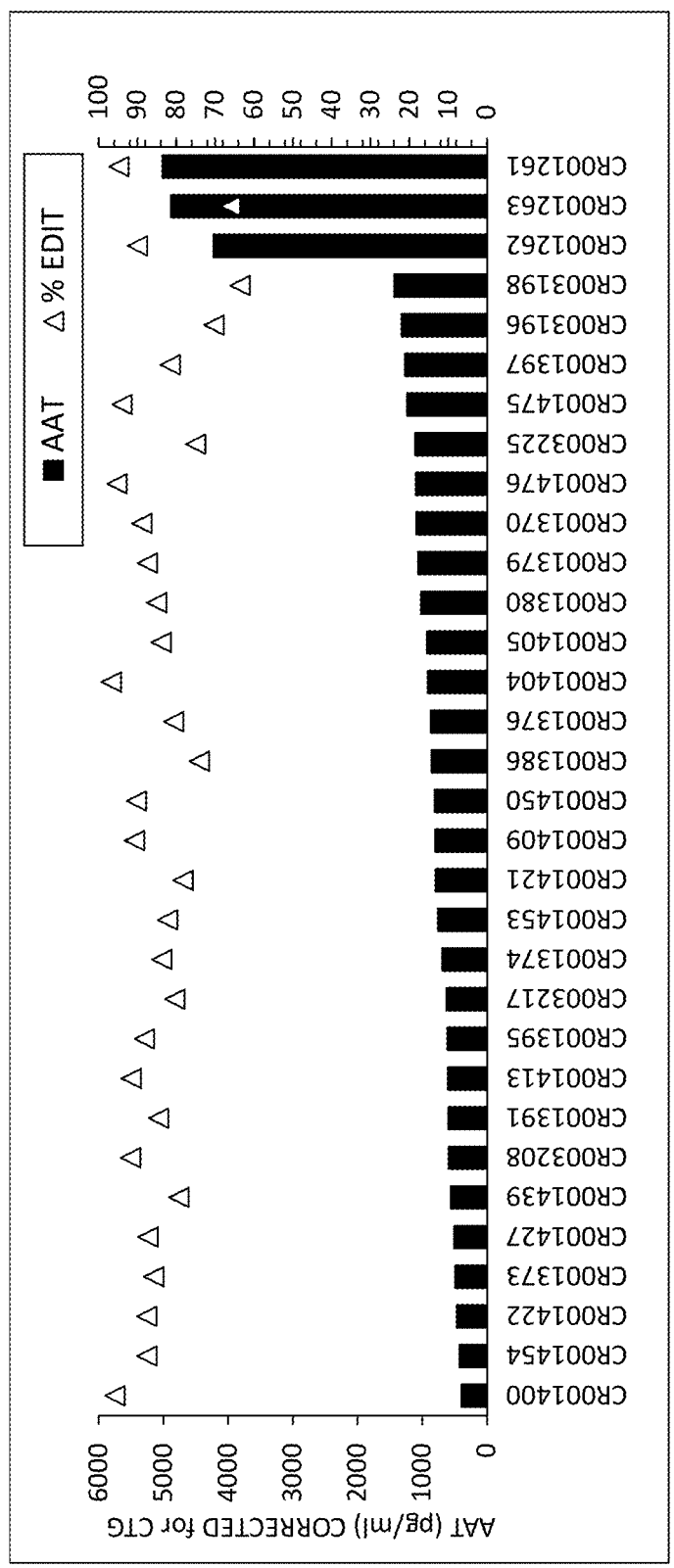
FIG. 2 shows percent editing (% edit) of AAT and levels of secreted AAT following administration of the guide sequences provided on the x-axis. CTG=CellTiter-Glo.

Selected guide sequences from each cell line were used to create a panel of 30 crRNAs for further analysis (Table 7). A schematic drawing overlaying chromosomal location of the selected SERPINA1 guides relative to exons 2-5 is presented in FIG. 1. Percent editing and AAT secretion levels are shown in FIG. 2.

TABLE 7

ELISA and western blot (WB) data for crRNAs targeting SERPINA1 in HUH7 cells

| GUIDE ID | % Edit | ELISA % Reduction | WB % Reduction |
|---|---|---|---|
| CR001370 | 89 | 78 | 16 |
| CR001373 | 86 | 90 | 37 |
| CR001374 | 84 | 86 | 28 |
| CR001376 | 81 | 83 | 42 |
| CR001379 | 87 | 78 | 58 |
| CR001380 | 85 | 79 | 49 |
| CR001386 | 74 | 74 | 43 |
| CR001391 | 74 | 74 | 45 |
| CR001392 | 64 | 71 | 37 |
| CR001395 | 88 | 88 | 47 |
| CR001397 | 82 | 75 | 40 |
| CR001400 | 96 | 92 | 57 |
| CR001404 | 97 | 82 | 47 |
| CR001405 | 84 | 81 | 70 |
| CR001409 | 91 | 84 | 70 |
| CR001413 | 92 | 88 | 72 |
| CR001421 | 78 | 84 | 55 |
| CR001422 | 88 | 91 | 36 |
| CR001427 | 87 | 60 | 66 |
| CR001439 | 79 | 89 | 54 |
| CR001450 | 90 | 84 | 68 |
| CR001453 | 82 | 85 | 49 |
| CR001475 | 94 | 75 | 0 |
| CR001476 | 95 | 78 | 16 |
| CR003196 | 70 | 74 | 50 |
| CR003208 | 92 | 88 | 68 |
| CR003214 | NA | NA | 59 |
| CR003217 | 80 | 87 | 23 |
| CR003225 | 75 | 78 | 25 |
| CR003226 | NA | NA | 38 |

2. Off Target Analysis of SERPINA1 Guides

An oligo insertion based assay (See, e.g., Tsai et al., Nature Biotechnology 33, 187-197; 2015) was used to determine potential off-target genomic sites cleaved by Cas9 targeting SERPINA1. The 30 guides in Table 7 (and two control guides with known off-target profiles) were screened in the HEK293-Cas9 cells as described above, and the off-target results were plotted in FIG. 3. The assay identified potential off-target sites for some of the crRNAs and identified others that had no detectable off-targets.

Example 3. Phenotypic Analysis

1. ELISA Analysis of Secreted Alpha-1 Antitrypsin

The hepatocellular carcinoma cell line, HUH7, was transfected as described in Example 1 with guides from Table 1 in quadruplicate. Two days post-transfection, one replicate was harvested for genomic DNA and analysis by NGS sequencing. All guides, including control guides, had percent edits greater than 70% with some guides reaching 95%. Six-days post-transfection one replicate was prepared for media harvest for analysis of secreted AAT by ELISA as previously described. All of the AAT crRNAs reduced the levels of AAT secreted into the media by a factor of 5 to 10-fold when compared to the control guides. The data for % edit for each guide and reduction of extra-cellular AAT is provided in Table 7.

2. Western Analysis of Intracellular Alpha-1 Antitrypsin

The hepatocellular carcinoma cell line, HUH7, was transfected as described in Example 1 with crRNA comprising the guides from Table 1. The transfected pools of cells were retained in tissue culture and passaged for further analysis. At eleven days post-transfection, cells were harvested and whole cell extracts (WCEs) were prepared and subjected to analysis by Western Blot as previously described.

As cells were passaged samples were collected and processed for NGS sequencing as described herein. Select samples from day 2, 23, 32 and 40 were compared (Table 8) for % editing over time. This result suggests that there was not a proliferative change associated with AAT editing in regards to HUH7 cell growth.

TABLE 8

Time course of % editing in HUH7 cells

| Guide | Day 2 | Day 23 | Day 32 | Day 40 |
|---|---|---|---|---|
| CR001261 | 95 | 96 | 97 | 96 |
| CR001263 | 66 | 70 | 71 | 70 |
| CR001373 | 86 | NA | 83 | 85 |
| CR001391 | 85 | 87 | 90 | 91 |
| CR001400 | 96 | 89 | 90 | 90 |
| CR001422 | 88 | 86 | 88 | 87 |
| CR001427 | 85 | 93 | 95 | 93 |
| CR001439 | 79 | 78 | 79 | 79 |
| CR003208 | 92 | 91 | 92 | 94 |

Figure 4:
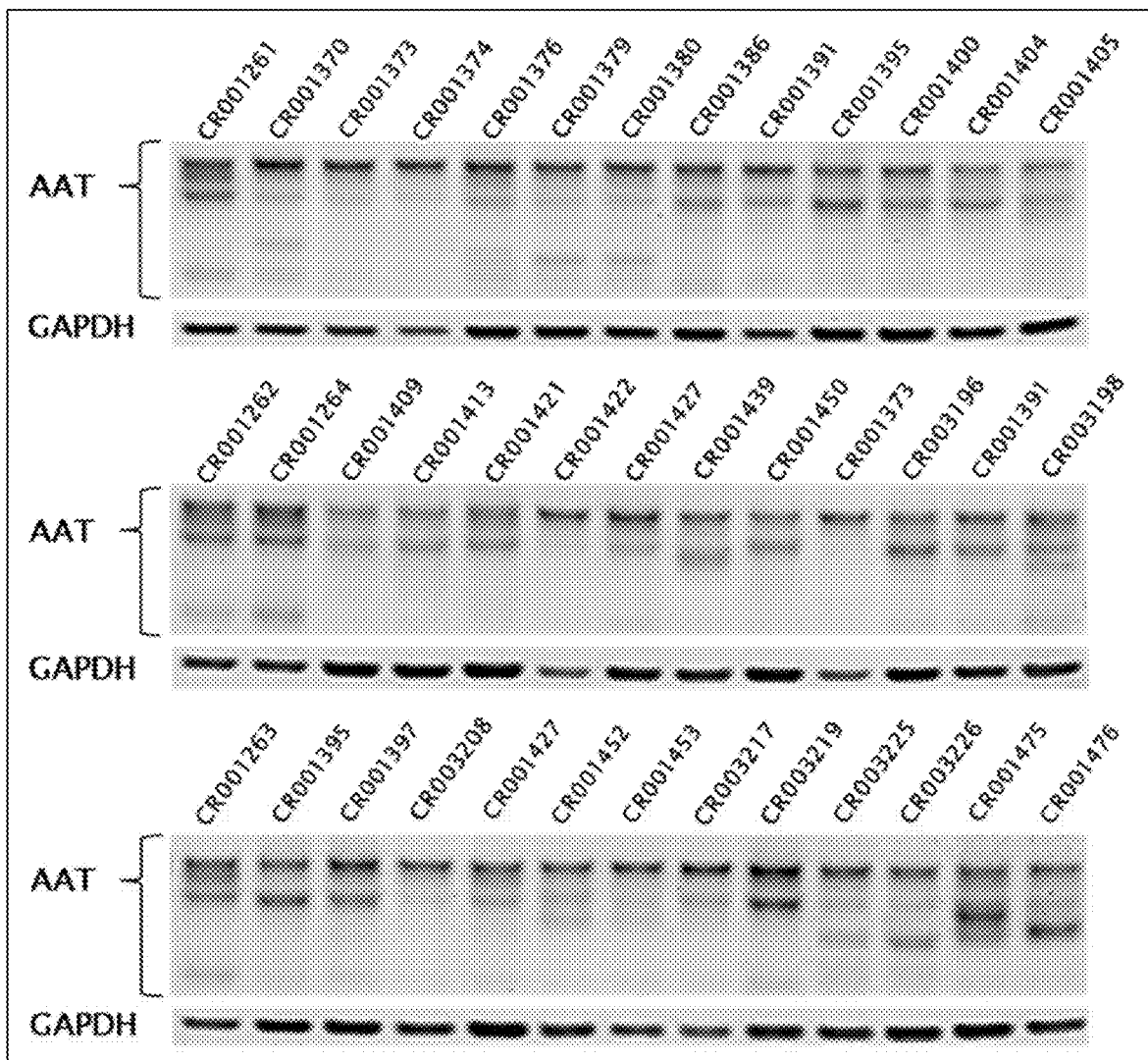
FIG. 4 shows western blot analysis of AAT-targeted guides in HUH7 cells.

WCEs were analyzed by Western Blot for reduction of AAT protein. Full length AAT protein has 418 amino acids, though the protein is heavily glycosylated prior to being secreted. Non-glycosylated AAT has a predicted molecular weight of 46 kD and a band at this molecular weight was observed in the control lanes in the Western Blot along with bands at 52 and 56 kD corresponding to various AAT protein species (FIG. 4).

Percent reduction of AAT protein was calculated using the Licor Odyssey Image Studio Ver 5.2 software. GAPDH was used as a loading control and probed simultaneously with AAT. A ratio was calculated for the densitometry values for GAPDH within each sample compared to the total region encompassing all three bands for AAT. Percent reduction of AAT protein was determined after the ratios were normalized to control lanes. Results are shown in Table 7.

3. Consolidated In Vitro Data for Select Guides

Focused data packages for individual guides were created by analyzing the data described herein. Lead candidates were characterized and rank ordered through a comparison of the reduction of secreted AAT (ELISA), reduction of total AAT protein versus production of extraneous bands (Western Blot), and off-target analysis. The homology, including any mismatches (mm) in sequence, to cynomolgus monkey is also represented. See, FIGS. 5 through 10.

Example 4. Lipid Nanoparticle (LNP) Delivery to Primary Human Hepatocytes (PHH) and HepG2 Cells Lipid nanoparticle formulations of Cas9 mRNA and modified sgRNAs targeting human SERPINA1 were tested on PHH and HepG2 cells in a dose response curve. PHH and HepG2 cells were plated as described in Example 1 (but at 15,000 PHH cells/well as opposed to 33,000/well). The cells were incubated at 37° C., 5% CO2 for 24 hours prior to treatment with LNPs. The LNPs used in the experiment were prepared as described in Example 1, each containing the sgRNA specified in FIGS. 11 and 12 and Cas9 mRNA. LNPs were incubated in hepatocyte maintenance media containing 6% cyno serum at 37° C. for 5 minutes. Post incubation the LNPs were added onto the cells in an 8 point 2-fold dose response curve starting at 100 ng mRNA. The cells were lysed 72 hours post treatment for NGS analysis as described in Example 1. The dose response curve data for the guide sequences in both cell types is shown in FIGS. 11 and 12. The data show that the formulations are effective for editing both HepG2 cells, as well as primary human hepatocytes, which are the intended in vivo cell target in humans.

Example 5. Lipid Nanoparticle (LNP) Delivery and Editing of the Human PiZ Variant in Vivo Five of the six LNP formulations tested in Example 4 and a control LNP comprising a sgRNA targeting the murine TTR gene were administered to transgenic mice harboring copies of the human PiZ variant. The PiZ transgenic mouse has been described previously (See e.g., Carlson J A, Rogers B B, Sifers R N, et al. Accumulation of PiZ alpha 1-antitrypsin causes liver damage in transgenic mice. J Clin Invest 1989; 83:1183-1190), and is believed to carry 7-8 concatemerized copies of the human PiZ variant in mice heterozygous for the concatemer (data not shown).

PiZ mice (mix of male and female) ranging from 15-39 weeks of age were used in this study. LNPs were dosed via the lateral tail vein in a volume of 0.2 mL per animal (n=5 for each group), at a dose of 4 mg/kg (4 mg of total RNA content per kg). Animals were euthanized two weeks post-administration of LNPs. Blood was collected for serum analysis prior to LNP administration and at necropsy. Liver tissue was collected at necropsy from each animal for protein and DNA extraction followed by protein quantification (ELISA and Western blot analyses for serum and tissue levels of PiZ protein, respectively) and NGS analysis using the reagents and methods described in Example 1. Table 9 below shows the sgRNAs formulated in each LNP tested.

TABLE 9

| sgRNA | LNP | target |
|---|---|---|
| G000407 | 641 | hAAT |
| G000408 | 642 | hAAT |
| G000409 | 643 | hAAT |
| G000413 | 644 | hAAT |
| G000414 | 645 | hAAT |
| G000282 | 647 | mTTR |

G000282 (* = PS linkage; 'm' = 2'-O-Me nucleotide):
(SEQ ID NO: 424)
mU*mU*mA*CAGCCACGUCUACAGCAGUUUUAGAmGmCmUmAmGmAmAmAm UmAmGmCAAGUUAAAAUAAGGCUAGUCCGUUAUCAmAmCmUmUmGmAmAm AmAmAmGmUmGmGmCmAmCmCmGmAmGmUmCmGmGmUmGmCmU*mU*mU* mU

As shown in FIG. 13A, robust editing of the PiZ variant of SERPINA1 (or TTR with respect to the murine control) was detected across each group, while no editing was detected in the vehicle control (TSS=Tris/sodium chloride/sucrose buffer). No editing was also detected in some animals within the experimental groups, and subsequent genotyping analysis (data not shown) revealed that these animals were negative for the PiZ transgene, and thus would not be expected to give rise to detectable editing, PiZ protein expression, or knockdown of PiZ secretion into serum. This was further confirmed by protein expression analysis (ELISA and Western blot; See FIGS. 13B and 13C).

Additionally, editing of the PiZ variant correlated with knockdown in serum levels in treated mice. Further, editing also correlated with a knockdown of PiZ protein in liver tissues as shown by Western blot (FIG. 13C). These data demonstrate that the formulations are effective for knocking down expression and secretion of the human PiZ allele in vivo.

What is claimed is:

1. A composition comprising a guide RNA comprising a guide sequence of SEQ ID NO: 42 or a guide sequence that is at least 90% identical to SEQ ID NO: 42 wherein the guide RNA is a single guide RNA (sgRNA) comprising 2'-O-methyl (2'-O-Me) modified nucleotides at the first three nucleotides at the 5' end and/or 2'-O-Me modified nucleotides at the last three nucleotides at the 3' end.

2. The composition of claim 1, wherein the guide sequence is SEQ ID NO: 42.

3. The composition of claim 2, wherein the guide RNA comprises a guide sequence of SEQ ID NO: 42 and further comprises SEQ ID NO: 141 at the 3' end of SEQ ID NO: 42.

4. The composition of claim 2, wherein the guide RNA comprises
mC*mA*mA*CCUCACGGAGAUUCCGGGUUUU
AGAmGmCmUmAmGmAmAmAmUmA
mGmCAAGUUAAAAUAAGGCUAGUCCGUUAUCA-
mAmCmUmUmGmAmAmAmAmAm GmUmGmGmC-
mAmCmCmGmAmGmUmCm
GmGmUmGmCmU*mU*mU*mU (SEQ ID NO: 138), wherein a * indicates a phosphorothioate (PS) linkage and a lower case "m" indicates that the nucleotide is 2'-O-Me modified.

5. The composition of claim 1, wherein the sgRNA comprises a guide sequence that has the modifications of SEQ ID NO: 130 or wherein the sgRNA comprises SEQ ID NO: 130.

6. The composition of claim 5, wherein each N in SEQ ID NO: 130 is any natural or non-natural nucleotide, wherein the N's form the guide sequence, and the guide sequence targets an RNA-guided DNA binding agent to the SERPINA1 gene.

7. The composition of claim 6, wherein each N in SEQ ID NO: 130 is collectively replaced with a guide sequence of SEQ ID NO: 42.

8. The composition of claim 1, wherein the guide RNA comprises at least one further modification comprising
   a. a 2'-O-methyl (2'-O-Me) modified nucleotide;
   b. a phosphorothioate (PS) bond between nucleotides;
   c. a 2'-fluoro (2'-F) modified nucleotide;
   d. a modification at one or more of the first five nucleotides at the 5' end;
   e. a modification at one or more of the last five nucleotides at the 3' end;
   f. PS bonds between the first four nucleotides;
   g. PS bonds between the last four nucleotides; or
   h. a combination of two or more of (a)-(g).

9. The composition of claim 8, wherein the at least one modification comprises phosphorothioate (PS) bonds between the first four nucleotides and/or between the last four nucleotides.

10. The composition of claim 1, wherein the guide RNA comprises a guide sequence that is at least 95% or 90% identical to SEQ ID NO: 42.

11. The composition of claim 10, wherein the guide RNA further comprises SEQ ID NO: 141 at the 3' end of the guide sequence.

12. The composition of claim 11, comprising the modification pattern of SEQ ID NO: 130.

13. The composition of claim 1, wherein the guide RNA is associated with a lipid nanoparticle (LNP).

14. The composition of claim 1, wherein the guide RNA and an RNA-guided DNA binding agent or a nucleic acid encoding an RNA-guided DNA binding agent are associated with a lipid nanoparticle (LNP).

15. The composition of claim 14, wherein the LNP comprises Lipid A (((9Z,12Z)-3-((4,4-bis(octyloxy)butanoyl)oxy)-2-((((3-(diethylamino)propoxy)carbonyl)oxy)methyl)propyl octadeca-9,12-dienoate) and/or PEG2k-DMG.

16. The composition of claim 1, wherein the composition further comprises an RNA-guided DNA binding agent or comprises an mRNA that encodes an RNA-guided DNA binding agent.

17. The composition of claim 16, wherein the RNA-guided DNA binding agent is Cas9 from S. pyogenes.

18. The composition of claim 1, wherein the composition is a pharmaceutical formulation and further comprises a pharmaceutically acceptable carrier.

19. The composition of claim 1, wherein the sgRNA comprises a sequence selected from SEQ ID NOs: 130, 410-414, and 416-421, wherein each N in the sequence is collectively replaced with a guide sequence of SEQ ID NO: 42 or a guide sequence that is at least or 90% identical to SEQ ID NO: 42.

20. A viral vector comprising the composition of claim 1.

21. A lipid nanoparticle comprising the composition of claim 1.

* * * * *

UNITED STATES PATENT AND TRADEMARK OFFICE
CERTIFICATE OF CORRECTION

| | | |
|---|---|---|
| PATENT NO. | : 11,549,107 B2 | Page 1 of 1 |
| APPLICATION NO. | : 16/446764 | |
| DATED | : January 10, 2023 | |
| INVENTOR(S) | : Odate et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Twentieth Day of May, 2025

Coke Morgan Stewart
*Acting Director of the United States Patent and Trademark Office*